United States Patent
Manoharan et al.

(10) Patent No.: US 9,453,222 B2
(45) Date of Patent: Sep. 27, 2016

(54) LIGAND-CONJUGATED MONOMERS

(71) Applicant: ALNYLAM PHARMACEUTICALS, INC., Cambridge, MA (US)

(72) Inventors: Muthiah Manoharan, Cambridge, MA (US); Venkitasamy Kesavan, Cambridge, MA (US); Kallanthottathil G. Rajeev, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 14/582,284

(22) Filed: Dec. 24, 2014

(65) Prior Publication Data

US 2015/0191726 A1 Jul. 9, 2015

Related U.S. Application Data

(63) Continuation of application No. 13/656,365, filed on Oct. 19, 2012, now Pat. No. 8,957,223, which is a continuation of application No. 12/497,262, filed on Jul. 2, 2009, now Pat. No. 8,404,862, which is a continuation of application No. 11/200,703, filed on Aug. 10, 2005, now Pat. No. 7,582,744.

(60) Provisional application No. 60/600,703, filed on Aug. 10, 2004.

(51) Int. Cl.
| | |
|---|---|
| C07F 9/06 | (2006.01) |
| A61K 31/7088 | (2006.01) |
| C12N 15/113 | (2010.01) |
| A61K 47/48 | (2006.01) |
| C12N 15/11 | (2006.01) |
| C12N 15/87 | (2006.01) |
| A61K 31/713 | (2006.01) |

(52) U.S. Cl.
CPC ......... *C12N 15/113* (2013.01); *A61K 31/7088* (2013.01); *A61K 31/713* (2013.01); *A61K 47/48023* (2013.01); *A61K 47/48046* (2013.01); *A61K 47/48107* (2013.01); *A61K 47/48123* (2013.01); *C07F 9/06* (2013.01); *C12N 15/111* (2013.01); *C12N 15/87* (2013.01); *C12N 2310/113* (2013.01); *C12N 2310/14* (2013.01); *C12N 2310/351* (2013.01); *C12N 2310/3515* (2013.01); *C12N 2320/32* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 5,519,134 A | 5/1996 | Acevedo et al. | |
| 5,646,126 A | 7/1997 | Cheng et al. | |
| 5,652,359 A | 7/1997 | Meyer, Jr. et al. | |
| 6,747,014 B2 | 6/2004 | Teng et al. | |
| 7,582,744 B2 | 9/2009 | Manoharan et al. | |
| 8,957,223 B2 * | 2/2015 | Manoharan | A61K 47/48023 548/413 |
| 2003/0175950 A1 | 9/2003 | McSwiggen | |
| 2004/0152112 A1 | 8/2004 | Croce et al. | |
| 2005/0107325 A1 | 5/2005 | Manoharan et al. | |
| 2005/0261218 A1 | 11/2005 | Esau et al. | |
| 2007/0123482 A1 | 5/2007 | Stoffel et al. | |

FOREIGN PATENT DOCUMENTS

| | | |
|---|---|---|
| WO | WO99203464 A1 | 3/1992 |
| WO | WO0044914 A1 | 8/2000 |
| WO | WO0136646 A1 | 5/2001 |
| WO | WO03/029459 A2 | 4/2003 |
| WO | WO03093449 A2 | 11/2003 |
| WO | WO2004011647 A1 | 2/2004 |
| WO | WO2004014933 A1 | 2/2004 |
| WO | WO2004080406 A2 | 9/2004 |
| WO | WO2004094595 A2 | 11/2004 |

OTHER PUBLICATIONS

Aoki et al., "Potential tumor-targeting peptide vector of histidylated oligolysine conjugated to a tumor-homing RGD motif" Cancer Gene Therapy 8:10:783-787 (2001).

Berger et at, "Universal bases for hybridization, replication and chain termination" Nucleic Acids Research 28 (15) :2911-2914 (2000).

Brotschi et al., "A Stable DNA Duplex Containing a Non-Hydrogen-Bonding and Non-Shape-Complementary Base Couple: Interstrand Stacking as the Stability Determining Factor" Agnew Chem. Int. Ed. 40:3012-3014 (2001).

Brummelkamp et al., "Stable suppression of tumorigenicity by virus-mediated RNA interference" Cancer Cell 2:243-247 (2000).

Calin et al,, "Frequent deletions and down-regulation of micro-RNA genes miR15 and miRl6 at 13q14 in chronic lymphocytic leukemia" Proc. Nat. Acad. Sci.USA 99:15524-15529 (2002).

Chang et al., "miR-122, a Mammalian Liver-Specific microRNA, is Processed her from and mRNA and May Downregulate the High Affinity Cationic Amino Acid Transporter CAT-1" RNA Biology 1(2):106-113 (2004).

Chang et al., "miR-122, a Mammalian Liver-Specific microRNA, is Processes from her and mRNA and May Downregulate the High Affinity Cationic Amino Acid Transporter CAT-1" RNA Biology 2(1):17-24 (2005).

Cheruvallath et al., "Use of Phenylacetyle Disulfide (PADS) in the Synthesis of Oligodeoxyribonucleotide Phoshorothioates" Nucleosides & Nucleotides 18(3):485-492 (1999).

(Continued)

*Primary Examiner* — Michael Barker
(74) *Attorney, Agent, or Firm* — Jeffrey N. Townes; LeClairRyan

(57) ABSTRACT

This invention relates composition and methods for making and using chemically modified oligonucleotides agents for inhibiting gene expression.

21 Claims, 25 Drawing Sheets

(56) References Cited

OTHER PUBLICATIONS

Colledge et al., "Disruption of c-mos causes parthenogenetic development of unfertilized mouse eggs" Nature 370:65-68 (1994).
Cormier et al., "Synthesis of hexanucleotide analogues containing diisopropylsilyl internucleotide linkages" Nucleic Acids Res. 16:4583-4594 (1988).
Doench et al., siRNAs can function as miRNAs Genes & Development 17:438-442 (2003).
Edge et al., "Synthetic Analogues of Polynucleotides. Part V. Analogues of Trinucleoside Diphosphates containing Carboxymethylthymidine," J. Chem. Soc. (C) 1933-1939 (1971).
Edge et al., "Synthetic Analogues of Polynucleotides. Part VIII. Analogues of Oligonucleotides containing Carboxymethylthymidine" J. Chem. Soc. Perkin Trans. 1:1991-1996 (1972).
Eis et al., "Accumulation of miR-155 and BIC RNA in human B cell lymphomas" Proc. Nat. Acad. Sci. USA 102 (10):3627-3632 (2005).
Gante, "Azapeptides" Synthesis 405-413 (1989).
Goodman et al., "Nanomolar Small Molecule Inhibtors for αvβ6, αvβ5, and αvβ3 Integrins" J. Med. Chem. 45:1045-1051 (2002).
Griffiths-Jones, "The microRNA Registry" Nucleic Acids Research 32:D109-D111 (2004).
Guckian et al., "Structure and Base Pairing Properties of a Replicable Nonpolar Isostere for Deoxyadenosine" J. Org. Chem. 63:9652-9656 (1998).
Hashimoto et al., "Parthenogenetic activation of oocytes in c-mos-deficient mice" Nature 370:67-71 (1994).
Haubner et al., "Glycosylated RGD-Containing Peptides: Tracer for Tumor Targeting and Angiogenesis Imaging with Improved Biokinetcs" J. Nucl. Med. 42(2):326-336 (2001).
John et al., "Human MicroRNA Targets" PLoS Biology 2(11):1862-1878 (2004); and correction in PLoS Biology 3:1328 (2005).
Johnson et al., "RAS Is Regulated by the let-7 MicroRNA Family" Cell 120:635-647 (2005).
Katajisto et al., "Solid-Phase Synthesis of Multiantennary Oligonucleotide Glycoconjugates Utilizing On-Support Oximation" Bioconjugate Chem. 15:890-896 (2004).
Kim et al., "Identification of many microRNAs that copurify with polyribosomes in mammalian neurons" Proc. Nat. Acad. Sci. USA 101(1):360-365 (2004).
Krek et al,, "Combinatorial microRNA target predictions" Nature Genetics 37(5):495-500 (2005).
Lam et al., "A new type of synthetic peptide library for identifying ligand-binding activity" Nature 354:82-84 (1991).
Lan et al., "Minor Groove Hydration is Critical to the Stability of DNA Duplexes" J. Am. Chem. Soc.122:6512-6513 (2000).
Lim et al., "Microarray analysis shows that some microRNAs downregulate large numbers of target mRNAs" Nature 433(17):769-773 (2005).
Limbach et al., "Summary: the modified nucleosides of RNA" Nucleic Acids Res. 22:2183-2196.
Liu et al., "Bi-stranded, multisite replication of a base pair between difluorotoluene and adenine: confirmation by 'inverse' sequencing" Chem. Biol. 4:919-926 (1997).
Loakes, "Survey and Summary: The Applications of Universal DNA base analogues" Nucleic Acid Res. 29:2437-2447 (2001).
Luedtke et al., "Cellular Uptake of Aminoglycosides, Guanidinoglycosides, and Poly-arginine" J. Am. Chem. Soc. 125:12374-12375 (2003).
Luedtke et al., "RNA—Ligand Interactions: Affinity and Specificity of Aminoglycosicle Dimers and Acridine Conjugates to the HIV-1 Rev Response Element" Biochemistry 42(39):11391-11403 (2003).
Manoharan, "Oligonueleotide Conjugates as Potential Antisense Drugs with Improved Uptake, Biodistribution, Targeted Delivery and Mechanism of Action" Antisense and Nucleic Acid Drug Development 12:103-128 (2002).
Matray et al., "Selective and Stable DNA Base Pairing without Hydrogen Bonds" J. Am. Chem. Soc.120:6191-6192 (1998).

McMinn et al., "Efforts toward Expansion of the Genetic Alphabet; DNA Polymerase Recognition of a Highly Stable, Self-Pairing Hydrophobic Base" J. Am. Chem. Soc. 121:11585-11586 (1999).
Metzler et al., "High Expression of Precursor MicroRNA-155/BIC RNA in Children with Burkitt Lymphoma" Genes, Chromosomes & Cancer 39:167-169 (2004).
Michael et al., "Reduced Accumulation of Specific MicroRNAs in Colorectal Neoplasia" Molecular Cancer Research 1:882-891 (2003).
Morales et al., "Importance of Terminal Base Pair Hydrogen-Bonding in 3'-End Proofreading by the Klenow Fragment of DNA Polyerasel" Biochem. 39:2626-2632 (2000).
Moran et al., "Difluorotoluene, a Nonpolar Isostere for Thymine, Codes Specifically and Efficiently for Adenine in DNA Replication" J. Am. Chem. Soc. 119:2056-2057 (1997).
Morrow et al., "Synthetic metallonucleases for RNA cleavage" Curr. Opin. Chem. Biol. 8:192-200 (2004).
Ogawa et at, "Efforts toward the Expansion of the Genetic Alphabet: Information Storage and Replication with Unnatural Hydrophobic Base Pairs" J. Am. Chem. Soc. 122:3274-3287 (2000).
Ogawa et al., "Rational Design of an Unnatural Base Pair with Increased Kinetic Selectivity" J. Am. Chem. Soc. 122:8803-8804 (2000).
Pfeffer et al., "Identification of microRNAs of the herpesvirus family", Nature Methods 2(4):269-276 (2005).
Pfeffer et al., "Identification of Virus-Encoded MicroRNAs" Science 304:734-736 (2004).
Poy et al., "A pancreatic islet-specific microRNA regulates insulin secretion" Nature 432:226-230 (2004).
Sempere et al, "Expression profiling of mammalian microRNAs uncovers a subset of brain expressed microRNAs with possible roles in murine and human neuronal differentiation" Genome Biology 5:R13 (2004).
Shih et al. "Profound defects in pancreatic β-cell function in mice with combined heterozygous mutation in Pdx-1, Hnf-1α, and Hnf-3β" Proc. Nat. Acad. Sci. USA 99(6):3818-3823 (2002).
Shingara et al., "MicroRNA Profiling by Array Analysis Reveals Critical BioMarkers" Ambion TechNotes 11(6) (2005).
Simeoni et al, "Insight into the mechanism of the peptide-based gene delivery system MPG: implications for delivery of siRNA into mammalian cells" Nucl. Acids Res. 31:2717-2724 (2003).
Stirchak, "Uncharged stereoregular nucleic acid analogs: 2. Morpholino nucleoside oligomers with carbamate internucleoside linkages" Nucleic Acids Res. 17:6129-6141 (1989).
Sulyok et al., "Solid-Phase Synthesis of a Nonpeptide RGD Mimetic Library: New Selective αvβ3 Integrin Antagonists" J. Med. Chem. 44:1938-1950 (2001).
Tae et al., "Efforts toward expansion of the genetic alphabet: replication of DNA with three base pairs" J. Am. Chem. Soc. 123:7439-7440 (2001).
Weizman et al., "2,2'-Bipyridine ligandoside: a novel building block for modifying DNA with intra-duplex metal complexes" J. Am. Chem. Soc.123:3375-3376 (2001).
Wu et al., "Efforts toward Expansion of the Genetic Alphabet: Optimization of Interbase Hydrophobic Interactions" J. Am. Chem. Soc. 122(32):7621-7632 (2000).
Zeng et al., "MicroRNAs and small interfering RNAs can inhibit mRNA expression by similar mechanisms" Proc. Nat. Acad. Sci. USA 100(17):9779-9784 (2003).
Zitzmann et al., "Arginine-Glycine-Aspartic Acid (RGD)-Peptide Binds to Both Tumor and Tumor-Endothelial Cells in Vivo" Cancer Res. 62:5139-5143 (2002).
Krützfeldt et al., "Specificity, Duplex Degradation and Subcellular Localization of Antagomirs", Nucleic Acids Research 35:2885-2892 (2007).
Bijsterbosch, "Modulation of plasma protein binding and in vivo liver cell uptake of phosphorothioate oligodeoxynucleotides by cholesterol conjugation", Nucleic Acids Research 28(14):2717-2725 (2000).
Letsinger et al., "Cholesteryl-conjugated oligonucleotides: Synthesis, properties, and activity as inhibitors of replication of human immunodeficiency virus in cell culture", Proc. Nat. Acad. Sci. USA 86:6553-6556 (1989).

(56) References Cited

OTHER PUBLICATIONS

Mackellar et al., "Synthesis and physical properties of anti-HIV antisense oligonucleotides bearing terminal lipophilic groups", Nucleic Acids Research 20(13):3411-3417 (1992).

Manoharan, "RNA interference and chemically modified siRNAs", Nucleic Acids Research Supplement 3:115-116 (2003).

Zhou et al., "Discovery of Short, 3'-Cholesterol-modified DNA Duplexes with Unique Antitumor Cell Activity", Cancer Research 54:5783-5787 (1994).

* cited by examiner

LIGAND-CONJUGATED MONOMERS

RELATED APPLICATIONS

This application is a continuation application of U.S. application Ser. No. 13/656,365, filed Oct. 19, 2012, which is a continuation application of U.S. application Ser. No. 12/497,262, filed Jul. 2, 2009, now U.S. Pat. No. 8,404,862, which is a continuation application of U.S. application Ser. No. 11/200,703, filed Aug. 10, 2005, now U.S. Pat. No. 7,582,744, which claims the benefit of U.S. Provisional Application No. 60/600,703, filed Aug. 10, 2004; all of which are herein incorporated by reference in their entirety.

TECHNICAL FIELD

This invention relates generally to chemically modified oligonucleotides useful for modulating gene expression. More particularly, the invention relates to single stranded chemically modified oligonucleotides for inhibiting gene expression and to methods of making and using the modified oligonucleotides.

BACKGROUND

A variety of nucleic acid species are capable of modifying gene expression. These include antisense RNA, siRNA, microRNA, RNA and DNA aptamers, and decoy RNAs. Each of these nucleic acid species can inhibit gene expression by a different mechanism.

SUMMARY

The invention features methods and compositions for modulating, either inhibiting or up-regulating, gene expression by using a conjugate of an oligonucleotide agent (a term which is defined below) and a ligand. The compositions include conjugated oligonucleotide agents as well as conjugated monomers that are the components of or can be used to make the conjugated oligonucleotide agents. The conjugated oligonucleotide agents can modify gene expression by targeting and binding to a nucleic acid, e.g., a pre-mRNA, an mRNA, a microRNA (miRNA), a mi-RNA precursor (pre-miRNA), or DNA, or to a protein. An oligonucleotide agent featured in the invention can be, e.g., an miRNA, antisense RNA, decoy RNA, DNA, or aptamer.

Thus, the invention features an oligonucleotide agent coupled to a ligand. The ligand can be attached to the oligonucleotide agent through a monomer, e.g., a chemically modified monomer that is integrated into the oligonucleotide agent. In a preferred embodiment, the coupling is by a tether or a linker (or both) as described herein, and the complex has the formula represented by:

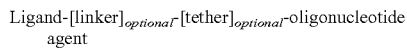

While, in most cases, embodiments are described with respect to an oligonucleotide agent including a number of nucleotides, the invention includes monomeric subunits having the structure:

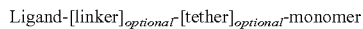

Methods of making and incorporating the monomers into the oligonucleotide agents and methods of using of those agents are included in the invention.

In preferred embodiments, the sugar, e.g., the ribose sugar of one or more of the nucleotides, (e.g., ribonucleotide, deoxynucleotide, or modified nucleotide) subunits of an oligonucleotide agent can be replaced with another moiety, e.g., a non-carbohydrate (preferably cyclic) carrier. A nucleotide subunit in which the sugar of the subunit has been so replaced is referred to herein as a sugar replacement modification subunit (SRMS). This is often referred to herein as a "tether." A cyclic carrier may be a carbocyclic ring system, i.e., all ring atoms are carbon atoms or a heterocyclic ring system, i.e., one or more ring atoms may be a heteroatom, e.g., nitrogen, oxygen, or sulfur. The cyclic carrier may be a monocyclic ring system, or may contain two or more rings, e.g. fused rings. The cyclic carrier may be a fully saturated ring system, or it may contain one or more double bonds.

The carriers further include (i) at least two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" as used herein refers to a constituent ring atom of the cyclic carrier, e.g., a carbon atom or a heteroatom (distinct from an atom which provides a backbone attachment point), that connects a selected moiety. The moiety can be, e.g., a ligand, e.g., a targeting or delivery moiety, or a moiety which alters a physical property. One of the most preferred moieties is a moiety which promotes entry into a cell, e.g., a lipophilic moiety, e.g., cholesterol. While not wishing to be bound by theory it is believed the attachment of a lipophilic agent increases the lipophilicity of an oligonucleotide agent. Optionally, the selected moiety is connected by an intervening tether to the cyclic carrier. Thus, it will often include a functional group, e.g., an amino group, or generally, provide a bond, that is suitable for incorporation or tethering of another chemical entity, e.g., a ligand to the constituent ring.

Incorporation of one or more SRMSs described herein into an oligonucleotide agent, particularly when tethered to an appropriate entity, can confer one or more new properties to the oligonucleotide agent and/or alter, enhance or modulate one or more existing properties in the oligonucleotide agent. E.g., it can alter one or more of lipophilicity or nuclease resistance. Incorporation of one or more SRMSs described herein into an oligonucleotide agent can, particularly when the SRMS is tethered to an appropriate entity, modulate, e.g., increase, binding affinity of an oligonucleotide agent to a target RNA, e.g., a pre-mRNA, mRNA, or miRNA of the subject or a pathogen of the subject. Incorporation of one or more SRMSs can alter distribution, target the oligonucleotide agent to a particular part of the body, modify the interaction with nucleic acid binding proteins (e.g., during RISC formation and strand separation), or increase sequence specificity, e.g, to inhibit off-site targeting.

Accordingly, in one aspect, the invention features, an oligonucleotide agent preferably comprising at least one subunit having the structure of formula (I):

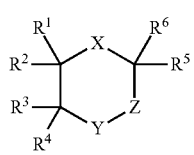

(I)

wherein:

X is N(CO)R$^7$, NR$^7$ or CH$_2$;
Y is NR$^8$, O, S, CR$^9$R$^{10}$, or absent;
Z is CR$^{11}$R$^{12}$ or absent;
Each of R$^1$, R$^2$, R$^3$, R$^4$, R$^9$, and R$^{10}$ is, independently, H, OR$^a$, OR$^b$, (CH$_2$)$_n$OR$^a$, or (CH$_2$)$_n$OR$^b$, provided that at least one of R$^1$, R$^2$, R$^3$, R$^4$, R$^9$, and R$^{10}$ is OR$^a$ or OR$^b$ and that at least one of R$^1$, R$^2$, R$^3$, R$^4$, R$^9$, and R$^{10}$ is (CH$_2$)$_n$OR$^a$, or (CH$_2$)$_n$OR$^b$ (when the SRMS is terminal, one of R$^1$, R$^2$, R$^3$, R$^4$, R$^9$, and R$^{10}$ will include R$^a$ and one will include R$^b$; when the SRMSS is internal, two of R$^1$, R$^2$, R$^3$, R$^4$, R$^9$, and R$^{10}$ will each include an R$^b$); further provided that preferably OR$^a$ may only be present with (CH$_2$)$_n$OR$^b$ and (CH$_2$)$_n$OR$^a$ may only be present with OR$^b$;

Each of R$^5$, R$^6$, R$^{11}$, and R$^{12}$ is, independently, H, C$_1$-C$_6$ alkyl optionally substituted with 1-3 R$^{13}$, or C(O)NHR$^7$; or R$^5$ and R$^{11}$ together are C$_3$-C$_8$ cycloalkyl optionally substituted with R$^{14}$;

R$^7$ can be a ligand, e.g., R$^7$ can be R$^d$, or R$^7$ can be a ligand tethered indirectly to the carrier, e.g., through a tethering moiety, e.g., C$_1$-C$_{20}$ alkyl substituted with NR$^c$R$^d$; or C$_1$-C$_{20}$ alkyl substituted with NHC(O)R$^d$;

R$^8$ is C$_1$-C$_6$ alkyl;
R$^{13}$ is hydroxy, C$_1$-C$_4$ alkoxy, or halo;
R$^{14}$ is NR$^c$R$^7$;
R$^a$ is:

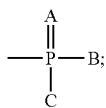

R$^b$ is:

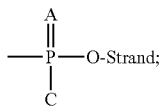

Each of A and C is, independently, O or S;
B is OH, O$^-$, or

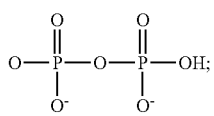

R$^c$ is H or C$_1$-C$_6$ alkyl;
R$^d$ is H or a ligand, e.g., a lipophilic ligand, e.g., cholesterol; and
n is 1-4.

Embodiments can include one or more of the following features:

R$^1$ can be CH$_2$OR$^a$ and R$^3$ can be OR$^b$; or R$^1$ can be CH$_2$OR$^a$ and R$^9$ can be OR$^b$; or R$^1$ can be CH$_2$OR$^a$ and R$^2$ can be OR$^b$.

R$^1$ can be CH$_2$OR$^b$ and R$^3$ can be OR$^b$; or R$^1$ can be CH$_2$OR$^b$ and R$^9$ can be OR$^b$; or R$^1$ can be CH$_2$OR$^b$ and R$^2$ can be OR$^b$; or R$^1$ can be CH$_2$OR$^b$ and R$^3$ can be OR$^a$; or R$^1$ can be CH$_2$OR$^b$ and R$^9$ can be OR$^a$; or R$^1$ can be CH$_2$OR$^b$ and R$^2$ can be OR$^a$.

R$^1$ can be OR$^a$ and R$^3$ can be CH$_2$OR$^b$; or R$^1$ can be OR$^a$ and R$^9$ can be CH$_2$OR$^b$; or R$^1$ can be OR$^a$ and R$^2$ can be CH$_2$OR$^b$.

R$^1$ can be OR$^b$ and R$^3$ can be CH$_2$OR$^b$; or R$^1$ can be OR$^b$ and R$^9$ can be CH$_2$OR$^b$; or R$^1$ can be OR$^b$ and R$^2$ can be CH$_2$OR$^b$; or R$^1$ can be OR$^b$ and R$^3$ can be CH$_2$OR$^a$; or R$^1$ can be OR$^b$ and R$^9$ can be CH$_2$OR$^a$; or R$^1$ can be OR$^b$ and R$^2$ can be CH$_2$OR$^a$.

R$^3$ can be CH$_2$OR$^a$ and R$^9$ can be OR$^b$; or R$^3$ can be CH$_2$OR$^a$ and R$^4$ can be OR$^b$.

R$^3$ can be CH$_2$OR$^b$ and R$^9$ can be OR$^b$; or R$^3$ can be CH$_2$OR$^b$ and R$^4$ can be OR$^b$; or R$^3$ can be CH$_2$OR$^b$ and R$^9$ can be OR$^a$; or R$^3$ can be CH$_2$OR$^b$ and R$^4$ can be OR$^a$.

R$^3$ can be OR$^b$ and R$^9$ can be CH$_2$OR$^a$; or R$^3$ can be OR$^b$ and R$^4$ can be CH$_2$OR$^a$; or R$^3$ can be OR$^b$ and R$^9$ can be CH$_2$OR$^b$; or R$^3$ can be OR$^b$ and R$^4$ can be CH$_2$OR$^b$.

R$^3$ can be OR$^a$ and R$^9$ can be CH$_2$OR$^b$; or R$^3$ can be OR$^a$ and R$^4$ can be CH$_2$OR$^b$.

R$^9$ can be CH$_2$OR$^a$ and R$^{10}$ can be OR$^b$.
R$^9$ can be CH$_2$OR$^b$ and R$^{10}$ can be OR$^b$; or R$^9$ can be CH$_2$OR$^b$ and R$^{10}$ can be OR$^a$.

In a preferred embodiment the ribose is replaced with a pyrroline scaffold or with a 4-hydroxyproline-derived scaffold, and X is N(CO)R$^7$ or NR$^7$, Y is CR$^9$R$^{10}$, and Z absent.

R$^1$ and R$^3$ can be cis or R$^1$ and R$^3$ can be trans.
n can be 1.
A can be O or S.
R$^1$ can be (CH$_2$)$_n$OR$^b$ and R$^3$ can be OR$^b$; or R$^1$ can be (CH$_2$)$_n$OR$^a$ and R$^3$ can be OR$^b$.

R$^7$ can be (CH$_2$)$_5$NHR$^d$ or (CH$_2$)$_5$NHR$^d$. R$^d$ can be chosen from a folic acid radical; a cholesterol radical; a carbohydrate radical; a vitamin A radical; a vitamin E radical; a vitamin K radical. Preferably, R$^d$ is a cholesterol radical.

R$^1$ can be OR$^b$ and R$^3$ can be (CH$_2$)$_n$OR$^b$; or R$^1$ can be OR$^b$ and R$^3$ can be (CH$_2$)$_n$OR$^a$; or R$^1$ can be OR$^a$ and R$^3$ can be (CH$_2$)$_n$OR$^b$; or R$^1$ can be (CH$_2$)$_n$OR$^b$ and R$^9$ can be OR$^a$.

R$^1$ and R$^9$ can be cis or R$^1$ and R$^9$ can be trans.

R$^1$ can be OR$^a$ and R$^9$ can be (CH$_2$)$_n$OR$^b$; or R$^1$ can be (CH$_2$)$_n$OR$^b$ and R$^9$ can be OR$^b$; or R$^1$ can be (CH$_2$)$_n$OR$^a$ and R$^9$ can be OR$^b$; or R$^1$ can be OR$^b$ and R$^9$ can be (CH$_2$)$_n$OR$^b$; or R$^1$ can be OR$^b$ and R$^9$ can be (CH$_2$)$_n$OR$^a$.

R$^3$ can be (CH$_2$)$_n$OR$^b$ and R$^9$ can be OR$^a$; or R$^3$ can be (CH$_2$)$_n$OR$^b$ and R$^9$ can be OR$^b$; or R$^3$ can be (CH$_2$)$_n$OR$^a$ and R$^9$ can be OR$^b$; or R$^3$ can be OR$^a$ and R$^9$ can be (CH$_2$)$_n$OR$^b$; or R$^3$ can be OR$^b$ and R$^9$ can be (CH$_2$)$_n$OR$^b$; or R$^3$ can be OR$^b$ and R$^9$ can be (CH$_2$)$_n$OR$^a$.

R$^3$ and R$^9$ can be cis or R$^3$ and R$^9$ can be trans.

In other preferred embodiments the ribose is replaced with a piperidine scaffold, and X is N(CO)R$^7$ or NR$^7$, Y is CR$^9$R$^{10}$, and Z is CR$^{11}$R$^{12}$.

R$^9$ can be (CH$_2$)$_n$OR$^b$ and R$^{10}$ can be OR$^a$.
n can be 1 or 2.
R$^9$ can be (CH$_2$)$_n$OR$^b$ and R$^{10}$ can be OR$^b$; or R$^9$ can be (CH$_2$)$_n$OR$^a$ and R$^{10}$ can be OR$^b$.
A can be O or S.
R$^7$ can be (CH$_2$)$_5$NHR$^d$ or (CH$_2$)$_5$NHR$^d$. R$^d$ can be selected from a folic acid radical; a cholesterol radical; a carbohydrate radical; a vitamin A radical; a vitamin E radical; a vitamin K radical. Preferably, R$^d$ is a cholesterol radical.

R$^3$ can be (CH$_2$)$_n$OR$^b$ and R$^4$ can be OR$^a$; or R$^3$ can be (CH$_2$)$_n$OR$^b$ and R$^4$ can be OR$^b$; or
R$^3$ can be (CH$_2$)$_n$OR$^a$ and R$^4$ can be OR$^b$.
R$^1$ can be (CH$_2$)$_n$OR$^b$ and R$^2$ can be OR$^a$; or R$^1$ can be (CH$_2$)$_n$OR$^b$ and R$^2$ can be OR$^b$; or R$^1$ can be (CH$_2$)$_n$OR$^a$ and R$^2$ can be OR$^b$.

$R^3$ can be $(CH_2)_nOR^b$ and $R^9$ can be $OR^a$.
$R^3$ and $R^9$ can be cis, or $R^3$ and $R^9$ can be trans.
$R^3$ can be $(CH_2)_nOR^b$ and $R^9$ can be $OR^b$; or $R^3$ can be $(CH_2)_nOR^b$ and $R^9$ can be $OR^a$; or $R^3$ can be $(CH_2)_nOR^a$ and $R^9$ can be $OR^b$.
$R^1$ can be $(CH_2)_nOR^b$ and $R^3$ can be $OR^a$.
$R^1$ and $R^3$ can be cis, or $R^1$ and $R^3$ can be trans.
$R^3$ can be $OR^a$ and $R^9$ can be $(CH_2)_nOR^b$.
$R^1$ can be $OR^a$ and $R^3$ can be $(CH_2)_nOR^b$.

In other preferred embodiments the ribose is replaced with a piperazine scaffold, and X is $N(CO)R^7$ or $NR^7$, Y is $NR^8$, and Z is $CR^{11}R^{12}$.
$R^1$ can be $(CH_2)_nOR^b$ and $R^3$ can be $OR^a$.
$R^1$ and $R^3$ can be cis or $R^1$ and $R^3$ can be trans.
n can be 1.
$R^1$ can be $(CH_2)_nOR^b$ and $R^3$ can be $OR^b$; or $R^1$ can be $(CH_2)_nOR^a$ and $R^3$ can be $OR^b$.
A can be O or S, preferably S.
$R^7$ can be $(CH_2)_5NHR^d$ or $(CH_2)_5NHR^d$. $R^d$ can be chosen from the group of a folic acid radical; a cholesterol radical; a carbohydrate radical; a vitamin A radical; a vitamin E radical; a vitamin K radical. Preferably, $R^d$ is a cholesterol radical.
$R^8$ can be $CH_3$.
$R^1$ can be $OR^a$ and $R^3$ can be $(CH_2)_nOR^b$.

In other preferred embodiments the ribose is replaced with a morpholino scaffold, and X is $N(CO)R^7$ or $NR^7$, Y is O, and Z is $CR^{11}R^{12}$.
$R^1$ can be $(CH_2)_nOR^b$ and $R^3$ can be $OR^a$.
$R^1$ and $R^3$ can be cis, or $R^1$ and $R^3$ can be trans.
n can be 1.
$R^1$ can be $(CH_2)_nOR^b$ and $R^3$ can be $OR^b$; of $R^1$ can be $(CH_2)_nOR^a$ and $R^3$ can be $OR^b$.
A can be O or S.
$R^7$ can be $(CH_2)_5NHR^d$ or $(CH_2)_5NHR^d$. $R^d$ can be chosen from the group of a folic acid radical; a cholesterol radical; a carbohydrate radical; a vitamin A radical; a vitamin E radical; a vitamin K radical. Preferably, $R^d$ is a cholesterol radical.
$R^8$ can be $CH_3$.
$R^1$ can be $OR^a$ and $R^3$ can be $(CH_2)_nOR^b$.

In other preferred embodiments the ribose is replaced with a decalin scaffold, and X is $CH_2$; Y is $CR^9R^{10}$; and Z is $CR^{11}R^{12}$; and $R^5$ and $R^{11}$ together are $C^6$ cycloalkyl.
$R^6$ can be $C(O)NHR^7$.
$R^{12}$ can be hydrogen.
$R^6$ and $R^{12}$ can be trans.
$R^3$ can be $OR^a$ and $R^9$ can be $(CH_2)_nOR^b$.
$R^3$ and $R^9$ can be cis, or $R^3$ and $R^9$ can be trans.
n can be 1 or 2.
$R^3$ can be $OR^b$ and $R^9$ can be $(CH_2)_nOR^b$; or $R^3$ can be $OR^b$ and $R^9$ can be $(CH_2)_nOR^a$.
A can be O or S.
$R^7$ can be $(CH_2)_5NHR^d$ or $(CH_2)_5NHR^d$. $R^d$ can be chosen from the group of a folic acid radical; a cholesterol radical; a carbohydrate radical; a vitamin A radical; a vitamin E radical; a vitamin K radical. Preferably, $R^d$ is a cholesterol radical.

In other preferred embodiments the ribose is replaced with a decalin/indane scaffold, e.g., X is $CH_2$; Y is $CR^9R^{10}$; and Z is $CR^{11}R^{12}$; and $R^5$ and $R^{11}$ together are $C^5$ cycloalkyl.
$R^6$ can be $CH_3$.
$R^{12}$ can be hydrogen.
$R^6$ and $R^{12}$ can be trans.
$R^3$ can be $OR^a$ and $R^9$ can be $(CH_2)_nOR^b$.
$R^3$ and $R^9$ can be cis, or $R^3$ and $R^9$ can be trans.
n can be 1 or 2.

$R^3$ can be $OR^b$ and $R^9$ can be $(CH_2)_nOR^a$; or $R^3$ can be $OR^b$ and $R^9$ can be $(CH_2)_nOR^a$.
A can be O or S.
$R^{14}$ can be $N(CH_3)R^7$. $R^7$ can be $(CH_2)_5NHR^d$ or $(CH_2)_5NHR^d$. $R^d$ can be chosen from the group of a folic acid radical; a cholesterol radical; a carbohydrate radical; a vitamin A radical; a vitamin E radical; a vitamin K radical. Preferably, $R^d$ is a cholesterol radical.

In another aspect, this invention features an oligonucleotide agent comprising at least one subunit having a structure of formula (II):

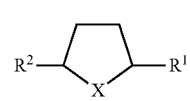

(II)

X is $N(CO)R^7$ or $NR^7$; Each of $R^1$ and $R^2$ is, independently, $OR^a$, $OR^b$, $(CH_2)_nOR^a$, or $(CH_2)_nOR^b$, provided that one of $R^1$ and $R^2$ is $OR^a$ or $OR^b$ and the other is $(CH_2)_nOR^a$ or $(CH_2)_nOR^b$ (when the SRMS is terminal, one of $R^1$ or $R^2$ will include $R^a$ and one will include $R^b$; when the SRMSS is internal, both $R^1$ and $R^2$ will each include an $R^b$); further provided that preferably $OR^a$ may only be present with $(CH_2)_nOR^b$ and $(CH_2)_nOR^a$ may only be present with $OR^b$;
$R^7$ is $C_1$-$C_{20}$ alkyl substituted with $NR^cR^d$;
$R^8$ is $C_1$-$C_6$ alkyl;
$R^{13}$ is hydroxy, $C_1$-$C_4$ alkoxy, or halo;
$R^{14}$ is $NR^cR^7$;
$R^a$ is:

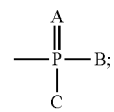

$R^b$ is

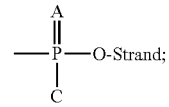

Each of A and C is, independently, O or S;
B is OH, O⁻, or

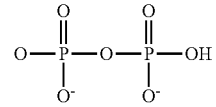

$R^c$ is H or $C_1$-$C_6$ alkyl;
$R^d$ is H or a ligand; and
n is 1-4.

The oligonucleotide agent of the conjugate is substantially single-stranded and comprises from about 12 to about 29 subunits, preferably about 15 to about 25 subunits. An oligonucleotide agent that is substantially single-stranded includes at least 60%, 70%, 80%, or 90% or more nucleotides that are not duplexed.

Embodiments can include one or more of the features described above.

In a further aspect, this invention features an oligonucleotide agent having at least one subunit comprising formula (I) or formula (II).

In one aspect, this invention features an oligonucleotide agent having at least two subunits comprising formula (I) and/or formula (II).

In another aspect, this invention provides a method of making an oligonucleotide agent described herein having at least one subunit comprising formula (I) and/or (II). In a further aspect, this invention provides a method of modulating expression of a target gene. The method includes administering an oligonucleotide agent described herein having at least one subunit comprising formula (I) and/or (II) to a subject.

In one aspect, this invention features a pharmaceutical composition having an oligonucleotide agent described herein having at least one subunit comprising formula (I) and/or (II) and a pharmaceutically acceptable carrier.

SRMSs or tethers described herein may be incorporated into any oligonucleotide agent described herein. An oligonucleotide agent may include one or more of the SRMSs described herein. An SRMS can be introduced at one or more points in an oligonucleotide agent. An SRMS can be placed at or near (within 1, 2, or 3 positions) the 3' or 5' end of the oligonucleotide. In some embodiments, it is preferred to not have an SRMS at or near (within 1, 2, or 3 positions of) the 5' end of the oligonucleotide. An SRMS can be internal, and will preferably be positioned in regions not critical for binding to the target.

In an embodiment, an oligonucleotide agent may have an SRMS at (or within 1, 2, or 3 positions of) the 3' end.

In another embodiment, an oligonucleotide agent may have an SRMS at an internal position. In other embodiments, an oligonucleotide agent may have an SRMS at the 3' end and an SRMS at an internal position.

Other modifications to sugars, bases, or backbones described herein can be incorporated into the oligonucleotide agents.

The oligonucleotide agents can take an architecture or structure described herein.

The oligonucleotide agent can be selected to target any of a broad spectrum of genes, including any of the genes described herein.

In a preferred embodiment the oligonucleotide agent has an architecture (architecture refers to one or more of the overall length) described herein. In addition to the SRMS-containing bases of the oligonucleotide agents described herein can include nuclease resistant monomers (NRMs).

In another aspect, the invention features an oligonucleotide agent to which is conjugated a lipophilic moiety, e.g., cholesterol, e.g., by conjugation to an SRMS of an oligonucleotide agent. In a preferred embodiment, the lipophilic moiety enhances entry of the oligonucleotide agent into a cell. In a preferred embodiment, the cell is part of an organism, tissue, or cell line, e.g., a primary cell line, immortalized cell line, or any type of cell line disclosed herein. Thus, the conjugated oligonucleotide agent can be used to inhibit expression of a target gene in an organism, e.g., a mammal, e.g., a human, or to inhibit expression of a target gene in a cell line or in cells which are outside an organism.

The lipophilic moiety can be chosen, for example, from the group consisting of a lipid, cholesterol, oleyl, retinyl, cholesteryl residues, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. A preferred lipophilic moiety is cholesterol.

The oligonucleotide agent can have at least one subunit having formula (I) or formula (II) incorporated into it. The oligonucleotide agent can have one or more of any of the features described herein. For example, when the subunit is of formula (I), $R^d$ can be cholesterol; X can be N(CO)$R^7$ or N$R^7$, Y can be C$R^9R^{10}$, and Z can be absent, and $R^1$ can be $(CH_2)_nOR^b$ and $R^3$ can be O$R^a$; X can be N(CO)$R^7$ or N$R^7$, Y can be C$R^9R^{10}$, and Z can be C$R^{11}R^{12}$, and $R^9$ can be $(CH_2)_nOR^b$ and $R^{10}$ can be O$R^a$; X can be N(CO)$R^7$ or N$R^7$, Y can be N$R^8$, and Z can be c$R^{11}R^{12}$, and $R^1$ can be $(CH_2)_nOR^b$ and $R^3$ can be O$R^a$; X can be $CH_2$; Y can be C$R^9R^{10}$; and Z can be C$R^{11}R^{12}$, in which $R^6$ can be C(O)NH$R^7$; or X can be $CH_2$; Y can be C$R^9R^{10}$; and Z can be C$R^{11}R^{12}$, in which $R^{11}$ or $R^{12}$ can be C(O)NH$R^7$ or $R^5$ and $R^{11}$ together can be $C_5$ or $C_6$ cycloalkyl substituted with N(CH3)$R^7$.

In a preferred embodiment, the lipophilic moiety, e.g., a cholesterol, enhances entry of the oligonucleotide agent into a synoviocyte, myocyte, keratinocyte, hepatocyte, leukocyte, endothelial cell (e.g., a kidney cell), B-cell, T-cell, epithelial cell, mesodermal cell, myeloid cell, neural cell, neoplastic cell, mast cell, or fibroblast cell. In certain aspects, a myocyte can be a smooth muscle cell or a cardiac myocyte, a fibroblast cell can be a dermal fibroblast, and a leukocyte can be a monocyte. In another preferred embodiment, the cell can be from an adherent tumor cell line derived from a tissue, such as bladder, lung, breast, cervix, colon, pancreas, prostate, kidney, liver, skin, or nervous system (e.g., central nervous system).

In another aspect, the invention provides, methods of inhibiting expression of a target gene by providing an oligonucleotide agent to which a lipophilic moiety is conjugated, e.g., a lipophilic conjugated oligonucleotide agent described herein, to a cell. In a preferred embodiment the conjugated oligonucleotide agent can be used to inhibit expression of a target gene in an organism, e.g., a mammal, e.g., a human, or to inhibit expression of a target gene in a cell line or in cells which are outside an organism. In the case of a whole organism, the method can be used to inhibit expression of a gene, e.g., a gene described herein, and treat a condition mediated by the gene. In the case of use on a cell which is not part of an organism, e.g., a primary cell line, secondary cell line, tumor cell line, or transformed or immortalized cell line, the oligonucleotide agent to which a lipophilic moiety is conjugated can be used to inhibit expression of a gene, e.g., one described herein. Cells which are not part of a whole organism can be used in an initial screen to determine if an oligonucleotide agent is effective in inhibiting expression of a gene. A test in cells which are not part of a whole organism can be followed by testing the oligonucleotide agent in a whole animal. In preferred embodiments, the oligonucleotide agent which is conjugated to a lipophilic moiety is administered to an organism, or contacted with a cell which is not part of an organism, in the absence of (or in a reduced amount of) other reagents that facilitate or enhance delivery, e.g., a compound which enhances transit through the cell membrane. (A reduced amount can be an amount of such reagent which is reduced in comparison to what would be needed to get an equal amount of nonconjugated oligonucleotide agent into the target cell). E.g., the oligonucleotide agent which is conjugated to a lipophilic moiety is administered to an organism, or contacted with a cell which is not part of an organism, in the absence (or reduced amount) of: an additional lipophilic moiety; a transfection agent, e.g., concentrations of an ion or other substance which substantially alters cell permeability to an oligonucleotide agent; a transfecting agent such as Lipofectamine™ (Invitrogen, Carlsbad, Calif.), Lipofectamine 2000™, TransIT-TKO™ (Minis, Madison, Wis.), FuGENE 6 (Roche, Indianapolis, Ind.), polyethylenimine, X-tremeGENE Q2 (Roche, Indianapolis, Ind.), DOTAP, DOSPER, Metafectene™ (Biontex, Munich, Germany), and the like.

In a preferred embodiment the oligonucleotide agent is suitable for delivery to a cell in vivo, e.g., to a cell in an organism. In another aspect, the oligonucleotide agent is suitable for delivery to a cell in vitro, e.g., to a cell in a cell line.

An oligonucleotide agent to which a lipophilic moiety is attached can target any gene described herein and can be delivered to any cell type described herein, e.g., a cell type in an organism, tissue, or cell line. Delivery of the oligonucleotide agent can be in vivo, e.g., to a cell in an organism, or in vitro, e.g., to a cell in a cell line.

In another aspect, the invention provides compositions of oligonucleotide agents described herein, and in particular compositions of an oligonucleotide agent to which a lipophilic moiety is conjugated, e.g., a lipophilic conjugated oligonucleotide agent described herein. In a preferred embodiment the composition is a pharmaceutically acceptable composition.

In preferred embodiments, the composition, e.g., pharmaceutically acceptable composition, is free of, has a reduced amount of, or is essentially free of other reagents that facilitate or enhance delivery, e.g., compounds which enhance transit through the cell membrane. (A reduced amount can be an amount of such reagent which is reduced in comparison to what would be needed to get an equal amount of nonconjugated oligonucleotide agent into the target cell). E.g., the composition is free of, has a reduced amount of, or is essentially free of: an additional lipophilic moiety; a transfection agent, e.g., concentrations of an ion or other substance which substantially alters cell permeability to an oligonucleotide agent; a transfecting agent such as Lipofectamine™ (Invitrogen, Carlsbad, Calif.), Lipofectamine 2000™, TransIT-TKO™ (Mirus, Madison, Wis.), FuGENE 6 (Roche, Indianapolis, Ind.), polyethylenimine, X-tremeGENE Q2 (Roche, Indianapolis, Ind.), DOTAP, DOSPER, Metafectene™ (Biontex, Munich, Germany), and the like.

In a preferred embodiment the composition is suitable for delivery to a cell in vivo, e.g., to a cell in an organism. In another aspect, the oligonucleotide agent is suitable for delivery to a cell in vitro, e.g., to a cell in a cell line.

The SRMS-containing oligonucleotide agents can be used in any of the methods described herein, e.g., to target any of the genes described herein or to treat any of the disorders described herein. They can be incorporated into any of the formulations, modes of delivery, delivery modalities, kits or preparations, e.g., pharmaceutical preparations, described herein. E.g, a kit which includes one or more of the oligonucleotide agents described herein, a sterile container in which the oligonucleotide agent is disclosed, and instructions for use.

The methods and compositions of the invention, e.g., the SRMS-containing oligonucleotide agents described herein, can be used with any of the oligonucleotide agents described herein. In addition, the methods and compositions of the invention can be used for the treatment of any disease or disorder described herein, and for the treatment of any subject, e.g., any animal, any mammal, such as any human.

The methods and compositions of the invention, e.g., the SRMS-containing oligonucleotide agents described herein, can be used with any dosage and/or formulation described herein, as well as with any route of administration described herein.

The non-ribose scaffolds, as well as monomers and dimers of the SRMSs described herein are within the invention.

An "oligonucleotide agent" refers to a single stranded oligomer or polymer of ribonucleic acid (RNA) or deoxyribonucleic acid (DNA) or both or modifications thereof, which is antisense with respect to its target. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

Oligonucleotide agents include both nucleic acid targeting (NAT) oligonucleotide agents and protein-targeting (PT) oligonucleotide agents. NAT and PT oligonucleotide agents refer to single stranded oligomers or polymers of ribonucleic acid (RNA) or deoxyribonucleic acid (DNA) or both or modifications thereof. This term includes oligonucleotides composed of naturally occurring nucleobases, sugars, and covalent internucleoside (backbone) linkages as well as oligonucleotides having non-naturally-occurring portions that function similarly. Such modified or substituted oligonucleotides are often preferred over native forms because of desirable properties such as, for example, enhanced cellular uptake, enhanced affinity for nucleic acid target, and/or increased stability in the presence of nucleases. NATs designed to bind to specific RNA or DNA targets have substantial complementarity, e.g., at least 70, 80, 90, or 100% complementary, with at least 10, 20, or 30 or more bases of a target nucleic acid, and include antisense RNAs, miRNAs, and other non-duplex structures which can modulate expression. Other NAT oligonucleotide agents include external guide sequence (EGS) oligonucleotides (oligozymes), DNAzymes, and ribozymes. The NAT oligonucleotide agents can target any nucleic acid, e.g., a miRNA, a pre-miRNA, a pre-mRNA, an mRNA, or a DNA. These NAT oligonucleotide agents may or may not bind via Watson-Crick complementarity to their targets. PT oligonucleotide agents bind to protein targets, preferably by virtue of three-dimensional interactions, and modulate protein activity. They include decoy RNAs, aptamers, and the like.

The compounds in accordance with this invention preferably comprise from about 5 to about 100 nucleobases, e.g., from about 8 to about 75 nucleobases, e.g., from about 8 to about 50 nucleobases. NAT oligonucleotide agents are preferably about 12 or about 15 nucleotides long, more preferably about 18, 19, 20, 21, 22, 23, 24, 25, 26, 27, 28, 29, or 30 nucleotides long. PT oligonucleotide agents are preferably about 18 nucleotides long, more preferably 23. Particularly preferred compounds are miRNAs and antisense oligonucleotides, even more preferably those comprising from about 12 to about 30 nucleobases.

While not wishing to be bound by theory, an oligonucleotide agent may act by one or more of a number of mechanisms, including a cleavage-dependent or cleavage-independent mechanism. A cleavage-based mechanism can be RNAse H dependent and/or can include RISC complex function. Cleavage-independent mechanisms include occupancy-based translational arrest, such as can be mediated by miRNAs, or binding of the oligonucleotide agent to a protein, as do aptamers. Oligonucleotide agents may also be used to alter the expression of genes by changing the choice of splice site in a pre-mRNA. Inhibition of splicing can also result in degradation of the improperly processed message, thus down-regulating gene expression.

An oligonucleotide agent can be administered, e.g., to a cell or to a human, in a single-stranded or double-stranded configuration. An oligonucleotide agent that is in a double-stranded configuration is bound to a substantially complementary oligonucleotide strand. Delivery of an oligonucleotide agent in a double stranded configuration may confer certain advantages on the oligonucleotide agent, such as an increased resistance to nucleases. When an oligonucleotide agent is presented in a double stranded configuration, one or both of the oligonucleotide agent and the substantially complementary strand can include modifications, e.g., any of the modifications described herein, including base modifications, sugar modifications, tethered ligands, and the like.

An oligonucleotide agent featured in the invention can target a substantially complementary miRNA. For example, an oligonucleotide agent can target an endogenous miRNA, such as an miRNA associated with a particular disease or disorder. In one embodiment, an oligonucleotide agent targets an miRNA that is upregulated in tumor cells, e.g., lung tumor cells. For example, the oligonucleotide agent can target miR-21 (Shingara et al., *Ambion TechNotes* 11(6), 2005). In another example, an oligonucleotide agent targets an miRNA that has been found to be upregulated in diffuse large B cell lymphoma (DLBCL) or in Burkitt's Lymphoma. For example, the oligonucleotide agent can target miR-155 (Eis et al., *Proc. Natl. Acad. Sci. U.S.A.* 102:3627-3632, 2005; Metzler et al., *Genes Chromosom. Cancer* 39:167-169, 2004). In another embodiment, an oligonucleotide agent targets an miRNA that is enriched in particular tissues or in particular cell types, e.g., in pancreatic islet cells. For example, the oligonucleotide agent can target miR-375, a pancreatic islet-specific miRNA that has been shown to suppress glucose-induced insulin secretion (Poy et al., *Nature* 432:226-230, 2004). In another embodiment, an miRNA oligonucleotide agent featured in the invention targets an endogenous miRNA that binds a gene for which underexpression is associated with disease. Targeting of such an miRNA with an miRNA oligonucleotide agent will result in upregulation of the disease-associated gene, thereby relieving symptoms of the disease or disorder.

Exemplary single stranded oligonucleotide agents can target RNAs encoding the following polypeptides: vascular endothelial growth factor (VEGF); Apolipoprotein B (ApoB); luciferase (luc); Androgen Receptor (AR); coagulation factor VII (FVII); hypoxia-inducible factor 1, alpha subunit (Hif-1α); placenta growth factor (PLGF); Lamin A/C; and green fluorescent protein (GFP). Exemplary single stranded oligonucleotide agents are shown in Table 1 below. Additional suitable miRNA targets are described, e.g., in John et al., *PLoS Biology* 2:1862-1879, 2004 (correction in *PLoS* 3:1328, 2005), and The microRNA Registry (Griffiths-Jones S., *NAR* 32:D109-D111, 2004).

TABLE 1

Exemplary oligonucleotide agents

| AL-SQ-NO: | Sequence (5'- 3' unless otherwise indicated) | SEQ ID NO: | Target |
|---|---|---|---|
| 3186 | GCACAUAGGAGAGAUGAGCUUs-Chol | 63 | VEGF |
| 3191 | Naproxen-sGUCAUCACACUGAAUACCAAUs-Chol | 64 | ApoB |
| 3209 | CAUCACACUGAAUACCAAUdTdTs-Chol | 65 | Luc |
| 3230 | oUsoCsoAoCoGoCoGoAoGoCoCoGoAoAoCoGoAoAoCsoAsoAsoAs-Chol | 66 | Mir-375 |
| 3234 | oCoUGGGAAAGoUoCAAGoCoCoCAoUdTsdT-Chol | 67 | AR |
| 3235 | oCoUGoUGoCAAGoUGoCoCoCAAGAoUdTsdT-Chol | 68 | AR |
| 3253 | GGAfUfCAfUfCfUfCAAGfUfCfUfUAfCdTsdT-Chol | 69 | FVII |
| 3256 | ACUGCAGGGUGAAGAAUUAdTsdTs-Chol | 70 | Hif-1α |
| 3257 | GCACAUAGGAGAGAUGAGCUsUs-Chol | 71 | VEGF |
| 3258 | GAACUGUGUGUGAGAGGUCCsUs-Chol | 72 | Luc |
| 3264 | CCAGGUUUUUUCUUACUUTsTs-Chol | 73 | VEGF |
| 3265 | UUCCUCAAAUCAAUUACCATsTs-Chol | 74 | VEGF |
| 3266 | GGAAGGCUCCCUUGAUGGAdTsdTs-Chol | 75 | VEGF |
| 3268 | GACACAGUGUGUUUGAUUUdTsdTs-Chol | 76 | Hif-1α |
| 3269 | UGCCAAGCCAGAUUCUCUUdTsdTs-Chol | 77 | PLGF |
| 3271 | CUCAGGAAUUCAGUGCCUUdTsdTs-Chol | 78 | PLGF |
| 3275 | CUGGACUUCCAGAAGAACAdTdT-Chol | 79 | Lamin A/C |
| 3150 | Chol-sGUCAUCACACUGAAUACCAAsU | 80 | ApoB |

TABLE 1-continued

Exemplary oligonucleotide agents

| AL-SQ-NO: | Sequence (5'- 3' unless otherwise indicated) | SEQ ID NO: | Target |
|---|---|---|---|
| 5225 | GUCAUCACACUGAAUACCAAUs-Chol | 81 | ApoB |
| 4967 | GcACcAUCUUCUUcAAGGACGs-Chol | 82 | GFP |
| 5225 | GUCAUCACACUGAAUACCAAUs-Chol | 81 | ApoB |
| 5221 | AGGUGUAUGGCUUCAACCCUGs-Chol | 83 | ApoB |
| 5255 | GUGAUCAGACUCAAUACGAAUs-Chol | 84 | ApoB |
| 5474 | GGAAUCoUoUAoUAoUoUoUGAUCoCAAs-Chol | 85 | ApoB |
| 4750 | CCACAUGAAGCAGCACGACUUs-Chol | 86 | GFP |
| 3148 | GUCAUCACACUGAAUACCAAUs-Thiochol | 87 | ApoB |
| 3208 | AUUGGUAUUCAGUGUGAUGAoCsoAsCs-Thiochol | 88 | ApoB |
| 3233 | AUUGGUAUUCAGUGUGAUGAoCsoAsCs-Thiochol | 88 | ApoB |
| 2774 | CUUACGCUGAGUACUUCGAdTdT-Thiochol | 89 | Luc |
| 2775 | UCGAAGUACUCAGCGUAAGdTdT-Thiochol | 90 | Luc |
| 3149 | Thiochol-sGUCAUCACACUGAAUACCAAsU | 91 | ApoB |
| 3207 | AUUGGUAUUCAGUGUGAUGAoCsoAsCs-Cholanic acid | 88 | ApoB |
| 3231 | GUCAUCACACUGAAUACCAAUs-Lithocholic I | 87 | ApoB |
| 3189 | GUCAUCACACUGAAUACCAAUs-Distearylglyceride | 87 | ApoB |
| 2767 | CUUACGCUGAGUACUUCGAdTdT-Distearylglyceride | 89 | Luc |
| 2768 | 3' Distearylglyceride-dTdTGAAUGCGACUCAUGAAGCU 5' | 92 | Luc |
| 3204 | Distearylglyceride-sGUCAUCACACUGAAUACCAAsU | 91 | ApoB |
| 2918 | Distearylglyceride-CUUACGCUGAGUACUUCGAdTdT | 89 | ApoB |
| 2919 | 3' dTdTGAAUGCGACUCAUGAAGCU-Distearylglyceride 5' | 92 | Luc |
| 3190 | GUCAUCACACUGAAUACCAAUs-Vitamin E | 87 | ApoB |
| 2920 | Vitamin E-CUUACGCUGAGUACUUCGA dTdT' | 89 | Luc |
| 2921 | 3' dTdTGAAUGCGACUCAUGAAGCU-Vitamin E 5' | 92 | ApoB |
| 3192 | Aminoalkyl-sGUCAUCACACUGAAUACCAAUs-Chol | 64 | ApoB |

"oN" (N = A, C, G or U) indicates 2'-O-Methyl modified nucleotide; "fN" (N = A, C, G or U) indicates 2'-deoxy-2'-fluoro modified nucleotide, "s" indicates phosphorothioate linkage; "Chol" indicates cholesterol conjugate; "Thiochol" indicates thiocholesterol conjugate; "Cholanic Acid" indicates 5β-cholanic acid conjugate; "Naproxen" indicates Naproxen conjugate; "Lithocholic I" indicates lithocholic acid derivative conjugate; "Distearylglyceride" indicates distearylglyceride conjugate; "Vitamin E" indicates vitamin E conjugate and "Aminoalkyl" indicates amino linker conjugate.

An oligonucleotide agent featured in the invention can include a nucleotide sequence that is substantially identical to a nucleotide sequence of an miRNA, such as an endogenous miRNA. An oligonucleotide sequence that is substantially identical to a second nucleotide sequence is 70%, 80%, 90%, or more identical to the second nucleotide sequence. Preferably, the agent is identical in sequence with an endogenous miRNA. An oligonucleotide agent that is substantially identical to a nucleotide sequence of an miRNA can be delivered to a cell or a human to replace or supplement the activity of an endogenous miRNA, such as when an miRNA deficiency is linked to a disease or disorder. In one embodiment, an oligonucleotide agent featured in the invention can have a nucleotide sequence that is substantially identical to an miRNA known to be down-regulated or lost in certain cancers. For example, an oligonucleotide agent can have a nucleotide sequence that is substantially identical to miR-15 (e.g., miR-15a or miR-15b) or miR-16, miRNAs known to be downregulated or lost in many cases of B cell chronic lymphocytic leukemia, mantle cell lymphoma, multiple myelomas and prostate cancer (Callin et al., *Proc. Natl. Acad. Sci.* 99:15524-15529, 2002). In another example, an oligonucleotide agent can have a nucleotide sequence that is substantially identical to miR-143 or miR-145, miRNAs known to be downregulated in many cases of adenomatous and cancer stages of colorectal neoplasia (Micheal et al., *Mol. Cancer Res.* 1:882-891, 2003). In yet another example, an oligonucleotide agent can have a nucleotide sequence that is substantially identical to let-7, an miRNA known to be downregulated in lung cancer tissue (Johnson et al., *Cell* 120:635-647, 2005). Oligonucleotide agents that are substantially identical to at least a portion of an miRNA, such as those described above, can be administered to a subject to treat the disease or disorder associated with the downregulation of miRNA expression. Other suitable oligonucleotide agents are substantially identical to miRNAs described, e.g., in John et al., *PLoS Biology* 2:1862-1879, 2004 (correction in *PLoS* 3:1328, 2005), and The microRNA Registry (Griffiths-Jones, *NAR* 32:D109-D111, 2004).

MicroRNA-Type Oligonucleotide Agents

Oligonucleotide agents include microRNAs (miRNAs). MicroRNAs are small noncoding RNA molecules that are capable of causing post-transcriptional silencing of specific genes in cells such as by the inhibition of translation or through degradation of the targeted mRNA. An miRNA can be completely complementary or can have a region of noncomplementarity with a target nucleic acid, consequently resulting in a "bulge" at the region of non-complementarity. The region of noncomplementarity (the bulge) can be flanked by regions of sufficient complementarity, preferably complete complementarity to allow duplex formation. Preferably, the regions of complementarity are at least 8 to 10 nucleotides long (e.g., 8, 9, or 10 nucleotides long). A miRNA can inhibit gene expression by repressing translation, such as when the microRNA is not completely complementary to the target nucleic acid, or by causing target RNA degradation, which is believed to occur only when the miRNA binds its target with perfect complementarity. The invention also can include double-stranded precursors of miRNAs that may or may not form a bulge when bound to their targets.

In a preferred embodiment an oligonucleotide agent featured in the invention can target an endogenous miRNA or pre-miRNA. The oligonucleotide agent featured in the invention can include naturally occurring nucleobases, sugars, and covalent internucleoside (backbone) linkages as well as oligonucleotides having non-naturally-occurring portions that function similarly. Such modified or substituted oligonucleotides are often preferred over native forms because of desirable properties such as, for example, enhanced cellular uptake, enhanced affinity for the endogenous miRNA target, and/or increased stability in the presence of nucleases. An oligonucleotide agent designed to bind to a specific endogenous miRNA has substantial complementarity, e.g., at least 70, 80, 90, or 100% complementary, with at least 10, 20, or 25 or more bases of the target miRNA.

A miRNA or pre-miRNA can be 18-100 nucleotides in length, and more preferably from 18-80 nucleotides in length. Mature miRNAs can have a length of 19-30 nucleotides, preferably 21-25 nucleotides, particularly 21, 22, 23, 24, or 25 nucleotides. MicroRNA precursors can have a length of 70-100 nucleotides and have a hairpin conformation. MicroRNAs can be generated in vivo from pre-miRNAs by enzymes called Dicer and Drosha that specifically process long pre-miRNA into functional miRNA. The microRNAs or precursor mi-RNAs featured in the invention can be synthesized in vivo by a cell-based system or can be chemically synthesized. MicroRNAs can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting. Methods of synthesis and chemical modifications are described in greater detail below.

Given a sense strand sequence (e.g., the sequence of a sense strand of a cDNA molecule), an miRNA can be designed according to the rules of Watson and Crick base pairing. The miRNA can be complementary to a portion of an RNA, e.g., a miRNA, a pre-miRNA, a pre-mRNA or an mRNA. For example, the miRNA can be complementary to the coding region or noncoding region of an mRNA or pre-mRNA, e.g., the region surrounding the translation start site of a pre-mRNA or mRNA, such as the 5' UTR. An miRNA oligonucleotide can be, for example, from about 12 to 30 nucleotides in length, preferably about 15 to 28 nucleotides in length (e.g., 16, 17, 18, 19, 20, 21, 22, 23, 24, or 25 nucleotides in length).

In particular, an miRNA or a pre-miRNA featured in the invention can have a chemical modification on a nucleotide in an internal (i.e., non-terminal) region having noncomplementarity with the target nucleic acid. For example, a modified nucleotide can be incorporated into the region of a miRNA that forms a bulge. The modification can include a ligand attached to the miRNA, e.g., by a linker (e.g., see diagrams OT-I through OT-IV below). The modification can, for example, improve pharmacokinetics or stability of a therapeutic miRNA, or improve hybridization properties (e.g., hybridization thermodynamics) of the miRNA to a target nucleic acid. In some embodiments, it is preferred that the orientation of a modification or ligand incorporated into or tethered to the bulge region of a miRNA is oriented to occupy the space in the bulge region. For example, the modification can include a modified base or sugar on the nucleic acid strand or a ligand that functions as an intercalator. These are preferably located in the bulge. The intercalator can be an aromatic, e.g., a polycyclic aromatic or heterocyclic aromatic compound. A polycyclic intercalator can have stacking capabilities, and can include systems with 2, 3, or 4 fused rings. The universal bases described below can be incorporated into the miRNAs. In some embodiments, it is preferred that the orientation of a modification or ligand incorporated into or tethered to the bulge region of a miRNA is oriented to occupy the space in the bulge region. This orientation facilitates the improved hybridization properties or an otherwise desired characteristic of the miRNA.

In one embodiment, an miRNA or a pre-miRNA can include an aminoglycoside ligand, which can cause the miRNA to have improved hybridization properties or improved sequence specificity. Exemplary aminoglycosides include glycosylated polylysine; galactosylated polylysine; neomycin B; tobramycin; kanamycin A; and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-S-acridine has an increased affinity for the HIV Rev-response element (RRE). In some embodiments the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent.

In one embodiment, the ligand can include a cleaving group that contributes to target gene inhibition by cleavage of the target nucleic acid. Preferably, the cleaving group is tethered to the miRNA in a manner such that it is positioned in the bulge region, where it can access and cleave the target RNA. The cleaving group can be, for example, a bleomycin (e.g., bleomycin-$A_5$, bleomycin-$A_2$, or bleomycin-$B_2$), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a miRNA or a pre-miRNA to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. The methods and compositions featured in the invention include miRNAs that inhibit target gene expression by a cleavage or non-cleavage dependent mechanism.

An miRNA or a pre-miRNA can be designed and synthesized to include a region of noncomplementarity (e.g., a region that is 3, 4, 5, or 6 nucleotides long) flanked by regions of sufficient complementarity to form a duplex (e.g., regions that are 7, 8, 9, 10, or 11 nucleotides long).

For increased nuclease resistance and/or binding affinity to the target, the miRNA sequences can include 2'-O-methyl, 2'-fluorine, 2'-O-methoxyethyl, 2'-O-aminopropyl, 2'-amino, and/or phosphorothioate linkages. Inclusion of locked nucleic acids (LNA), 2-thiopyrimidines (e.g., 2-thio-U), 2-amino-A, G-clamp modifications, and ethylene nucleic acids (ENA), e.g., 2'-4'-ethylene-bridged nucleic acids, can also increase binding affinity to the target. The inclusion of furanose sugars in the oligonucleotide backbone can also decrease endonucleolytic cleavage. An miRNA or a pre-miRNA can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3' end of oligonucleotide. Even small alkyl chains, aryl groups, or heterocyclic conjugates or modified sugars (D-ribose, deoxyribose, glucose etc.) can block 3'-5'-exonucleases.

The 5'-terminus can be blocked with an aminoalkyl group, e.g., a 5'-O-alkylamino substituent. Other 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5' end of oligonucleotide. Even small alkyl chains, aryl groups, or heterocyclic conjugates or modified sugars (D-ribose, deoxyribose, glucose etc.) can block 3'-5'-exonucleases.

In one embodiment, an miRNA or a pre-miRNA includes a modification that improves targeting, e.g. a targeting modification described herein. Examples of modifications that target miRNA molecules to particular cell types include carbohydrate sugars such as galactose, N-acetylgalactosamine, mannose; vitamins such as folates; other ligands such as RGDs and RGD mimics; and small molecules including naproxen, ibuprofen or other known protein-binding molecules.

An miRNA or a pre-miRNA can be constructed using chemical synthesis and/or enzymatic ligation reactions using procedures known in the art. For example, an miRNA or a pre-miRNA can be chemically synthesized using naturally occurring nucleotides or variously modified nucleotides designed to increase the biological stability of the molecules or to increase the physical stability of the duplex formed between the miRNA or a pre-miRNA and target nucleic acids, e.g., phosphorothioate derivatives and acridine substituted nucleotides can be used. Other appropriate nucleic acid modifications are described herein. Alternatively, the miRNA or pre-miRNA nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Antisense-Type Oligonucleotide Agents

The single-stranded oligonucleotide agents featured in the invention include antisense nucleic acids. An "antisense" nucleic acid includes a nucleotide sequence that is complementary to a "sense" nucleic acid encoding a gene expression product, e.g., complementary to the coding strand of a double-stranded cDNA molecule or complementary to an RNA sequence, e.g., a pre-mRNA, mRNA, miRNA, or pre-miRNA. Accordingly, an antisense nucleic acid can form hydrogen bonds with a sense nucleic acid target.

Given a coding strand sequence (e.g., the sequence of a sense strand of a cDNA molecule), antisense nucleic acids can be designed according to the rules of Watson and Crick base pairing. The antisense nucleic acid molecule can be complementary to a portion of the coding or noncoding region of an RNA, e.g., a pre-mRNA or mRNA. For example, the antisense oligonucleotide can be complementary to the region surrounding the translation start site of a pre-mRNA or mRNA, e.g., the 5' UTR. An antisense oligonucleotide can be, for example, about 10 to 25 nucleotides in length (e.g., 11, 12, 13, 14, 15, 16, 18, 19, 20, 21, 22, 23, or 24 nucleotides in length). An antisense oligonucleotide can also be complementary to a miRNA or pre-miRNA.

An antisense nucleic acid can be constructed using chemical synthesis and/or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and target nucleic acids, e.g., phosphorothioate derivatives and acridine substituted nucleotides can be used. Other appropriate nucleic acid modifications are described herein. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

An antisense agent can include ribonucleotides only, deoxyribonucleotides only (e.g., oligodeoxynucleotides), or both deoxyribonucleotides and ribonucleotides. For example, an antisense agent consisting only of ribonucleotides can hybridize to a complementary RNA, and prevent access of the translation machinery to the target RNA transcript, thereby preventing protein synthesis. An antisense molecule including only deoxyribonucleotides, or deoxyribonucleotides and ribonucleotides, e.g., DNA sequence flanked by RNA sequence at the 5' and 3' ends of the antisense agent, can hybridize to a complementary RNA, and the RNA target can be subsequently cleaved by an enzyme, e.g., RNAse H. Degradation of the target RNA prevents translation. The flanking RNA sequences can include 2'-O-methylated nucleotides, and phosphorothioate linkages, and the internal DNA sequence can include phosphorothioate internucleotide linkages. The internal DNA sequence is preferably at least five nucleotides in length when targeting by RNAseH activity is desired.

For increased nuclease resistance, an antisense agent can be further modified by inverting the nucleoside at the 3'-terminus with a 3'-3' linkage. In another alternative, the 3'-terminus can be blocked with an aminoalkyl group.

In one embodiment, an antisense oligonucleotide agent includes a modification that improves targeting, e.g. a targeting modification described herein.

Decoy-Type Oligonucleotide Agents

An oligonucleotide agent featured in the invention can be a decoy nucleic acid, e.g., a decoy RNA. A decoy nucleic acid resembles a natural nucleic acid, but is modified in such a way as to inhibit or interrupt the activity of the natural nucleic acid. For example, a decoy RNA can mimic the natural binding domain for a ligand. The decoy RNA therefore competes with natural binding target for the binding of a specific ligand. The natural binding target can be an endogenous nucleic acid, e.g., a pre-miRNA, miRNA, prem-RNA, mRNA or DNA. For example, it has been shown that over-expression of HIV trans-activation response (TAR) RNA can act as a "decoy" and efficiently bind HIV tat protein, thereby preventing it from binding to TAR sequences encoded in the HIV RNA.

In one embodiment, a decoy RNA includes a modification that improves targeting, e.g. a targeting modification described herein.

The chemical modifications described above for miRNAs and antisense RNAs, and described elsewhere herein, are also appropriate for use in decoy nucleic acids.

Aptamer-Type Oligonucleotide Agents

An oligonucleotide agent featured in the invention can be an aptamer. An aptamer binds to a non-nucleic acid ligand, such as a small organic molecule or protein, e.g., a transcription or translation factor, and subsequently modifies (e.g., inhibits) activity. An aptamer can fold into a specific structure that directs the recognition of the targeted binding site on the non-nucleic acid ligand. An aptamer can contain any of the modifications described herein.

In one embodiment, an aptamer includes a modification that improves targeting, e.g. a targeting modification described herein.

The chemical modifications described above for miRNAs and antisense RNAs, and described elsewhere herein, are also appropriate for use in decoy nucleic acids.

The details of one or more embodiments of the invention are set forth in the accompanying drawings and the description below. Other features and advantages of the invention will be apparent from the description and drawings, and from the claims. This application incorporates all cited references, patents, and patent applications by references in their entirety for all purposes.

DESCRIPTION OF DRAWINGS

In FIG. 3A, panel 1 shows pyrroline-based SRMSs, and panel 2 shows 3-hydroxyproline-based SRMSs; in FIG. 3B, panel 3 shows piperidine-based SRMSs; in FIG. 3C, panel 4 shows morpholine and piperazine-based SRMSs; and in FIG. 3D, panel 5 shows decalin-based SRMSs. $R_1$ is succinate or phosphoramidate and $R_2$ is H or a conjugate ligand.

DETAILED DESCRIPTION

Figure 1:
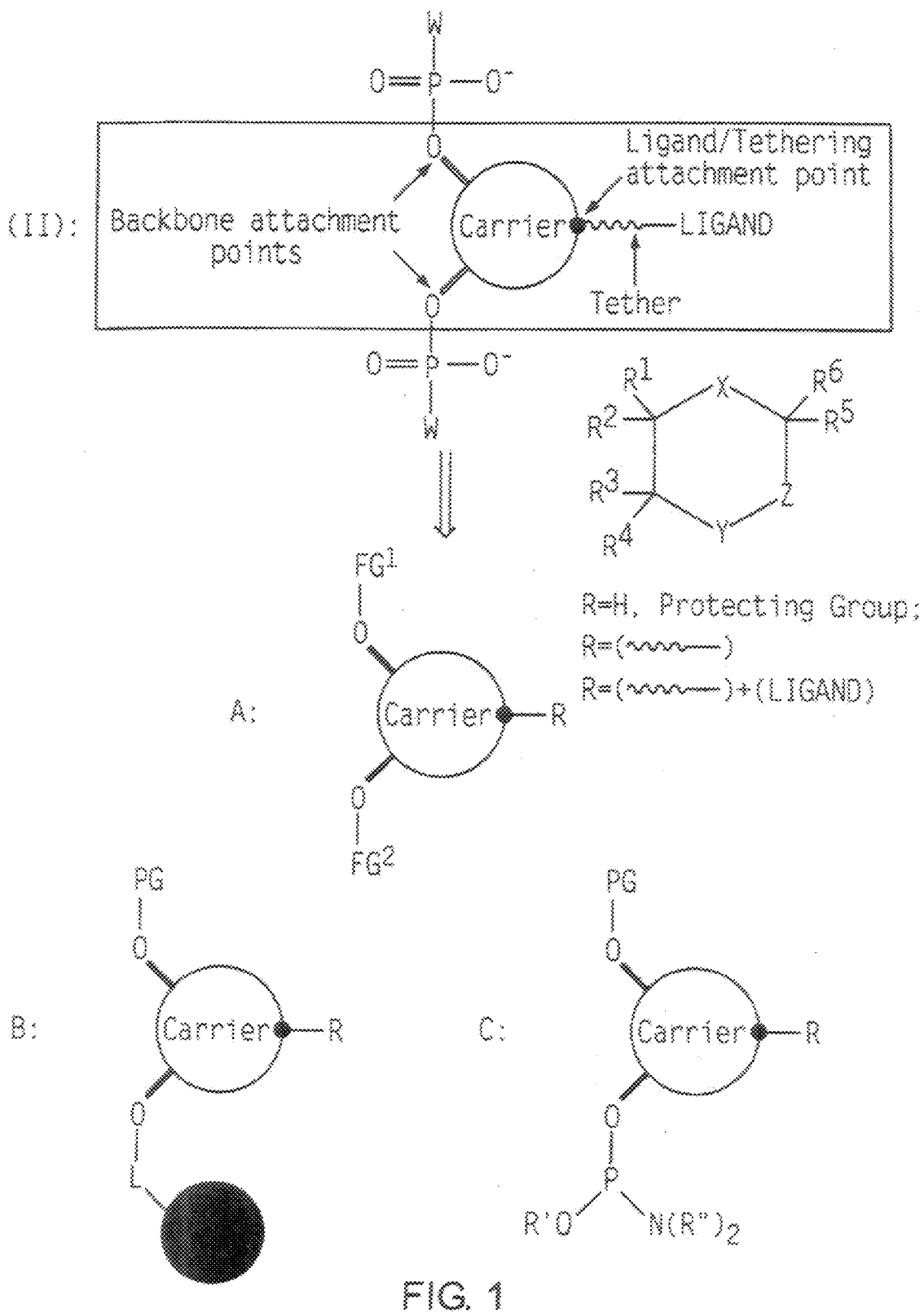
FIG. 1 a general synthetic scheme for incorporation of SRMS monomers into an oligonucleotide.

In a typical embodiment, the subject is a mammal such as a cow, horse, mouse, rat, dog, pig, goat, or a primate. The subject can be a dairy mammal (e.g., a cow, or goat) or other farmed animal (e.g., a chicken, turkey, sheep, pig, fish, shrimp). In a much preferred embodiment, the subject is a human, e.g., a normal individual or an individual that has, is diagnosed with, or is predicted to have a disease or disorder.

Further, because oligonucleotide agent-mediated modulation persists for several days after administering the oligonucleotide agent composition, in many instances it is possible to administer the composition with a frequency of less than once per day, or, for some instances, only once for the entire therapeutic regimen. For example, treatment of some cancer cells may be mediated by a single bolus administration, whereas a chronic viral infection may require regular administration, e.g., once per week or once per month. For example, treatment of diffuse large B cell lymphoma (DLBCL) or Burkitt's lymphoma may be treated with a single bolus administration of a single-stranded oligonucleotide agent, e.g., a single-stranded oligonucleotide agent that targets miR-155.

A number of exemplary routes of delivery are described that can be used to administer an oligonucleotide agent to a subject. In addition, the oligonucleotide agent can be formulated according to an exemplary method described herein.

Ligand-Conjugated Monomer Subunits and
Monomers for Oligonucleotide Synthesis

DEFINITIONS

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH(alkyl) and —NH(alkyl)$_2$ radicals respectively. The term "aralkylamino" refers to a —NH(aralkyl) radical. The term "alkoxy" refers to an —O-alkyl radical, and the terms "cycloalkoxy" and "aralkoxy" refer to an —O-cycloalkyl and O-aralkyl radicals respectively. The term "siloxy" refers to a $R_3SiO$— radical. The term "mercapto" refers to an SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl, and decalin.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom can be substituted. The cycloalkenyl groups herein described may also contain fused rings. Fused rings are rings that share a common carbon-carbon bond or a common carbon atom (e.g., spiro-fused rings). Examples of cycloalkenyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocycloalkenyl groups herein described may also contain fused rings. Fused rings are rings that share a common carbon-carbon bond or a common carbon atom (e.g., spiro-fused rings). Examples of heterocycloalkenyl include but are not limited to tetrahydropyridyl and dihydropyran.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The terms "adeninyl, cytosinyl, guaninyl, thyminyl, and uracilyl" and the like refer to radicals of adenine, cytosine, guanine, thymine, and uracil.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

General

An oligonucleotide agent, e.g., a conjugated oligonucleotide agent, containing a preferred, but nonlimiting ligand-conjugated monomer subunit is presented as formula (II) below and in the scheme in FIG. 1. The carrier (also referred to in some embodiments as a "linker") can be a cyclic or acyclic moiety and includes two "backbone attachment points" (e.g., hydroxyl groups) and a ligand. The ligand can be directly attached (e.g., conjugated) to the carrier or indirectly attached (e.g., conjugated) to the carrier by an intervening tether (e.g., an acyclic chain of one or more atoms; or a nucleobase, e.g., a naturally occurring nucleobase optionally having one or more chemical modifications, e.g., an unusual base; or a universal base). The carrier therefore also includes a "ligand or tethering attachment point" for the ligand and tether/tethered ligand, respectively.

The ligand-conjugated monomer subunit may be the 5' or 3' terminal subunit of the RNA molecule, i.e., one of the two "W" groups may be a hydroxyl group, and the other "W" group may be a chain of two or more unmodified or modified ribonucleotides. Alternatively, the ligand-conjugated monomer subunit may occupy an internal position, and both "W" groups may be one or more unmodified or modified ribonucleotides. More than one ligand-conjugated monomer subunit may be present in a RNA molecule, e.g., an oligonucleotide agent. Preferred positions for inclusion of a tethered ligand-conjugated monomer subunit, e.g., one in which a lipophilic moiety, e.g., cholesterol, is tethered to the carrier are at the 3' terminus, the 5' terminus, or at an internal position.

(II)

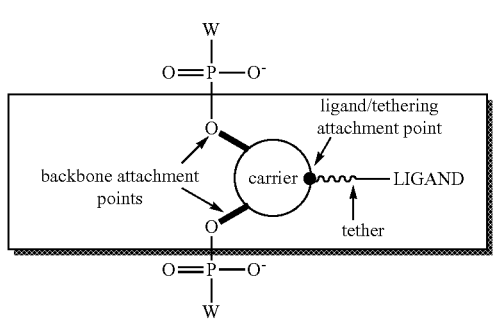

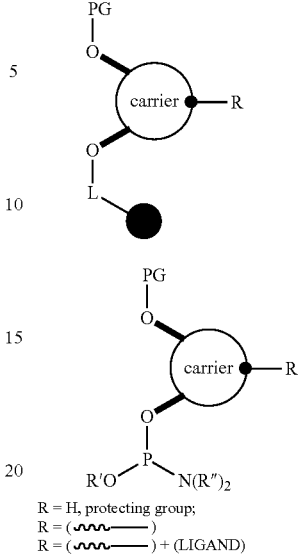

R = H, protecting group;
R = (~~~~)
R = (~~~~) + (LIGAND)

The modified RNA molecule of formula (II) can be obtained using oligonucleotide synthetic methods known in the art. In a preferred embodiment, the modified RNA molecule of formula (II) can be prepared by incorporating one or more of the corresponding monomer compounds (see, e.g., A, B, and C below and in the scheme in FIG. 1) into a growing strand, utilizing, e.g., phosphoramidite or H-phosphonate coupling strategies.

The monomers, e.g., a ligand-conjugated monomers, generally include two differently functionalized hydroxyl groups ($OFG^1$ and $OFG^2$), which are linked to the carrier molecule (see A below and in FIG. 1), and a ligand/tethering attachment point. As used herein, the term "functionalized hydroxyl group" means that the hydroxyl proton has been replaced by another substituent. As shown in representative structures B and C below and in FIG. 1, one hydroxyl group ($OFG^1$) on the carrier is functionalized with a protecting group (PG). The other hydroxyl group ($OFG^2$) can be functionalized with either (1) a liquid or solid phase synthesis support reagent (solid circle) directly or indirectly through a linker, L, as in B, or (2) a phosphorus-containing moiety, e.g., a phosphoramidite as in C. The tethering attachment point may be connected to a hydrogen atom, a suitable protecting group, a tether, or a tethered ligand at the time that the monomer is incorporated into the growing strand (see variable "R" in A below). Thus, the tethered ligand can be, but need not be attached to the monomer at the time that the monomer is incorporated into the growing strand. In certain embodiments, the tether, the ligand or the tethered ligand may be linked to a "precursor" ligand-conjugated monomer subunit after a "precursor" ligand-conjugated monomer subunit has been incorporated into the strand. The wavy line used below (and elsewhere herein) refers to a connection, and can represent a direct bond between the moiety and the attachment point or a tethering molecule which is interposed between the moiety and the attachment point. Directly tethered means the moiety is bound directly to the attachment point. Indirectly tethered means that there is a tether molecule interposed between the attachment point and the moiety.

A

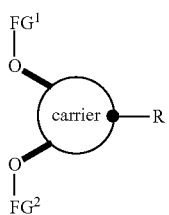

The ($OFG^1$) protecting group may be selected as desired, e.g., from T. W. Greene and P. G. M. Wuts, *Protective Groups in Organic Synthesis*, 2d. Ed., John Wiley and Sons (1991). The protecting group is preferably stable under amidite synthesis conditions, storage conditions, and oligonucleotide synthesis conditions. Hydroxyl groups, —OH, are nucleophilic groups (i.e., Lewis bases), which react through the oxygen with electrophiles (i.e., Lewis acids). Hydroxyl groups in which the hydrogen has been replaced with a protecting group, e.g., a triarylmethyl group or a trialkylsilyl group, are essentially unreactive as nucleophiles in displacement reactions. Thus, the protected hydroxyl group is useful in preventing e.g., homocoupling of compounds exemplified by structure C during oligonucleotide synthesis. In some embodiments, a preferred protecting group is the dimethoxytrityl group. In other embodiments, a preferred protecting group is a silicon-based protecting group having the formula below:

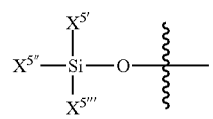

Figure 2A:
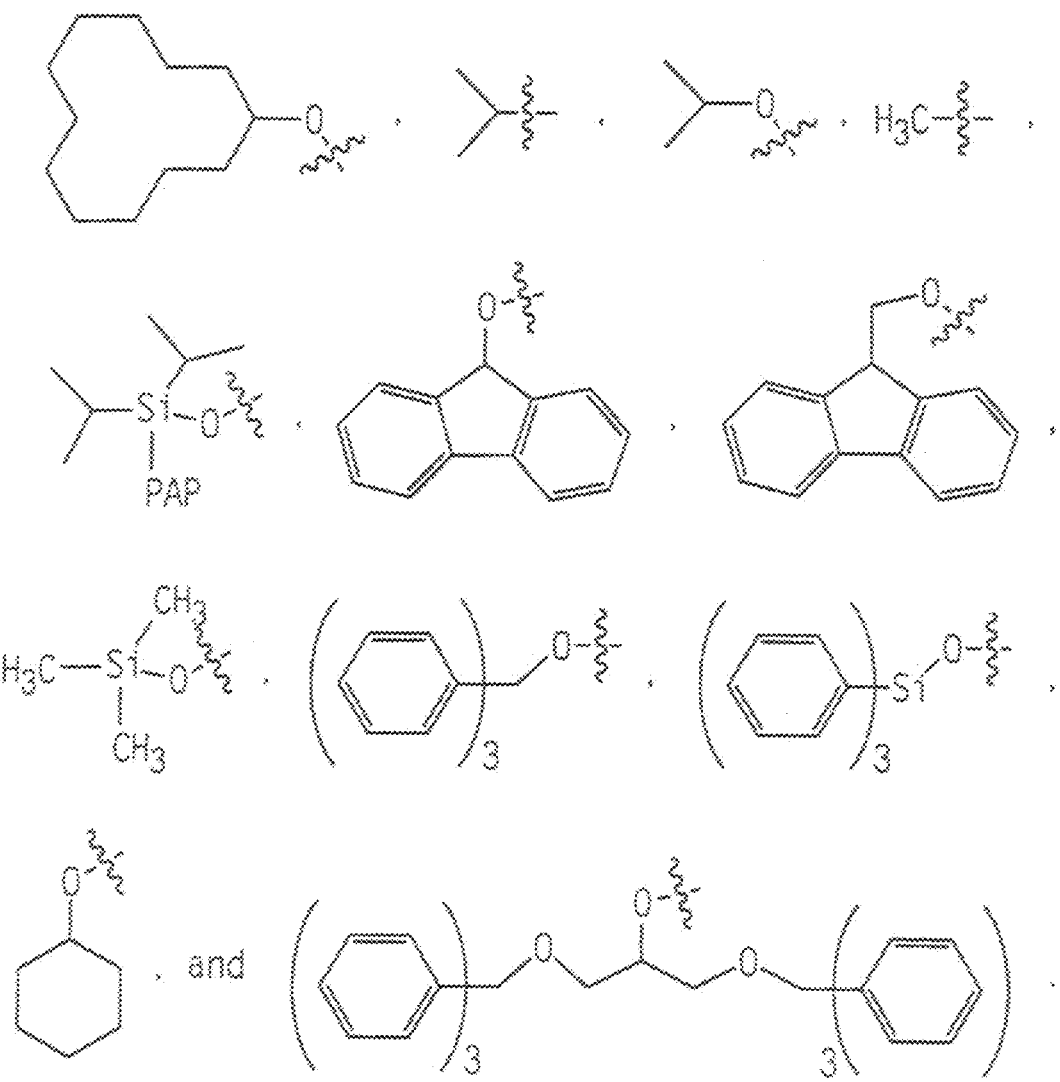
FIG. 2A is a list of substituents that may be present on silicon in $OFG^1$.

$X^{5'}$, $X^{5''}$, and $X^{5'''}$ can be selected from substituted or unsubstituted alkyl, cycloalkyl, aryl, araklyl, heteroaryl, alkoxy, cycloalkoxy, aralkoxy, aryloxy, heteroaryloxy, or siloxy (i.e., $R_3SiO$—, the three "R" groups can be any combination of the above listed groups). $X^{5'}$, $X^{5''}$, and $X^{5'''}$ may all be the same or different; also contemplated is a combination in which two of $X^{5'}$, $X^{5''}$, and $X^{5'''}$ are identical and the third is different. In certain embodiments $X^{5'}$, $X^{5''}$, and $X^{5'''}$ include at least one alkoxy or siloxy groups and may be any one of the groups listed in FIG. 2A, a preferred combination includes $X^{5'}$, $X^{5''}$=trimethylsiloxy and $X^{5'''}$=1,3-(triphenylmethoxy)-2-propoxy or cyclododecyloxy.

Other preferred combinations of $X^{5'}$, $X^{5''}$, and $X^{5'''}$ include those that result in $OFG^1$ groups that meet the deprotection and stability criteria delineated below. The group is preferably stable under amidite synthesis conditions, storage conditions, and oligonucleotide synthesis conditions. Rapid removal, i.e., less than one minute, of the silyl group from e.g., a support-bound oligonucleotide is desirable because it can reduce synthesis times and thereby reduce exposure time of the growing oligonucleotide chain to the reagents. Oligonucleotide synthesis can be improved if the silyl protecting group is visible during deprotection, e.g., from the addition of a chromophore silyl substituent.

Selection of silyl protecting groups can be complicated by the competing demands of the essential characteristics of stability and facile removal, and the need to balance these competitive goals. Most substituents that increase stability can also increase the reaction time required for removal of the silyl group, potentially increasing the level of difficulty in removal of the group.

The addition of alkoxy and siloxy substituents to $OFG^1$ silicon-containing protecting groups increases the susceptibility of the protecting groups to fluoride cleavage of the silylether bonds. Increasing the steric bulk of the substituents preserves stability while not decreasing fluoride lability to an equal extent. An appropriate balance of substituents on the silyl group makes a silyl ether a viable nucleoside protecting group.

Candidate $OFG^1$ silicon-containing protecting groups may be tested by exposing a tetrahydrofuran solution of a preferred carrier bearing the candidate $OFG^1$ group to five molar equivalents of tetrahydrofuran at room temperature. The reaction time may be determined by monitoring the disappearance of the starting material by thin layer chromatography.

When the $OFG^2$ in B includes a linker, e.g., a relatively long organic linker, connected to a soluble or insoluble support reagent, solution or solid phase synthesis techniques can be employed to build up a chain of natural and/or modified ribonucleotides once $OFG^1$ is deprotected and free to react as a nucleophile with another nucleoside or monomer containing an electrophilic group (e.g., an amidite group). Alternatively, a natural or modified ribonucleotide or oligoribonucleotide chain can be coupled to monomer C via an amidite group or H-phosphonate group at $OFG^2$. Subsequent to this operation, $OFG^1$ can be deblocked, and the restored nucleophilic hydroxyl group can react with another nucleoside or monomer containing an electrophilic group. R' can be substituted or unsubstituted alkyl or alkenyl. In preferred embodiments, R' is methyl, allyl or 2-cyanoethyl. R" may a $C_1$-$C_{10}$ alkyl group, preferably it is a branched group containing three or more carbons, e.g., isopropyl.

$OFG^2$ in B can be hydroxyl functionalized with a linker, which in turn contains a liquid or solid phase synthesis support reagent at the other linker terminus. The support reagent can be any support medium that can support the monomers described herein. The monomer can be attached to an insoluble support via a linker, L, which allows the monomer (and the growing chain) to be solubilized in the solvent in which the support is placed. The solubilized, yet immobilized, monomer can react with reagents in the surrounding solvent; unreacted reagents and soluble by-products can be readily washed away from the solid support to which the monomer or monomer-derived products is attached. Alternatively, the monomer can be attached to a soluble support moiety, e.g., polyethylene glycol (PEG) and liquid phase synthesis techniques can be used to build up the chain. Linker and support medium selection is within skill of the art. Generally the linker may be —C(O)(CH$_2$)$_q$C(O)—, or —C(O)(CH$_2$)$_q$S—, in which q can be 0, 1, 2, 3, or 4; preferably, it is oxalyl, succinyl or thioglycolyl. Standard control pore glass solid phase synthesis supports can not be used in conjunction with fluoride labile 5' silyl protecting groups because the glass is degraded by fluoride with a significant reduction in the amount of full-length product. Fluoride-stable polystyrene based supports or PEG are preferred.

The ligand/tethering attachment point can be any divalent, trivalent, tetravalent, pentavalent or hexavalent atom. In some embodiments, ligand/tethering attachment point can be a carbon, oxygen, nitrogen or sulfur atom. For example, a ligand/tethering attachment point precursor functional group can have a nucleophilic heteroatom, e.g., —SH, —NH$_2$, secondary amino, ONH$_2$, or NH$_2$NH$_2$. As another example, the ligand/tethering attachment point precursor functional group can be an olefin, e.g., —CH=CH$_2$ or a Diels-Alder diene or dienophile and the precursor functional group can be attached to a ligand, a tether, or tethered ligand using, e.g., transition metal catalyzed carbon-carbon (for example olefin metathesis) processes or cycloadditions (e.g., Diels-Alder). As a further example, the ligand/tethering attachment point precursor functional group can be an electrophilic moiety, e.g., an aldehyde. When the carrier is a cyclic carrier, the ligand/tethering attachment point can be an endocyclic atom (i.e., a constituent atom in the cyclic moiety, e.g., a nitrogen atom) or an exocyclic atom (i.e., an atom or group of atoms attached to a constituent atom in the cyclic moiety).

The carrier can be any organic molecule containing attachment points for $OFG^1$, $OFG^2$, and the ligand. In certain embodiments, carrier is a cyclic molecule and may contain heteroatoms (e.g., O, N or S). E.g., carrier molecules may include aryl (e.g., benzene, biphenyl, etc.), cycloalkyl (e.g., cyclohexane, cis or trans decalin, etc.), or heterocyclyl (piperazine, pyrrolidine, etc.). In other embodiments, the carrier can be an acyclic moiety, e.g., based on serinol. Any of the above cyclic systems may include substituents in addition to $OFG^1$, $OFG^2$, and the ligand.

Sugar-Based Monomers

In some embodiments, the carrier molecule is an oxygen containing heterocycle. Preferably the carrier is a ribose sugar as shown in structure LCM-I. In this embodiment, the ligand-conjugated monomer is a nucleoside.

LCM-I

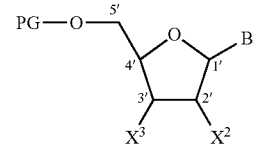

"B" represents a nucleobase, e.g., a naturally occurring nucleobase optionally having one or more chemical modifications, e.g., and unusual base; or a universal base.

As used herein, an "unusual" nucleobase can include any one of the following:
2-methyladeninyl,
N6-methyladeninyl,
2-methylthio-N6-methyladeninyl,
N6-isopentenyladeninyl,
2-methylthio-N6-isopentenyladeninyl,
N6-(cis-hydroxyisopentenyl)adeninyl,
2-methylthio-N6-(cis-hydroxyisopentenyl) adeninyl,
N6-glycinylcarbamoyladeninyl,
N6-threonylcarbamoyladeninyl,
2-methylthio-N6-threonyl carbamoyladeninyl,
N6-methyl-N6-threonylcarbamoyladeninyl, N6-hydroxynorvalylcarbamoyladeninyl,
2-methylthio-N6-hydroxynorvalyl carbamoyladeninyl,
N6,N6-dimethyladeninyl,
3-methylcytosinyl,
5-methylcytosinyl,
2-thiocytosinyl,
5-formylcytosinyl,
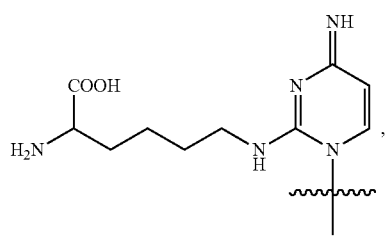 [SMILES: *n1ccc(=N)nc1NCCCCC(N)C(=O)O]
N4-methylcytosinyl,
5-hydroxymethylcytosinyl,
1-methylguaninyl,
N2-methylguaninyl,
7-methylguaninyl,
N2,N2-dimethylguaninyl,
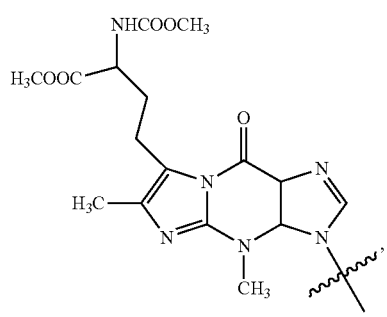
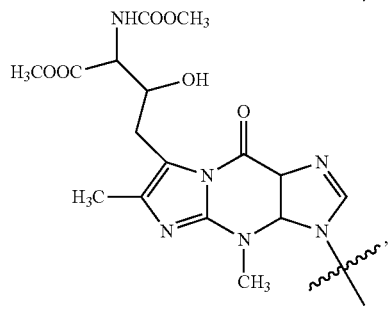
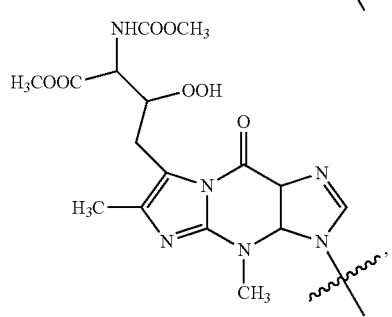
-continued
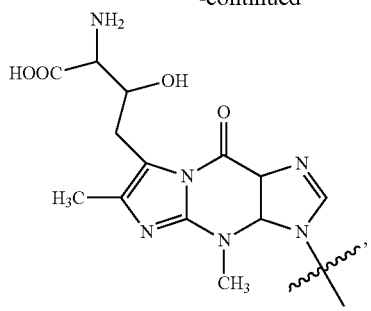
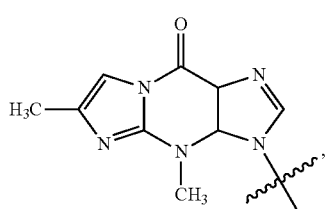
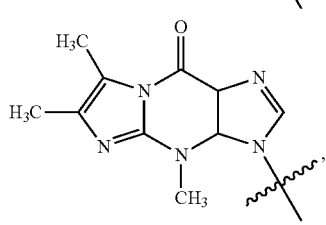
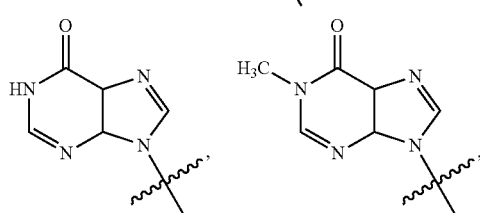
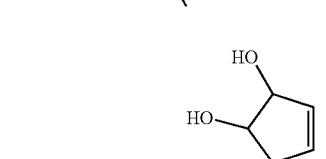
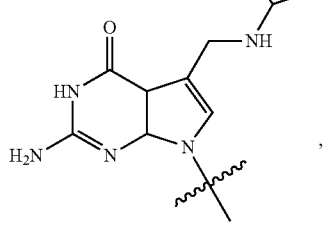
,
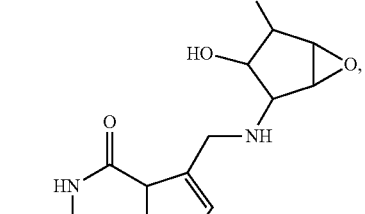

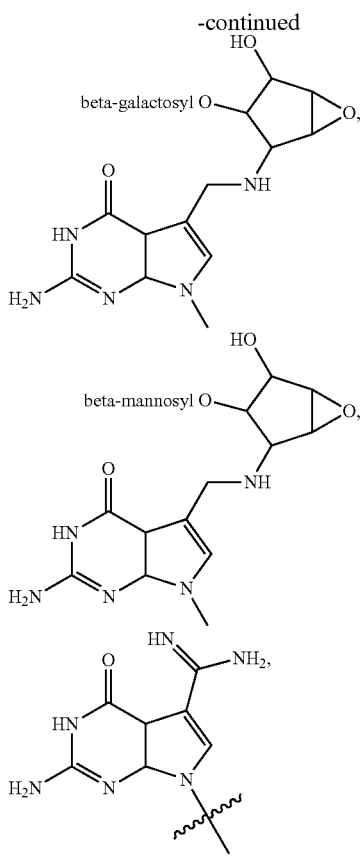

N2,7-dimethylguaninyl,
N2,N2,7-trimethylguaninyl,
1-methylguaninyl,
7-cyano-7-deazaguaninyl,
7-aminomethyl-7-deazaguaninyl,
pseudouracilyl,
dihydrouracilyl,
5-methyluracilyl,
1-methylpseudouracilyl,
2-thiouracilyl,
4-thiouracilyl,
2-thiothyminyl
5-methyl-2-thiouracilyl,
3-(3-amino-3-carboxypropyl)uracilyl,
5-hydroxyuracilyl,
5-methoxyuracilyl,
uracilyl 5-oxyacetic acid,
uracilyl 5-oxyacetic acid methyl ester,
5-(carboxyhydroxymethyl)uracilyl,
5-(carboxyhydroxymethyl)uracilyl methyl ester,
5-methoxycarbonylmethyluracilyl,
5-methoxycarbonylmethyl-2-thiouracilyl,
5-aminomethyl-2-thiouracilyl,
5-methylaminomethyluracilyl,
5-methylaminomethyl-2-thiouracilyl,
5-methylaminomethyl-2-selenouracilyl,
5-carbamoylmethyluracilyl,
5-carboxymethylaminomethyluracilyl,
5-carboxymethylaminomethyl-2-thiouracilyl,
3-methyluracilyl,
1-methyl-3-(3-amino-3-carboxypropyl) pseudouracilyl,
5-carboxymethyluracilyl,
5-methyldihydrouracilyl, or
3-methylpseudouracilyl.

A universal base can form base pairs with each of the natural DNA/RNA bases, exhibiting relatively little discrimination between them. In general, the universal bases are non-hydrogen bonding, hydrophobic, aromatic moieties which can stabilize e.g., duplex RNA or RNA-like molecules, via stacking interactions. A universal base can also include hydrogen bonding substituents.

As used herein, a "universal base" can include anthracenes, pyrenes or any one of the following:

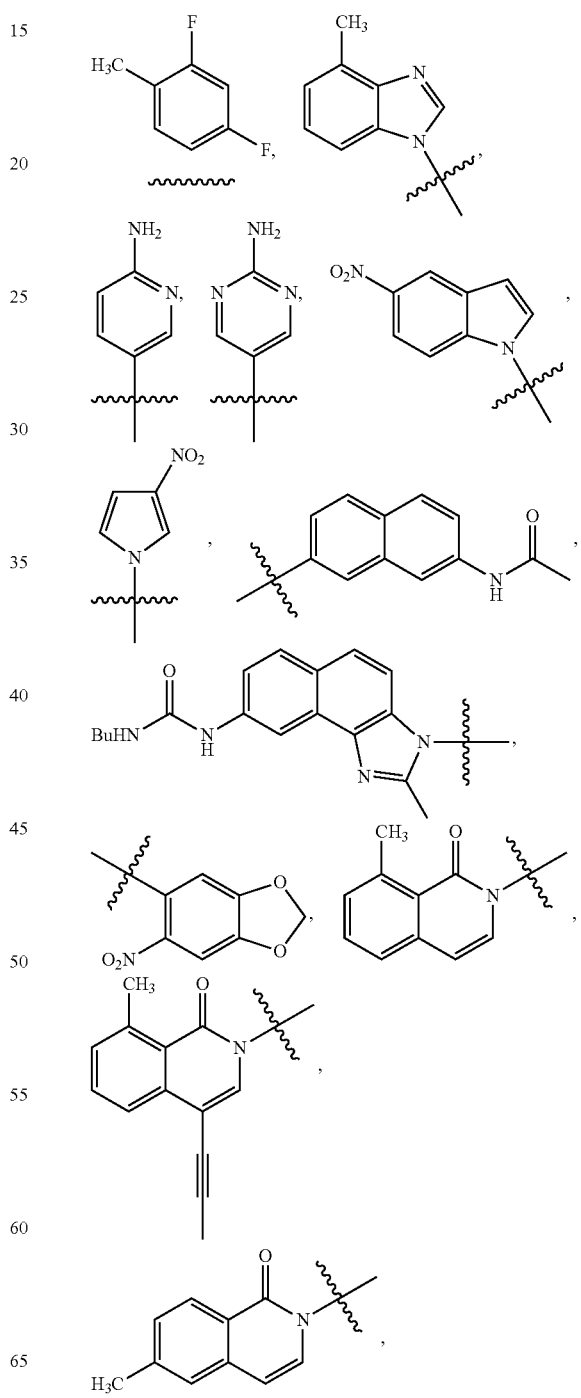

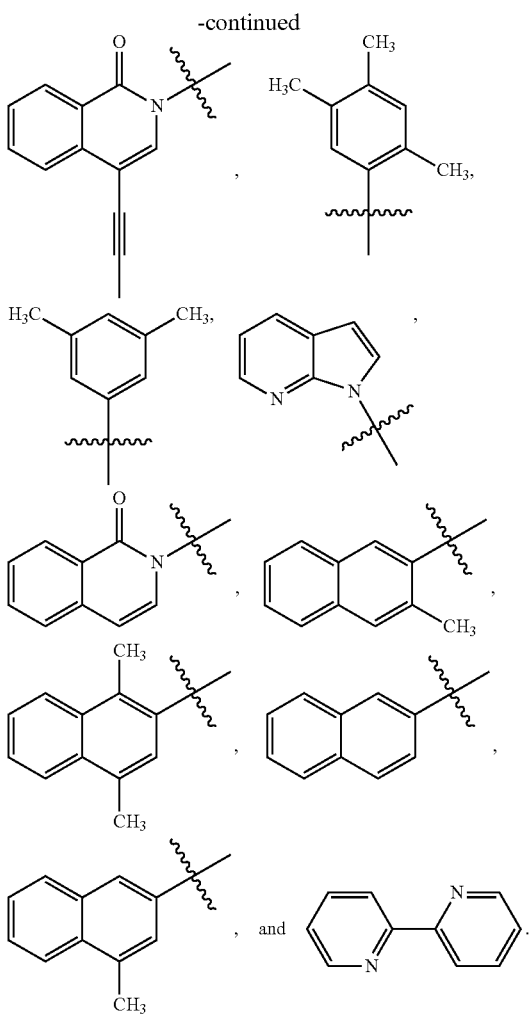

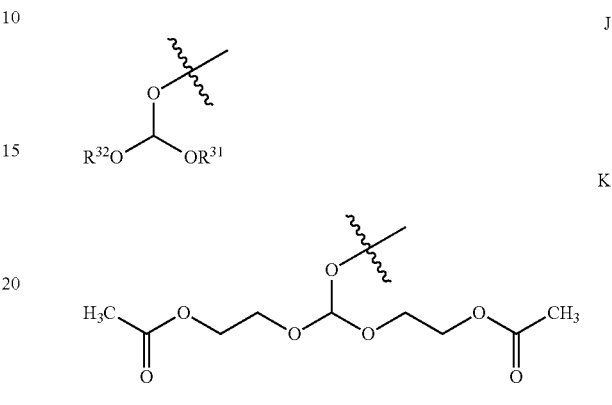

In some embodiments, B can form part of a tether that connects a ligand to the carrier. For example, the tether can be B—CH=CH—C(O)NH—(CH$_2$)$_5$—NHC(O)-LIGAND. In a preferred embodiment, the double bond is trans, and the ligand is a substituted or unsubstituted cholesterolyl radical (e.g., attached through the D-ring side chain or the C-3 hydroxyl); an aralkyl moiety having at least one sterogenic center and at least one substituent on the aryl portion of the aralkyl group; or a nucleobase. In certain embodiments, B, in the tether described above, is uracilyl or a universal base, e.g., an aryl moiety, e.g., phenyl, optionally having additional substituents, e.g., one or more fluoro groups. B can be substituted at any atom with the remainder of the tether.

X$^2$ can include "oxy" or "deoxy" substituents in place of the 2'-OH or be a ligand or a tethered ligand.

Examples of "oxy"-substituents include alkoxy or aryloxy (OR, e.g., R=H, alkyl, cycloalkyl, aryl, aralkyl, heteroaryl, sugar, or protecting group); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; O-PROTECTED AMINE (AMINE=NH$_2$; alkylamino, dialkylamino, heterocyclyl, arylamino, diaryl amino, heteroaryl amino, or diheteroaryl amino, ethylene diamine, polyamino) and aminoalkoxy, O(CH$_2$)$_n$PROTECTED AMINE, (e.g., AMINE=NH$_2$; alkylamino, dialkylamino, heterocyclyl, arylamino, diaryl amino, heteroaryl amino, or diheteroaryl amino, ethylene diamine, polyamino), and orthoester. Amine protecting groups can include formyl, amido, benzyl, allyl, etc.

Figure 2B:
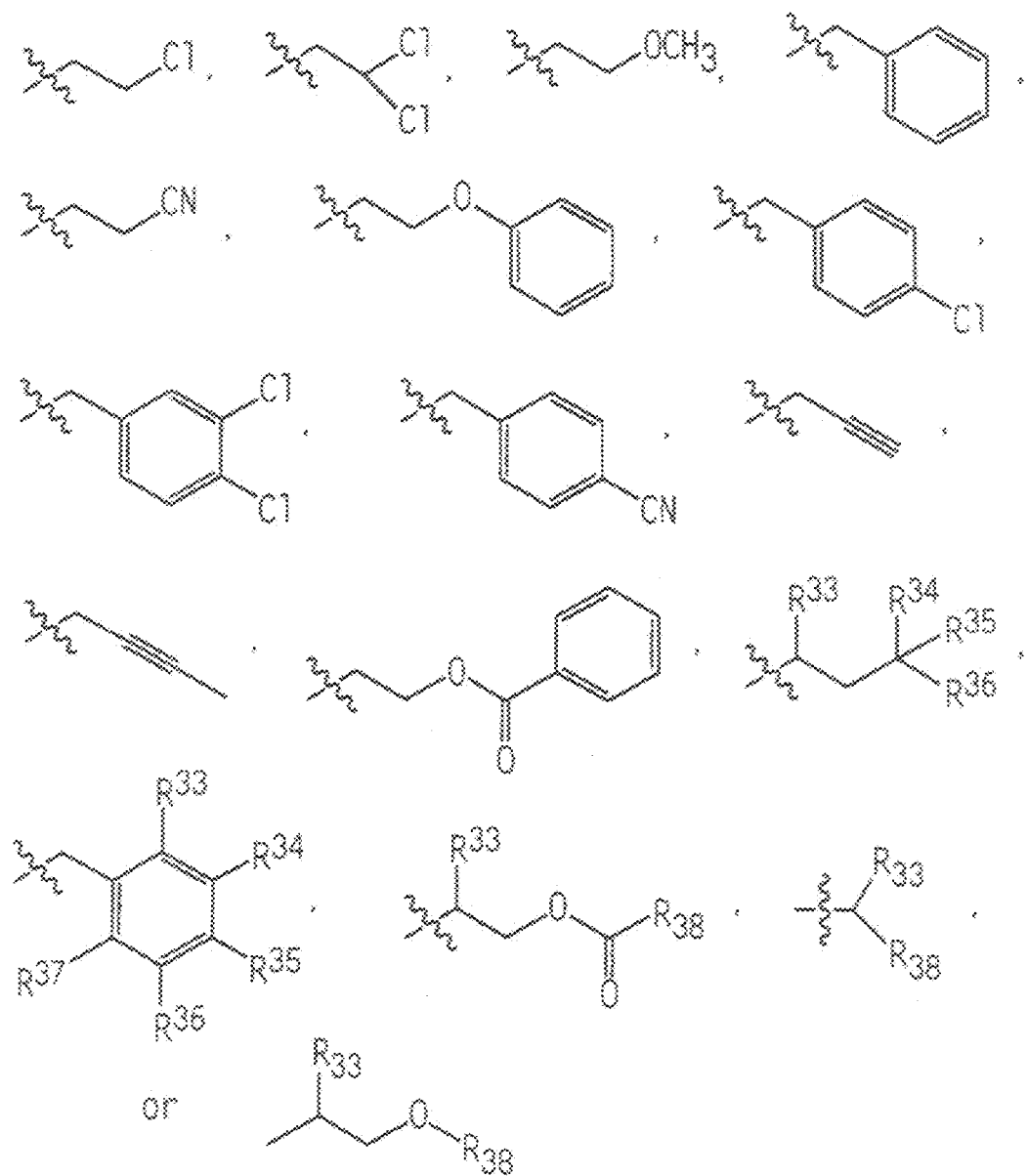
FIG. 2B is a list of substituents that may be present on the C2'-orthoester group.
Figure 3A:
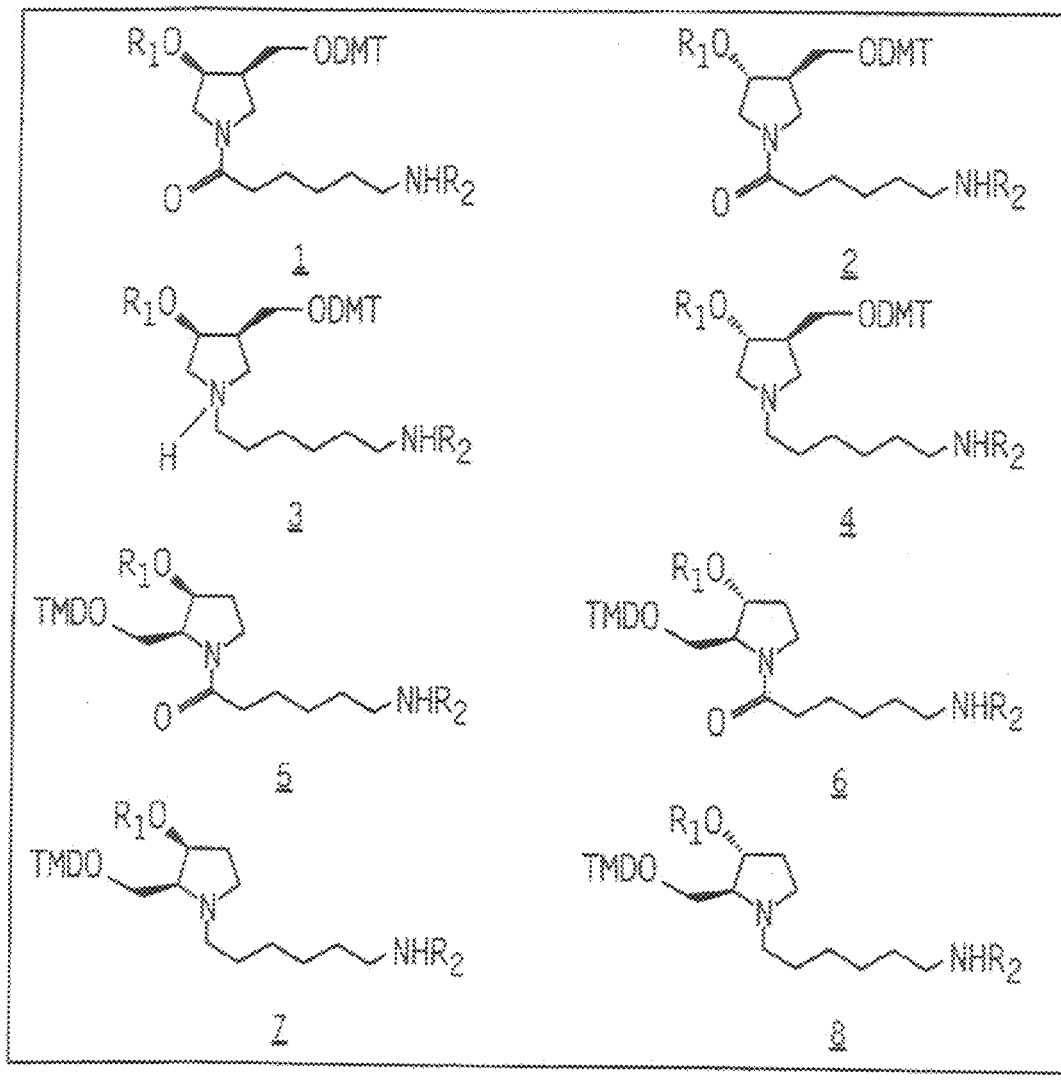
FIGS. 3A-3D depict representative cyclic, sugar replacement monomer subunit (SRMS) carriers.
Figure 3A:
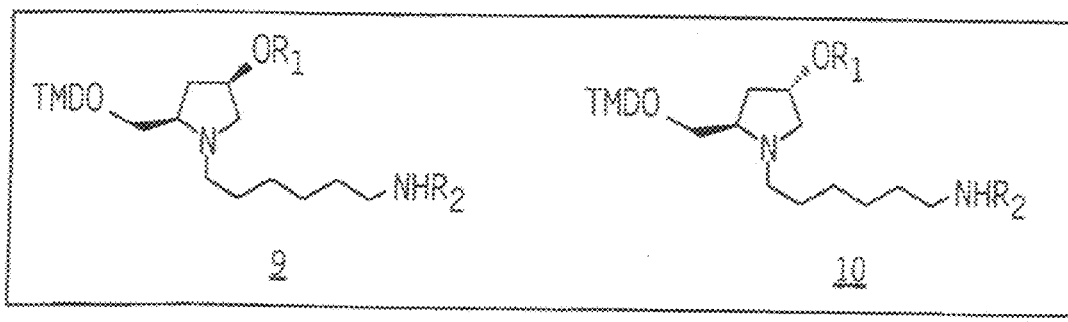
Figure 3B:
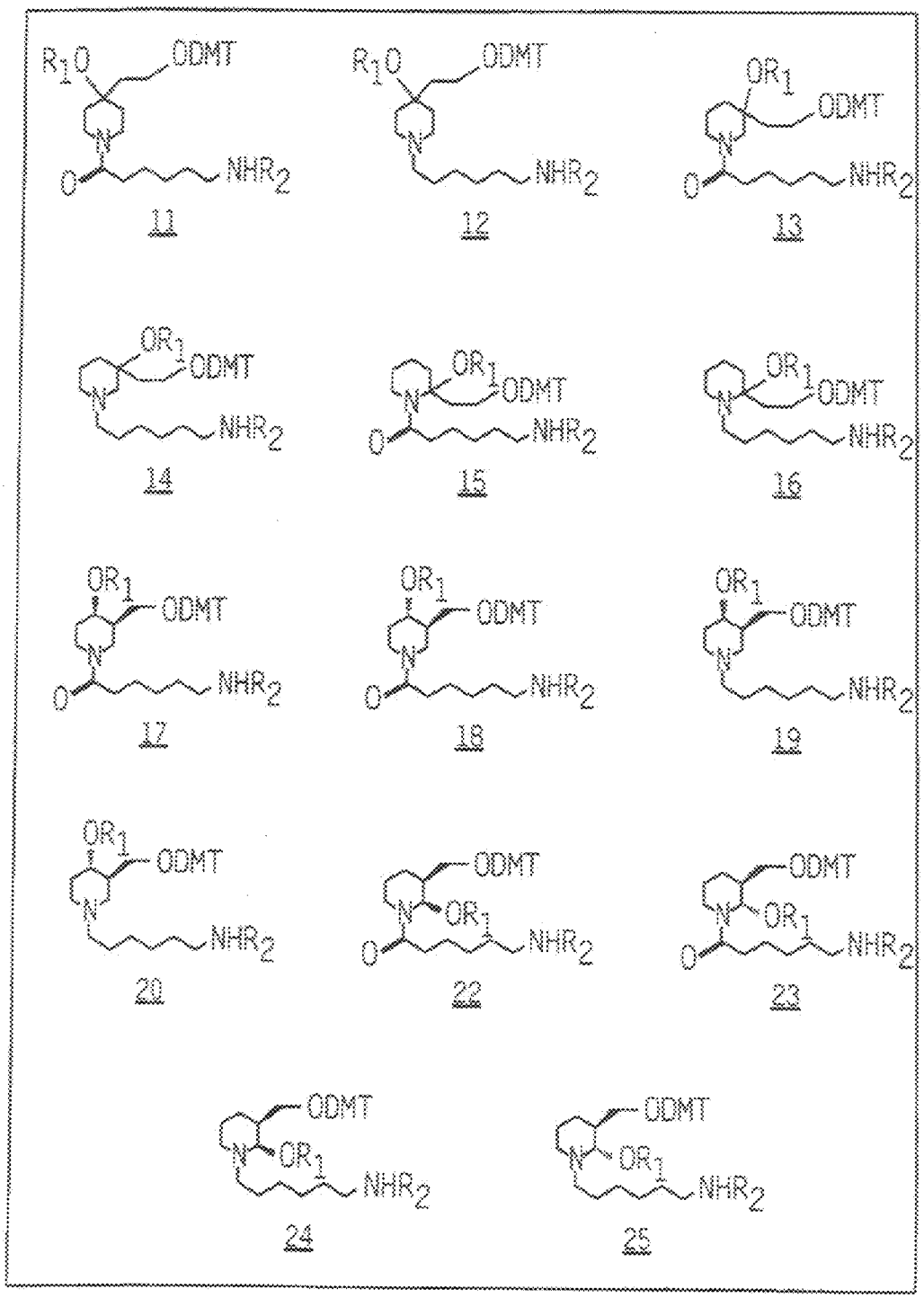
Figure 3C:
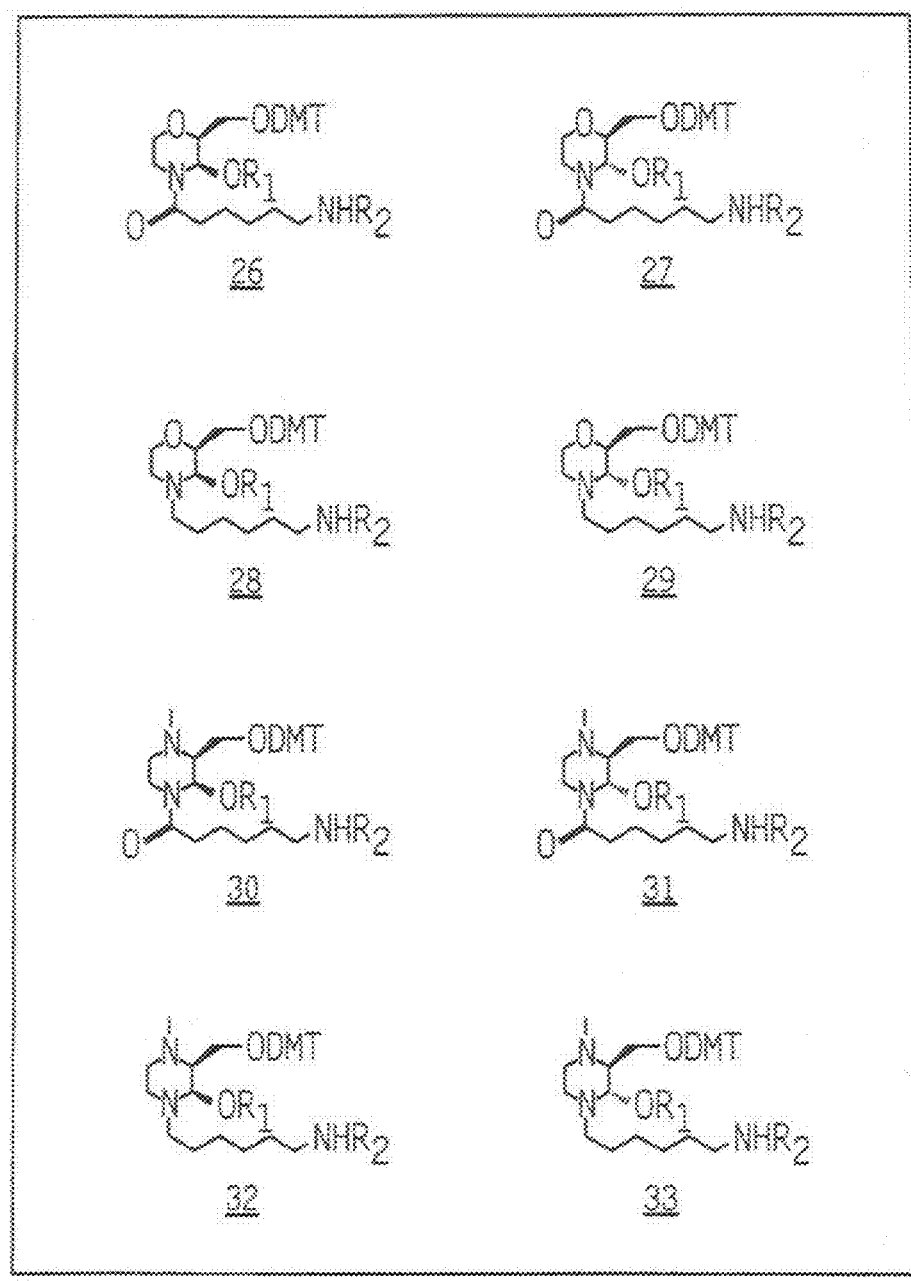
Figure 3D:
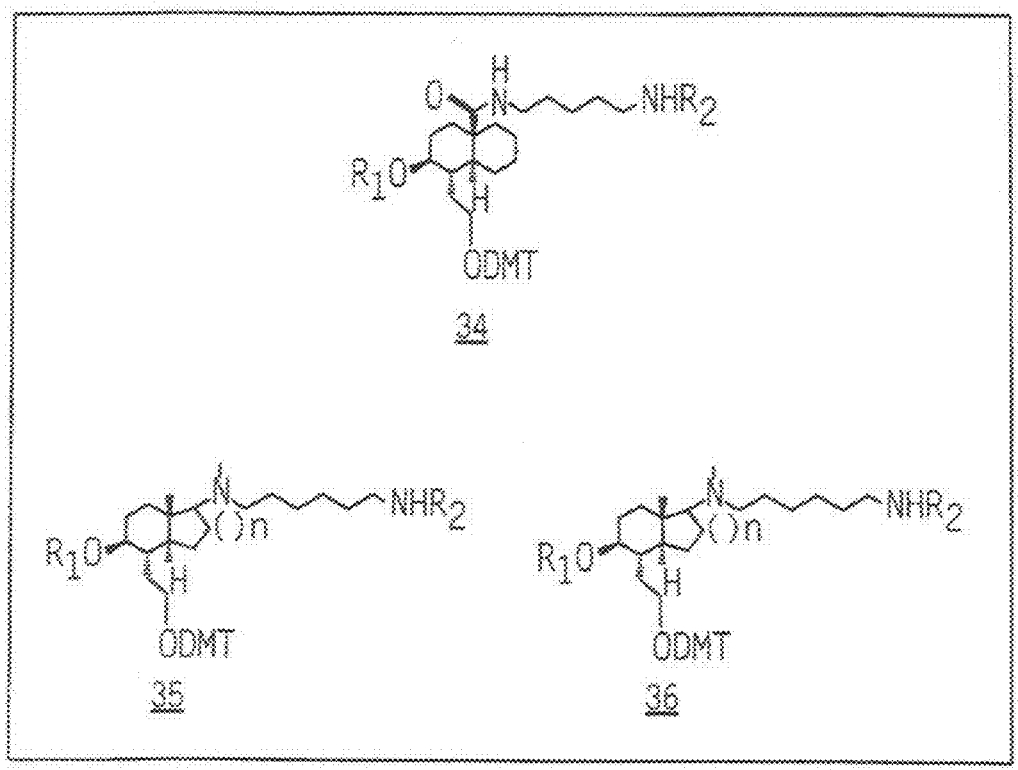

Preferred orthoesters have the general formula J. The groups R$^{31}$ and R$^{32}$ may be the same or different and can be any combination of the groups listed in FIG. 2B. A preferred orthoester is the "ACE" group, shown below as structure K.

"Deoxy" substituents include hydrogen (i.e. deoxyribose sugars); halo (e.g., fluoro); protected amino (e.g. NH$_2$; alkylamino, dialkylamino, heterocyclyl, arylamino, diaryl amino, heteroaryl amino, diheteroaryl amino, or amino acid in which all amino are protected); fully protected polyamino (e.g., NH(CH$_2$CH$_2$NH)$_n$CH$_2$CH$_2$-AMINE, wherein AMINE=NH$_2$; alkylamino, dialkylamino, heterocyclyl, arylamino, diaryl amino, heteroaryl amino, or diheteroaryl amino and all amino groups are protected), —NHC(O)R (R=alkyl, cycloalkyl, aryl, aralkyl, heteroaryl or sugar), cyano; alkyl-thio-alkyl; thioalkoxy; and alkyl, cycloalkyl, aryl, alkenyl and alkynyl, which may be optionally substituted with e.g., a protected amino functionality. Preferred substitutents are 2'-methoxyethyl, 2'-OCH3, 2'-O-allyl, 2'-C— allyl, and 2'-fluoro.

X$^3$ is as described for OFG$^2$ above.

PG can be a triarylmethyl group (e.g., a dimethoxytrityl group) or Si(X$^{5'}$)(X$^{5''}$)(X$^{5'''}$) in which (X$^{5'}$), (X$^{5''}$), and (X$^{5'''}$) are as described elsewhere.

Sugar Replacement-Based Monomers

Cyclic sugar replacement-based monomers, e.g., sugar replacement-based ligand-conjugated monomers, are also referred to herein as sugar replacement monomer subunit (SRMS) monomer compounds. Preferred carriers have the general formula (LCM-2) provided below. (In that structure preferred backbone attachment points can be chosen from R$^1$ or R$^2$; R$^3$ or R$^4$; or R$^9$ and R$^{10}$ if Y is CR$^9$R$^{10}$ (two positions are chosen to give two backbone attachment points, e.g., R$^1$ and R$^4$, or R$^4$ and R$^9$). Preferred tethering attachment points include R$^7$; R$^5$ or R$^6$ when X is CH$_2$. The carriers are described below as an entity, which can be incorporated into a strand. Thus, it is understood that the structures also encompass the situations wherein one (in the case of a terminal position) or two (in the case of an internal position) of the attachment points, e.g., R$^1$ or R$^2$; R$^3$ or R$^4$; or R$^9$ or R$^{10}$ (when Y is CR$^9$R$^{10}$), is connected to the phosphate, or modified phosphate, e.g., sulfur containing, backbone. E.g., one of the above-named R groups can be —CH$_2$—, wherein one bond is connected to the carrier and one to a backbone atom, e.g., a linking oxygen or a central phosphorus atom.

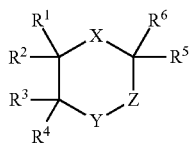
(LCM-2)

in which,

X is N(CO)R$^7$, NR$^7$ or CH$_2$;

Y is NR$^8$, O, S, CR$^9$R$^{10}$;

Z is CR$^{11}$R$^{12}$ or absent;

Each of R$^1$, R$^2$, R$^3$, R$^4$, R$^9$, and R$^{10}$ is, independently, H, OR$^a$, or (CH$_2$)$_n$OR$^b$, provided that at least two of R$^1$, R$^2$, R$^3$, R$^4$, R$^9$, and R$^{10}$ are OR$^a$ and/or (CH$_2$)$_n$OR$^b$;

Each of R$^5$, R$^6$, R$^{11}$, and R$^{12}$ is, independently, a ligand, H, C$_1$-C$_6$ alkyl optionally substituted with 1-3 R$^{13}$, or C(O)NHR$^7$; or R$^5$ and R$^{11}$ together are C$_3$-C$_8$ cycloalkyl optionally substituted with R$^{14}$;

R$^7$ can be a ligand, e.g., R$^7$ can be R$^d$, or R$^7$ can be a ligand tethered indirectly to the carrier, e.g., through a tethering moiety, e.g., C$_1$-C$_{20}$ alkyl substituted with NR$^c$R$^d$; or C$_1$-C$_{20}$ alkyl substituted with NHC(O)R$^d$;

R$^8$ is H or C$_1$-C$_6$ alkyl;

R$^{13}$ is hydroxy, C$_1$-C$_4$ alkoxy, or halo;

R$^{14}$ is NR$^c$R$^7$;

R$^{15}$ is C$_1$-C$_6$ alkyl optionally substituted with cyano, or C$_2$-C$_6$ alkenyl;

R$^{16}$ is C$_1$-C$_{10}$ alkyl;

R$^{17}$ is a liquid or solid phase support reagent;

L is —C(O)(CH$_2$)$_q$C(O)—, or —C(O)(CH$_2$)$_q$S—;

R$^a$ is a protecting group, e.g., CAr$_3$; (e.g., a dimethoxytrityl group) or Si(X$^{5'}$)(X$^{5''}$)(X$^{5'''}$) in which (X$^{5'}$), (X$^{5''}$), and (X$^{5'''}$) are as described elsewhere.

R$^b$ is P(O)(O$^-$)H, P(OR$^{15}$)N(R$^{16}$)$_2$ or L-R$^{17}$;

R$^c$ is H or C$_1$-C$_6$ alkyl;

R$^d$ is H or a ligand;

Each Ar is, independently, C$_6$-C$_{10}$ aryl optionally substituted with C$_1$-C$_4$ alkoxy;

n is 1-4; and q is 0-4.

Exemplary carriers include those in which, e.g., X is N(CO)R$^7$ or NR$^7$, Y is CR$^9$R$^{10}$, and Z is absent; or X is N(CO)R$^7$ or NR$^7$, Y is CR$^9$R$^{10}$, and Z is CR$^{11}$R$^{12}$; or X is N(CO)R$^7$ or NR$^7$, Y is NR$^8$, and Z is CR$^{11}$R$^{12}$; or X is N(CO)R$^7$ or NR$^7$, Y is O, and Z is CR$^{11}$R$^{12}$; or X is CH$_2$; Y is CR$^9$R$^{10}$; Z is CR$^{11}$R$^{12}$, and R$^5$ and R$^{11}$ together form C$_6$ cycloalkyl (H, z=2), or the indane ring system, e.g., X is CH$_2$; Y is CR$^9$R$^{10}$; Z is cR$^{11}$R$^{12}$, and R$^5$ and R$^{11}$ together form C$_5$ cycloalkyl (H, z=1).

In certain embodiments, the carrier may be based on the pyrroline ring system or the 4-hydroxyproline ring system, e.g., X is N(CO)R$^7$ or NR$^7$, Y is CR$^9$R$^{10}$, and Z is absent (D). OFG$^1$ is preferably attached to a primary carbon, e.g., an exocyclic alkylene group, e.g., a methylene group, connected to one of the carbons in the five-membered ring (—CH$_2$OFG$^1$ in D). OFG$^2$ is preferably attached directly to one of the carbons in the five-membered ring (—OFG$^2$ in D). For the pyrroline-based carriers, —CH$_2$OFG$^1$ may be attached to C-2 and OFG$^2$ may be attached to C-3; or —CH$_2$OFG$^1$ may be attached to C-3 and OFG$^2$ may be attached to C-4. In certain embodiments, CH$_2$OFG$^1$ and OFG$^2$ may be geminally substituted to one of the above-referenced carbons. For the 3-hydroxyproline-based carriers, —CH$_2$OFG$^1$ may be attached to C-2 and OFG$^2$ may be attached to C-4. The pyrroline- and 4-hydroxyproline-based monomers may therefore contain linkages (e.g., carbon-carbon bonds) wherein bond rotation is restricted about that particular linkage, e.g. restriction resulting from the presence of a ring. Thus, CH$_2$OFG$^1$ and OFG$^2$ may be cis or trans with respect to one another in any of the pairings delineated above Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). The tethering attachment point is preferably nitrogen. Preferred examples of carrier D include the following:

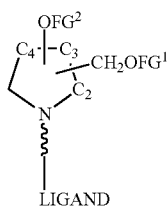
D

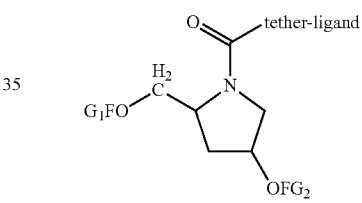

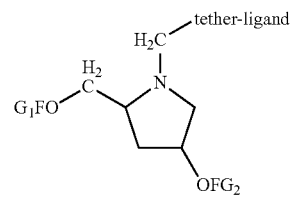

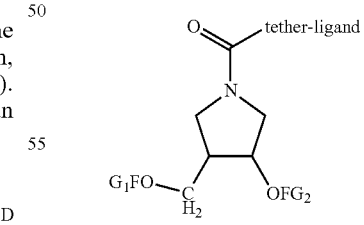

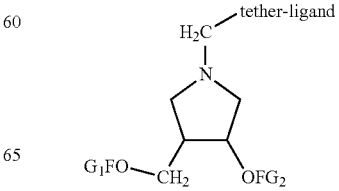

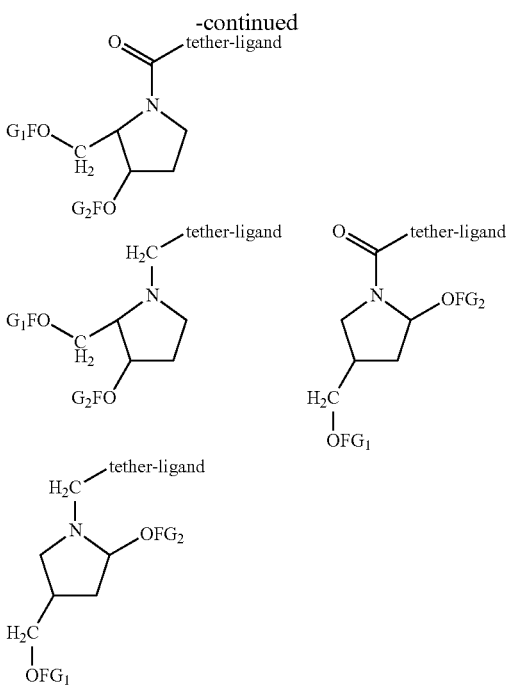

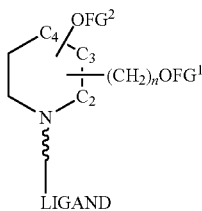

In certain embodiments, the carrier may be based on the piperidine ring system (E), e.g., X is N(CO)$R^7$ or $NR^7$, Y is $CR^9R^{10}$, and Z is $CR^{11}R^{12}$. $OFG^1$ is preferably

E attached to a primary carbon, e.g., an exocyclic alkylene group, e.g., a methylene group (n=1) or ethylene group (n=2), connected to one of the carbons in the six-membered ring [—$(CH_2)_n OFG^1$ in E]. $OFG^2$ is preferably attached directly to one of the carbons in the six-membered ring (—$OFG^2$ in E). —$(CH_2)_n OFG^1$ and $OFG^2$ may be disposed in a geminal manner on the ring, i.e., both groups may be attached to the same carbon, e.g., at C-2, C-3, or C-4. Alternatively, —$(CH_2)_n OFG^1$ and $OFG^2$ may be disposed in a vicinal manner on the ring, i.e., both groups may be attached to adjacent ring carbon atoms, e.g., —$(CH_2)_n OFG^1$ may be attached to C-2 and $OFG^2$ may be attached to C-3; —$(CH_2)_n OFG^1$ may be attached to C-3 and $OFG^2$ may be attached to C-2; —$(CH_2)_n OFG^1$ may be attached to C-3 and $OFG^2$ may be attached to C-4; or —$(CH_2)_n OFG^1$ may be attached to C-4 and $OFG^2$ may be attached to C-3. The piperidine-based monomers may therefore contain linkages (e.g., carbon-carbon bonds) wherein bond rotation is restricted about that particular linkage, e.g. restriction resulting from the presence of a ring. Thus, —$(CH_2)_n OFG^1$ and $OFG^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing $CH_2 OFG^1$ and $OFG^2$ can both have the R configuration; or both have the S configuration; or one center can have the R configuration and the other center can have the S configuration and vice versa). The tethering attachment point is preferably nitrogen.

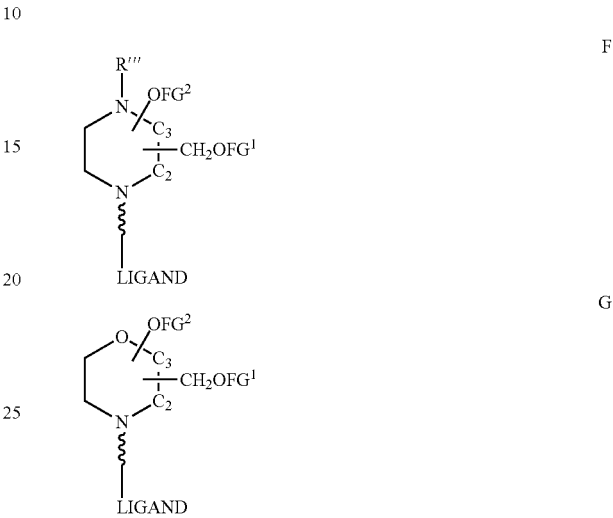

In certain embodiments, the carrier may be based on the piperazine ring system (F), e.g., X is N(CO)$R^7$ or $NR^7$, Y is $NR^8$, and Z is $CR^{11}R^{12}$, or the morpholine ring system (G), e.g., X is N(CO)$R^7$ or $NR^7$, Y is O, and Z is $CR^{11}R^{12}$. $OFG^1$ is preferably attached to a primary carbon, e.g., an exocyclic alkylene group, e.g., a methylene group, connected to one of the carbons in the six-membered ring (—$CH_2 OFG^1$ in F or G). $OFG^2$ is preferably attached directly to one of the carbons in the six-membered rings (—$OFG^2$ in F or G). For both F and G, —$CH_2 OFG^1$ may be attached to C-2 and $OFG^2$ may be attached to C-3; or vice versa. In certain embodiments, $CH_2 OFG^1$ and $OFG^2$ may be geminally substituted to one of the above-referenced carbons. The piperazine- and morpholine-based monomers may therefore contain linkages (e.g., carbon-carbon bonds) wherein bond rotation is restricted about that particular linkage, e.g. restriction resulting from the presence of a ring. Thus, $CH_2 OFG^1$ and $OFG^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing $CH_2 OFG^1$ and $OFG^2$ can both have the R configuration; or both have the S configuration; or one center can have the R configuration and the other center can have the S configuration and vice versa). R''' can be, e.g., $C_1$-$C_6$ alkyl, preferably $CH_3$. The tethering attachment point is preferably nitrogen in both F and G.

In certain embodiments, the carrier may be based on the decalin ring system, e.g., X is $CH_2$; Y is $CR^9R^{10}$; Z is $CR^{11}R^{12}$, and $R^5$ and $R^{11}$ together form $C_6$ cycloalkyl (H, z=2), or the indane ring system, e.g., X is $CH_2$; Y is $CR^9R^{10}$; Z is $CR^{11}R^{12}$, and $R^5$ and $R^{11}$ together form $C_5$ cycloalkyl (H, z=1). $OFG^1$ is preferably attached to a primary carbon,

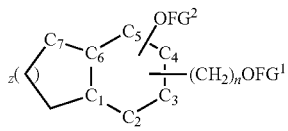

H e.g., an exocyclic methylene group (n=1) or ethylene group (n=2) connected to one of C-2, C-3, C-4, or C-5 [—(CH$_2$)$_n$OFG$^1$ in H]. OFG$^2$ is preferably attached directly to one of C-2, C-3, C-4, or C-5 (—OFG$^2$ in H). —(CH$_2$)$_n$OFG$^1$ and OFG$^2$ may be disposed in a geminal manner on the ring, i.e., both groups may be attached to the same carbon, e.g., at C-2, C-3, C-4, or C-5. Alternatively, —(CH$_2$)$_n$OFG$^1$ and OFG$^2$ may be disposed in a vicinal manner on the ring, i.e., both groups may be attached to adjacent ring carbon atoms, e.g., —(CH$_2$)$_n$OFG$^1$ may be attached to C-2 and OFG$^2$ may be attached to C-3; —(CH$_2$)$_n$OFG$^1$ may be attached to C-3 and OFG$^2$ may be attached to C-2; —(CH$_2$)$_n$OFG$^1$ may be attached to C-3 and OFG$^2$ may be attached to C-4; or —(CH$_2$)$_n$OFG$^1$ may be attached to C-4 and OFG$^2$ may be attached to C-3; —(CH$_2$)$_n$OFG$^1$ may be attached to C-4 and OFG$^2$ may be attached to C-5; or —(CH$_2$)$_n$OFG$^1$ may be attached to C-5 and OFG$^2$ may be attached to C-4. The decalin or indane-based monomers may therefore contain linkages (e.g., carbon-carbon bonds) wherein bond rotation is restricted about that particular linkage, e.g. restriction resulting from the presence of a ring. Thus, —(CH$_2$)$_n$OFG$^1$ and OFG$^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). In a preferred embodiment, the substituents at C-1 and C-6 are trans with respect to one another. The tethering attachment point is preferably C-6 or C-7.

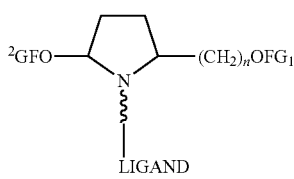

J

Other carriers may include those based on 3-hydroxyproline (J). Thus, —(CH$_2$)$_n$OFG$^1$ and OFG$^2$ may be cis or trans with respect to one another. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). The tethering attachment point is preferably nitrogen.

Representative cyclic, sugar replacement-based carriers are shown in FIG. 3.

Sugar Replacement-Based Monomers (Acyclic)

Acyclic sugar replacement-based monomers, e.g., sugar replacement-based ligand-conjugated monomers, are also referred to herein as sugar replacement monomer subunit (SRMS) monomer compounds. Preferred acyclic carriers can have formula LCM-3 or LCM-4 below.

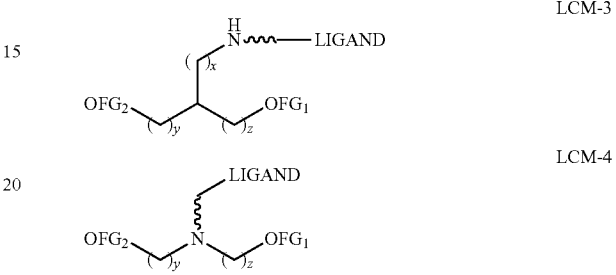

In some embodiments, each of x, y, and z can be, independently of one another, 0, 1, 2, or 3. In formula LCM-3, when y and z are different, then the tertiary carbon can have either the R or S configuration. In preferred embodiments, x is zero and y and z are each 1 in formula LCM-3 (e.g., based on serinol), and y and z are each 1 in formula LCM-3. Each of formula LCM-3 or LCM-4 below can optionally be substituted, e.g., with hydroxy, alkoxy, perhaloalkyl.

Tethers

In certain embodiments, a moiety, e.g., a ligand may be connected indirectly to the carrier via the intermediacy of an intervening tether. Tethers are connected to the carrier at a tethering attachment point (TAP) and may include any C$_1$-C$_{100}$ carbon-containing moiety, (e.g. C$_1$-C$_{75}$, C$_1$-C$_{50}$, C$_1$-C$_{20}$, C$_1$-C$_{10}$; C$_1$, C$_2$, C$_3$, C$_4$, C$_5$, C$_6$, C$_7$, C$_8$, C$_9$, or C$_{10}$), preferably having at least one nitrogen atom. In preferred embodiments, the nitrogen atom forms part of a terminal amino or amido (NHC(O)—) group on the tether, which may serve as a connection point for the ligand. Preferred tethers (underlined) include TAP-(CH$_2$)$_n$NH—; TAP-C(O)(CH$_2$)$_n$NH—; TAP-NR'''(CH$_2$)$_n$NH—, TAP-C(O)—(CH$_2$)$_n$—C(O)—; TAP-C(O)—(CH$_2$)$_n$—C(O)O—; TAP-C(O)—O—; TAP-C(O)—(CH$_2$)$_n$—NH—C(O)—; TAP-C(O)—(CH$_2$)$_n$—; TAP-C(O)—NH—; TAP-C(O)—; TAP-(CH$_2$)$_n$—C(O)—; TAP-(CH$_2$)$_n$—C(O)O—; TAP-(CH$_2$)$_n$—; or TAP-(CH$_2$)$_n$—NH—C(O)—; in which n is 1-20 (e.g., 1, 2, 3, 4, 5, 6, 7, 8, 9, 10, 11, 12, 13, 14, 15, 16, 17, 18, 19, or 20) and R'''' is C$_1$-C$_6$ alkyl. Preferably, n is 5, 6, or 11. In other embodiments, the nitrogen may form part of a terminal oxyamino group, e.g., —ONH$_2$, or hydrazino group, —NHNH$_2$. The tether may optionally be substituted, e.g., with hydroxy, alkoxy, perhaloalkyl, and/or optionally inserted with one or more additional heteroatoms, e.g., N, O, or S. Preferred tethered ligands may include, e.g., TAP-(CH$_2$)$_n$NH(LIGAND); TAP-C(O)(CH$_2$)$_n$NH(LIGAND); TAP-NR''''(CH$_2$)$_n$NH(LIGAND); TAP-(CH$_2$)$_n$ONH(LIGAND); TAP-C(O)(CH$_2$)$_n$ONH(LIGAND); TAP-NR''''(CH$_2$)$_n$ONH(LIGAND); TAP-(CH$_2$)$_n$NHNH$_2$(LIGAND), TAP-C(O)(CH$_2$)$_n$NHNH$_2$(LIGAND); TAP- NR""(CH$_2$)$_n$NHNH$_2$(LIGAND); TAP-C(O)—(CH$_2$)$_n$—C(O)(LIGAND); TAP-C(O)—(CH$_2$)$_n$—C(O)O(LIGAND); TAP-C(O)—O(LIGAND); TAP-C(O)—(CH$_2$)$_n$—NH—C(O)(LIGAND); TAP-C(O)—(CH$_2$)$_n$(LIGAND); TAP-C(O)—NH(LIGAND); TAP-C(O)(LIGAND); TAP-(CH$_2$)$_n$—C(O)(LIGAND); TAP-(CH$_2$)$_n$—C(O)O(LIGAND); TAP-(CH$_2$)$_n$(LIGAND); or TAP-(CH$_2$)$_n$—NH—C(O)(LIGAND). In some embodiments, amino terminated tethers (e.g., NH$_2$, ONH$_2$, NH$_2$NH$_2$) can form an imino bond (i.e., C=N) with the ligand. In some embodiments, amino terminated tethers (e.g., NH$_2$, ONH$_2$, NH$_2$NH$_2$) can acylated, e.g., with C(O)CF$_3$.

In some embodiments, the tether can terminate with a mercapto group (i.e., SH) or an olefin (e.g., CH=CH$_2$). For example, the tether can be TAP-(CH$_2$)$_n$—SH, TAP-C(O)(CH$_2$)$_n$SH, TAP-(CH$_2$)$_n$—(CH=CH$_2$), or TAP-C(O)(CH$_2$)$_n$(CH=CH$_2$), in which n can be as described elsewhere. In certain embodiments, the olefin can be a Diels-Alder diene or dienophile. The tether may optionally be substituted, e.g., with hydroxy, alkoxy, perhaloalkyl, and/or optionally inserted with one or more additional heteroatoms, e.g., N, O, or S. The double bond can be cis or trans or E or Z.

In other embodiments the tether may include an electrophilic moiety, preferably at the terminal position of the tether. Preferred electrophilic moieties include, e.g., an aldehyde, alkyl halide, mesylate, tosylate, nosylate, or brosylate, or an activated carboxylic acid ester, e.g. an NHS ester, or a pentafluorophenyl ester. Preferred tethers (underlined) include TAP-(CH$_2$)$_n$CHO; TAP-C(O)(CH$_2$)$_n$CHO; or TAP-NR""(CH$_2$)$_n$CHO, in which n is 1-6 and R"" is C$_1$-C$_6$ alkyl; or TAP-(CH$_2$)$_n$C(O)ONHS; TAP-C(O)(CH$_2$)$_n$C(O)ONHS; or TAP-NR""(CH$_2$)$_n$C(O)ONHS, in which n is 1-6 and R"" is C$_1$-C$_6$ alkyl; TAP-(CH$_2$)$_n$C(O)OC$_6$F$_5$; TAP-C(O)(CH$_2$)$_n$C(O)OC$_6$F$_5$; or TAP-NR""(CH$_2$)$_n$C(O)OC$_6$F$_5$, in which n is 1-11 and R"" is C$_1$-C$_6$ alkyl; or —(CH$_2$)$_n$CH$_2$LG; TAP-C(O)(CH$_2$)$_n$CH$_2$LG; or TAP-NR""(CH$_2$)$_n$CH$_2$LG, in which n can be as described elsewhere and R"" is C$_1$-C$_6$ alkyl (LG can be a leaving group, e.g., halide, mesylate, tosylate, nosylate, brosylate). Tethering can be carried out by coupling a nucleophilic group of a ligand, e.g., a thiol or amino group with an electrophilic group on the tether.

In other embodiments, it can be desirable for the ligand-conjugated monomer or a ligand-conjugated monomer to include a phthalimido group (K) at the terminal position of the tether.

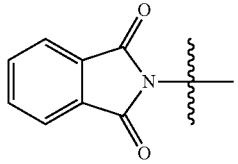

K

In other embodiments, other protected amino groups can be at the terminal position of the tether, e.g., alloc, monomethoxy trityl (MMT), trifluoroacetyl, Fmoc, or aryl sulfonyl (e.g., the aryl portion can be ortho-nitrophenyl or ortho, para-dinitrophenyl).

Any of the tethers described herein may further include one or more additional linking groups, e.g., —O—(CH$_2$)$_n$—, —(CH$_2$)$_n$—SS—, —(CH$_2$)$_n$—, or —(CH=CH)—.

Tethered Ligands

A wide variety of entities can be tethered to an oligonucleotide agent, e.g., to the carrier of a ligand-conjugated monomer. Examples are described below in the context of a ligand-conjugated monomer but that is only one preferred embodiment. Entities can be coupled at other points to an oligonucleotide agent.

A ligand tethered to an oligonucleotide agent (e.g., an oligonucleotide agent targeting an miRNA) can have a favorable effect on the agent. For example, the ligand can improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting.

A tethered ligand can include one or more modified bases or sugars that can function as intercalators. These are preferably located in an internal region, such as in a bulge of a miRNA/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand.

In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a miRNA to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage.

A tethered ligand can be an aminoglycoside ligand, which can cause an oligonucleotide agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-S-acridine has an increased affinity for the HIV Rev-response element (RRE). In some embodiments the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent, e.g., an oligonucleotide agent targeting an miRNA or pre-miRNA.

A tethered ligand can be a poly-arginine peptide, peptoid or peptidomimetic, which can enhance the cellular uptake of an oligonucleotide agent.

Preferred moieties are ligands, which are coupled, preferably covalently, either directly or indirectly via an intervening tether, to the ligand-conjugated carrier. In preferred embodiments, the ligand is attached to the carrier via an intervening tether. As discussed above, the ligand or tethered ligand may be present on the monomer when the monomer is incorporated into the growing strand. In some embodiments, the ligand may be incorporated into a "precursor" a ligand-conjugated monomer subunit after a "precursor" a ligand-conjugated monomer has been incorporated into the growing strand. For example, a monomer having, e.g., an amino-terminated tether, e.g., TAP-$(CH_2)_n NH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer subunit by coupling the electrophilic group of the ligand with the terminal nucleophilic group of the precursor monomer subunit tether.

In preferred embodiments, a ligand alters the distribution, targeting or lifetime of an oligonucleotide agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics.

Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic.

Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl) glycerol, 1,3-bis-O(octadecyl)glycerol), geranyloxyhexyl group, hexadecylglycerol, borneol, menthol, 1,3-propanediol, heptadecyl group, palmitic acid, stearic acid (e.g., gyceryl distearate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the oligonucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Peptides that target markers enriched in proliferating cells can be used. E.g., RGD containing peptides and peptidomimetics can target cancer cells, in particular cells that exhibit an $I_v\theta_3$ integrin. Thus, one could use RGD peptides, cyclic peptides containing RGD, RGD peptides that include D-amino acids, as well as synthetic RGD mimics. In addition to RGD, one can use other moieties that target the $I_v$-$\theta_3$ integrin ligand. Generally, such ligands can be used to control proliferating cells and angiogeneis. Preferred conjugates of this type include an oligonucleotide agent that targets PECAM-1, VEGF, or other cancer gene, e.g., a cancer gene described herein.

The oligonucleotide agents of the invention are particularly useful when targeted to the liver. For example, a single stranded oligonucleotide agent featured in the invention can target an miRNA enriched in the liver, and the oligonucleotide agent can include a ligand for enhanced delivery to the liver. An oligonucleotide agent can be targeted to the liver by incorporation of a monomer derivatized with a ligand which targets to the liver. For example, a liver-targeting agent can be a lipophilic moiety. Preferred lipophilic moieties include lipid, cholesterols, oleyl, retinyl, or cholesteryl residues. Other lipophilic moieties that can function as liver-targeting agents include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

An oligonucleotide agent can also be targeted to the liver by association with a low-density lipoprotein (LDL), such as lactosylated LDL. Polymeric carriers complexed with sugar residues can also function to target oligonucleotide agents to the liver.

A targeting agent that incorporates a sugar, e.g., galactose and/or analogues thereof, is particularly useful. These agents target, in particular, the parenchymal cells of the liver (see Table 2). For example, a targeting moiety can include more than one or preferably two or three galactose moieties, spaced about 15 angstroms from each other. The targeting moiety can alternatively be lactose (e.g., three lactose moieties), which is glucose coupled to a galactose. The targeting moiety can also be N-Acetyl-Galactosamine, N-Ac-Glucosamine. A mannose or mannose-6-phosphate targeting moiety can be used for macrophage targeting.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long (see Table 2, for example).

TABLE 2

Exemplary Cell Permeation Peptides

| Cell Permeation Peptide | Amino acid Sequence | Reference |
|---|---|---|
| Penetratin | RQIKIWFQNRRMKWKK (SEQ ID NO: 1) | Derossi et al., J. Biol. Chem. 269:10444, 1994 |
| Tat fragment (48-60) | GRKKRRQRRRPPQC (SEQ ID NO: 2) | Vives et al., J. Biol. Chem., 272:16010, 1997 |

TABLE 2-continued

Exemplary Cell Permeation Peptides

| Cell Permeation Peptide | Amino acid Sequence | Reference |
|---|---|---|
| Signal Sequence-based peptide | GALFLGWLGAAGSTMGAWSQPKKKRKV (SEQ ID NO: 3) | Chaloin et al., Biochem. Biophys. Res. Commun., 243:601, 1998 |
| PVEC | LLIILRRRIRKQAHAHSK (SEQ ID NO: 4) | Elmquist et al., Exp. Cell Res., 269:237, 2001 |
| Transportan | GWTLNSAGYLLKINLKALAALAKKIL (SEQ ID NO: 5) | Pooga et al., FASEB J., 12:67, 1998 |
| Amphiphilic model peptide | KLALKLALKALKAALKLA (SEQ ID NO: 6) | Oehlke et al., Mol. Ther., 2:339, 2000 |
| $Arg_9$ | RRRRRRRRR (SEQ ID NO: 7) | Mitchell et al., J. Pept. Res., 56:318, 2000 |
| Bacterial cell wall permeating | KFFKFFKFFK (SEQ ID NO: 8) | |
| LL-37 | LLGDFFRKSKEKIGKEFKRIVQRIKDFLRN LVPRTES (SEQ ID NO: 9) | |
| Cecropin P1 | SWLSKTAKKLENSAKKRISEGIAIAIQGGPR (SEQ ID NO: 10) | |
| α-defensin | ACYCRIPACIAGERRYGTCIYQGRLWAFCC (SEQ ID NO: 11) | |
| b-defensin | DHYNCVSSGGQCLYSACPIFTKIQGTCYR GKAKCCK (SEQ ID NO: 12) | |
| Bactenecin | RKCRIVVIRVCR (SEQ ID NO: 13) | |
| PR-39 | RRRPRPPYLPRPRPPPFFPPRLPPRIPPGFP PRFPPRFPGKR-NH2 (SEQ ID NO: 14) | |
| Indolicidin | ILPWKWPWWPWRR-NH2 (SEQ ID NO: 15) | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:16). An RFGF analogue (e.g., amino acid sequence AALLPVLLAAP (SEQ ID NO:17)) containing a hydrophobic MTS can also be a targeting moiety. The peptide moiety can be a "delivery" peptide, which can carry large polar molecules including peptides, oligonucleotides, and proteins across cell membranes. For example, sequences from the HIV Tat protein (GRKKRRQRRRPPQ (SEQ ID NO:18)) and the Drosophila Antennapedia protein (RQIKIWFQNRRMKWKK (SEQ ID NO:19)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an oligonucleotide agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an oligonucleotide agent (e.g., an oligonucleotide agent targeting an miRNA or pre-miRNA) to tumors of a variety of other tissues, including the lung, kidney, spleen, or liver (Aoki et al., Cancer Gene Therapy 8:783-787, 2001). Preferably, the RGD peptide will facilitate targeting of an oligonucleotide agent to the kidney. The RGD peptide can be linear or cyclic, and can be modified, e.g., glycosylated or methylated to facilitate targeting to specific tissues. For example, a glycosylated RGD peptide can deliver an oligonucleotide agent to a tumor cell expressing $\alpha_v\beta_3$ (Haubner et al., *Jour. Nucl. Med.*, 42:326-336, 2001).

Peptides that target markers enriched in proliferating cells can be used. E.g., RGD containing peptides and peptidomimetics can target cancer cells, in particular cells that exhibit an $I_v\theta_3$ integrin. Thus, one could use RGD peptides, cyclic peptides containing RGD, RGD peptides that include D-amino acids, as well as synthetic RGD mimics. In addition to RGD, one can use other moieties that target the $I_v$-$\theta_3$ integrin ligand. Generally, such ligands can be used to control proliferating cells and angiogeneis. Preferred conjugates of this type include an oligonucleotide agent that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., *Nucl. Acids Res.* 31:2717-2724, 2003).

In one embodiment, a targeting peptide tethered to a ligand-conjugated monomer can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, $H_2A$ peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number of helix destabilization residues will be utilized (e.g., proline, or cyclic monomeric units). The capping residue will be considered (for example Gly is an exemplary N-capping residue) and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

In some embodiments, the peptide can have a cationic and/or a hydrophobic moiety.

In some embodiments, the ligand can be any of the nucleobases described herein.

In some embodiments, the ligand can be a substituted amine, e.g. dimethylamino. In some embodiments, the substituted amine can be quaternized, e.g., by protonation or alkylation, rendering it cationic. In some embodiments, the substituted amine can be at the terminal position of a relatively hydrophobic tether, e.g., alkylene.

In some embodiments, the ligand can be one of the following triterpenes:

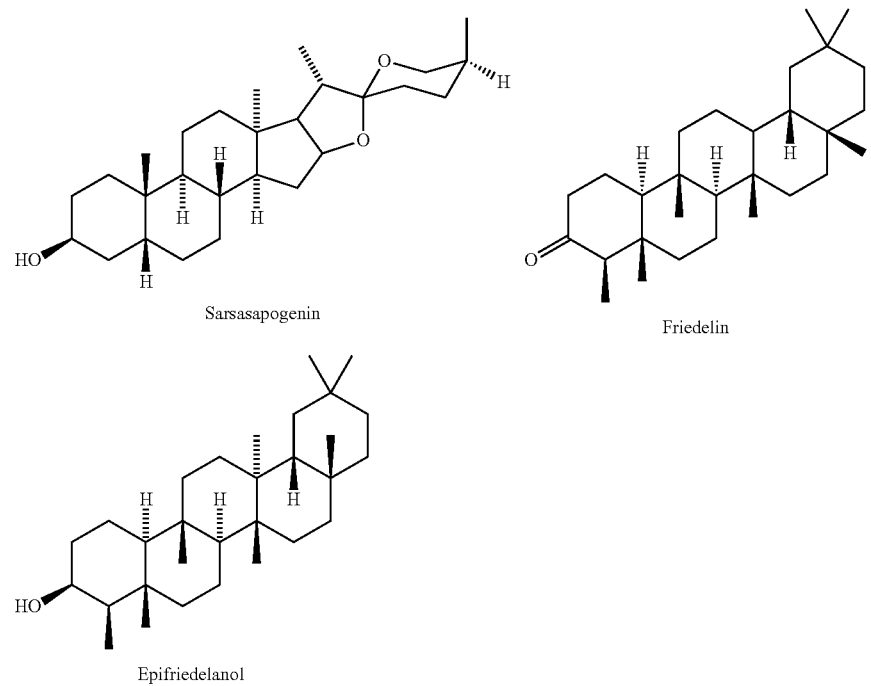

Sarsasapogenin

Friedelin

Epifriedelanol

-continued

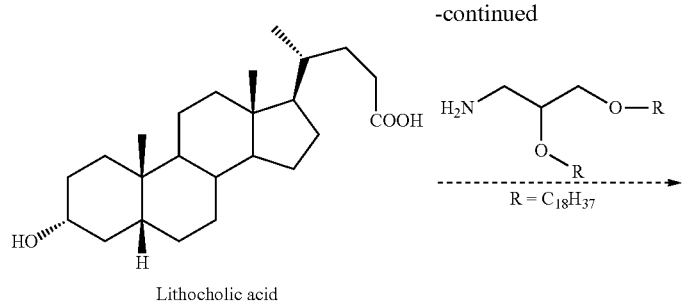
Lithocholic acid

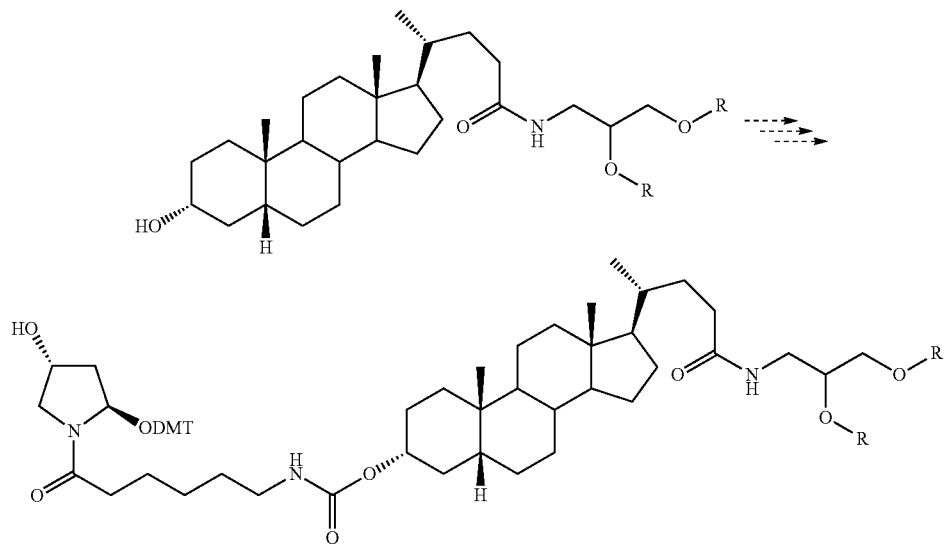

In some embodiments, the ligand can be substituted or unsubstituted cholesterol, or a stereoisomer thereof or one of the following steroids:

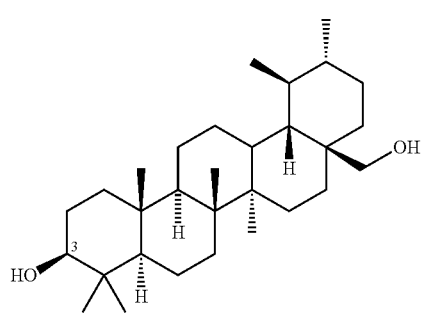
Uvaol

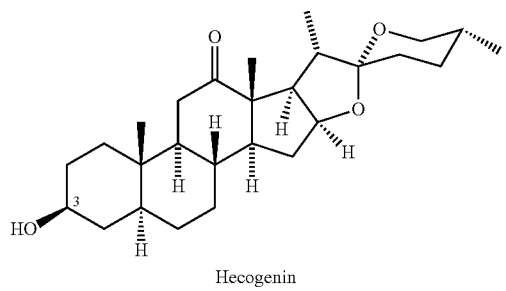
Hecogenin

-continued

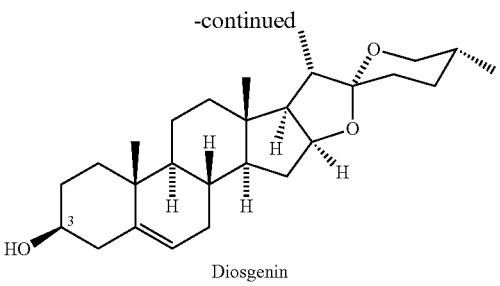
Diosgenin

In some embodiments, a tethered ligand can contain one or more atoms than the corresponding untethered or uncoupled ligand (e.g., one or more protons of a heteroatom-based functional group or an entire heteroatom-based functional group may be displaced from the uncoupled ligand during coupling of a ligand to a carrier or tether). For example, the proton of the 3-hydroxy group of cholesterol can be replaced by a tether (e.g., Chol-3-OH (uncoupled) and Chol-3-O-tether (coupled)) or the entire 3-hydroxy group of cholesterol can be replaced by a sulfur atom (e.g., Chol-3-OH (uncoupled) and Chol-3-S-tether (coupled, e.g., thiocholesterol)).

Methods for Making Oligonucleotide Agents

A listing of ribonucleosides containing the unusual bases described herein are described in "The RNA Modification Database" maintained by Pamela F. Crain, Jef Rozenski and James A. McCloskey; Departments of Medicinal Chemistry and Biochemistry, University of Utah, Salt Lake City, Utah 84112, USA.

The 5' silyl protecting group can be used in conjunction with acid labile orthoesters at the 2' position of ribonucleosides to synthesize oligonucleotides via phosphoramidite chemistry. Final deprotection conditions are known not to significantly degrade RNA products. Functional groups on the unusual and universal bases are blocked during oligonucleotide synthesis with protecting groups that are compatible with the operations being performed that are described herein. All syntheses can be conducted in any automated or manual synthesizer on large, medium, or small scale. The syntheses may also be carried out in multiple well plates or glass slides.

The 5'-O-silyl group can be removed via exposure to fluoride ions, which can include any source of fluoride ion, e.g., those salts containing fluoride ion paired with inorganic counterions e.g., cesium fluoride and potassium fluoride or those salts containing fluoride ion paired with an organic counterion, e.g., a tetraalkylammonium fluoride. A crown ether catalyst can be utilized in combination with the inorganic fluoride in the deprotection reaction. Preferred fluoride ion source are tetrabutylammonium fluoride or aminehydrofluorides (e.g., combining aqueous HF with triethylamine in a dipolar aprotic solvent, e.g., dimethylformamide).

The choice of protecting groups for use on the phosphite triesters and phosphotriesters can alter the stability of the triesters towards fluoride. Methyl protection of the phosphotriester or phosphitetriester can stabilize the linkage against fluoride ions and improve process yields.

Since ribonucleosides have a reactive 2' hydroxyl substituent, it can be desirable to protect the reactive 2' position in RNA with a protecting group that is compatible with a 5'-O-silyl protecting group, e.g. one stable to fluoride. Orthoesters meet this criterion and can be readily removed in a final acid deprotection step that can result in minimal RNA degradation.

Tetrazole catalysts can be used in the standard phosphoramidite coupling reaction. Preferred catalysts include e.g. tetrazole, S-ethyl-tetrazole, p-nitrophenyltetrazole.

The general process is as follows. Nucleosides are suitably protected and functionalized for use in solid-phase or solution-phase synthesis of RNA oligonucleotides. The 2'-hydroxyl group in a ribonucleotide can be modified using a tris orthoester reagent. The 2'-hydroxyl can be modified to yield a 2'-O-orthoester nucleoside by reacting the ribonucleoside with the tris orthoester reagent in the presence of an acidic catalyst, e.g., pyridinium p-toluene sulfonate. This reaction is known to those skilled in the art. The product can then be subjected to further protecting group reactions (e.g., 5'-O-silylation) and functionalizations (e.g., 3'-O-phosphitylation) to produce a desired reagent (e.g., nucleoside phosphoramidite) for incorporation within an oligonucleotide or polymer by reactions known to those skilled in the art.

Preferred orthoesters include those comprising ethylene glycol ligands which are protected with acyl or ester protecting groups. Specifically, the preferred acyl group is acetyl. The nucleoside reagents may then be used by those skilled in the art to synthesize RNA oligonucleotides on commercially available synthesizer instruments, e.g., Gene Assembler Plus (Pharmacia), 380B (Applied Biosystems). Following synthesis (either solution-phase or solid-phase) of an oligonucleotide or polymer, the product can be subjected to one or more reactions using non-acidic reagents. One of these reactions may be strong basic conditions, for example, 40% methylamine in water for 10 minutes at 55° C., which will remove the acyl protecting groups from the ethylene glycol ligands but leave the orthoester moiety attached. The resultant orthoester may be left attached when the polymer or oligonucleotide is used in subsequent applications, or it may be removed in a final mildly-acidic reaction, for example, 10 minutes at 55° C. in 50 mM acetic acid, pH 3.0, followed by addition of equal volume of 150 mM TRIS buffer for 10 minutes at 55° C.

Universal bases are described in "Survey and Summary: The Applications of Universal DNA base analogues" Loakes, D., *Nucleic Acid Research* 2001, 29, 2437, which is incorporated by reference in its entirety. Specific examples are described in the following: Liu, D.; Moran, S.; Kool, E. T. *Chem. Biol.*, 1997, 4, 919-926; Morales, J. C.; Kool, E. T. *Biochemistry*, 2000, 39, 2626-2632; Matray, T, J.; Kool, E. T. *J. Am. Chem. Soc.*, 1998, 120, 6191-6192; Moran, S. Ren, R. X.-F.; Rumney IV, S.; Kool, E. T. *J. Am. Chem. Soc.*, 1997, 119, 2056-2057; Guckian, K. M.; Morales, J. C.; Kool, E. T. *J. Org. Chem.*, 1998, 63, 9652-9656; Berger, M.; Wu. Y.; Ogawa, A. K.; McMinn, D. L.; Schultz, P. G.; Romesberg, F. E. *Nucleic Acids Res.*, 2000, 28, 2911-2914; Ogawa, A. K.; Wu, Y.; McMinn, D. L.; Liu, J.; Schultz, P. G.; Romesberg, F. E. *J. Am. Chem. Soc.*, 2000, 122, 3274-3287; Ogawa, A. K.; Wu. Y.; Berger, M.; Schultz, P. G.; Romesberg, F. E. *J. Am. Chem. Soc.*, 2000, 122, 8803-8804; Tae, E. L.; Wu, Y.; Xia, G.; Schultz, P. G.; Romesberg, F. E. *J. Am. Chem. Soc.*, 2001, 123, 7439-7440; Wu, Y.; Ogawa, A. K.; Berger, M.; McMinn, D. L.; Schultz, P. G.; Romesberg, F. E. *J. Am. Chem. Soc.*, 2000, 122, 7621-7632; McMinn, D. L.; Ogawa. A. K.; Wu, Y.; Liu, J.; Schultz, P. G.; Romesberg, F. E. *J. Am. Chem. Soc.*, 1999, 121, 11585-11586; Brotschi, C.; Haberli, A.; Leumann, C, J. *Angew. Chem. Int. Ed.*, 2001, 40, 3012-3014; Weizman, H.; Tor, Y. *J. Am. Chem. Soc.*, 2001, 123, 3375-3376; Lan, T.; McLaughlin, L. W. *J. Am. Chem. Soc.*, 2000, 122, 6512-13.

As discussed above, the monomers and methods described herein can be used in the preparation of modified RNA molecules, or polymeric molecules comprising any combination of monomer compounds described herein and/or natural or modified ribonucleotides in which one or more subunits contain an unusual or universal base. Modified RNA molecules include e.g. those molecules containing a chemically or stereochemically modified nucleoside (e.g., having one or more backbone modifications, e.g., phosphorothioate or P-alkyl; having one or more sugar modifications, e.g., 2'-OCH$_3$ or 2'-F; and/or having one or more base modifications, e.g., 5-alkylamino or 5-allylamino) or a nucleoside surrogate.

Coupling of 5'-hydroxyl groups with phosphoramidites forms phosphite ester intermediates, which in turn are oxidized e.g., with iodine, to the phosphate diester. Alternatively, the phosphites may be treated with, e.g., sulfur, selenium, amino, and boron reagents to form modified phosphate backbones. Linkages between the monomers described herein and a nucleoside or oligonucleotide chain can also be treated with iodine, sulfur, selenium, amino, and boron reagents to form unmodified and modified phosphate backbones respectively. Similarly, the monomers described herein may be coupled with nucleosides or oligonucleotides containing any of the modifications or nucleoside surrogates described herein.

Figure 4:
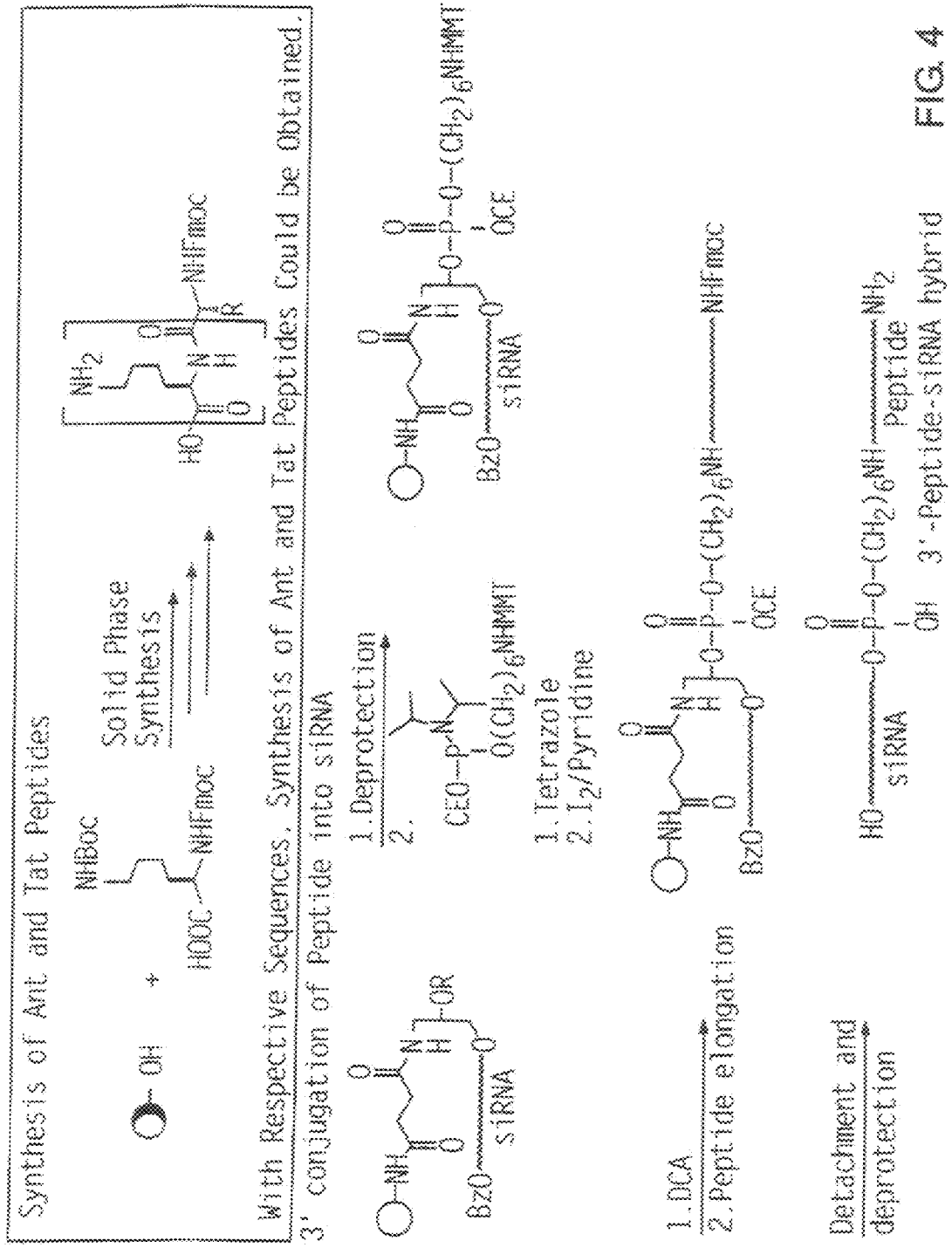
FIG. 4 is a general reaction scheme for 3' conjugation of peptide into an oligonucleotide agent.
Figure 5:
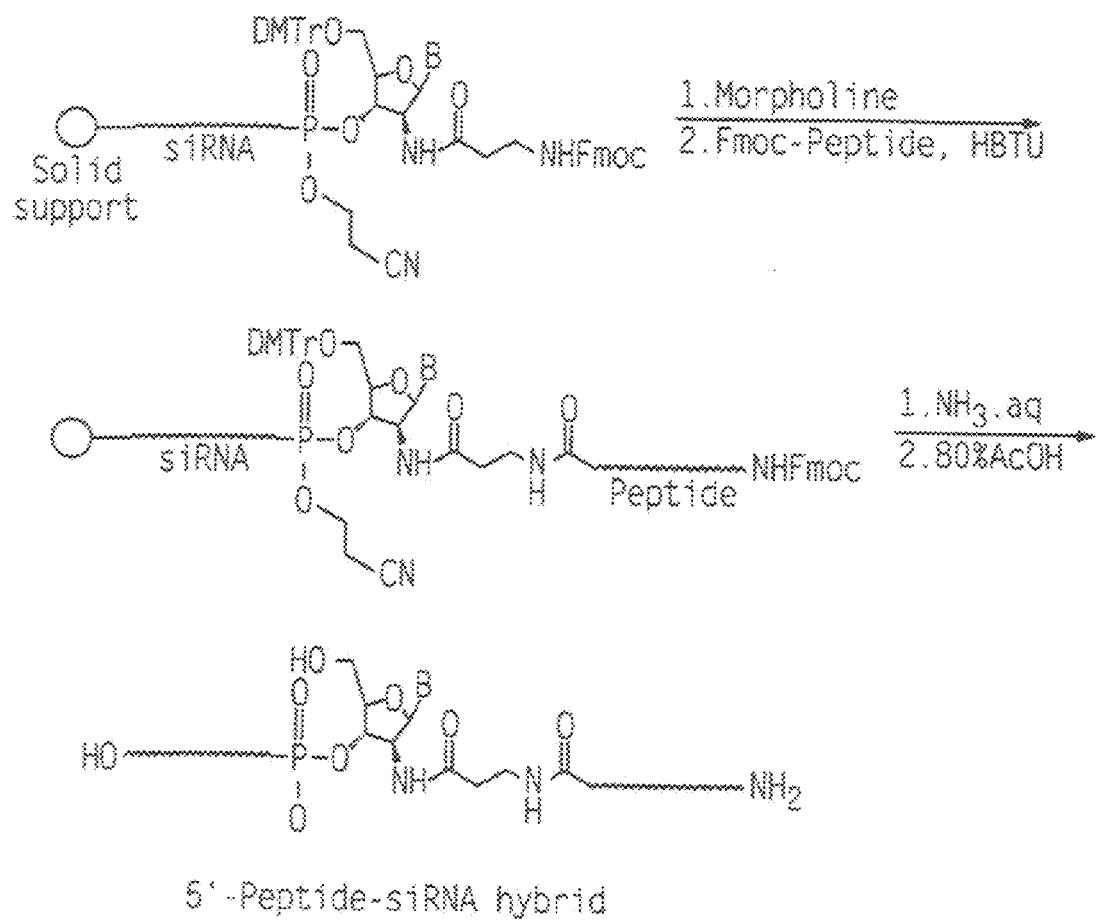
FIG. 5 is a general reaction scheme for 5' conjugation of peptide into an oligonucleotide agent.

The synthesis and purification of oligonucleotide peptide conjugates can be performed by established methods. See, for example, Trufert et al., Tetrahedron, 52:3005, 1996; and Manoharan, "Oligonucleotide Conjugates in Antisense Technology," in *Antisense Drug Technology*, ed. S. T. Crooke, Marcel Dekker, Inc., 2001. Exemplary methods are shown in FIGS. 4 and 5.

Figure 6:
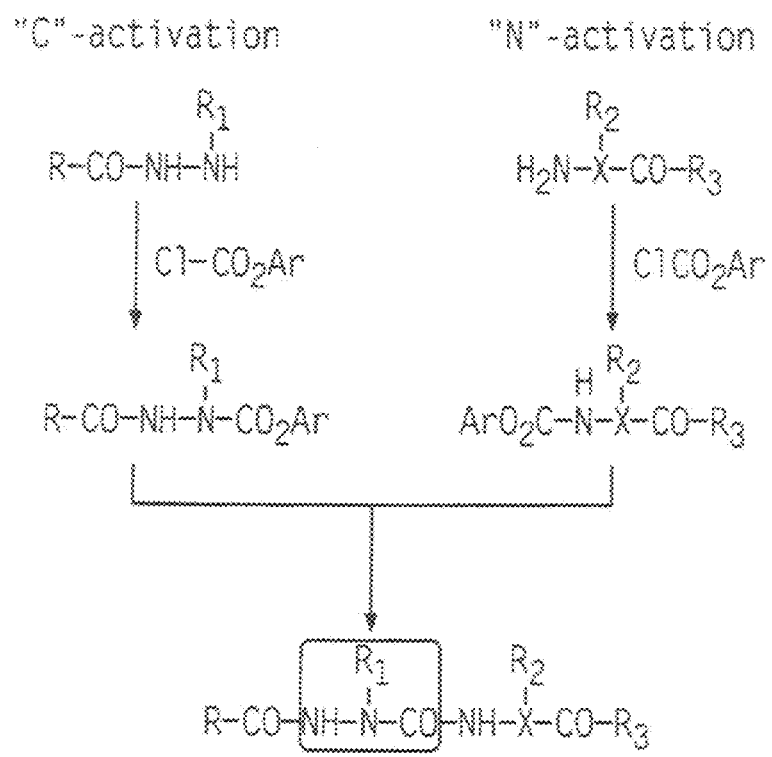
FIG. 6 is a general reaction scheme for the synthesis of aza-peptides.

In one embodiment of the invention, a peptidomimetic can be modified to create a constrained peptide that adopts a distinct and specific preferred conformation, which can increase the potency and selectivity of the peptide. For example, the constrained peptide can be an azapeptide (Gante, *Synthesis,* 1989, 405-413). An azapeptide is synthesized by replacing the α-carbon of an amino acid with a nitrogen atom without changing the structure of the amino acid side chain. For example, the azapeptide can be synthesized by using hydrazine in traditional peptide synthesis coupling methods, such as by reacting hydrazine with a "carbonyl donor," e.g., phenylchloroformate. A general azapeptide synthesis is shown in FIG. 6.

Figure 7:
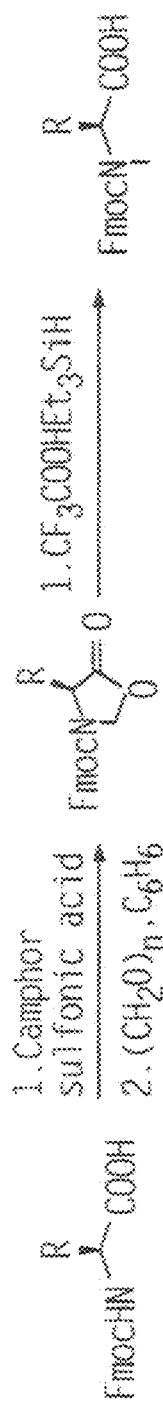
FIG. 7 is a general reaction scheme for the synthesis of N-methyl amino acids and peptides.
Figure 7:
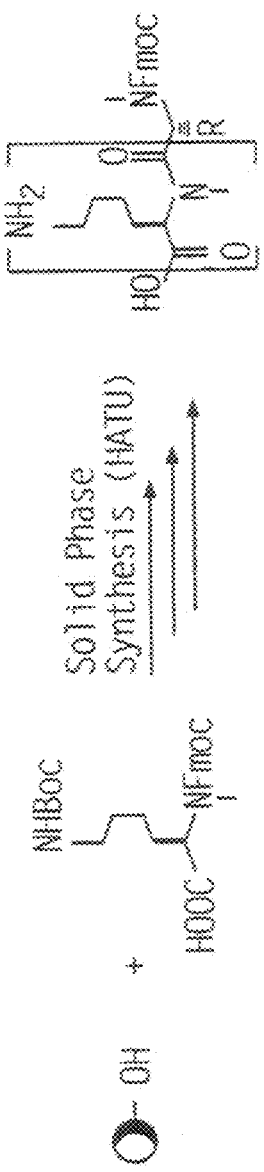

In one embodiment of the invention, a peptide or peptidomimetic (e.g., a peptide or peptidomimetic tethered to an ligand-conjugated monomer) can be an N-methyl peptide. N-methyl peptides are composed of N-methyl amino acids, which provide an additional methyl group in the peptide backbone, thereby potentially providing additional means of resistance to proteolytic cleavage. N-methyl peptides can by synthesized by methods known in the art (see, for example, Lindgren et al., Trends Pharmacol. Sci. 21:99, 2000; *Cell Penetrating Peptides: Processes and Applications*, Langel, ed., CRC Press, Boca Raton, Fla., 2002; Fische et al., Bioconjugate. Chem. 12: 825, 2001; Wander et al., J. Am. Chem. Soc., 124:13382, 2002). For example, an Ant or Tat peptide can be an N-methyl peptide. An exemplary synthesis is shown in FIG. 7.

Figure 8:
FIG. 8 is a general reaction scheme for the synthesis of β-methyl amino acids and Ant and Tat peptides.
Figure 8:
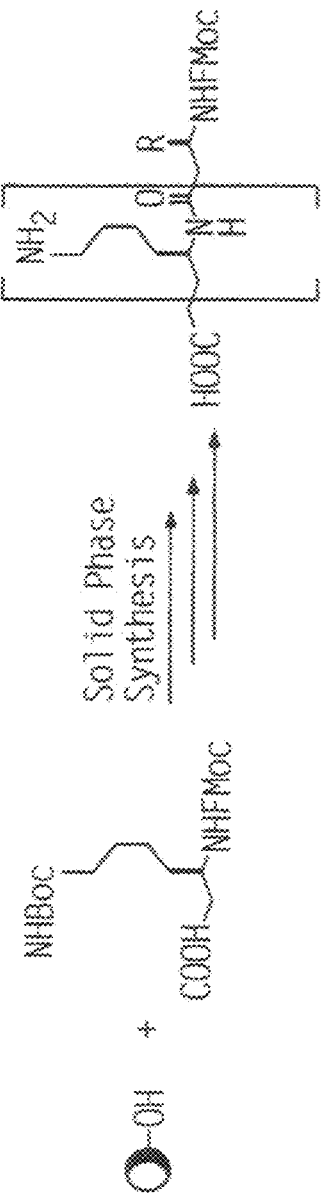

In one embodiment of the invention, a peptide or peptidomimetic (e.g., a peptide or peptidomimetic tethered to a ligand-conjugated monomer) can be a β-peptide. β-peptides form stable secondary structures such as helices, pleated sheets, turns and hairpins in solutions. Their cyclic derivatives can fold into nanotubes in the solid state. β-peptides are resistant to degradation by proteolytic enzymes. β-peptides can be synthesized by methods known in the art. For example, an Ant or Tat peptide can be a β-peptide. An exemplary synthesis is shown in FIG. 8.

Figure 9:
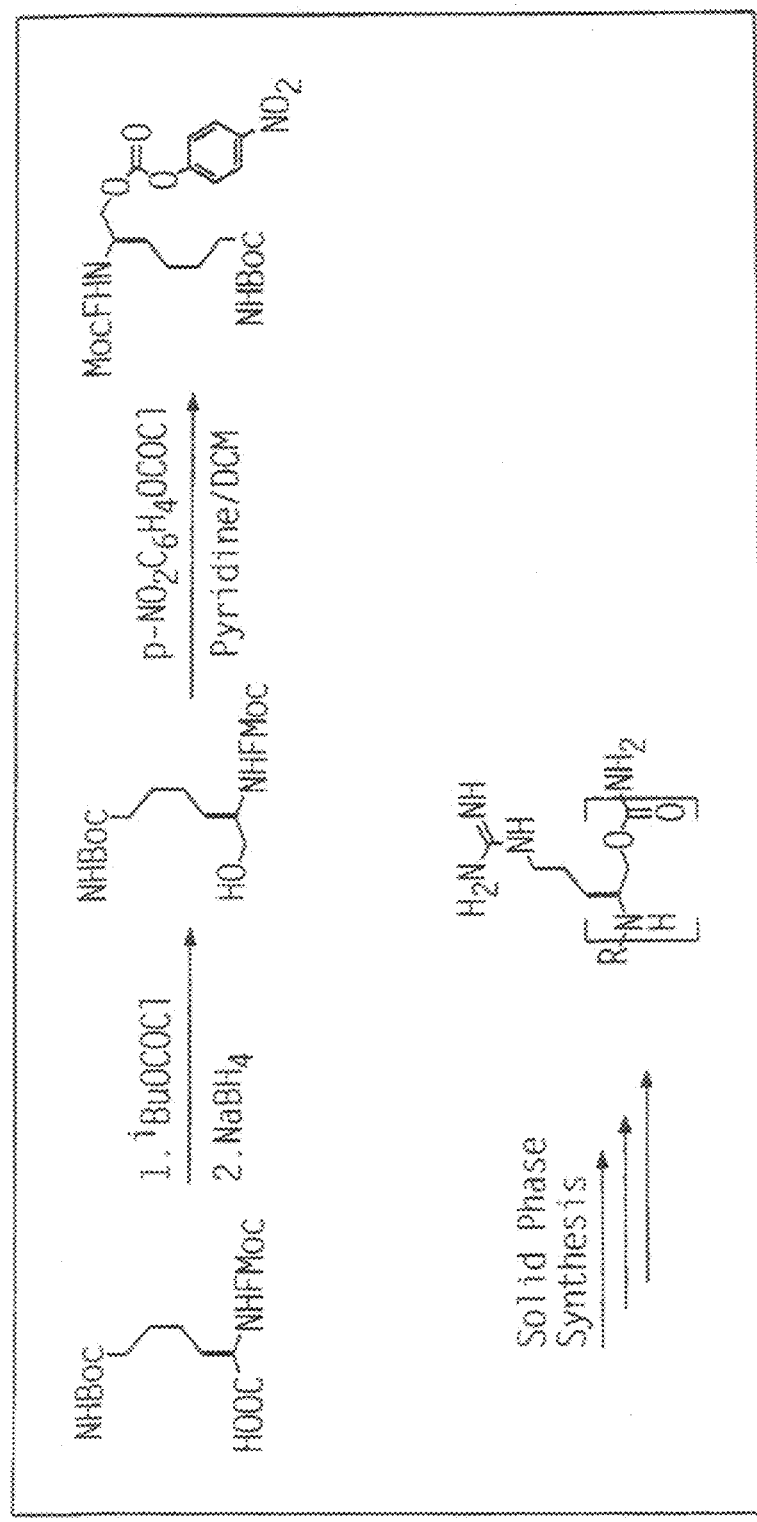
FIG. 9 is a general reaction scheme for the synthesis of Ant and Tat oligocarbamates.

In one embodiment of the invention, a peptide or peptidomimetic (e.g., a peptide or peptidomimetic tethered to a ligand-conjugated monomer) can be a oligocarbamate. Oligocarbamate peptides are internalized into a cell by a transport pathway facilitated by carbamate transporters. For example, an Ant or Tat peptide can be an oligocarbamate. An exemplary synthesis is shown in FIG. 9.

Figure 10:
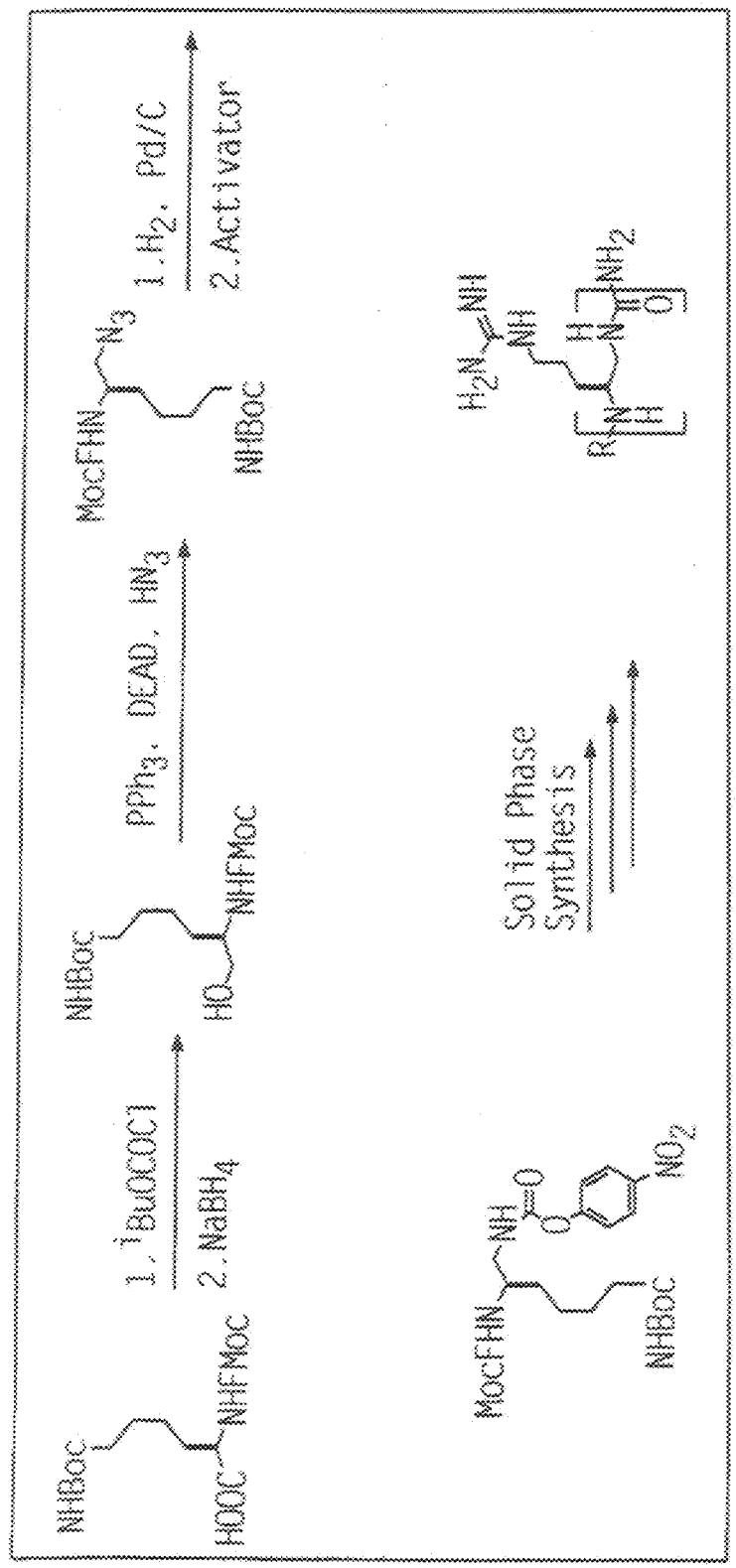
FIG. 10 is a general reaction scheme for the synthesis of Ant and Tat oligoureas.

In one embodiment of the invention, a peptide or peptidomimetic (e.g., a peptide or peptidomimetic tethered to a ligand-conjugated monomer) can be an oligourea conjugate (or an oligothiourea conjugate), in which the amide bond of a peptidomimetic is replaced with a urea moiety. Replacement of the amide bond provides increased resistance to degradation by proteolytic enzymes, e.g., proteolytic enzymes in the gastrointestinal tract. In one embodiment, an oligourea conjugate is tethered to an oligonucleotide agent for use in oral delivery. The backbone in each repeating unit of an oligourea peptidomimetic can be extended by one carbon atom in comparison with the natural amino acid. The single carbon atom extension can increase peptide stability and lipophilicity, for example. An oligourea peptide can therefore be advantageous when an oligonucleotide agent is directed for passage through a bacterial cell wall, or when an oligonucleotide agent must traverse the blood-brain barrier, such as for the treatment of a neurological disorder. In one embodiment, a hydrogen bonding unit is conjugated to the oligourea peptide, such as to create an increased affinity with a receptor. For example, an Ant or Tat peptide can be an oligourea conjugate (or an oligothiourea conjugate). An exemplary synthesis is shown in FIG. 10.

The siRNA peptide conjugates of the invention can be affiliated with, e.g., tethered to, ligand-conjugated monomers occurring at various positions on an oligonucleotide agent. For example, a peptide can be terminally conjugated, on either the sense or the antisense strand, or a peptide can be bisconjugated (one peptide tethered to each end, one conjugated to the sense strand, and one conjugated to the antisense strand). In another option, the peptide can be internally conjugated, such as in the loop of a short hairpin oligonucleotide agent. In yet another option, the peptide can be affiliated with a complex, such as a peptide-carrier complex.

A peptide-carrier complex consists of at least a carrier molecule, which can encapsulate one or more oligonucleotide agents (such as for delivery to a biological system and/or a cell), and a peptide moiety tethered to the outside of the carrier molecule, such as for targeting the carrier complex to a particular tissue or cell type. A carrier complex can carry additional targeting molecules on the exterior of the complex, or fusogenic agents to aid in cell delivery. The one or more oligonucleotide agents encapsulated within the carrier can be conjugated to lipophilic molecules, which can aid in the delivery of the agents to the interior of the carrier.

Figure 11:
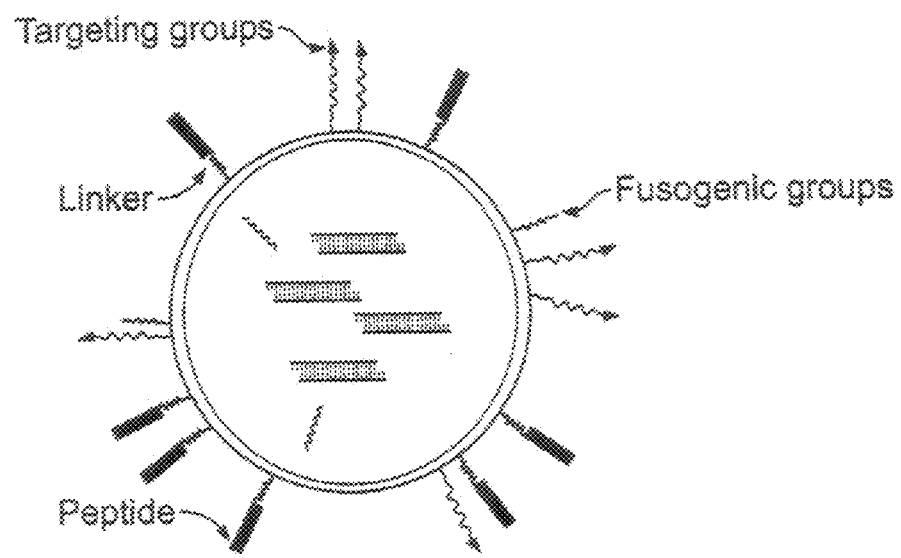
FIG. 11 is a schematic representation of peptide carriers.
Figure 11:
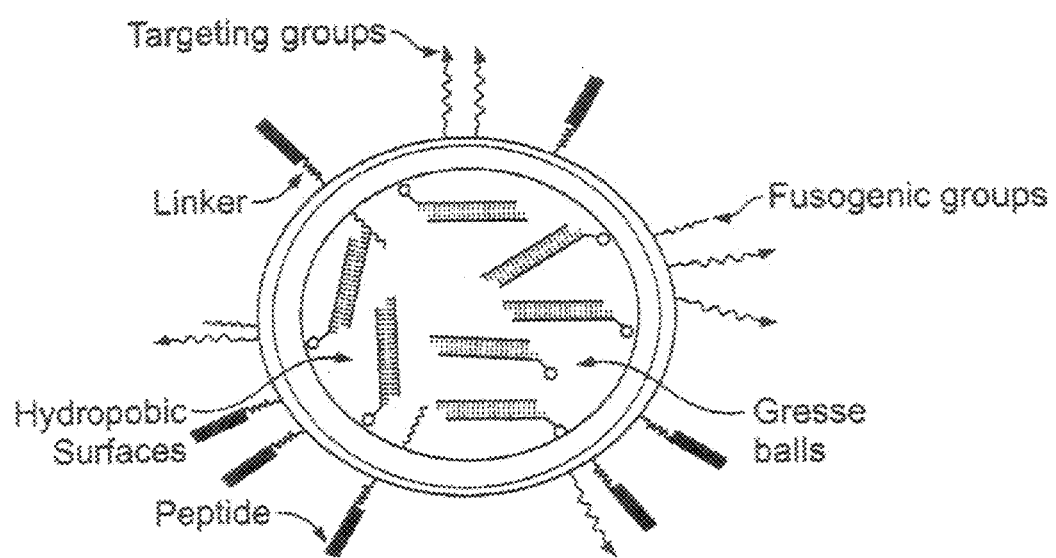
Figure 12:
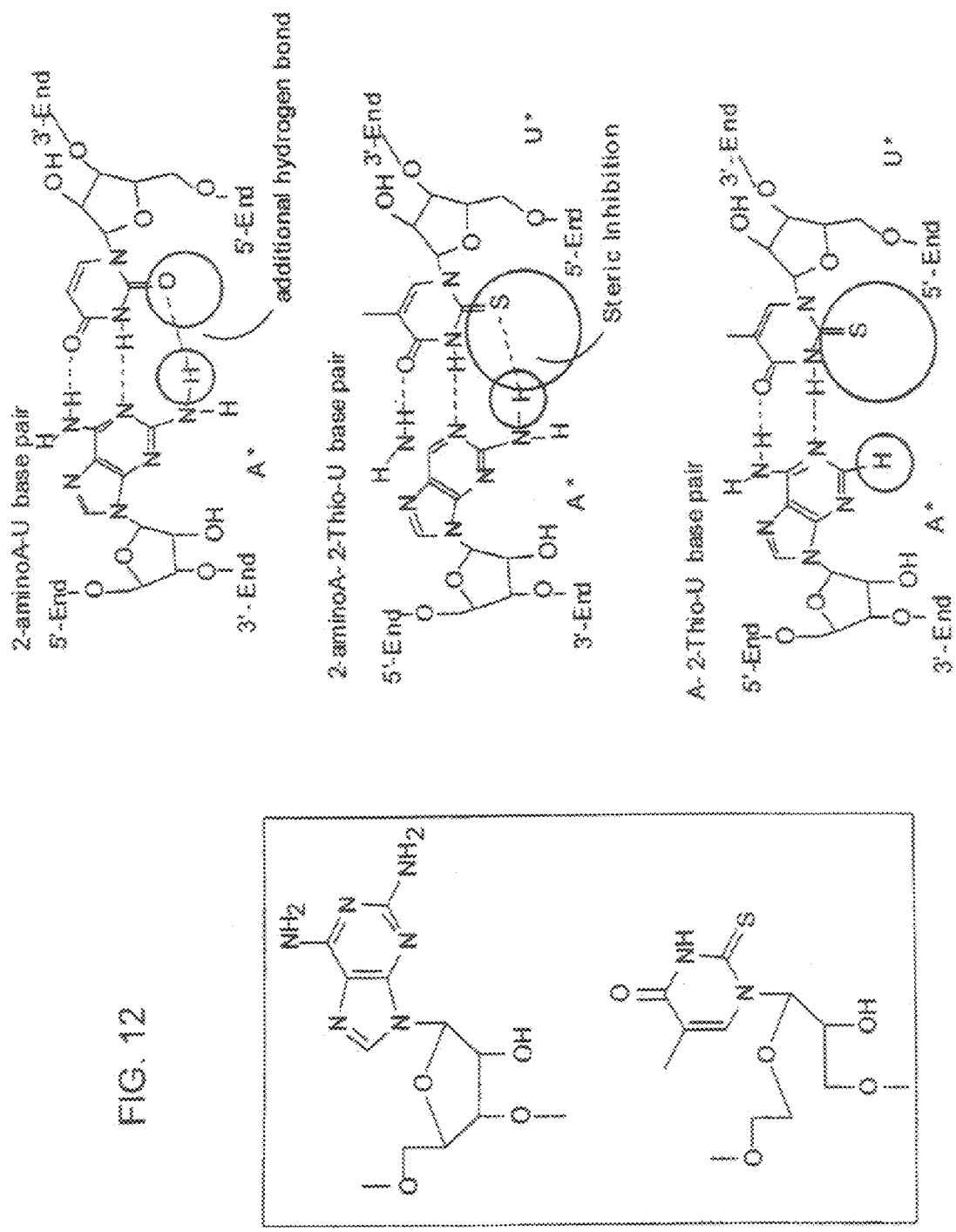
FIG. 12 is a list of representative cholesterol-tethered SRMS monomers.
Figure 13:
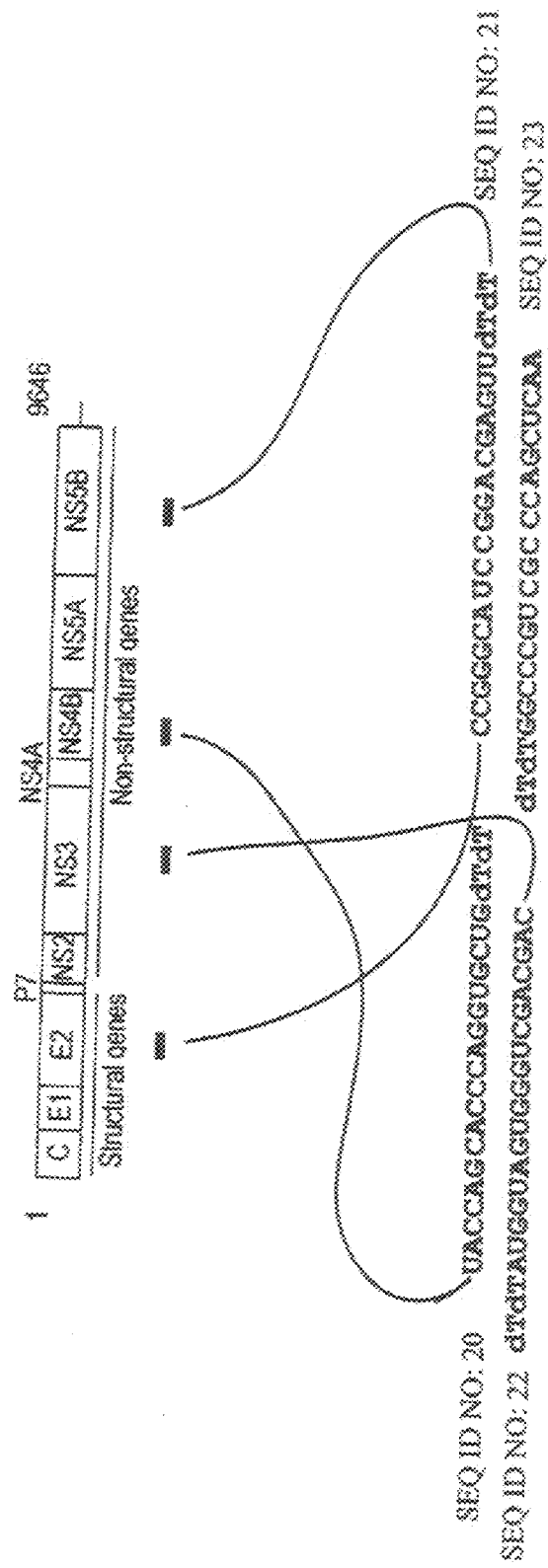
FIG. 13 shows LCMS data for a 3' cholesterol conjugate after PAGE purification.

A carrier molecule or structure can be, for example, a micelle, a liposome (e.g., a cationic liposome), a nanoparticle, a microsphere, or a biodegradable polymer. A peptide moiety can be tethered to the carrier molecule by a variety of linkages, such as a disulfide linkage, an acid labile linkage, a peptide-based linkage, an oxyamino linkage or a hydrazine linkage. For example, a peptide-based linkage can be a GFLG peptide. Certain linkages will have particular advantages, and the advantages (or disadvantages) can be considered depending on the tissue target or intended use. For example, peptide based linkages are stable in the blood stream but are susceptible to enzymatic cleavage in the lysosomes. A schematic of preferred carriers is shown in FIG. 11.

The protected monomer compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Other synthetic chemistry transformations, protecting groups (e.g., for hydroxyl, amino, etc. present on the bases) and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The protected monomer compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds described herein can also contain linkages (e.g., carbon-carbon bonds, carbon-nitrogen bonds, e.g., amides) or substituents that can restrict bond rotation, e.g. restriction resulting from the presence of a ring or double bond. Accordingly, all cis/trans, E/Z isomers, and rotational isomers (rotamers) are expressly included herein. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Representative ligand-conjugated monomers and typical syntheses for preparing ligand-conjugated monomers and related compounds described herein are provided below. As discussed elsewhere, protecting groups for ligand-conjugated monomer hydroxyl groups, e.g., OFG$^1$, include but are not limited to the dimethoxytrityl group (DMT). For example, it can be desirable in some embodiments to use silicon-based protecting groups as a protecting group for OFG$^1$. Silicon-based protecting groups can therefore be used in conjunction with or in place of the DMT group as necessary or desired. Thus, the ligand-conjugated monomers and syntheses delineated below, which feature the DMT protecting group as a protecting group for OFG$^1$, is not to be construed as limiting in any way to the invention.

Synthesis of Pyrroline Carrier

Scheme 1. Synthesis of cis-(-(3S,4R)-pyrrolidine diol

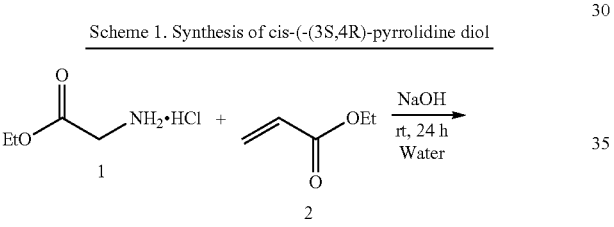

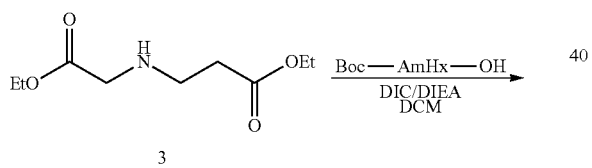

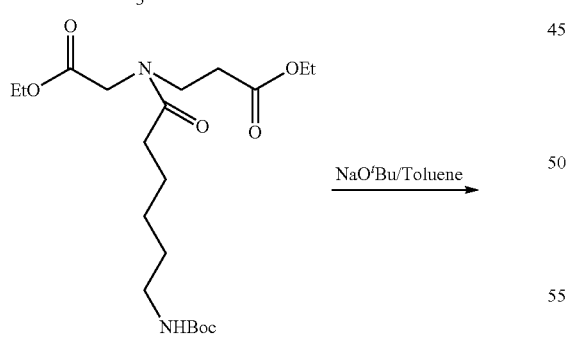

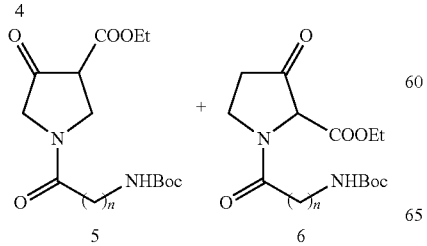

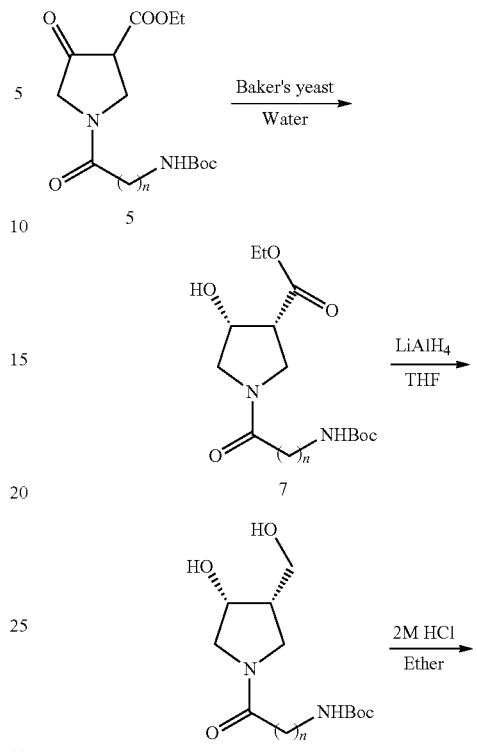

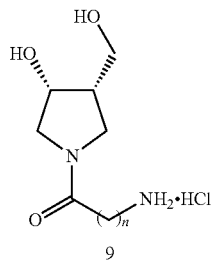

Scheme 2. Synthesis of cis-(-(2R, 3S)-pyrrolidine diol

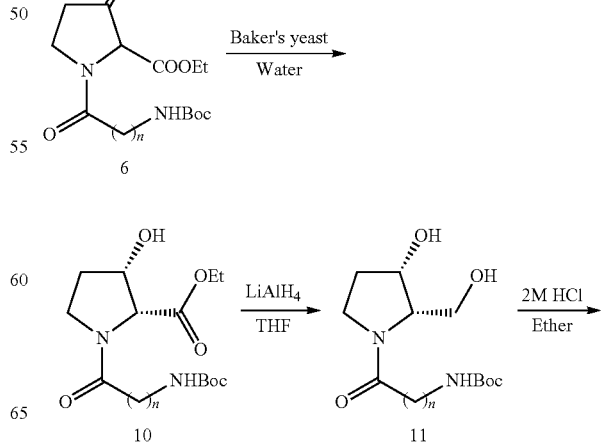

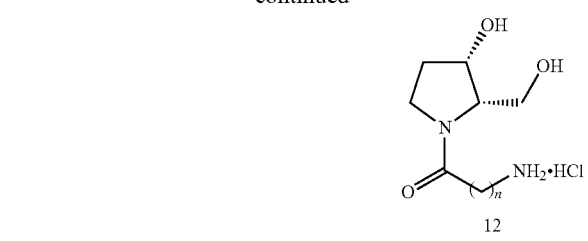
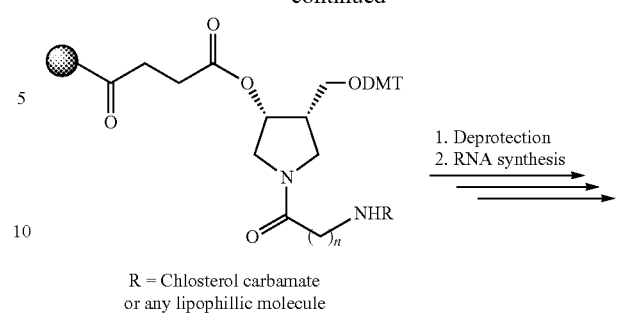
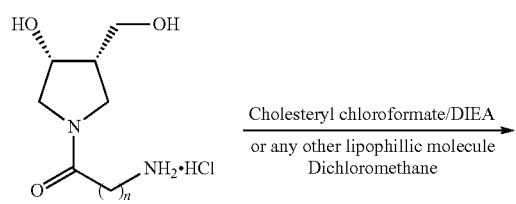
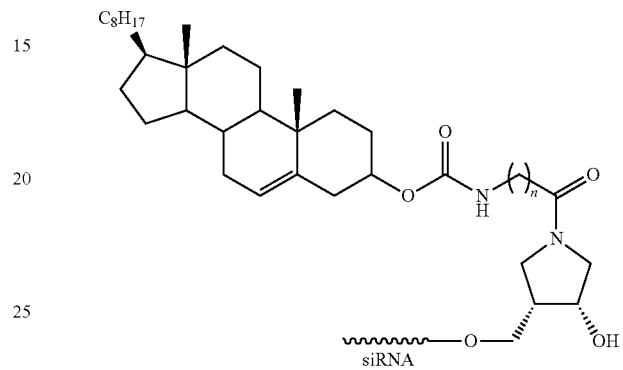
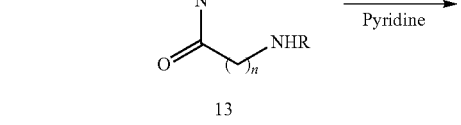
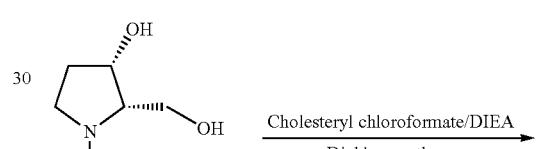
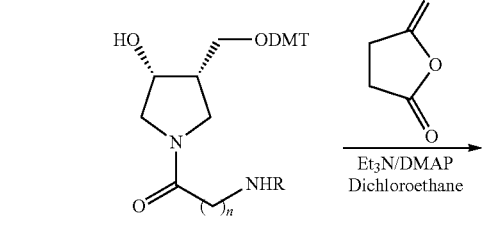
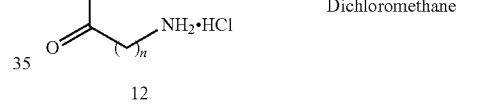
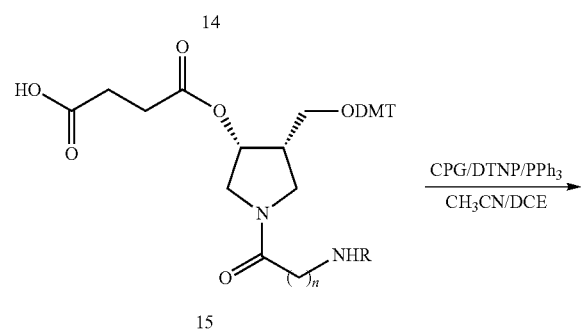
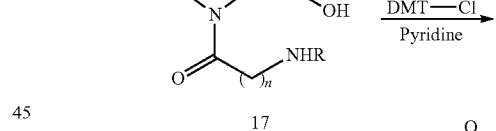
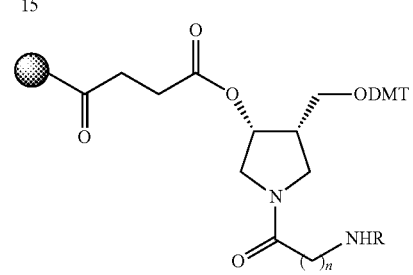
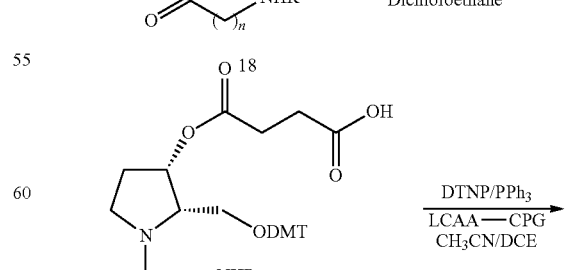

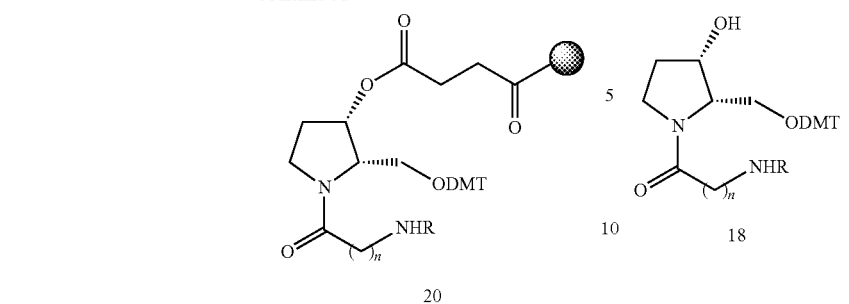
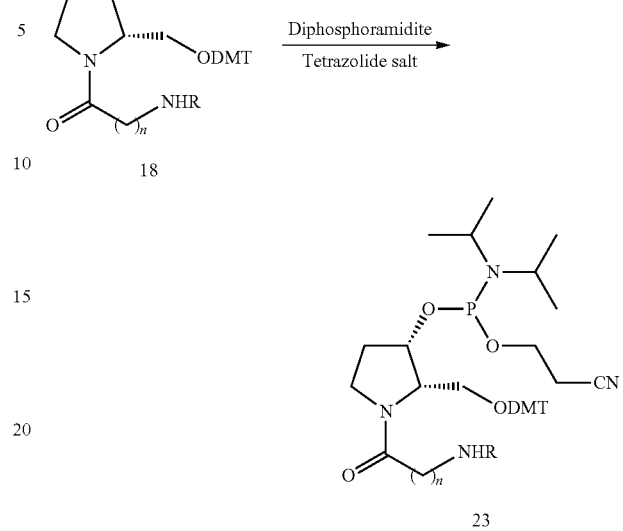
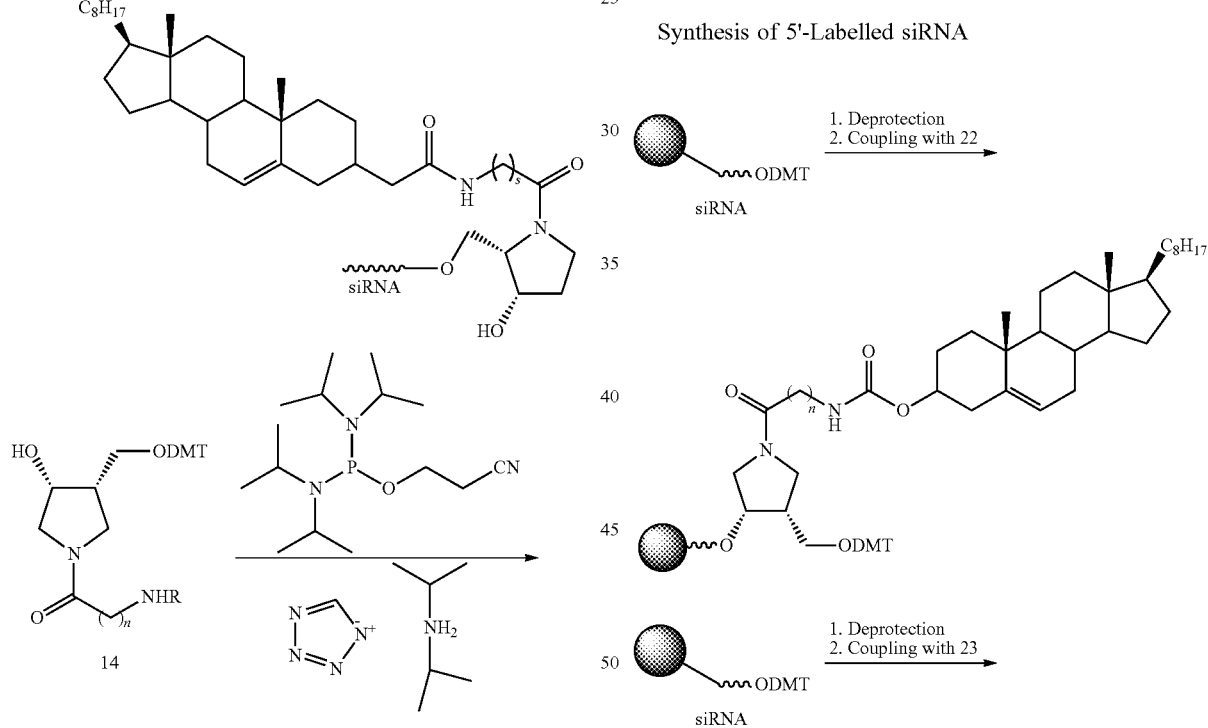
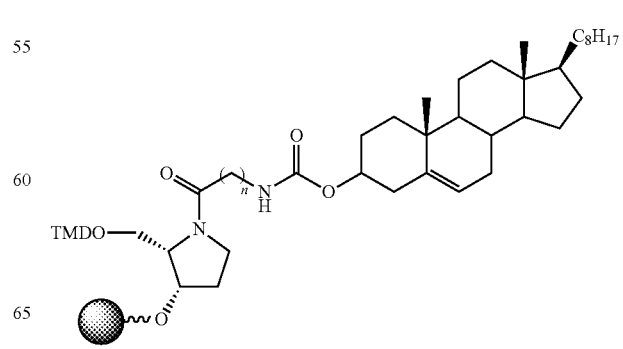
Synthesis of 5'-Labelled siRNA

-continued
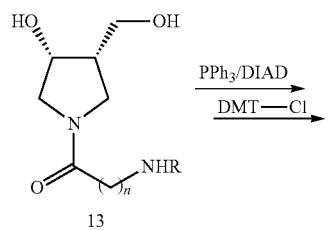
13
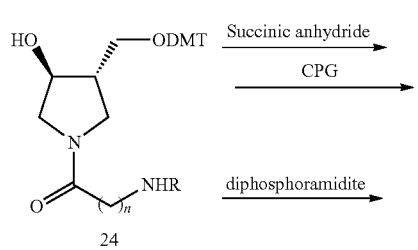
24
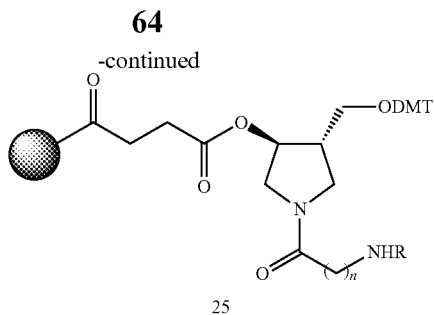
25
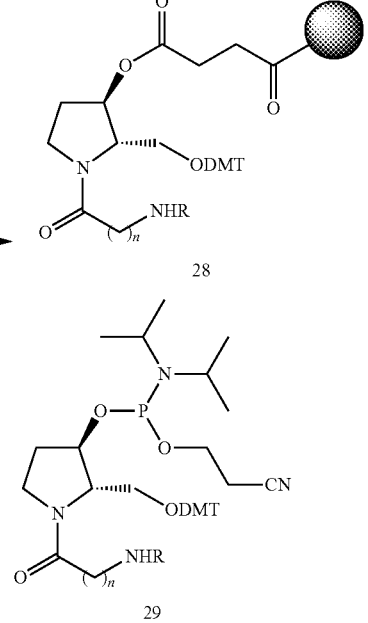
26
25 & 26 can be used for 3',5'-conjugation respectively.
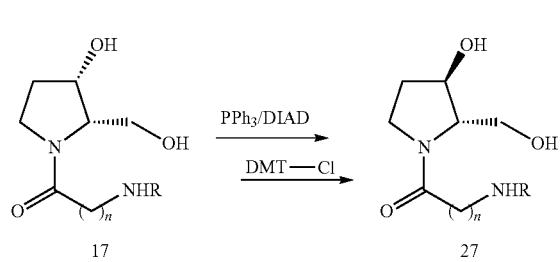
17     27
28
29

Synthesis of Phthalimido Derivative
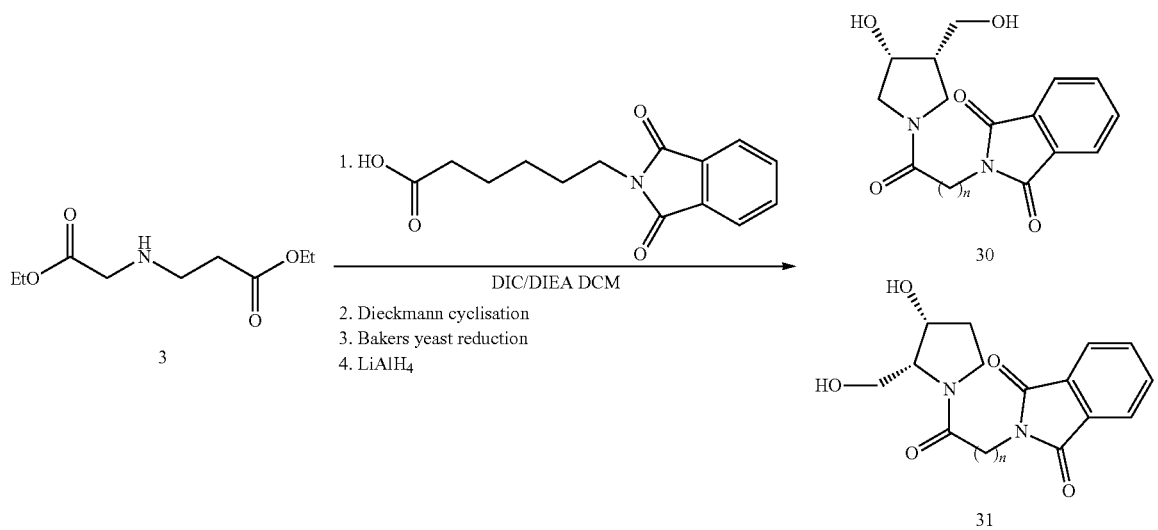
30 and 31 can be converted to similar derivatives as shown in schemes 2-4 for 3' and 5' conjugation of siRNA
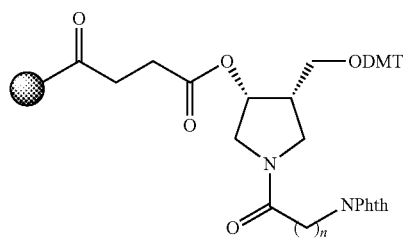
32
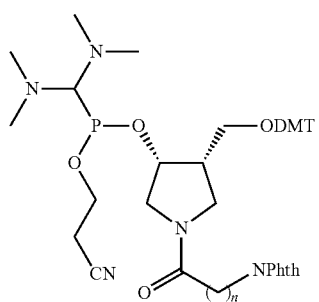
33
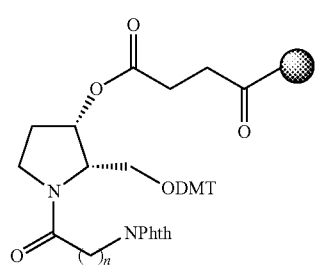
34
-continued
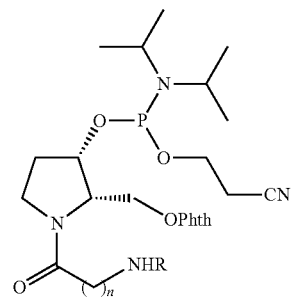
35
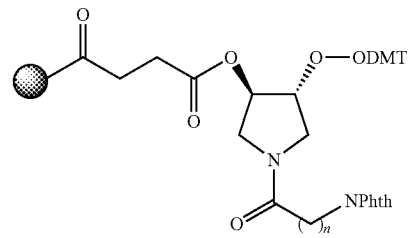
36
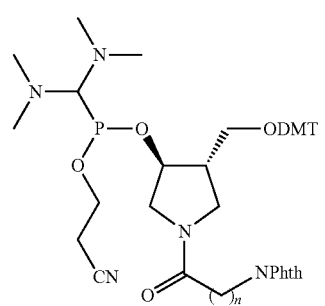
37

67
-continued
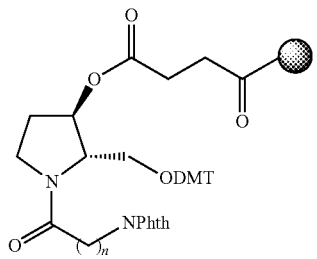
38
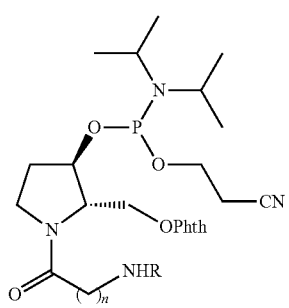
39
Synthesis of Thalimido Derivative
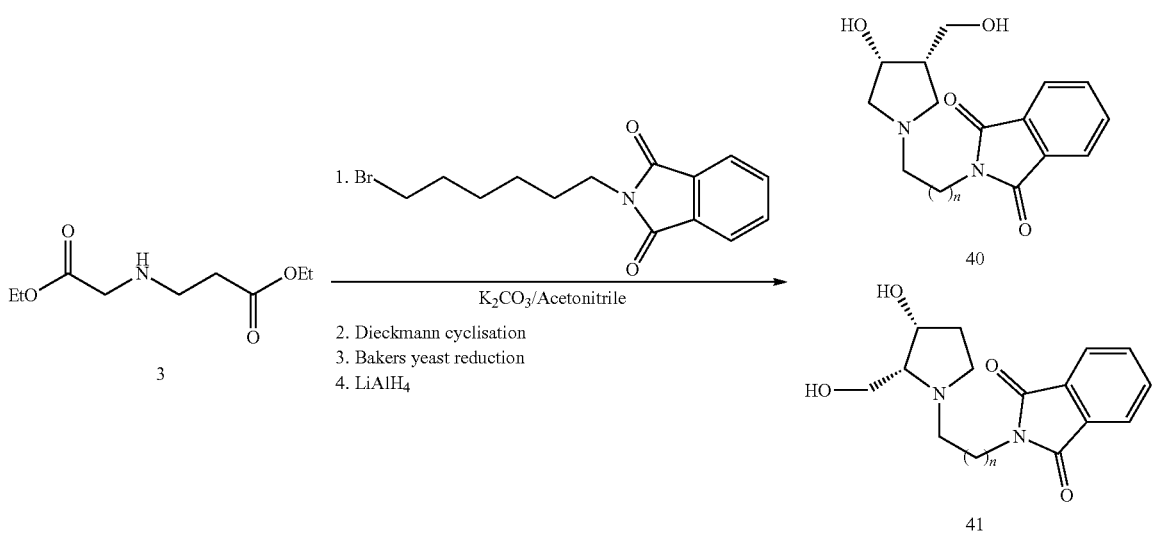
40 and 41 can be converted to similar derivatives as shown in schemes 2-4 for 3' and 5' conjugation of siRNA
68
-continued
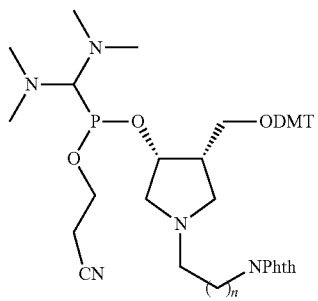
43
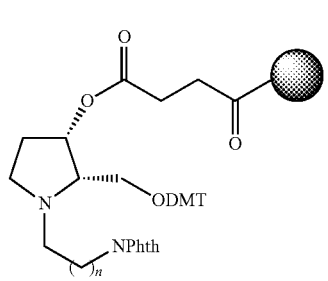
44
-continued
45

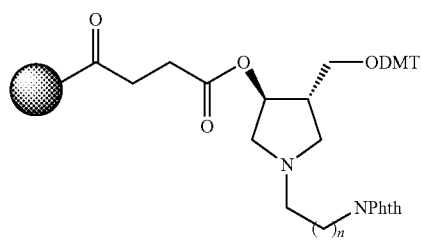
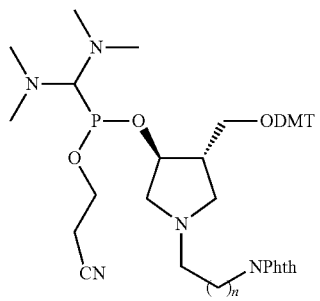
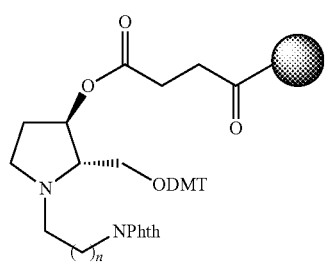
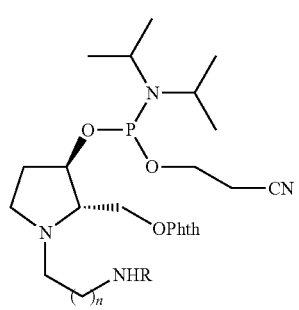
Synthesis of N-Alkyl Pyrroline Derivatives
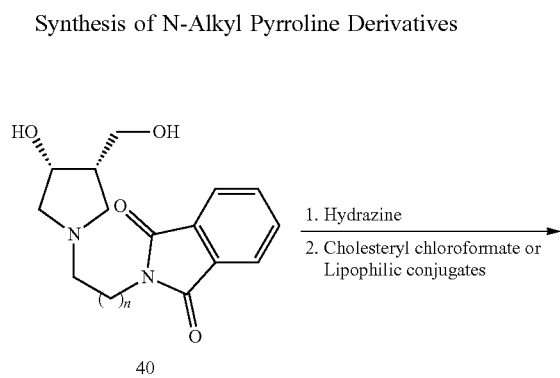
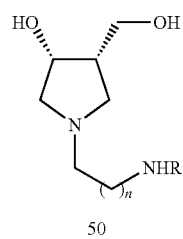
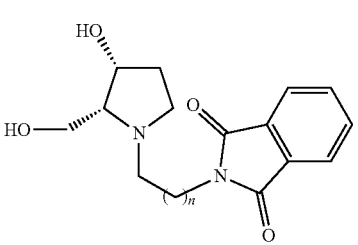
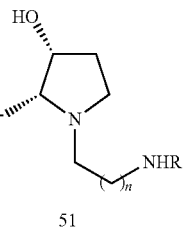
Intermediates 50 and 51 can be converted to analogs which could be conjugated with siRNA using similar reactions
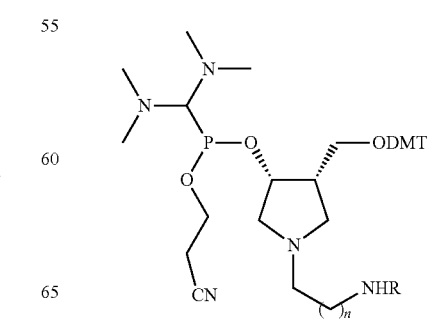

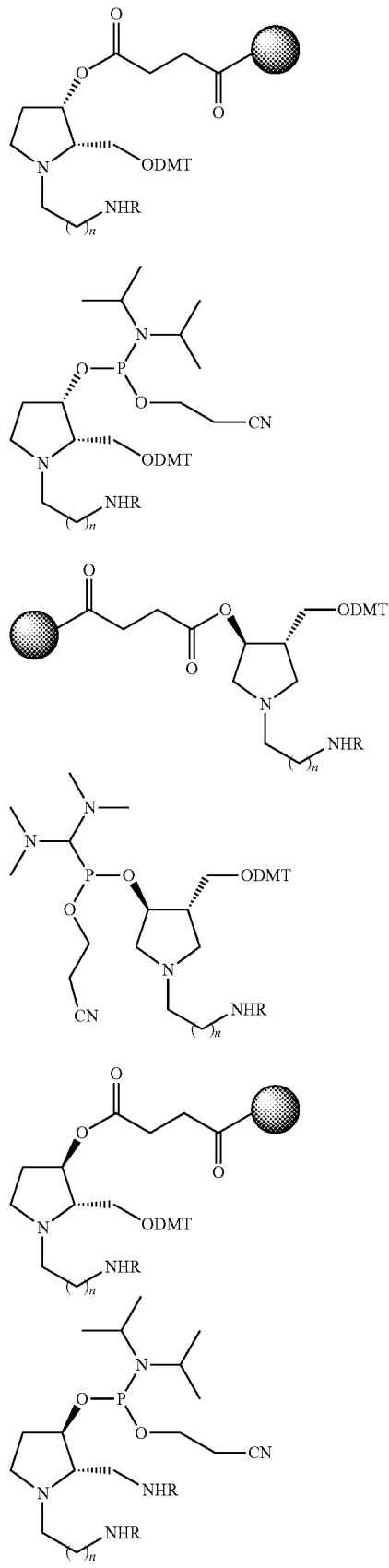
Piperidine Series Ligands:
Similar to Pyrroline Series Piperidine Series can be Synthesised
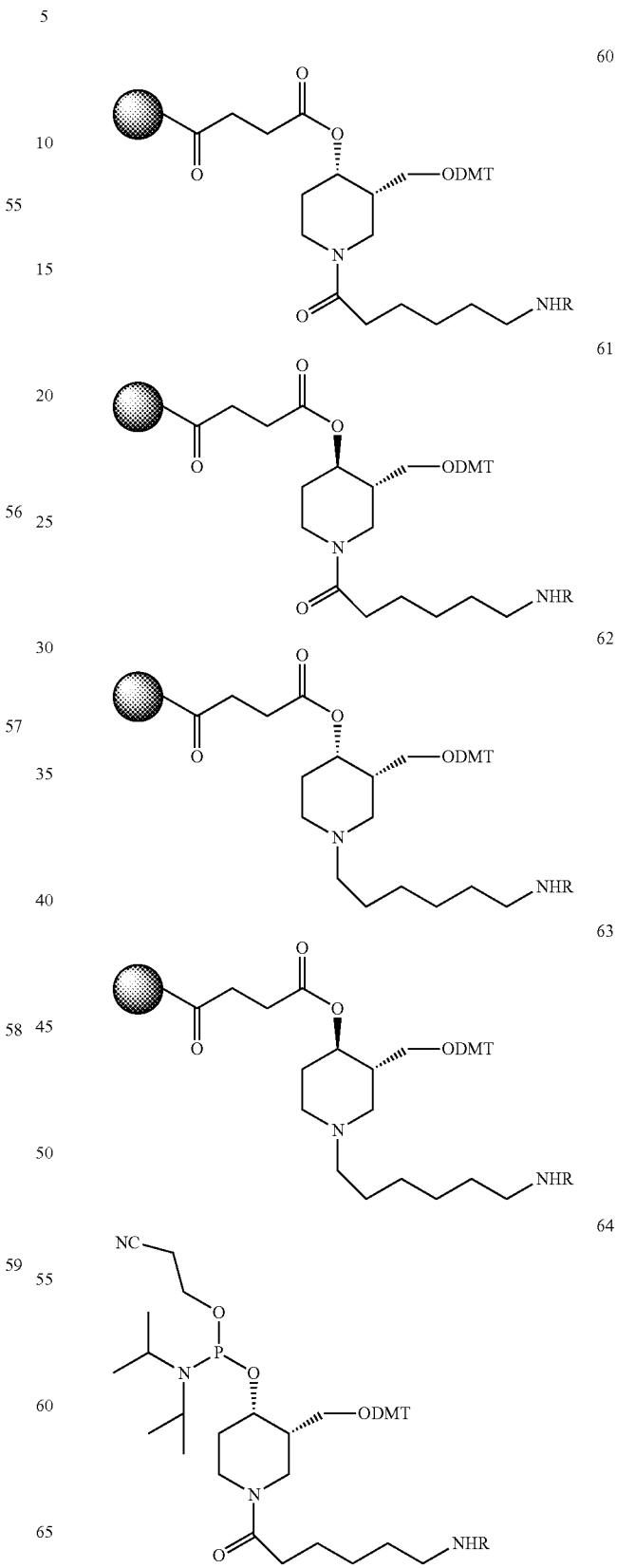

65
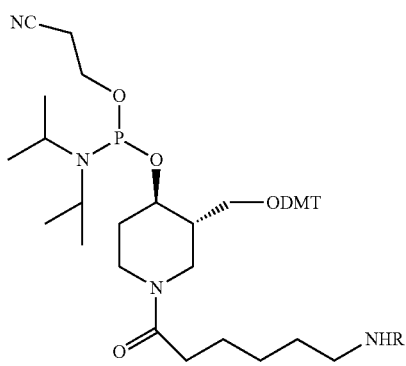
66
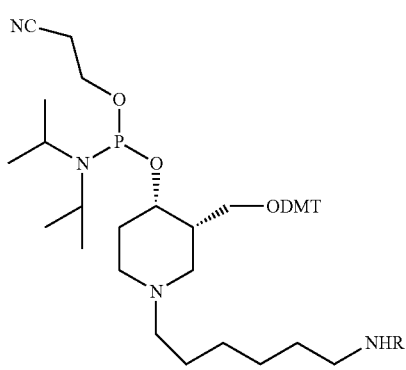
67
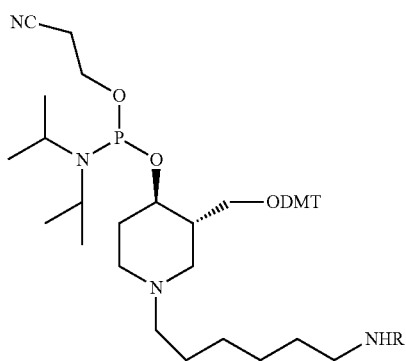
Piperidine Series Ligands:
Similar to Pyrroline Series Piperidine Series can be Synthesised
68
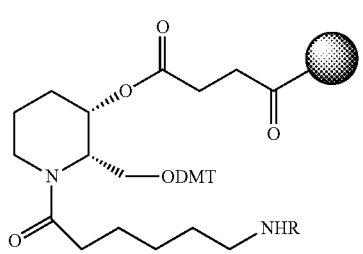
69
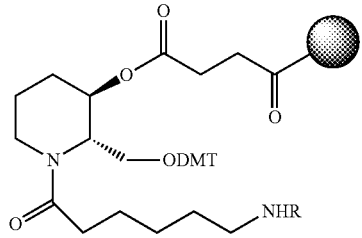
70
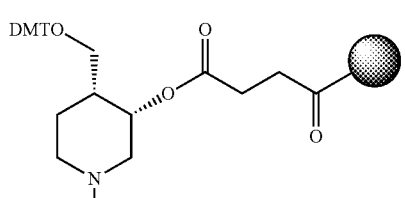
71
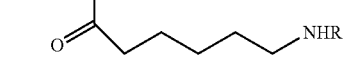
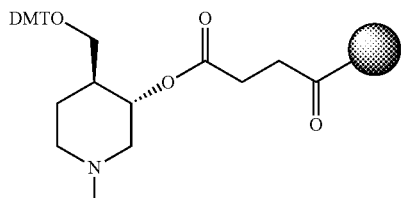
72
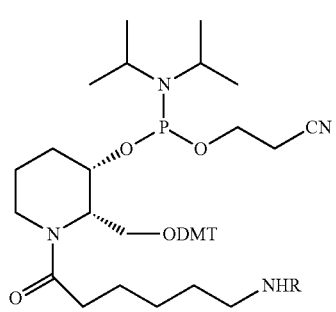
73
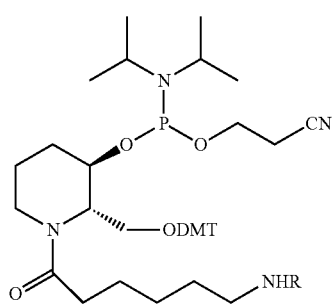

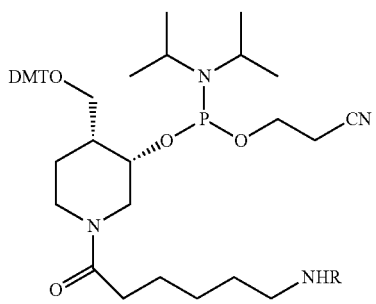
75
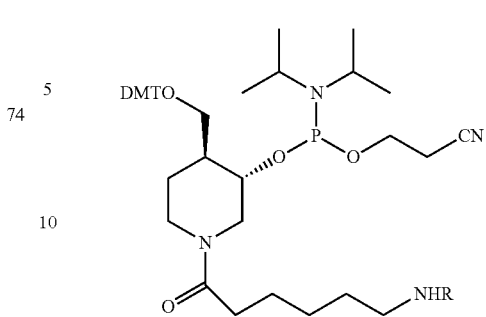
76
Hydroxy Proline Series Linkers:
From Commercially Available Cis-3-Hydroxy Proline and (s)-Pyrrolidone Carboxylate
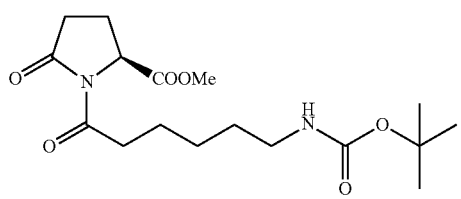
77
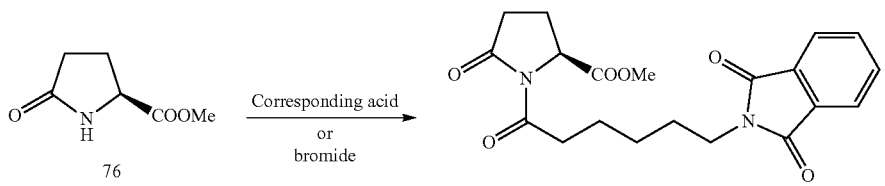
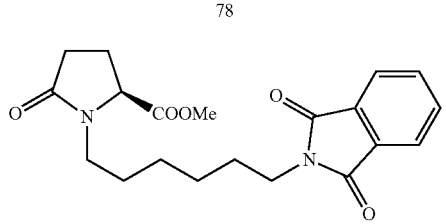
79
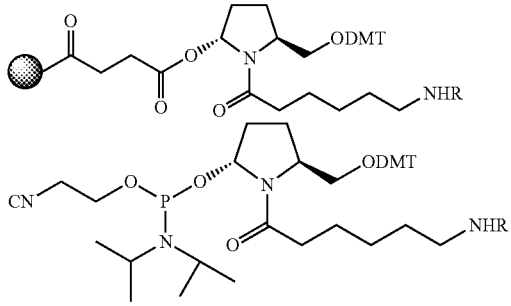
80
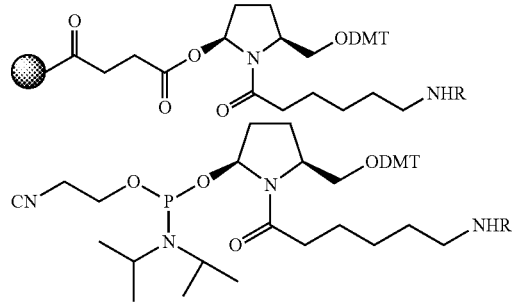
81
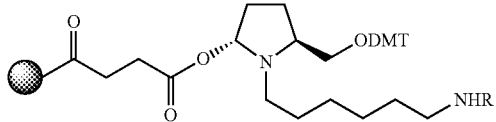
85

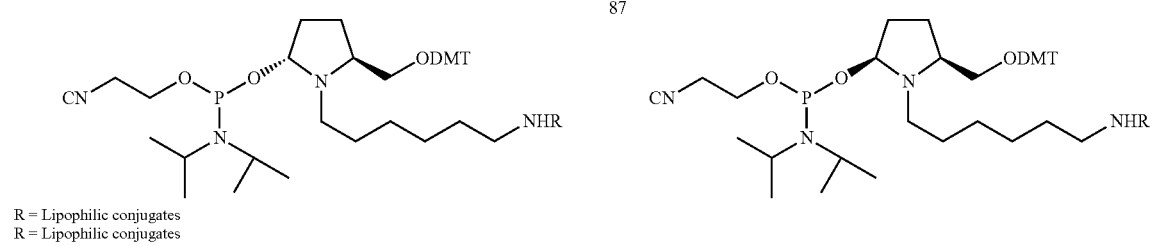
Phthalimide Derivative to Stabilise siRNA
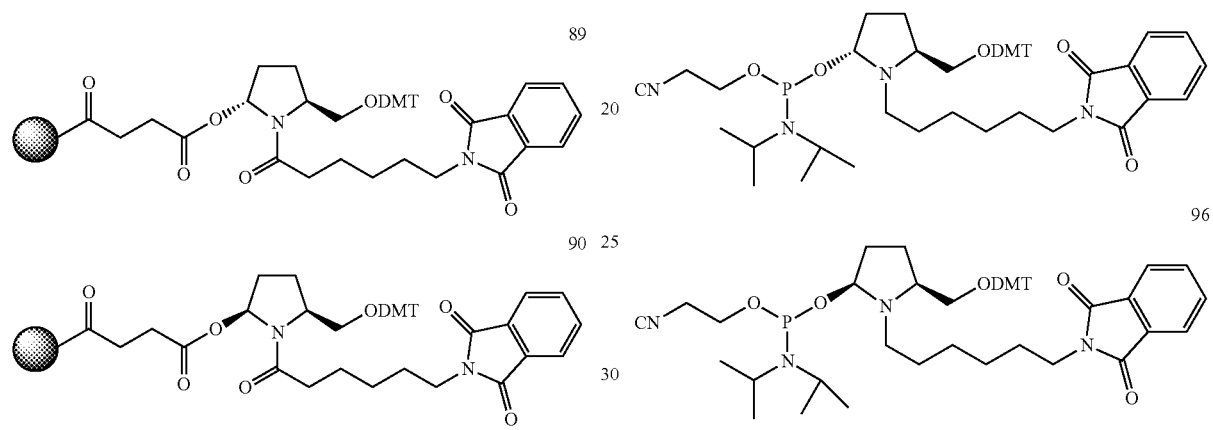
4-hydroxy Proline Derivatives
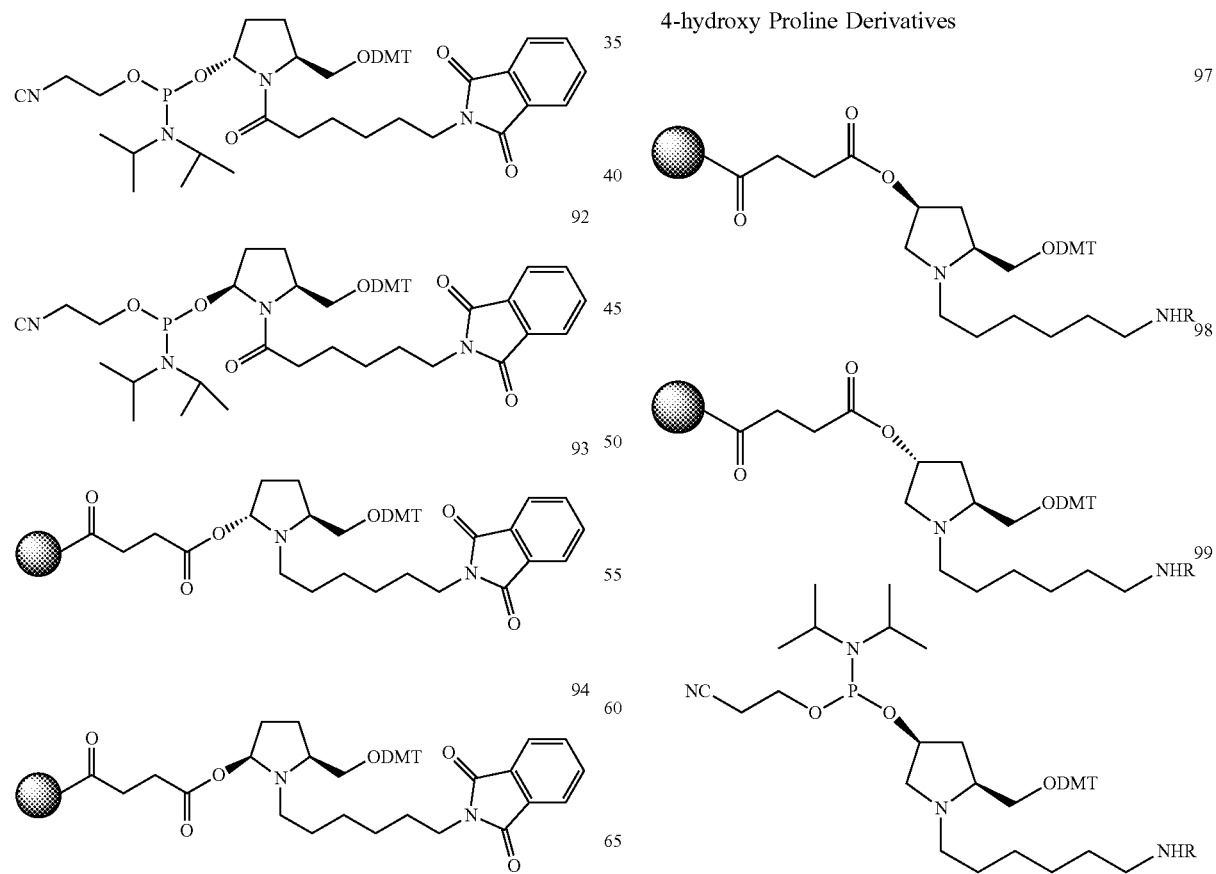

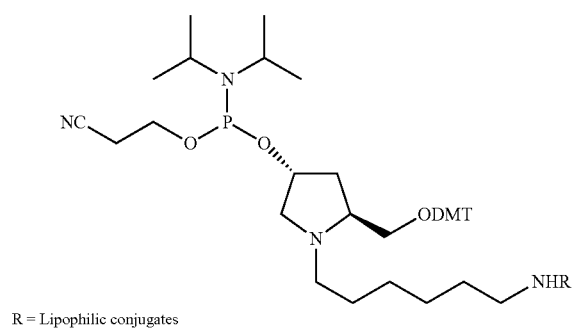
R = Lipophilic conjugates
Phthalimido Derivatives
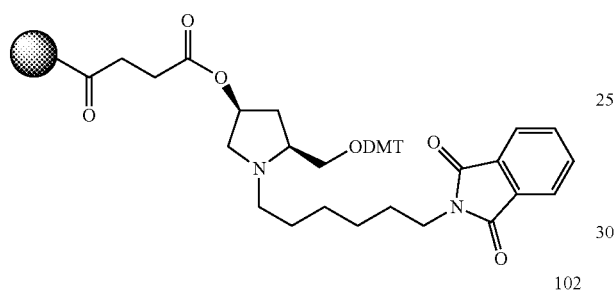
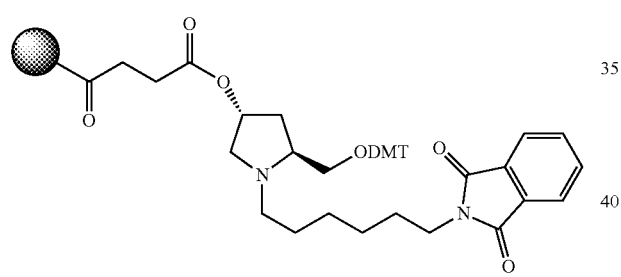
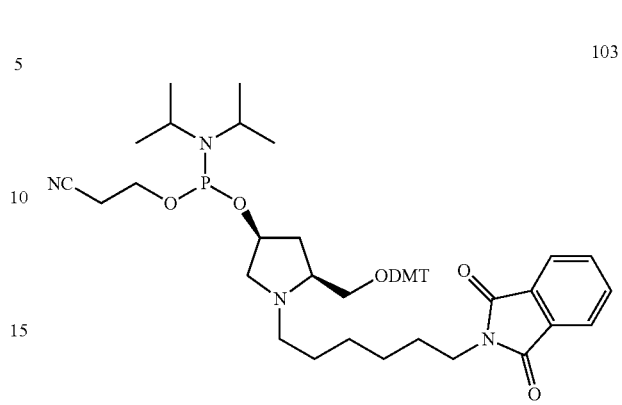
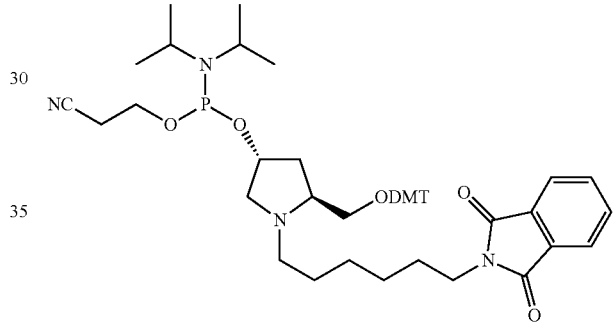
Synthesis of 6-Membered Linker
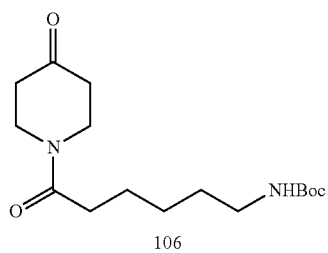
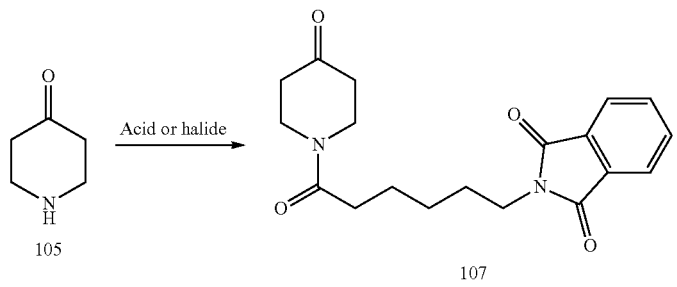

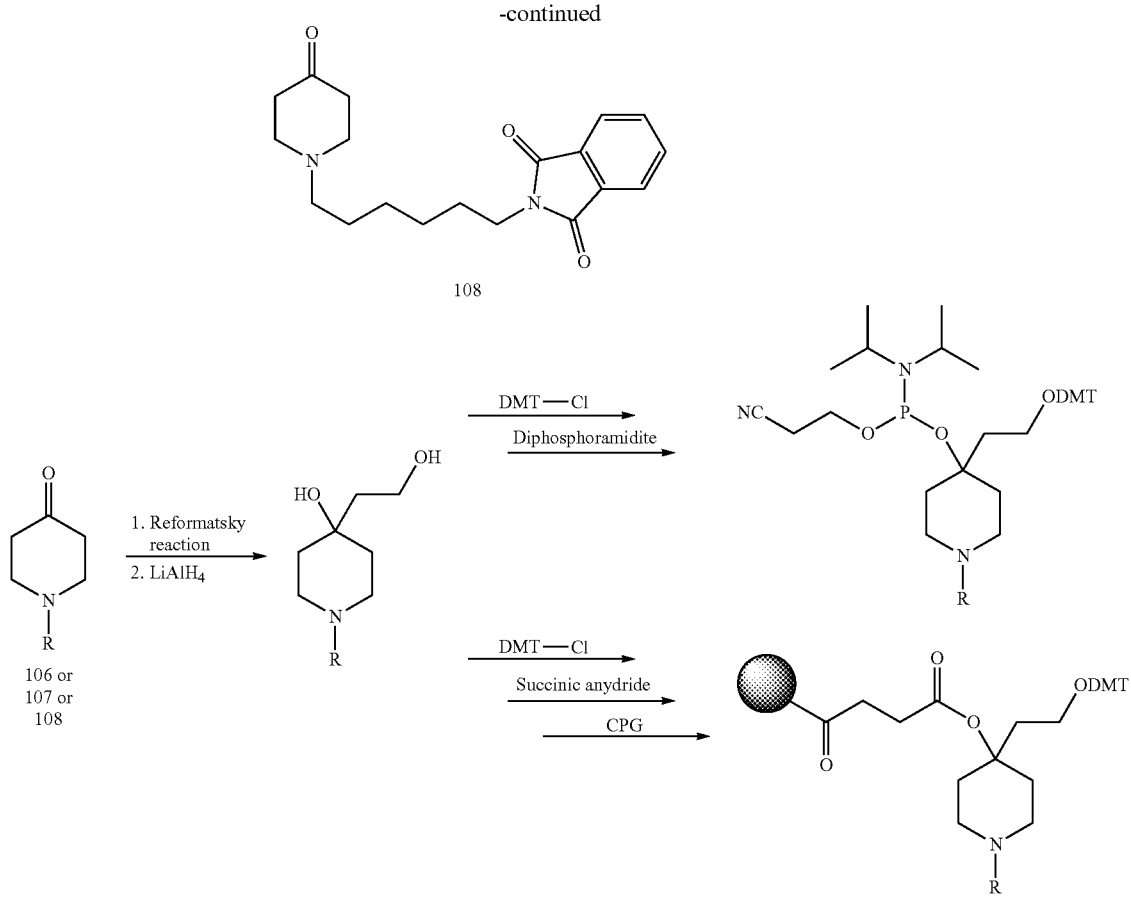
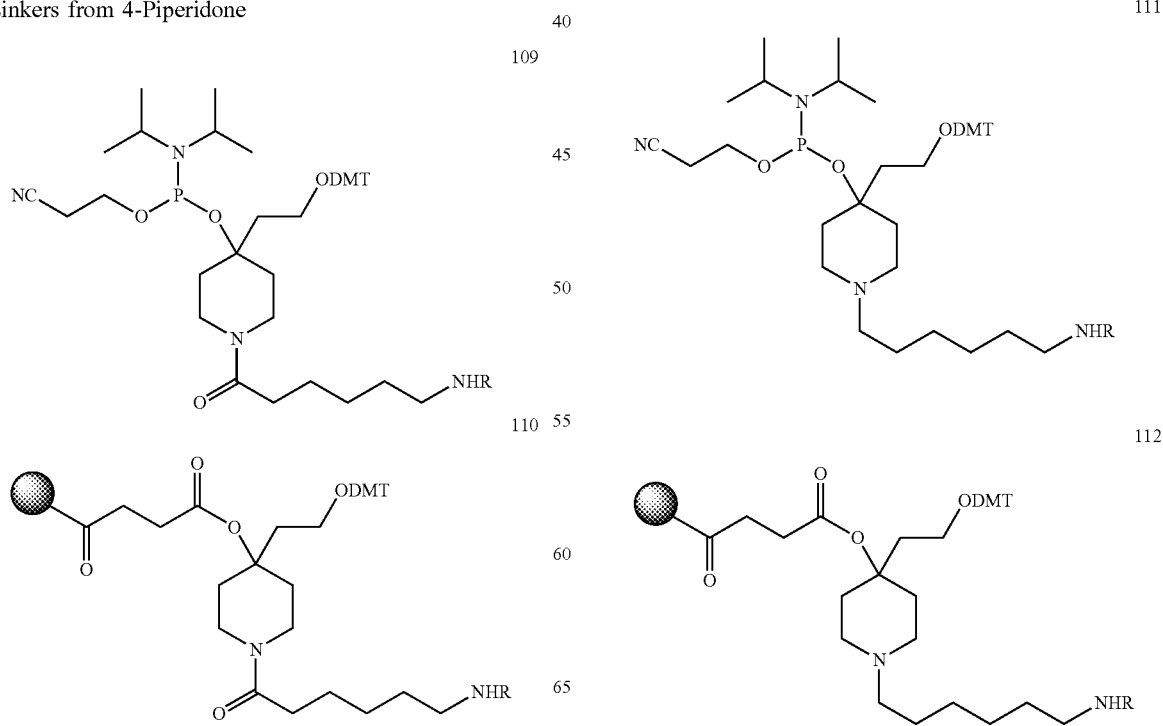
Similar Reaction can be Carried Out with 2-Piperidone and 3-Piperidone
Linkers from 4-Piperidone

84
Linkers from 3-Piperidone
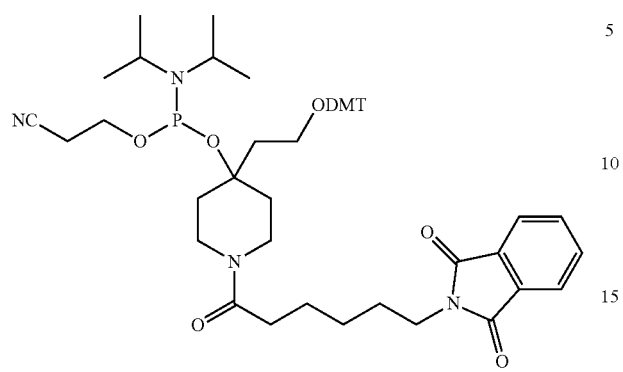
113
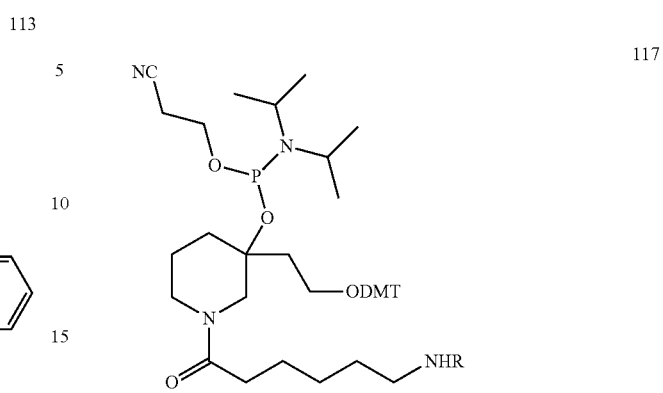
117
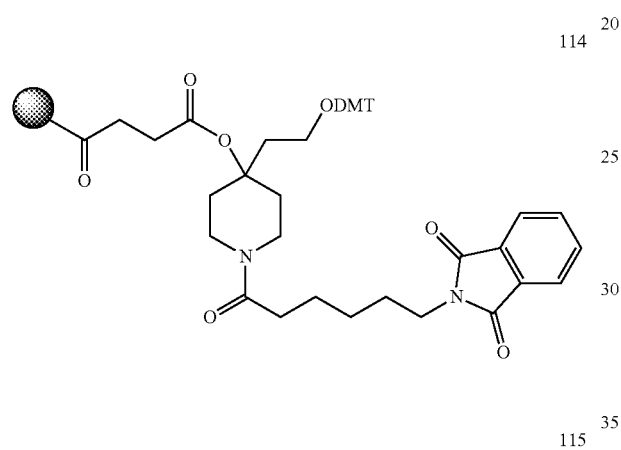
114
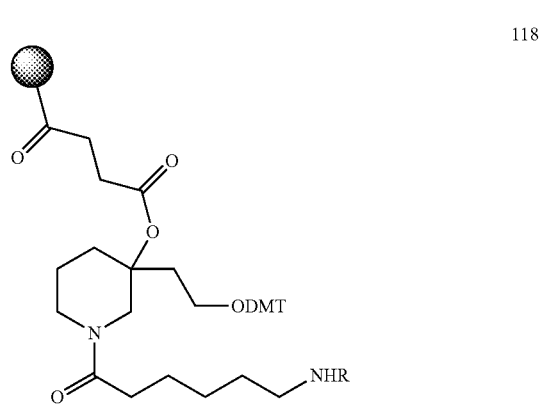
118
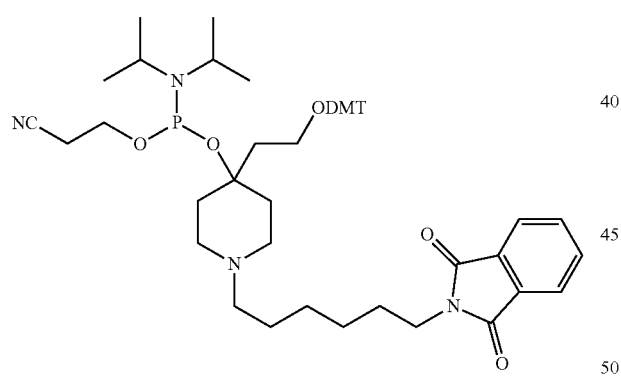
115
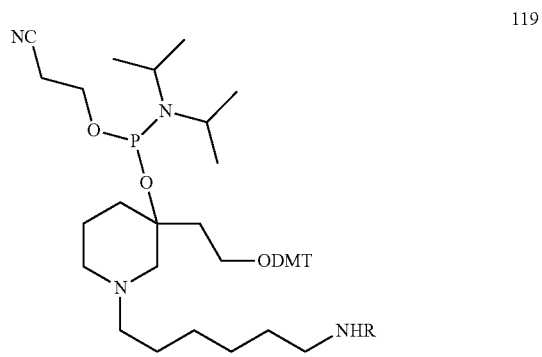
119
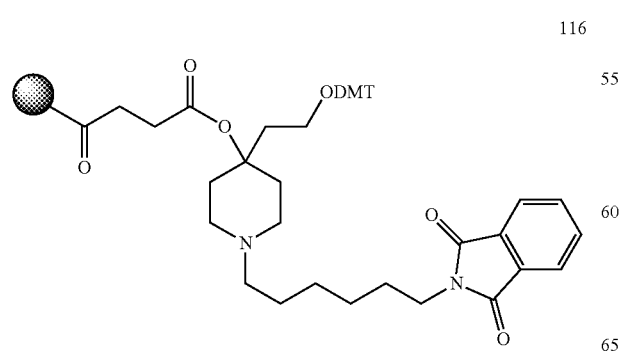
116
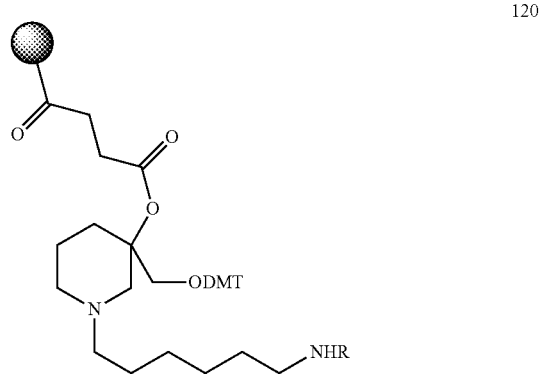
120

85
-continued
121
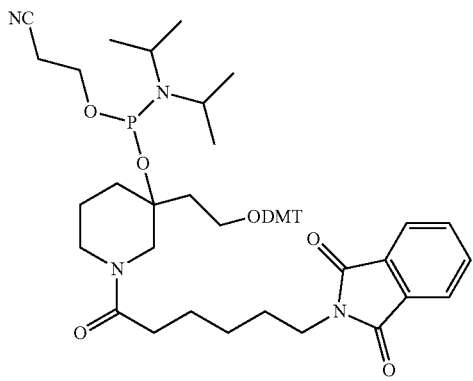
122
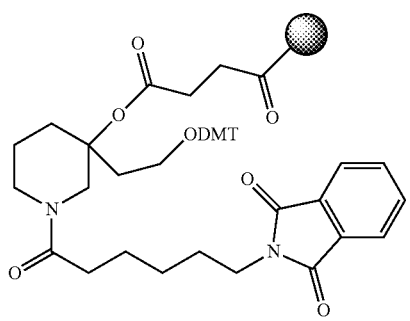
123
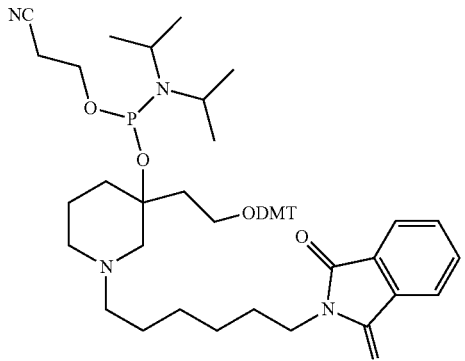
124
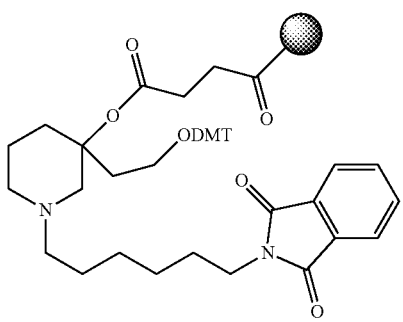
86
Linkers from 2-Piperidone
125
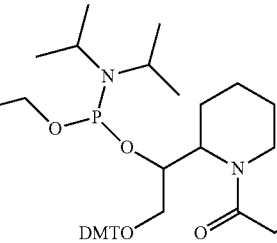
126
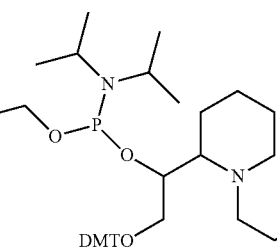
127
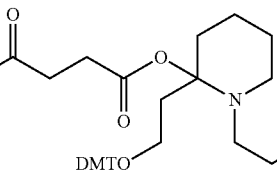
128
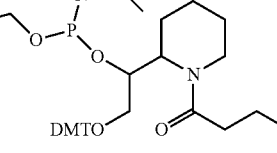
129
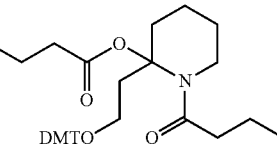
130

87
-continued
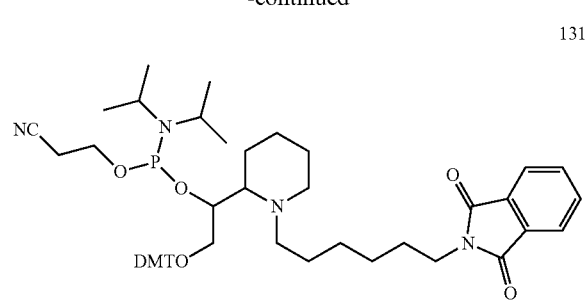
131
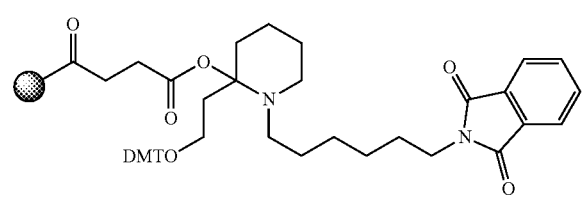
132
Conjugation Through Decalin System
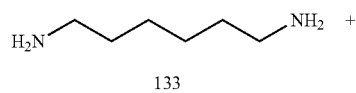
133
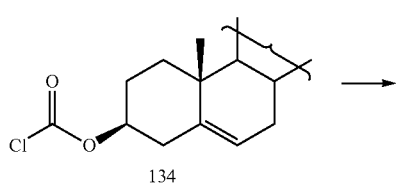
134
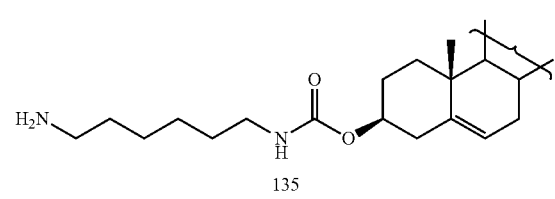
135
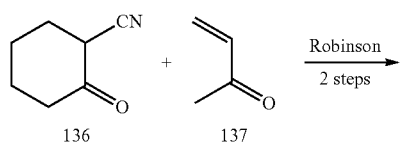
136  137
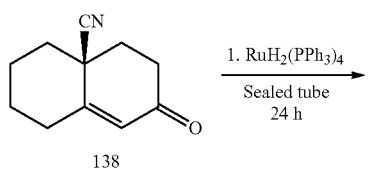
138
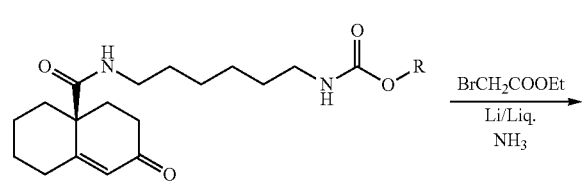
R = Cholesterol
139
88
-continued
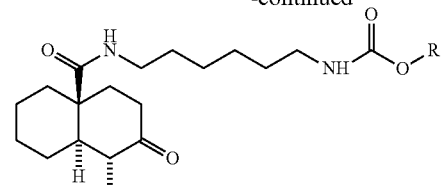
140
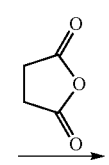
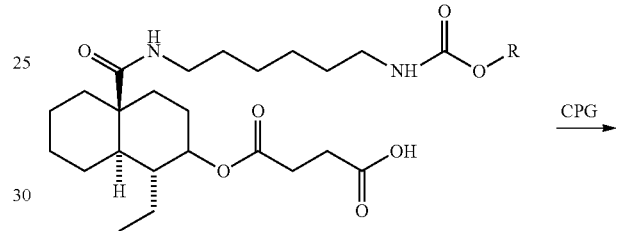
141
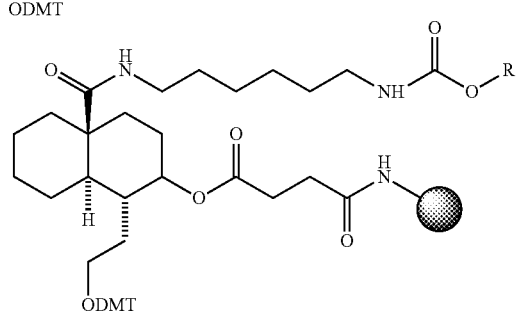
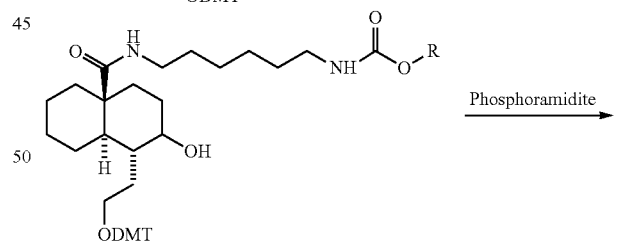
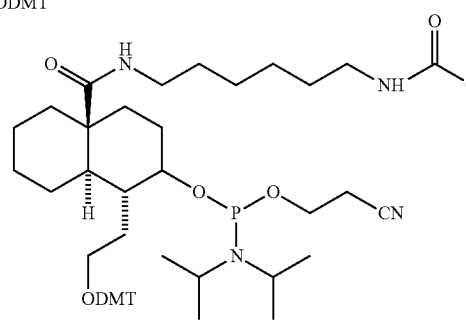

89
Conjugates from Decalin System:
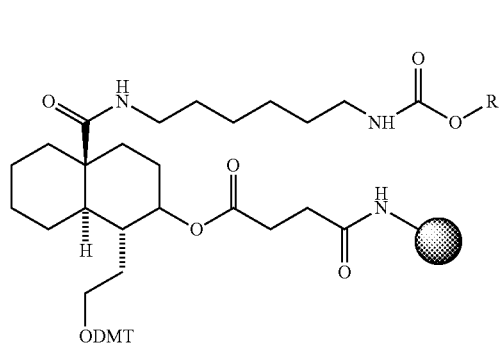
142
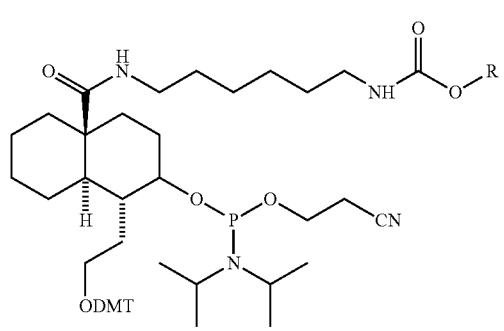
143
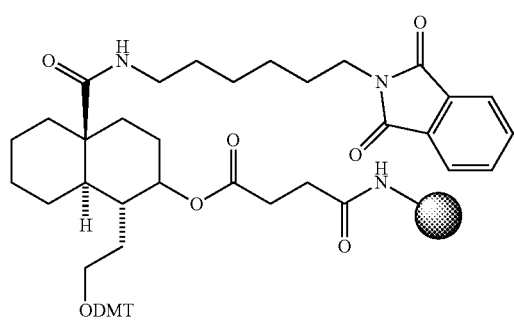
144
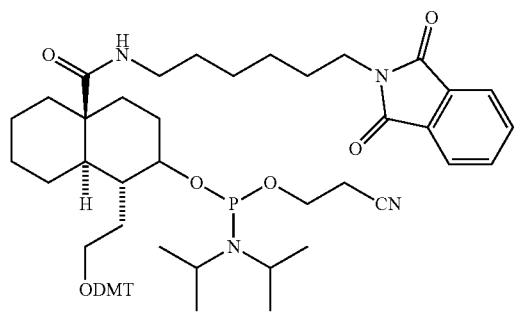
145
R = Lipophilic conjugates
90
Decalin Linker from Wieland-Miescher Ketone
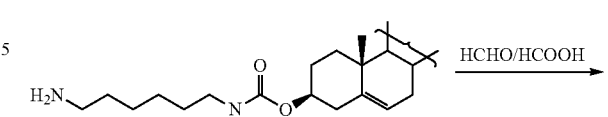
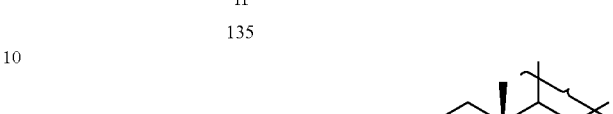
135
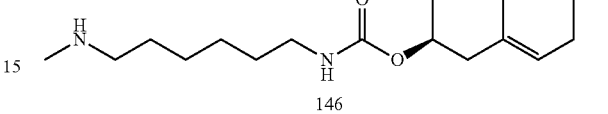
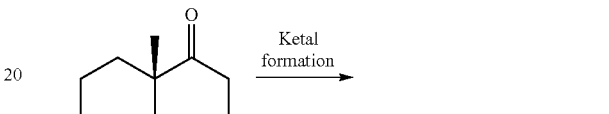
146
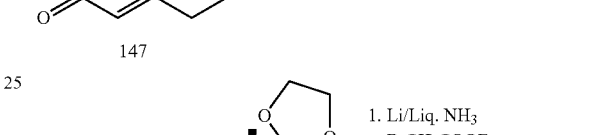
147
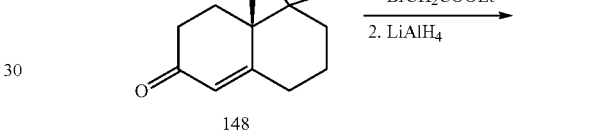
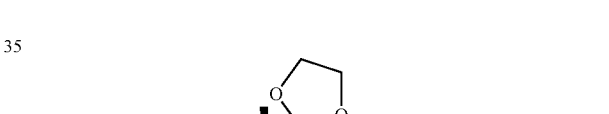
148
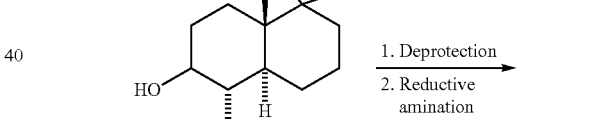
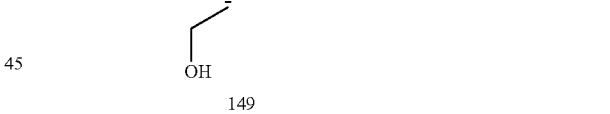
149
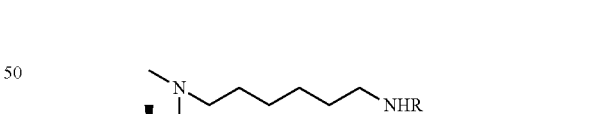
150
Ligand on CPG
or
Phosphoramidite

Conjugates from Wieland-Miescher Ketone
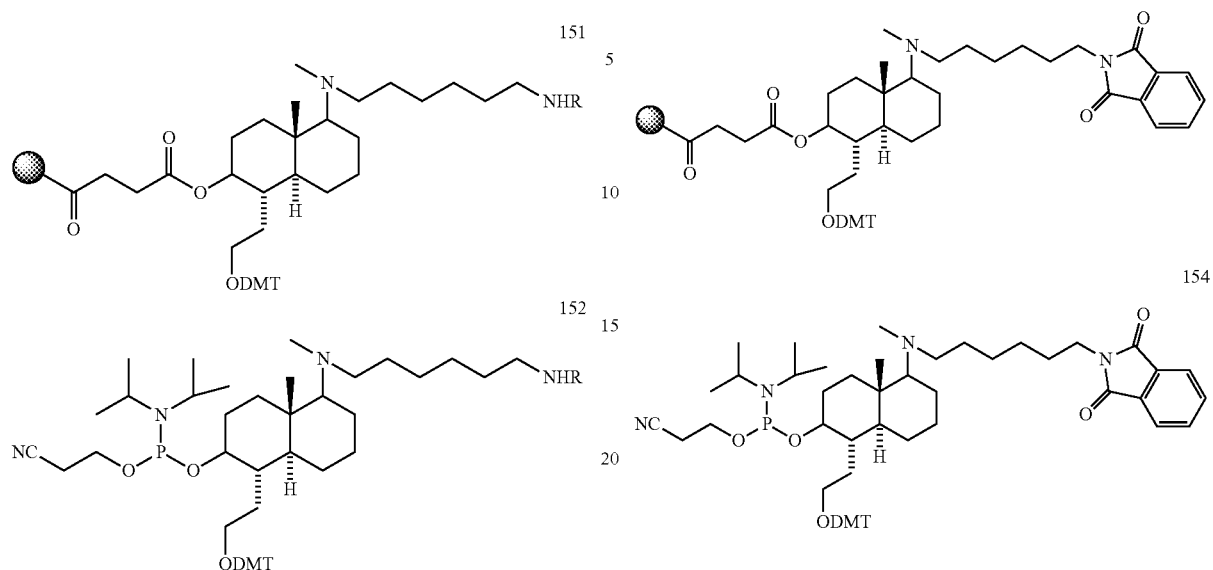
Synthesis of Pyrroline Linker:
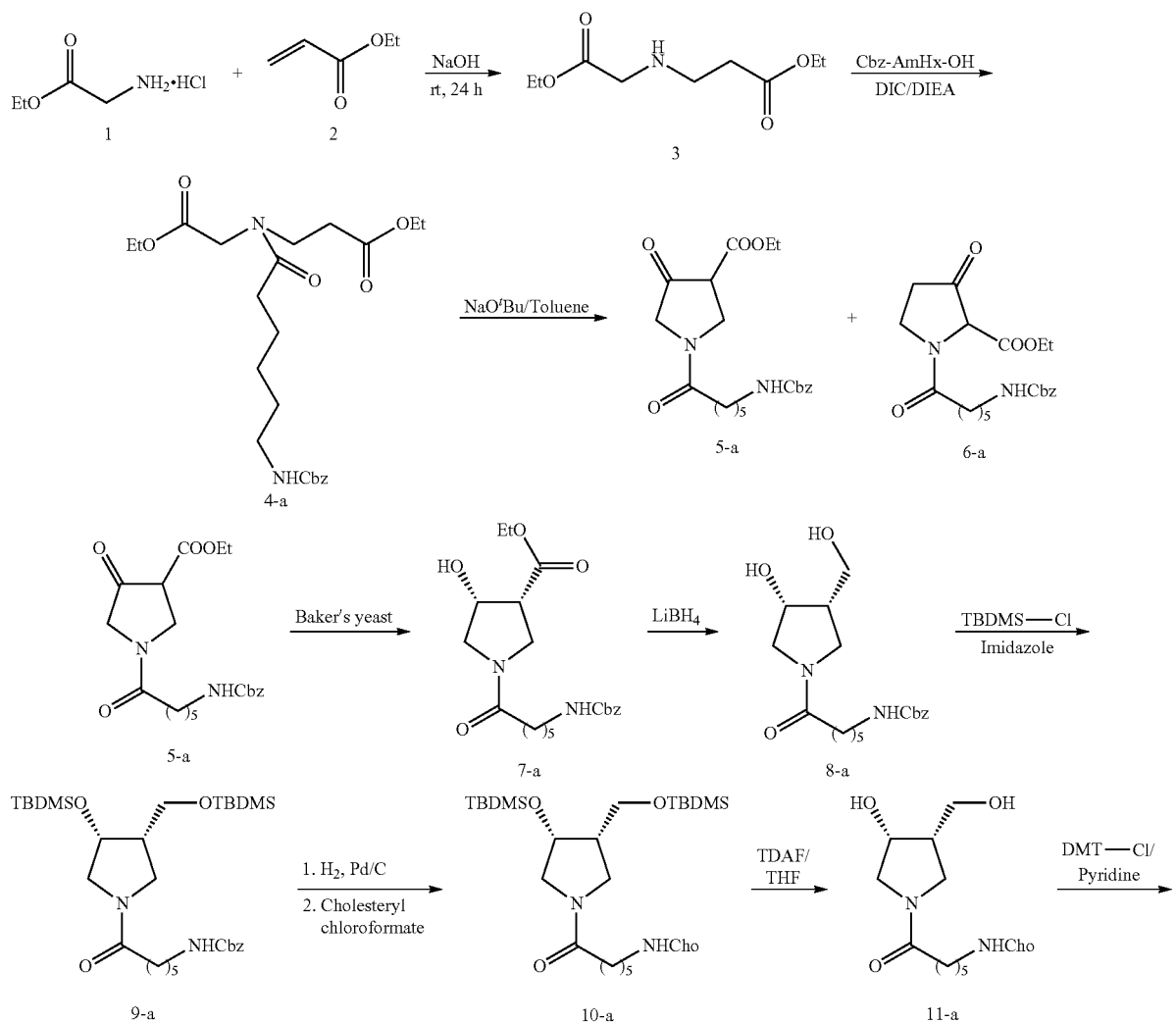

93
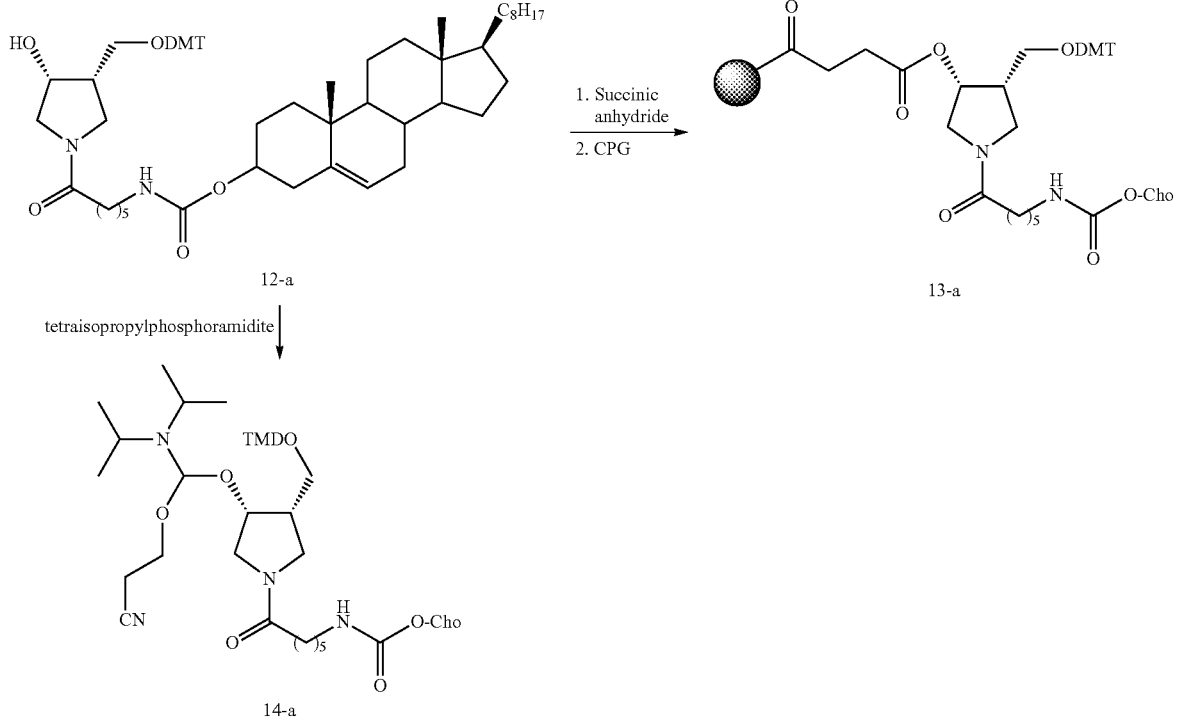
94
Solid Phase Synthesis and Post-Synthesis Conjugation:
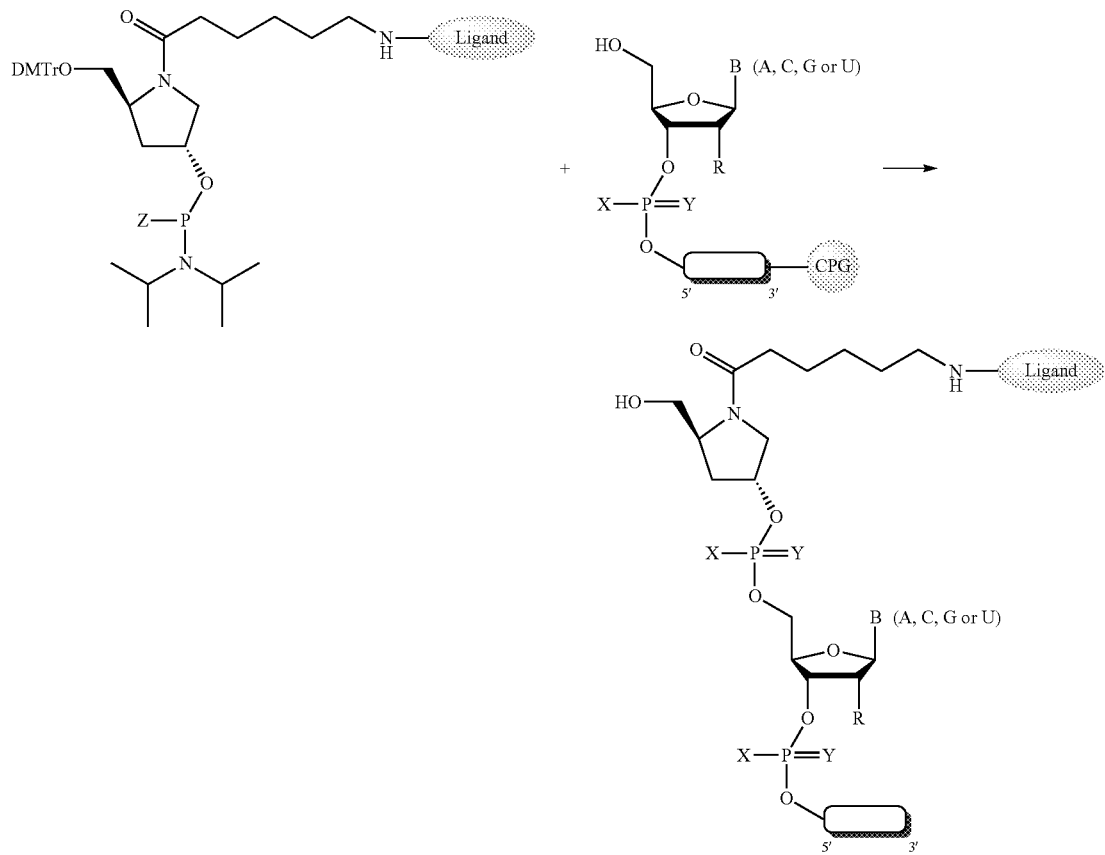

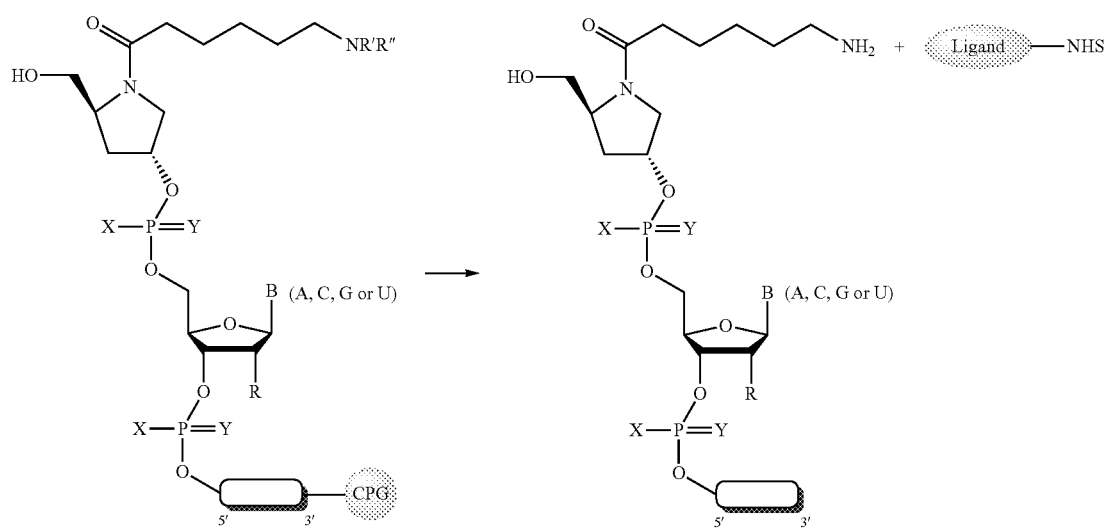
Exemplary Ligand Conjugated Monomers
LCM—E.g.—
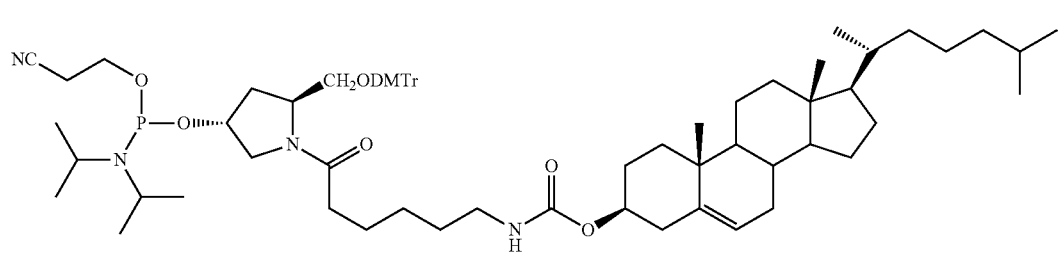
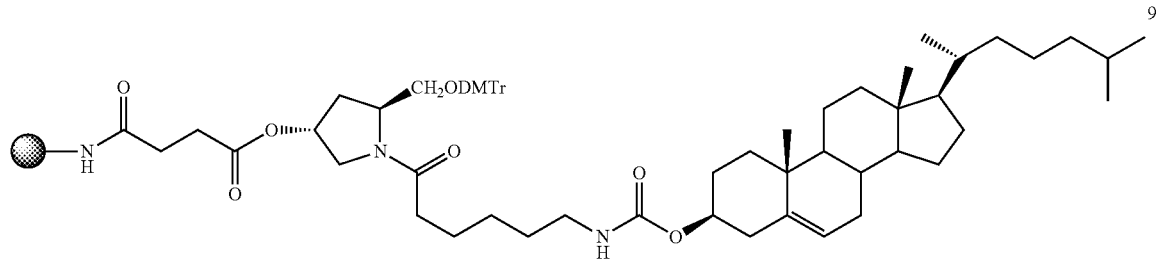
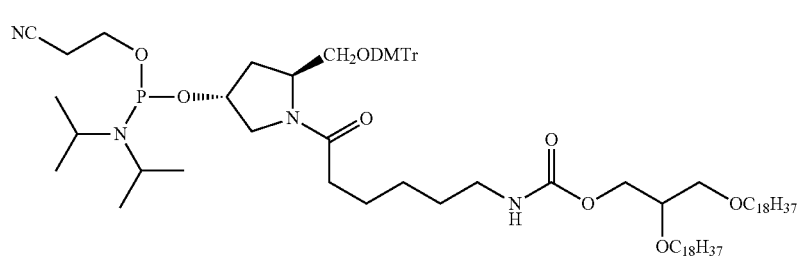

15
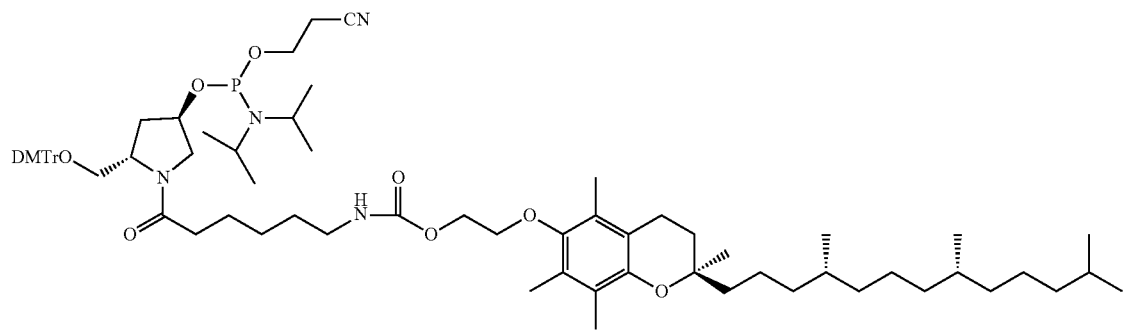
20
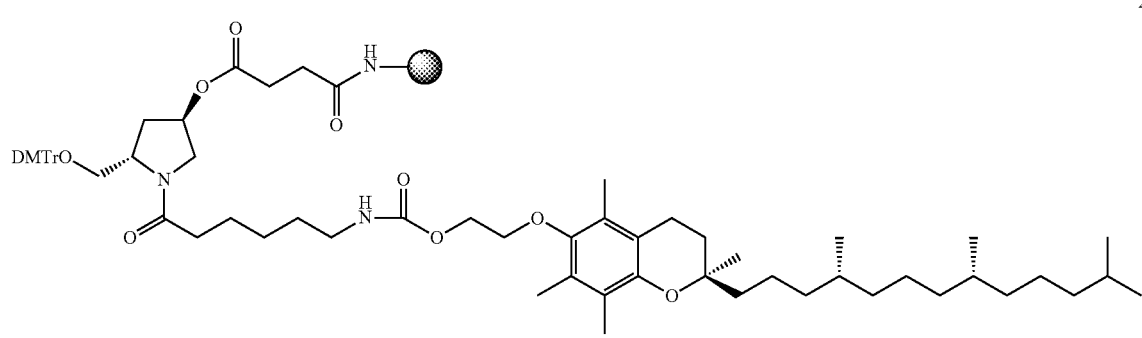
22
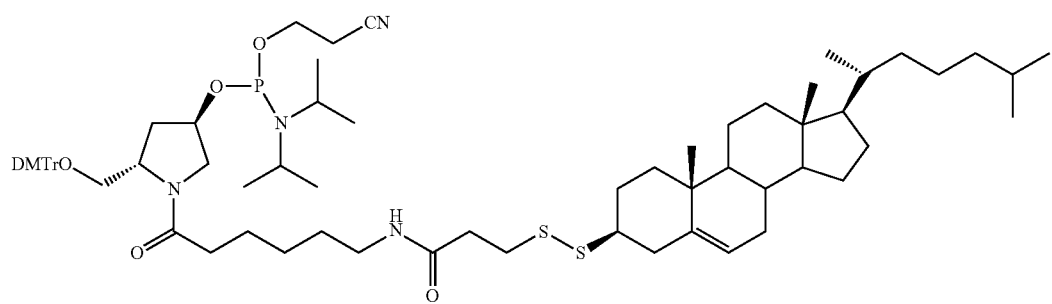
26
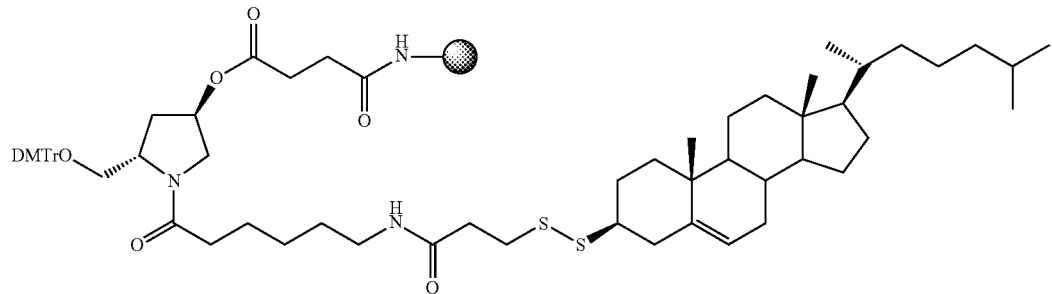
28

-continued
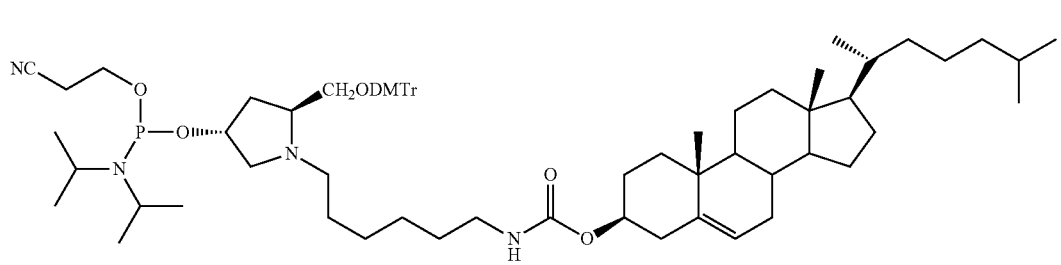
33
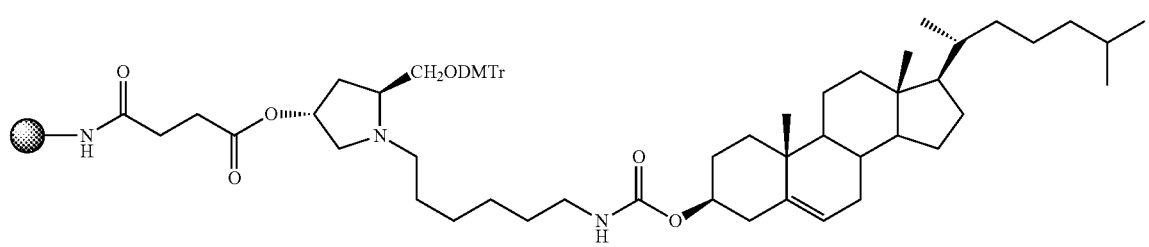
35
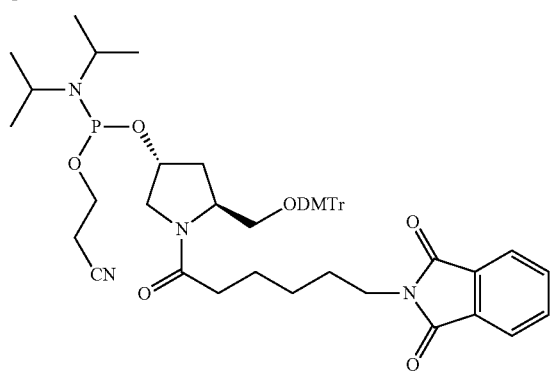
45a
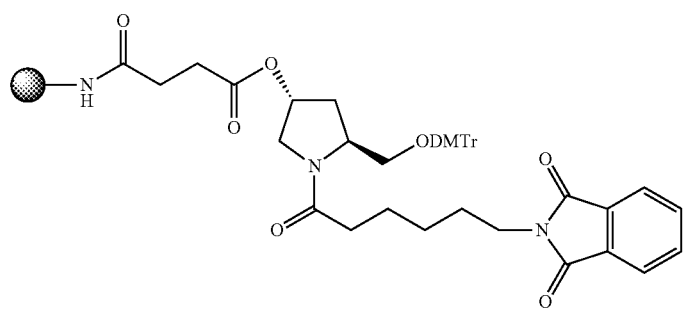
46a

3
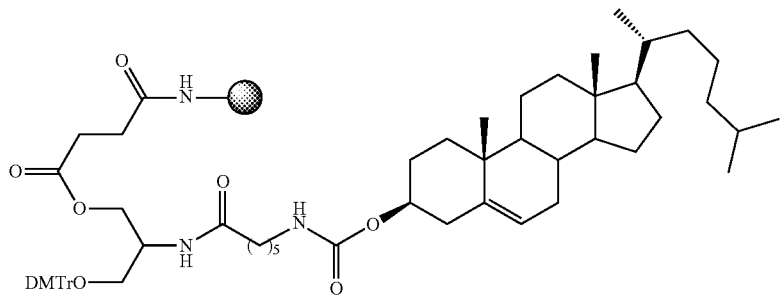
55
4
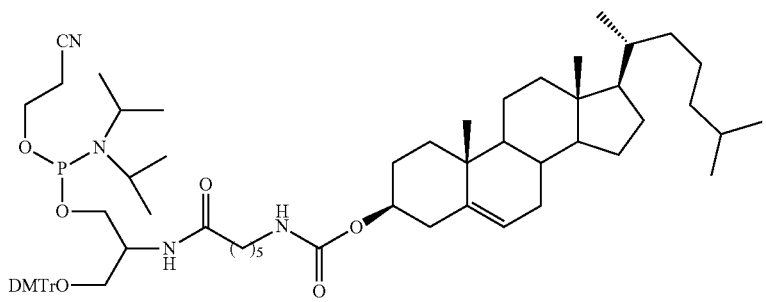
56
5
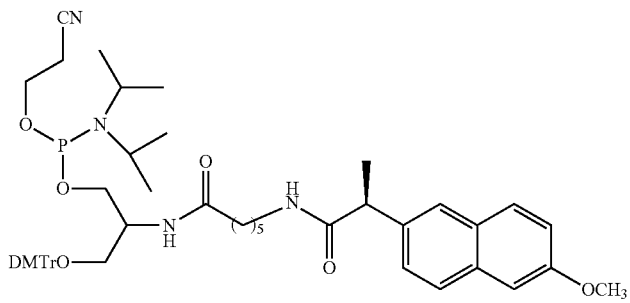
209a
6
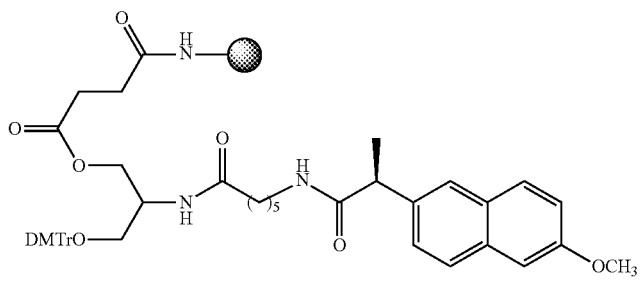
208a

7
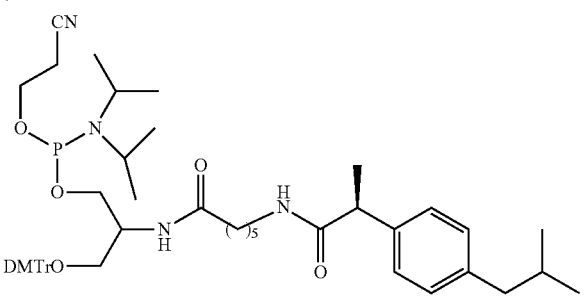
209b
8
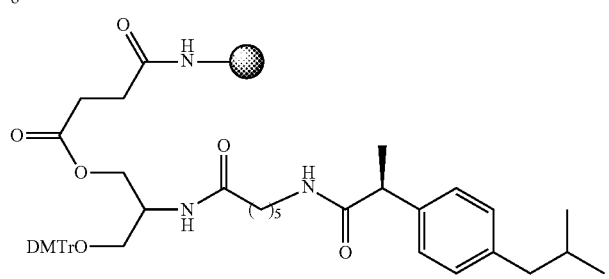
208b
9
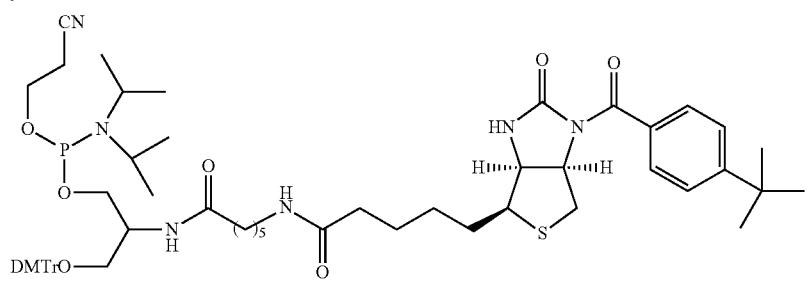
223
0
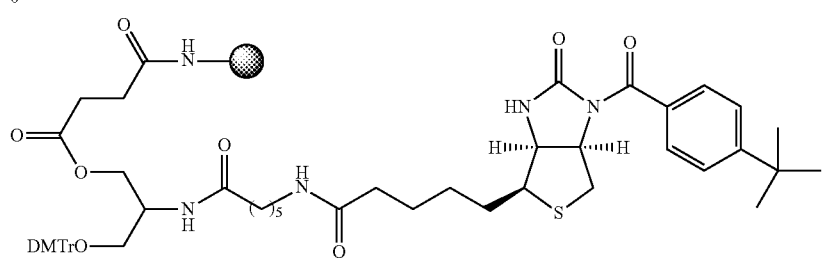
224
1
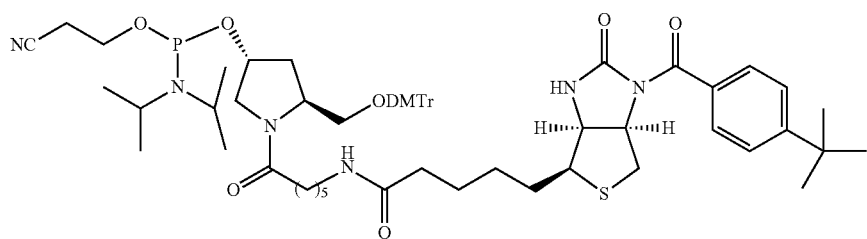
229a 2 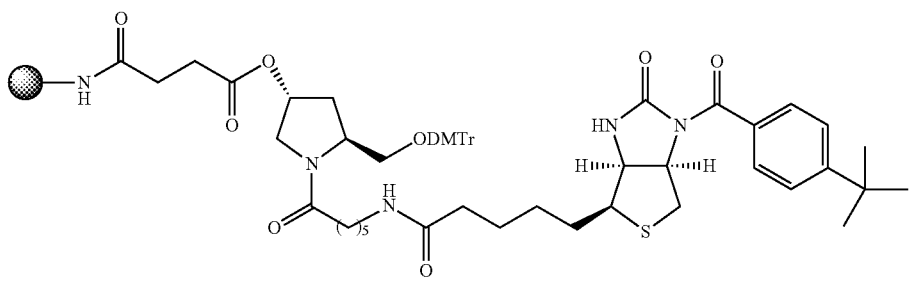 230a
3 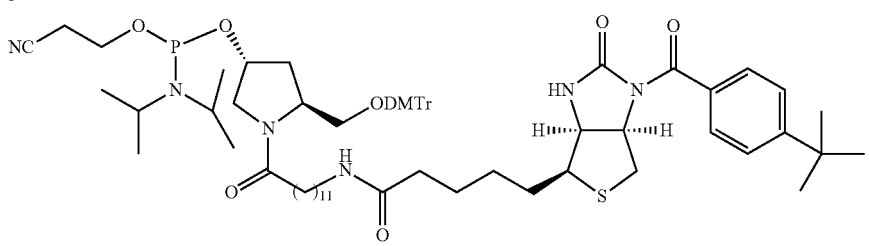 229b
4 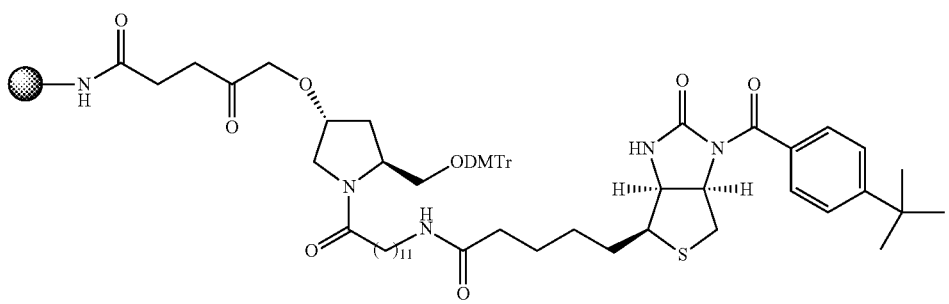 230b
5 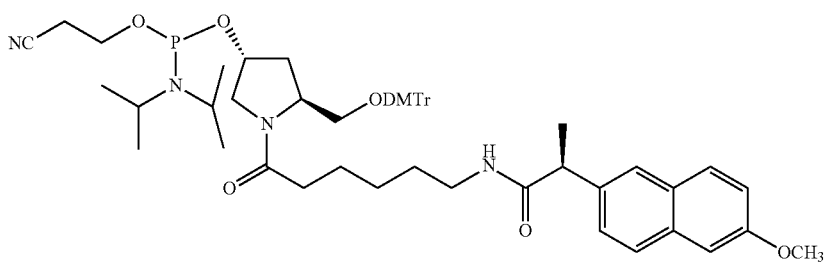 212a
6 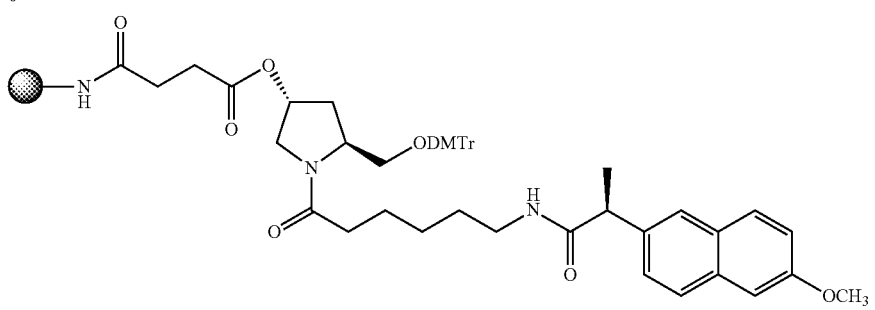 211a 7
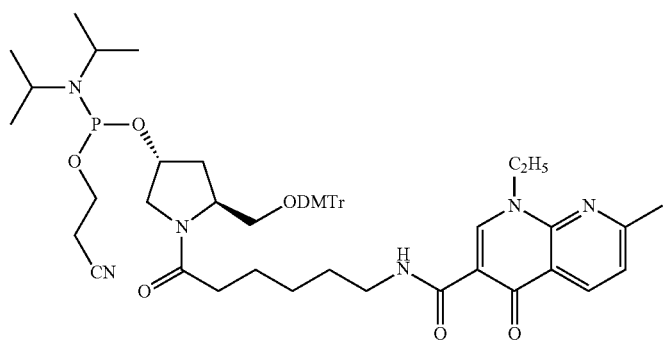
100
8
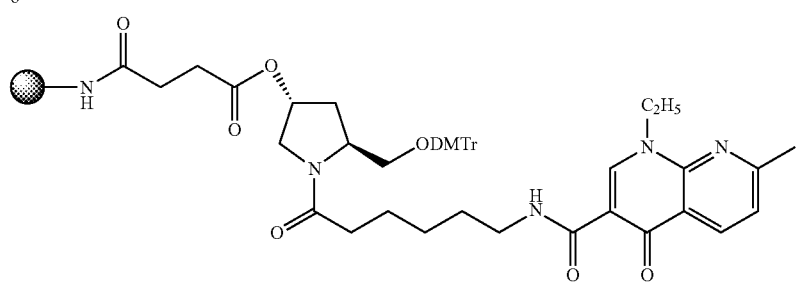
102
9
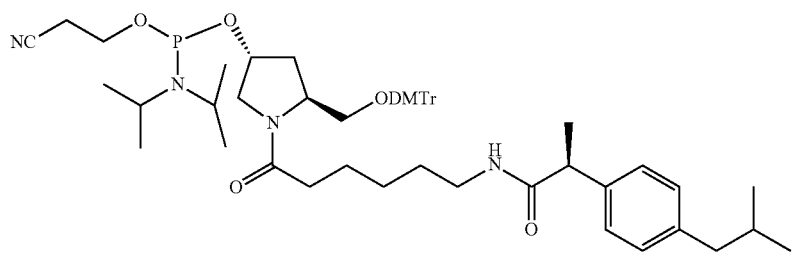
212b
0
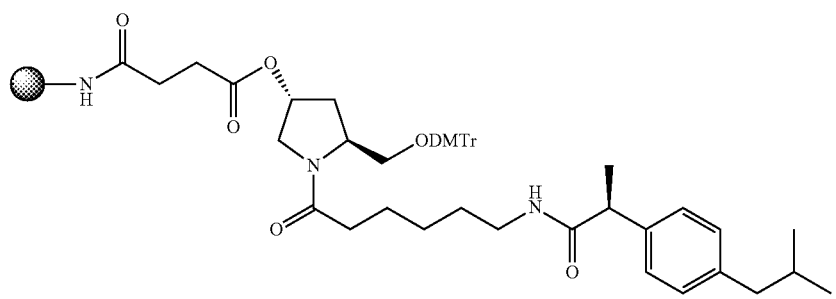
211b
1
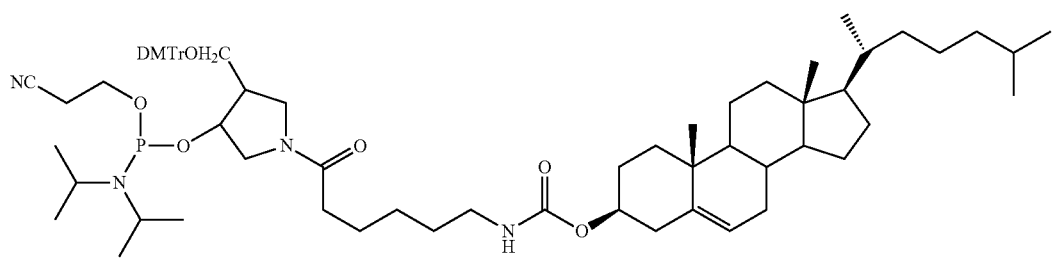
67

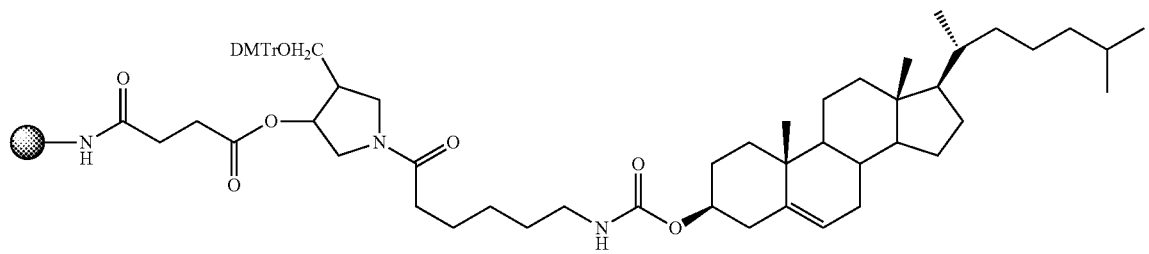
69
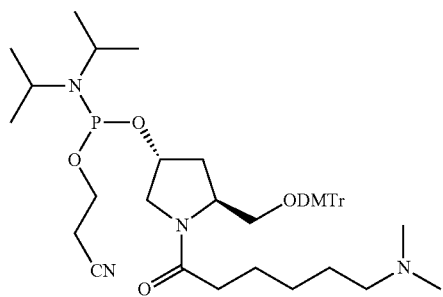
95
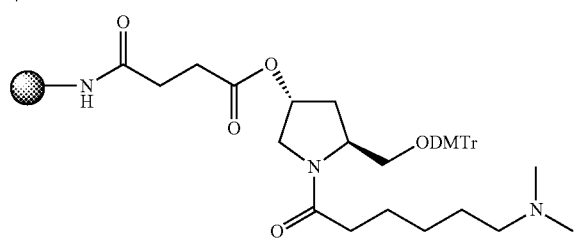
97
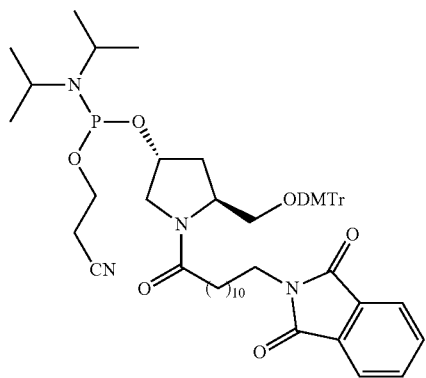
45b

6
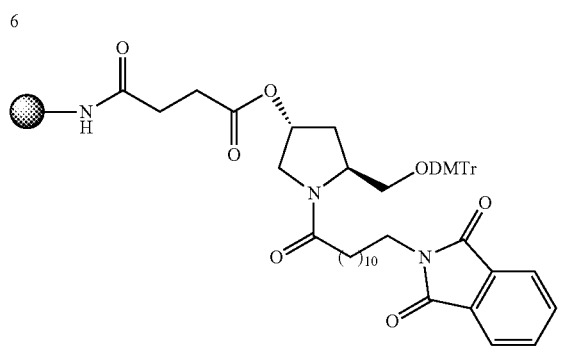
7
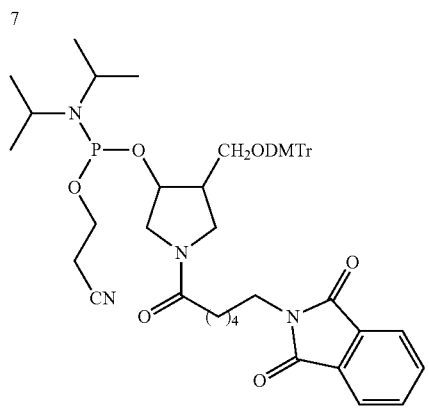
8
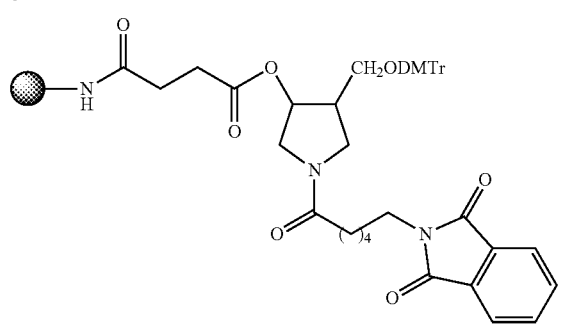
9
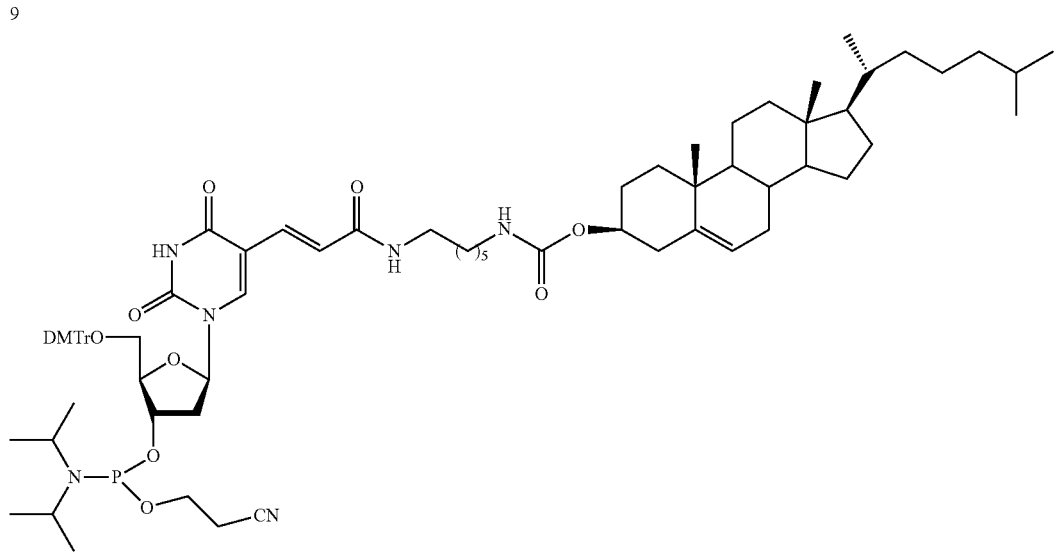

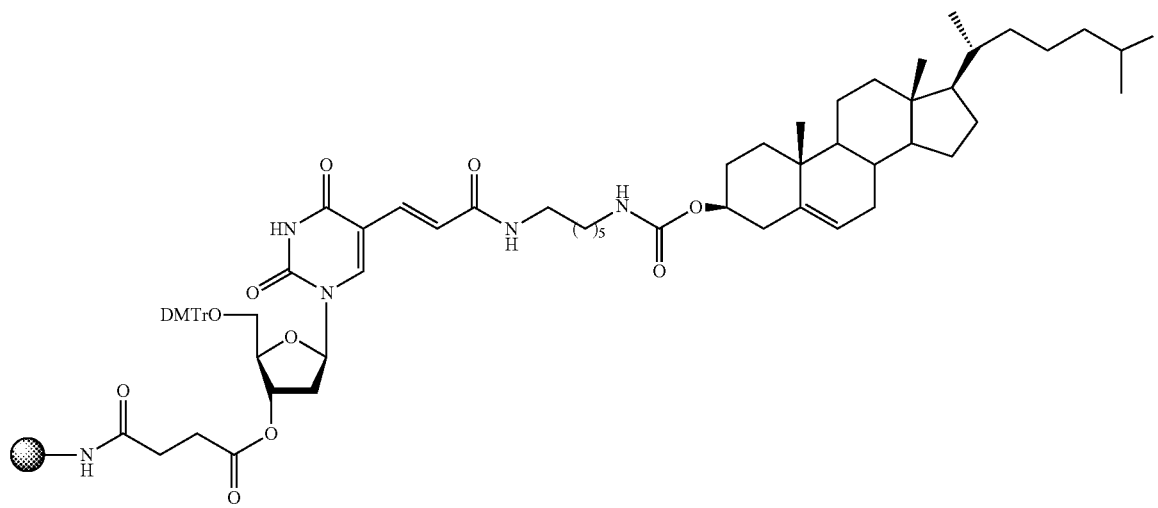
215a
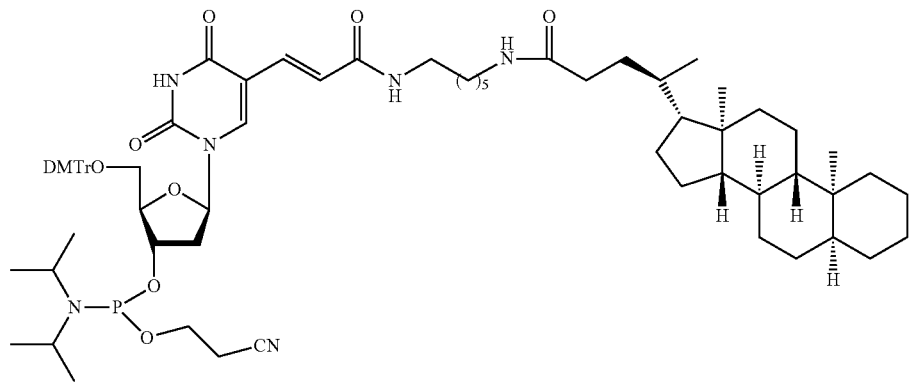
216b
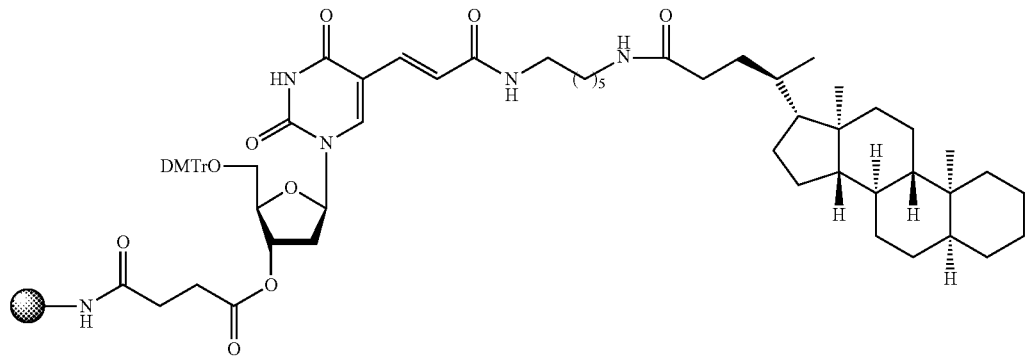
215b

3
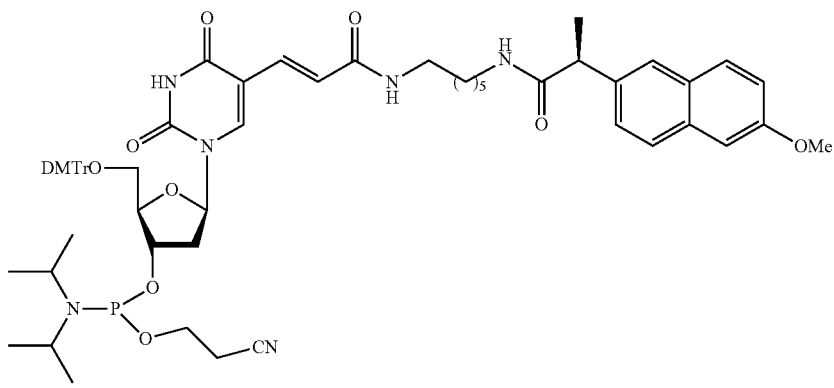
243a
4
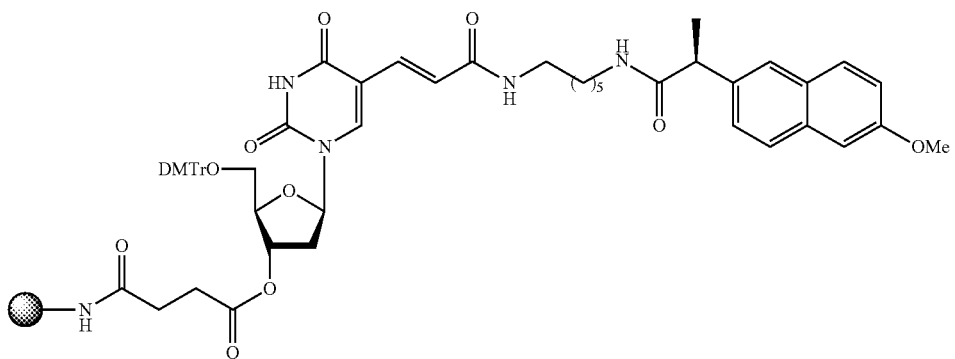
242a
5
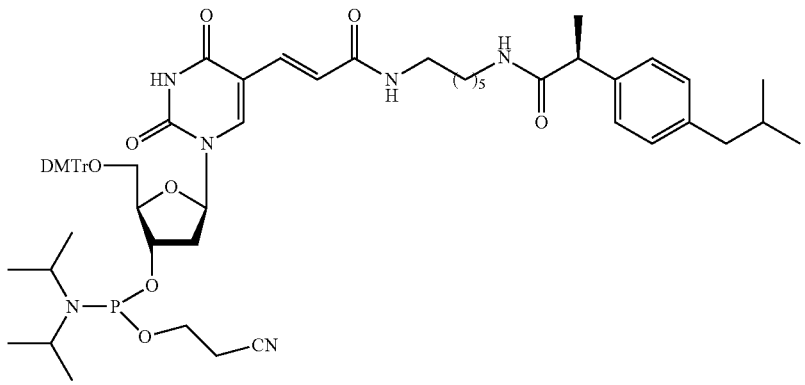
243b
6
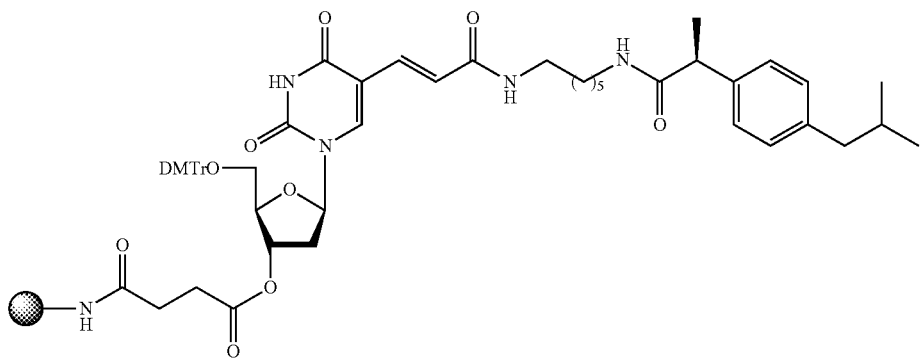
242b

7
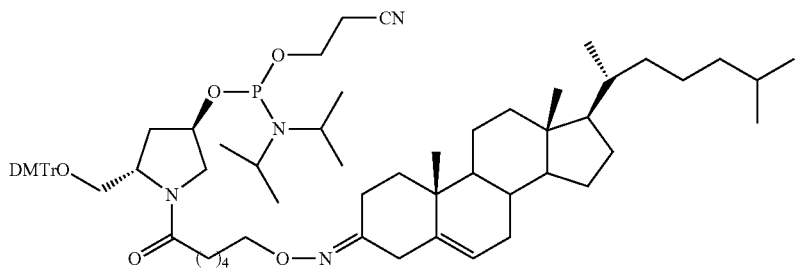
236a
8
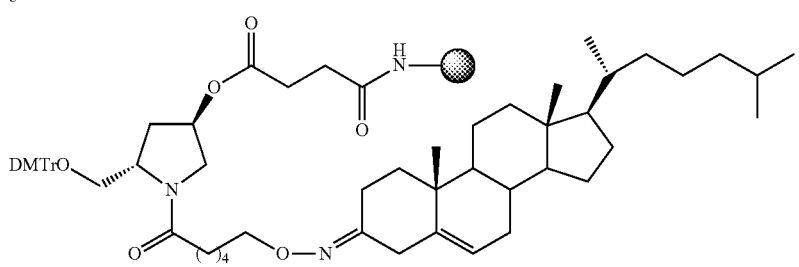
237a
9
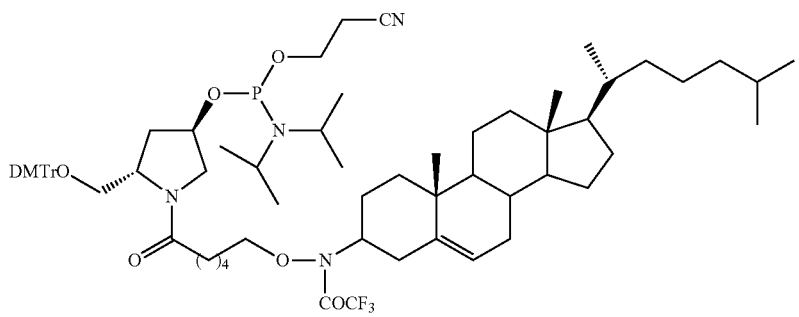
239a
0
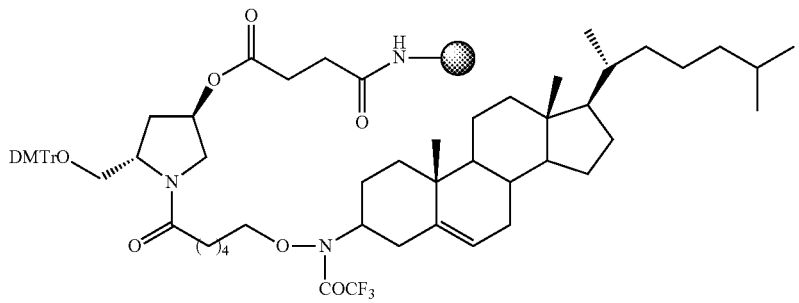
240a
1
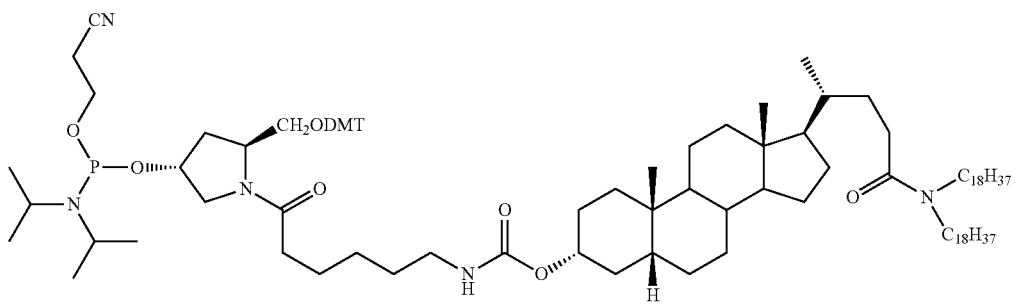
85

2.
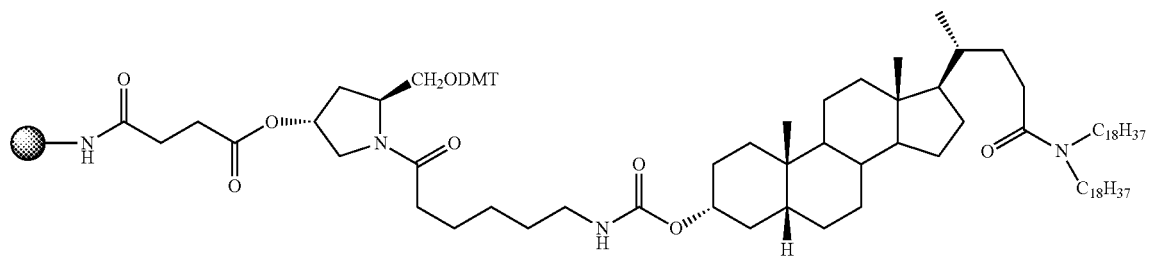
87
3.
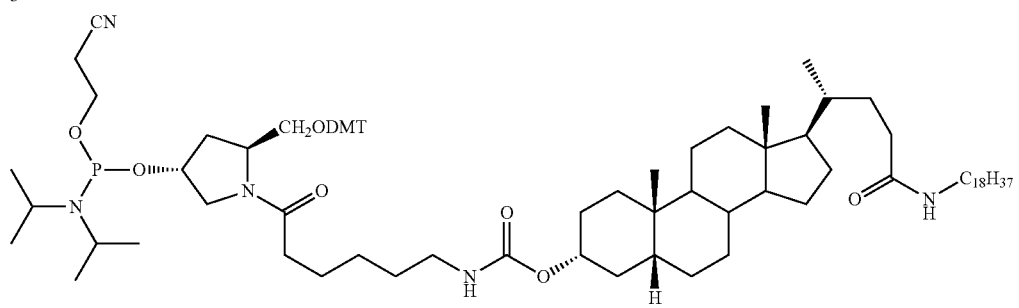
91
4.
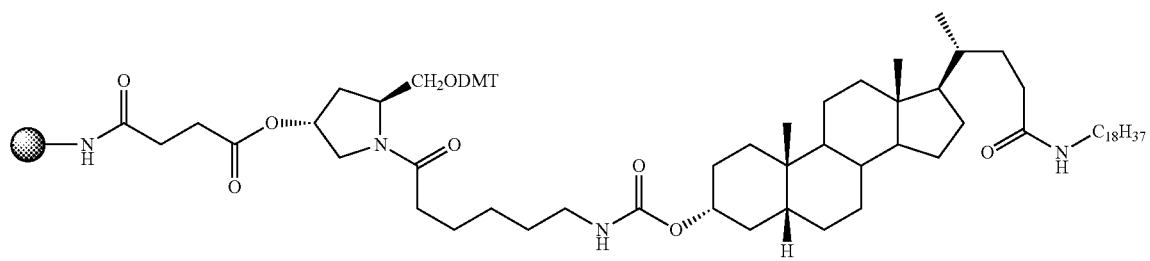
93
5.
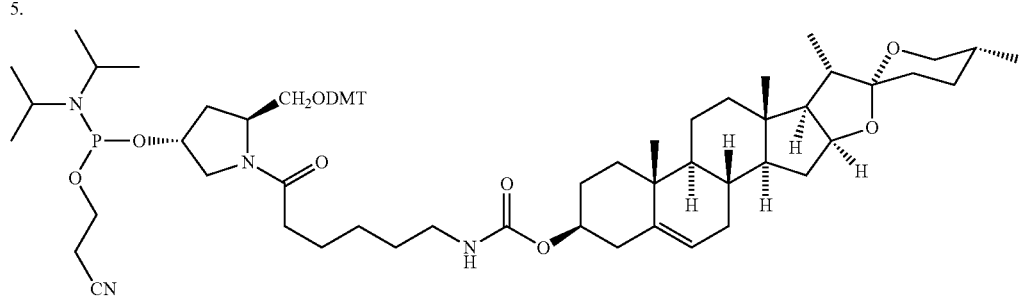
Diosgenin
106
6.
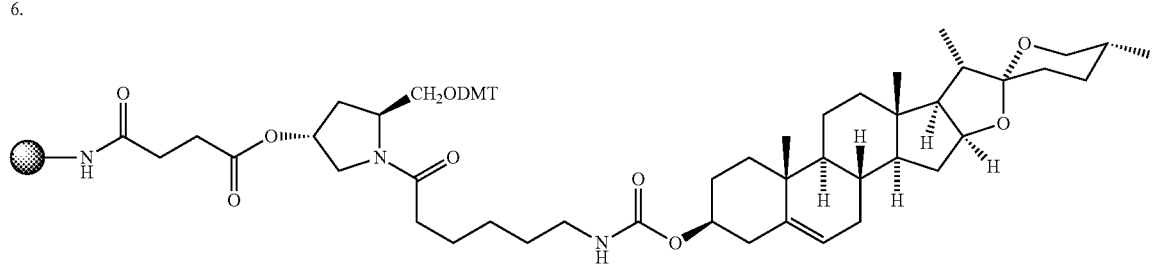
Diosgenin
108

7

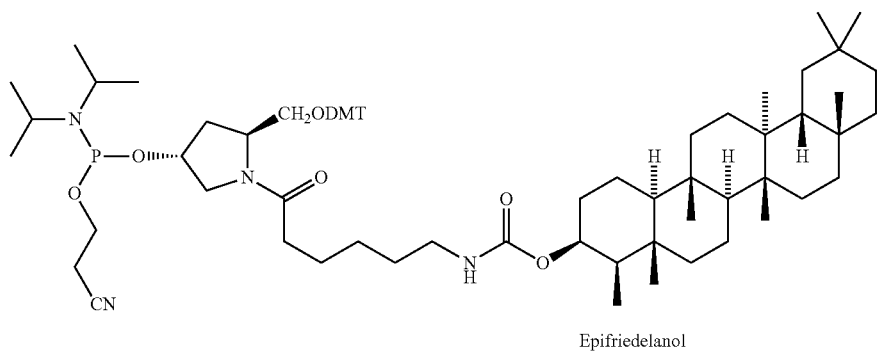

112

Epifriedelanol

8

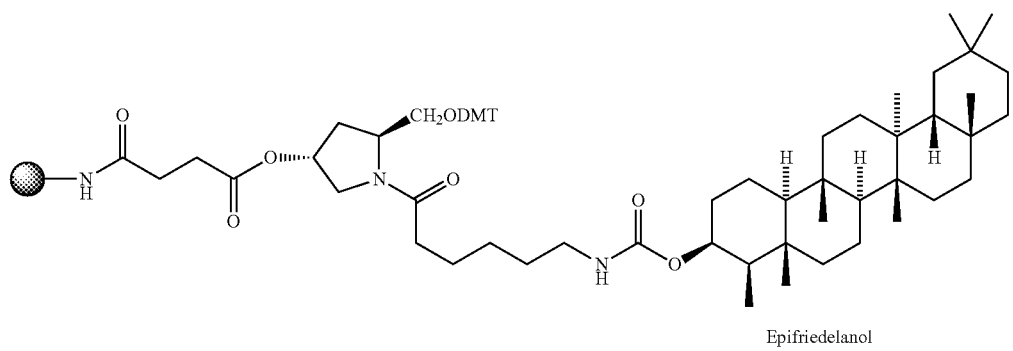

114

Epifriedelanol

Conjugation of Ligands to Oligonucleotide Agents

The conjugation of a ligand to an oligonucleotide agent, e.g., an oligonucleotide agent that targets an miRNA or pre-miRNA can have a favorable effect on the modulating effect of the agent. For example, the agent can improve pharmacokinetics, stability, and/or tissue specificity.

In some embodiments, an oligonucleotide agent (referred to as "NA" in formula OT-I through OT-IV below, e.g., RNA, DNA, chimeric RNA-DNA, DNA-RNA, RNA-DNA-RNA, or DNA-RNA-DNA) can be chemically modified by conjugating a moiety that includes a ligand having one or more chemical linkages for attachment of the ligand (L) to the oligonucleotide or nucleic acid. The ligand of an oligonucleotide agent can be coupled by one or both of a tether and linker. In the diagram below, exemplary chemical linkages are represented as X, Y, and Z. These can be part of the tether or linker.

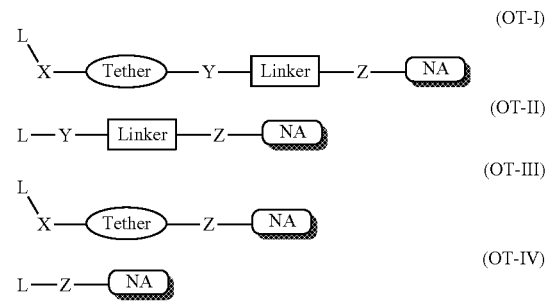

(OT-I)
(OT-II)
(OT-III)
(OT-IV)

Ligands can be attached at one or both of the 3' end, the 5' end, and internal positions. In certain embodiments, the oligonucleotide agent can be chemically modified by conjugating one or more moieties having formula OT-I. Table 3, shows a variety of conjugates.

TABLE 3

TABLE 3-continued

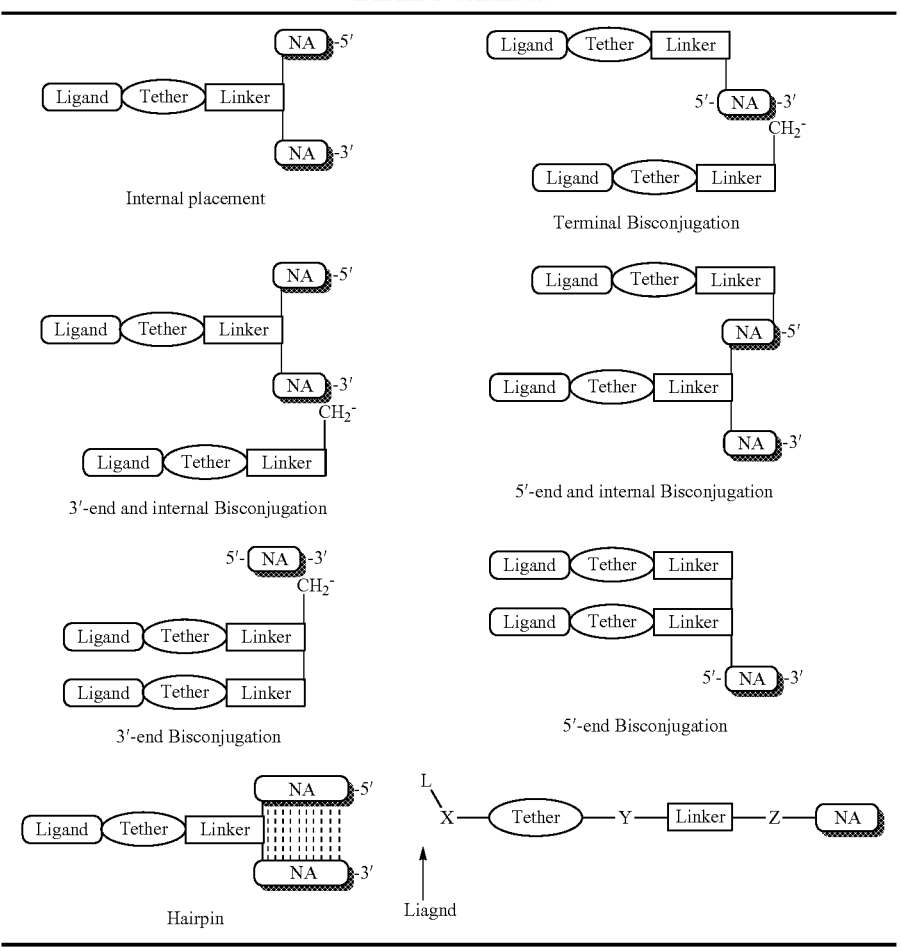

Exemplary ligands are listed in Table 4 and are discussed elsewhere herein. The exemplary ligands (L) shown in Table 4 are preferred.

TABLE 4

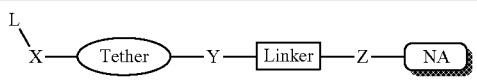

L =
Cholesterol
Thiocholesterol
5β-Cholanic Acid
Cholic acid
Lithocholic acid
Biotin
Vitamin E
Naproxen
Ibuprofen
Amines (mono, di, tri, tetraalkyl or aryl)
Folate
Sugar (N-Acetylgalactosamine, galactosamine, galactose, Mannose)
—$(CH_2)_n NQ_1 Q_2$, where n = 0-40, $Q_1$, $Q_2$ = H, Me or Et; $Q_1$ = H, $Q_2$ = H, Me, Et or aryl
—$(CH_2)_p CH=CH(CH_2)_q NQ_1 Q_2$, where p and/or q = 0-40, $Q_1$, $Q_2$ = H, Me or Et; $Q_1$ = H, $Q_2$ = H, Me, Et or aryl with E and/or Z configuration
—$(CH_2)_p CH\equiv CH(CH_2)_q NQ_1 Q_2$, where p and/or q = 0-40, $Q_1$, $Q_2$ = H, Me or Et; $Q_1$ = H, $Q_2$ = H, Me, Et or aryl
—$(CH_2)_p CH=CH(CH_2)_q CH=CH(CH_2)_r NQ_1 Q_2$, where p, q and/or r = 0-40, $Q_1$, $Q_2$ = H, Me or Et; $Q_1$ = H, $Q_2$ = H, Me, Et or aryl with E and/or Z configuration
—$O(CH_2)_m (OCH_2 CH_2)_n$—OR, where m, n = 0-40 and R=H, Me, $NQ_1 Q_2$, —C(O)NR'R" —C(S)NR'R"
—$NH(CH_2)_m (OCH_2 CH_2)_n$—OR, where m, n = 0-40 and R=H, Me, $NQ_1 Q_2$, —C(O)NR'R" —C(S)NR'R"
—$O(CH_2)_m (NHCH_2 CH_2)_n$—R, where m, n = 0-40 and R=H, OH, Me, $NQ_1 Q_2$, —C(O)NR'R" —C(S)NR'R"

TABLE 4-continued

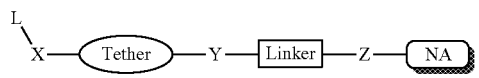

—NH(CH$_2$)$_m$(NHCH$_2$CH$_2$)$_n$—R, where m, n = 0-40 and R=H, OH, Me, NQ$_1$Q$_2$, —C(O)NR'R" —C(S)NR'R"
Dialkylglycerol (sn3, sn1, sn2 and racemic) with number of methylene varies from 0-40
Dlacylglycerol (sn3, sn1, sn2 and racemic) with number of methylene varies from 0-40
Dialkylglycerol (sn3, sn1, sn2 and racemic) with number of methylene varies from 0-40 and the alkyl chian contains one or more double bonds with E and/or Z isomers
Dlacylglycerol (sn3, sn1, sn2 and racemic) with number of methylene varies from 0-40 and the alkyl chian contains one or more double bonds with E and/or Z isomers
Lipids Exemplary X, Y, and Z moieties are shown in Table 5. The X, Y, and Z moieties can be selected independently of one another.

TABLE 5

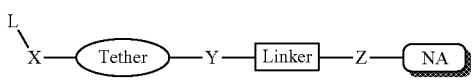

| X = | Y = | Z = |
|---|---|---|
| —NHC(O)— | —NHC(O)— | —NHC(O)— |
| —C(O)NH— | —C(O)NH— | —C(O)NH— |
| —OC(O)NH— | —OC(O)NH— | —OC(O)NH— |
| —NHC(O)O— | —NHC(O)O— | —NHC(O)O— |
| —O— | —O— | —O— |
| —S— | —S— | —S— |
| —SS— | —SS— | —SS— |
| —S(O)— | —S(O)— | —S(O)— |
| —S(O$_2$)— | —S(O$_2$)— | —S(O$_2$)— |
| —NHC(O)NH— | —NHC(O)NH— | —NHC(O)NH— |
| —NHC(S)NH— | —NHC(S)NH— | —NHC(S)NH— |
| —C(O)O— | —C(O)O— | —C(O)O— |
| —OC(O)— | —OC(O)— | —OC(O)— |
| —NHC(S)— | —NHC(S)— | —NHC(S)— |
| —NHC(S)O— | —NHC(S)O— | —NHC(S)O— |
| —C(S)NH— | —C(S)NH— | —C(S)NH— |
| —OC(S)NH— | —OC(S)NH— | —OC(S)NH— |
| —NHC(S)O— | —NHC(S)O— | —NHC(S)O— |
| —CH$_2$— | —CH$_2$— | —CH$_2$— |
| —CH$_2$CH=CH— | —CH$_2$CH=CH— | —CH$_2$CH=CH— |
| —C(O)CH=CH— | —C(O)CH=CH— | —C(O)CH=CH— |
| —NH—CH$_2$CH=CH— | —NH—CH$_2$CH=CH— | —NH—CH$_2$CH=CH— |
| —O—P(O)(OH)—O— | —O—P(O)(OH)—O— | —O—P(O)(OH)—O— |
| —O—P(S)(OH)—O— | —O—P(S)(OH)—O— | —O—P(S)(OH)—O— |
| —O—P(S)(SH)—O— | —O—P(S)(SH)—O— | —O—P(S)(SH)—O— |
| —S—P(O)(OH)—O— | —S—P(O)(OH)—O— | —S—P(O)(OH)—O— |
| —O—P(O)(OH)—S— | —O—P(O)(OH)—S— | —O—P(O)(OH)—S— |
| —S—P(O)(OH)—S— | —S—P(O)(OH)—S— | —S—P(O)(OH)—S— |
| —O—P(S)(OH)—S— | —O—P(S)(OH)—S— | —O—P(S)(OH)—S— |
| —S—P(S)(OH)—O— | —S—P(S)(OH)—O— | —S—P(S)(OH)—O— |
| —O—P(O)(R)—O— | —O—P(O)(R)—O— | —O—P(O)(R)—O— |
| —O—P(S)(R)—O— | —O—P(S)(R)—O— | —O—P(S)(R)—O— |
| —S—P(O)(R)—O— | —S—P(O)(R)—O— | —S—P(O)(R)—O— |
| —S—P(S)(R)—O— | —S—P(S)(R)—O— | —S—P(S)(R)—O— |
| —S—P(O)(R)—S— | —S—P(O)(R)—S— | —S—P(O)(R)—S— |
| —O—P(S)(R)—S— | —O—P(S)(R)—S— | —O—P(S)(R)—S— |

R = Alkyl, fluroalkyl, aryl or aralkyl

Exemplary tethers are shown in Table 7.
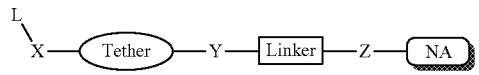
Tether:
—$(CH_2)_n$—, where n = 1-40
—$(CH_2—CH_2O)_n$—, where n = 1-20
—$O(CH_2—CH_2O)_n$—, where n = 1-20
—$(CH_2—CH_2NH)_n$—, where n = 1-20
—$NH(CH_2—CH_2NH)_n$—, where n = 1-20
—$(CH_2)_l[(CH=CH)_m(CH_2)_n]_p(CH=CH)_q(CH_2)_r$—,
where l, m, n, p, q and/or r = 0-20
—$(CH_2)_l[(C≡C)_m(CH_2)n]_p(C≡C)_q(CH_2)_r$—,
where l, m, n, p, q and/or r = 0-20
Linker =
3'-end     5'-end     interior
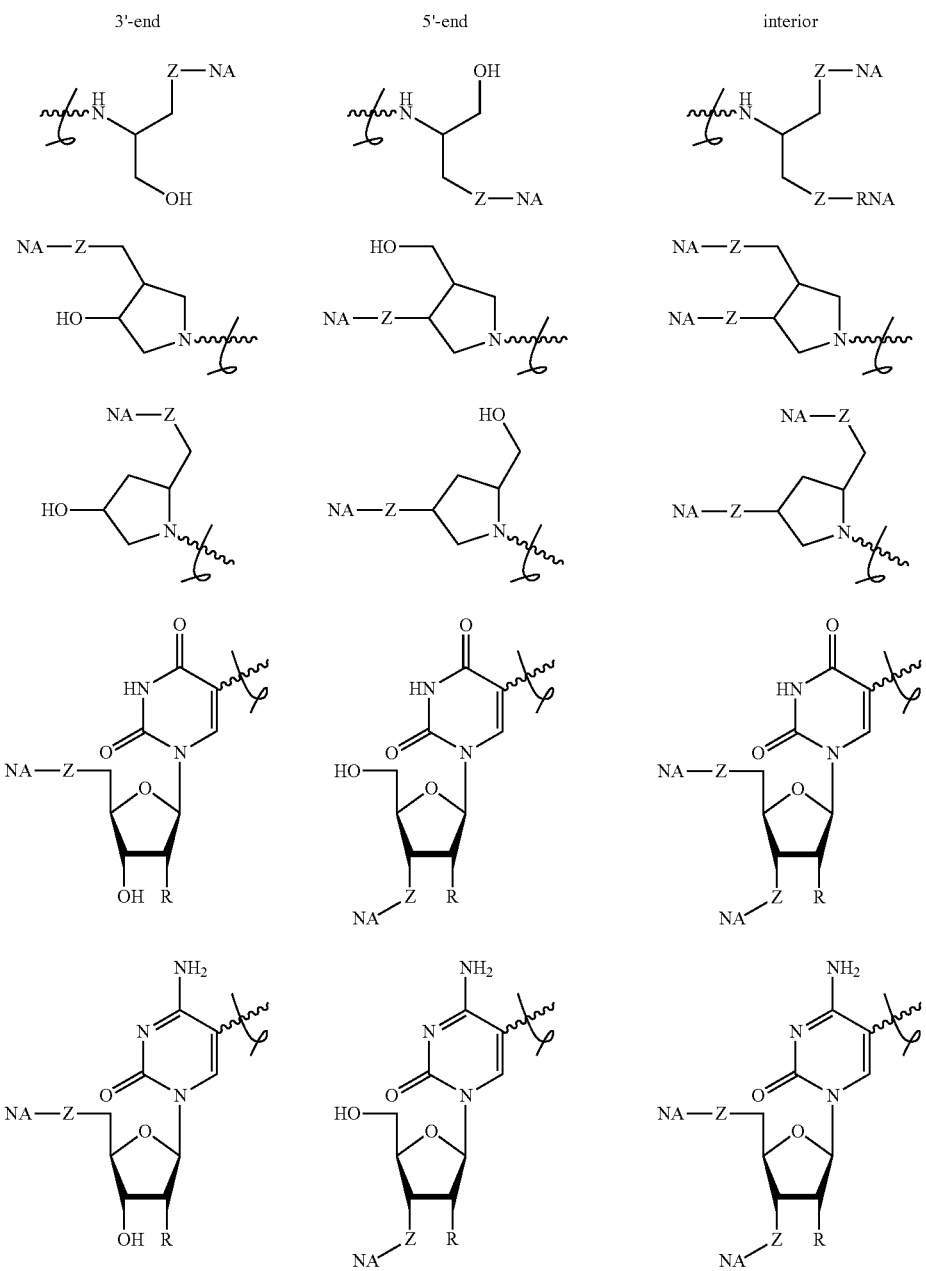

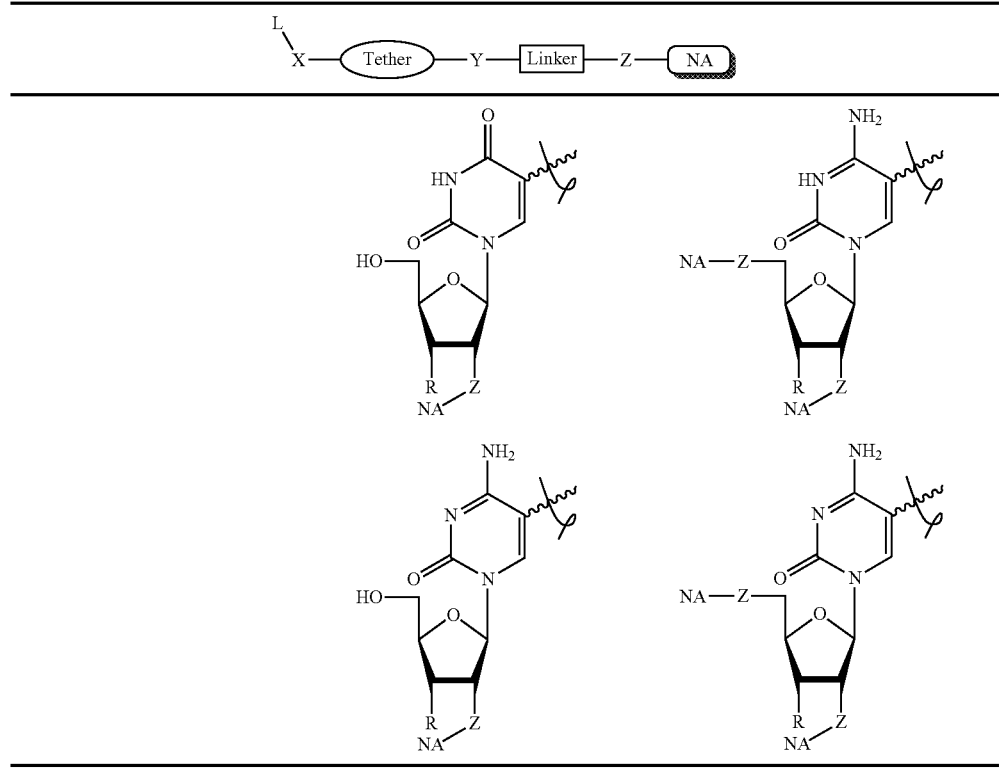

Compounds described herein can be prepared by methods described herein or by conventional methods from commercially available reagents and starting materials.

Compound 1 is prepared as reported by Fraser et al. (Tetrahedron Lett. 41:1523, 2000). Steps (ii), (iii) (a), (iii) (c), (iv), (v) and (vii) are performed according to literature procedure (Fraser et al., Tetrahedron Lett. 41:1523, 2000). Step (iii) (b) and (v) (b) are performed as reported in the literature (Bioorg. Med. Chem. Lett. 13:1713, 2003). Step (iv) is performed as reported in the literature (Corey and Venkateswarlu, J. Am. Chem. Soc. 94:6190, 1972).

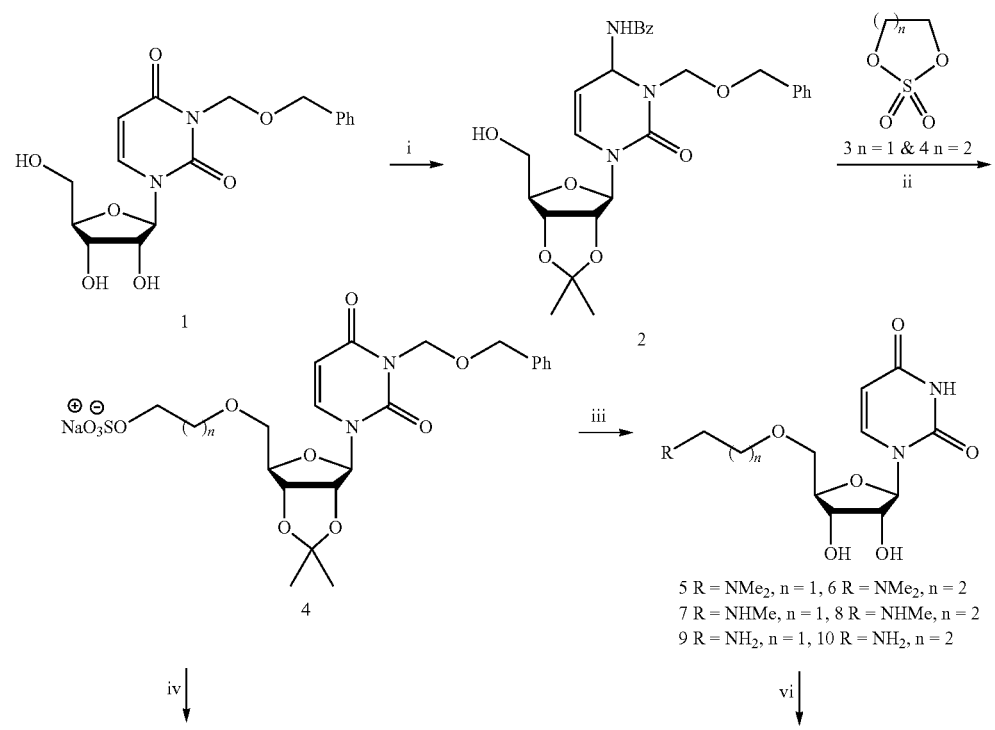

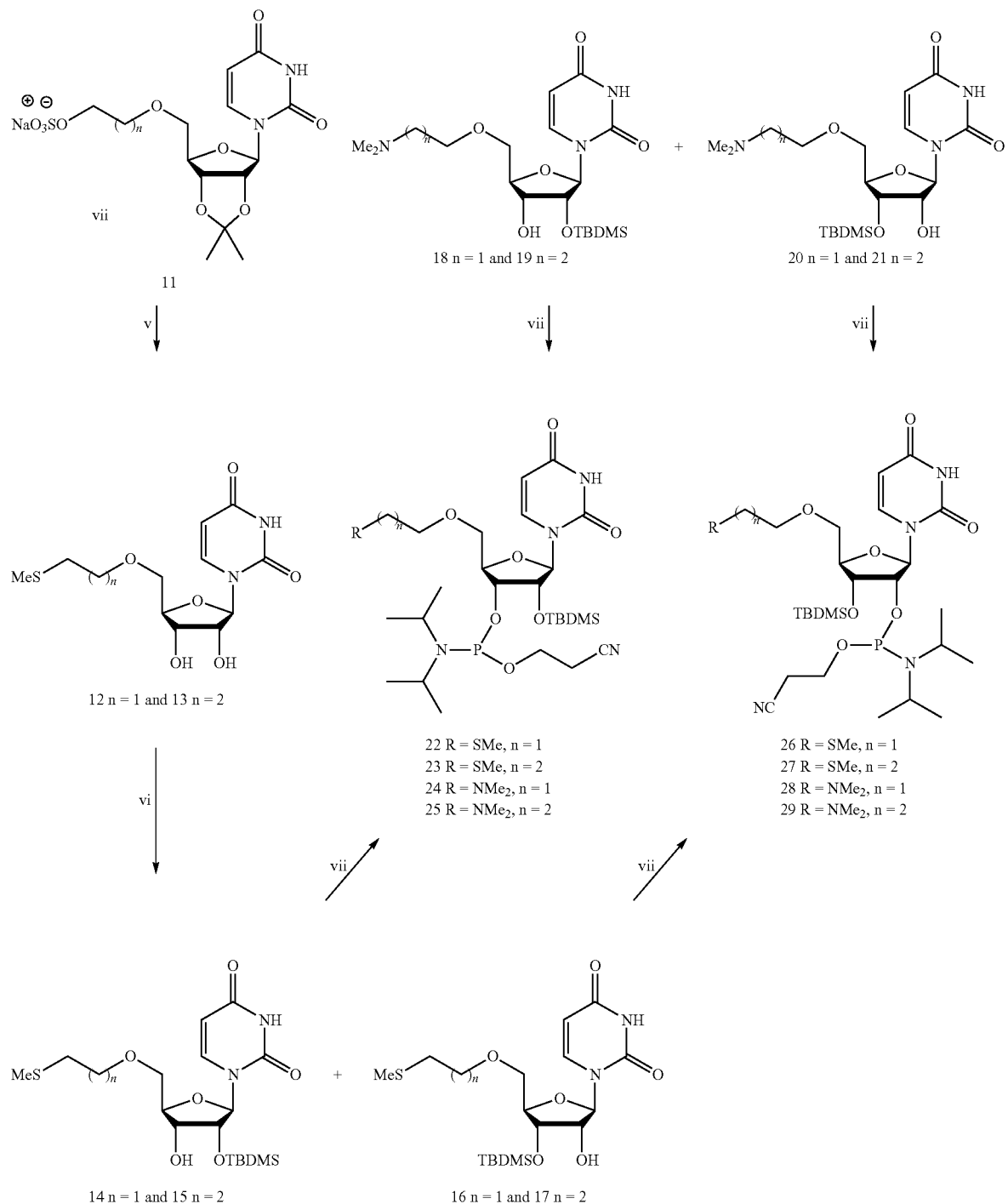

a(i) 2,2-Di-O-methylpropane, PTSA; (ii) NaH/DMF, 3 or 4, -45° C. to rt; (iii) (a) NH3, NH2Me or NHMe2, THF, autoclave, (b) HCOOH—H2O and (c) Pd(OH), EtOH, AcOH, H2 at 55 psi; (iv) Pd(OH), EtOH, AcOH, H2 at 55 psi; (v) NaSMe/DMF, 80° C. and (b) HCOOH—H2O (vi) TBDMS—Cl, Imidazole/Py; (vii) diisopropylamine tetrazolide, 2-cyanoethyl-N,N,N′,N′-tetraisopropylphosphoramidite/CH2Cl2

The synthesis of certain compounds is described in scheme 2, below. Step (i) is performed as reported in Dubowchik and Radia (Tetrahedron Lett., 38:5257, 1997); step (ii) is performed as reported in Corey and Venkateswarlu (J. Am. Chem. Soc. 94:6190, 1972); step (iii) is performed as reported in Fraser et al. (Tetrahedron Lett. 41:1523, 2000) and step (iv) is performed as described in Miller et al. (Current Protocol in Nucleic Acids Chemistry, 2000, 2.5.1-2.5.36, John Wiley and Sons, Inc.).

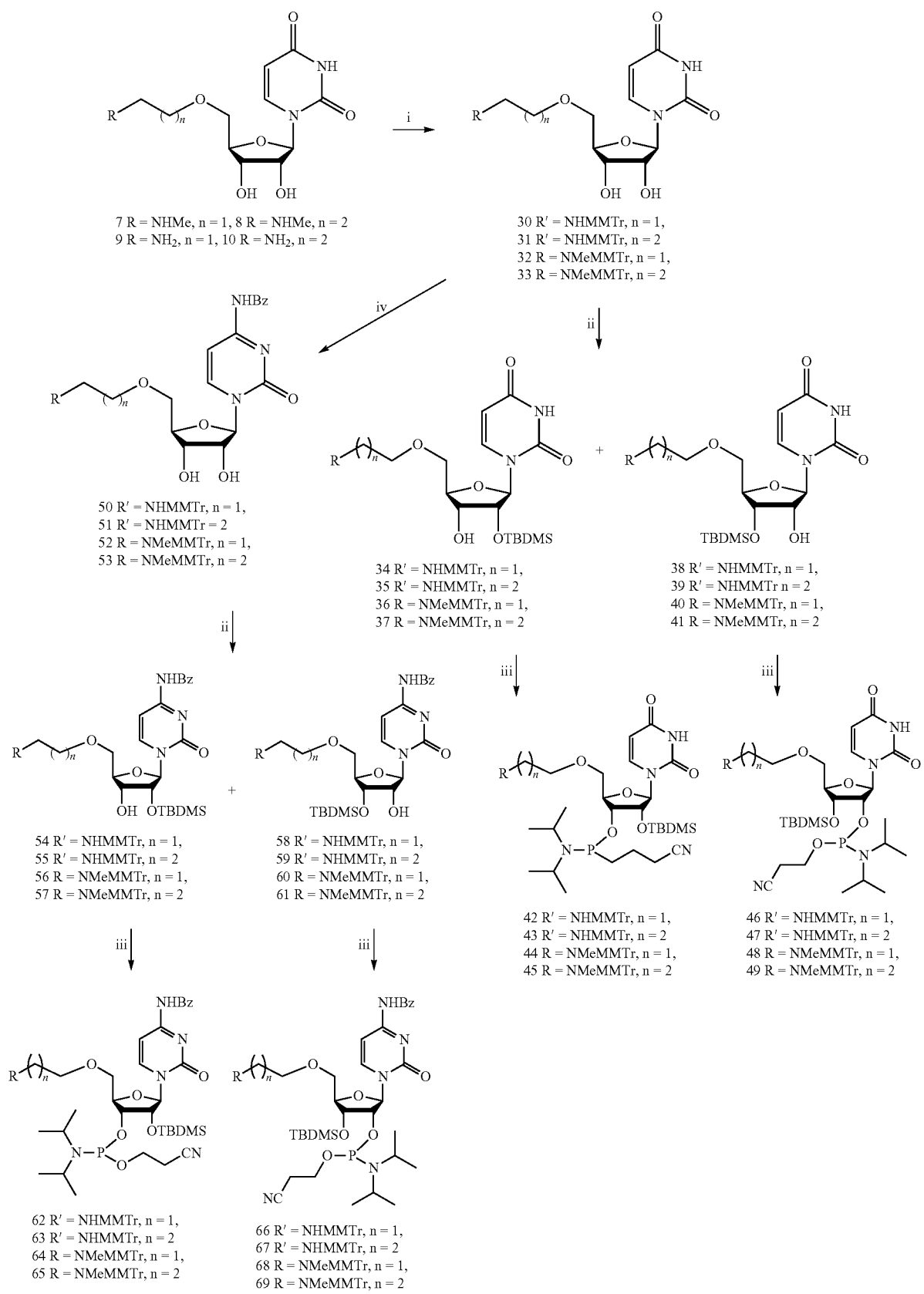
Scheme 2[a]
[a] (i) MMTr—Cl, TEA/CH₂Cl₂; (ii) TBDMS—Cl, Imidazole/Py; (iii) diisopropylamine tetrazolide, 2-cyanoethyl-N,N,N',N',-tetraisopropylphosphoramidite/CH₂Cl₂; (iv) (a) Ac₂O/Py, (b) Triazole, TEA, 4-chlorophenyl dichlorophosphate/MeCN, (c) NH₄OH and (d) Pentaflurophenyl benzoate/Py The synthesis of certain compounds is performed as described in Scheme 3, below. Step (i) is performed as described in Miller et al. (Current Protocol in Nucleic Acids Chemistry, 2000, 2.5.1-2.5.36, John Wiley and Sons, Inc.); step (ii) is performed as reported in the Corey and Venkateswarlu (J. Am. Chem. Soc. 94:6190, 1972) and step (iii) is performed as reported by Fraser et al. (Tetrahedron Lett. 41:1523, 2000).

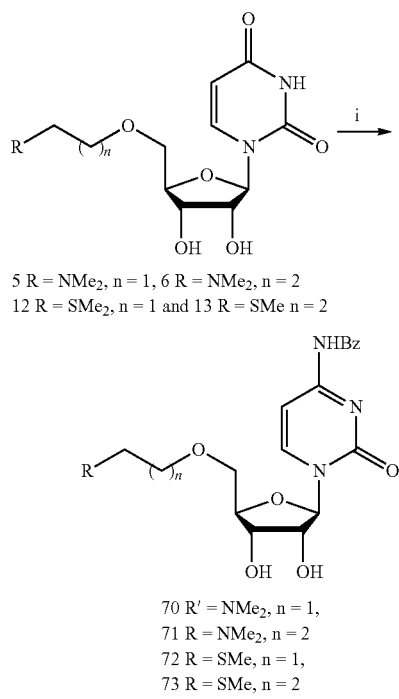

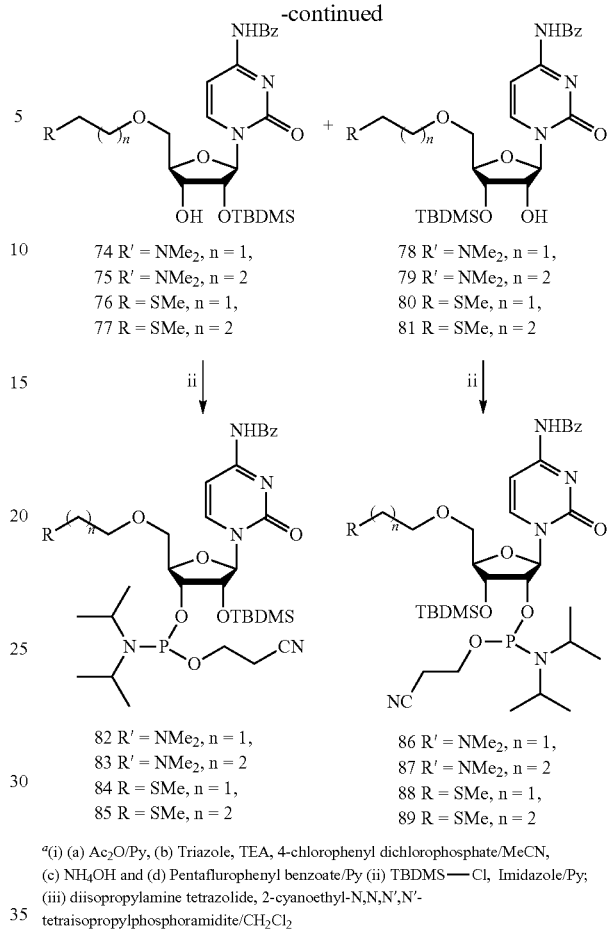

$^a$(i) (a) Ac$_2$O/Py, (b) Triazole, TEA, 4-chlorophenyl dichlorophosphate/MeCN, (c) NH$_4$OH and (d) Pentaflurophenyl benzoate/Py (ii) TBDMS—Cl, Imidazole/Py; (iii) diisopropylamine tetrazolide, 2-cyanoethyl-N,N,N′,N′-tetraisopropylphosphoramidite/CH$_2$Cl$_2$ The synthesis of certain compounds is performed as described in Scheme 4 below. Step (ii) is performed as reported in Corey and Venkateswarlu (J. Am. Chem. Soc. 94:6190, 1972) and step (iii) is performed as reported by Fraser et al. (Tetrahedron Lett. 41:1523, 2000).

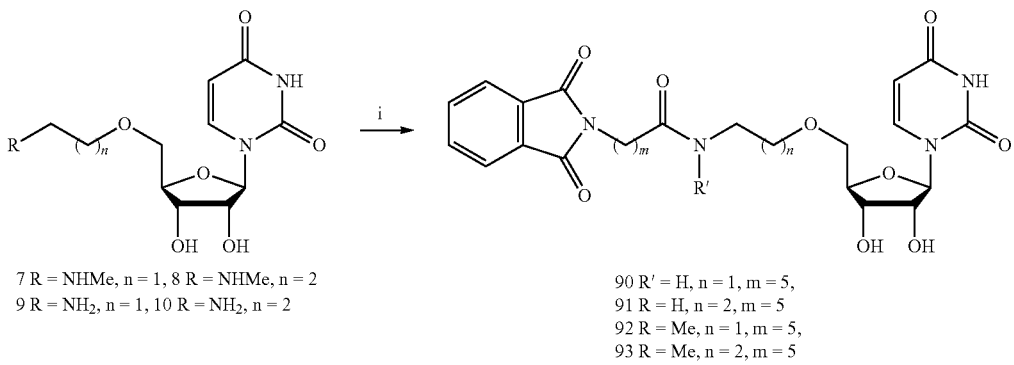

-continued

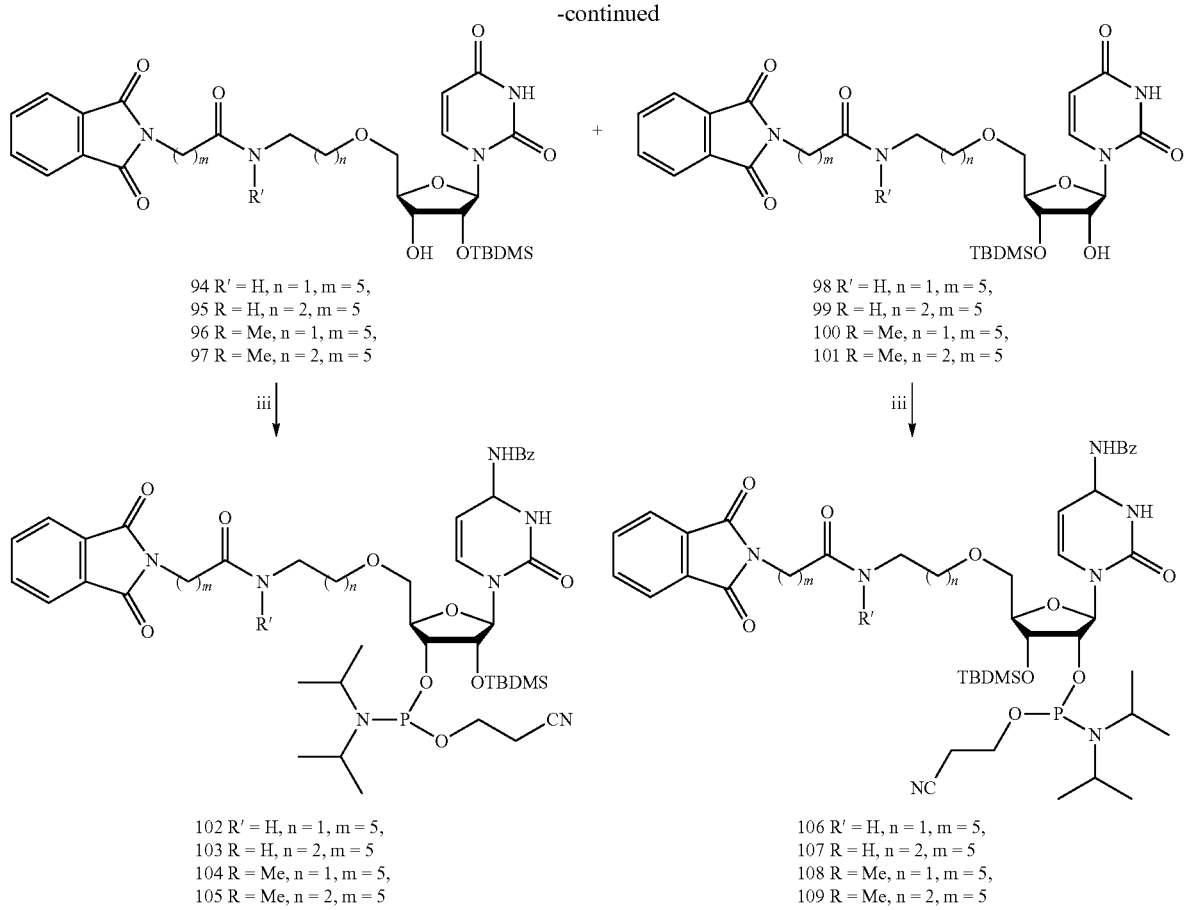

94 R' = H, n = 1, m = 5,
95 R = H, n = 2, m = 5
96 R = Me, n = 1, m = 5,
97 R = Me, n = 2, m = 5

98 R' = H, n = 1, m = 5,
99 R = H, n = 2, m = 5
100 R = Me, n = 1, m = 5,
101 R = Me, n = 2, m = 5

102 R' = H, n = 1, m = 5,
103 R = H, n = 2, m = 5
104 R = Me, n = 1, m = 5,
105 R = Me, n = 2, m = 5

106 R' = H, n = 1, m = 5,
107 R = H, n = 2, m = 5
108 R = Me, n = 1, m = 5,
109 R = Me, n = 2, m = 5

$^a$(i) N-Phthalimido-6-aminocaproic acid, DCC, DMAP, HOBT; (ii) TBDMS-Cl, Imidazole/Py; (iii) diisopropylamine tetrazolide, 2-cyanoethyl-N,N,N',N'-tetraisopropylphosphoramidite/CH$_2$Cl$_2$ The synthesis of certain compounds is described in Scheme 5, below. Step (i) is performed as described in Miller et al. (Current Protocol in Nucleic Acids Chemistry, 2000, 2.5.1-2.5.36, John Wiley and Sons, Inc.); step (ii) is performed as described in Corey and Venkateswarlu (J. Am. Chem. Soc. 94:6190, 1972) and step (iii) is performed as reported by Fraser et al. (Tetrahedron Lett. 41:1523, 2000).

Scheme 5$^a$

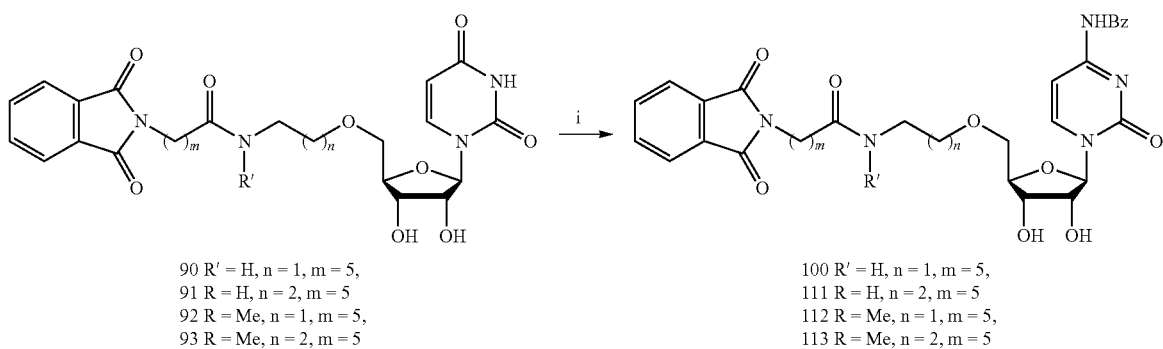

90 R' = H, n = 1, m = 5,
91 R = H, n = 2, m = 5
92 R = Me, n = 1, m = 5,
93 R = Me, n = 2, m = 5

100 R' = H, n = 1, m = 5,
111 R = H, n = 2, m = 5
112 R = Me, n = 1, m = 5,
113 R = Me, n = 2, m = 5

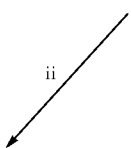

-continued

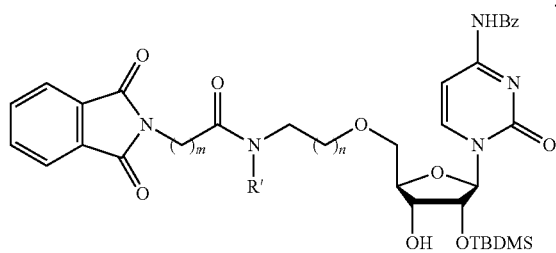

114 R' = H, n = 1, m = 5,
115 R = H, n = 2, m = 5
116 R = Me, n = 1, m = 5,
117 R = Me, n = 2, m = 5

118 R' = H, n = 1, m = 5,
119 R = H, n = 2, m = 5
120 R = Me, n = 1, m = 5,
121 R = Me, n = 2, m = 5

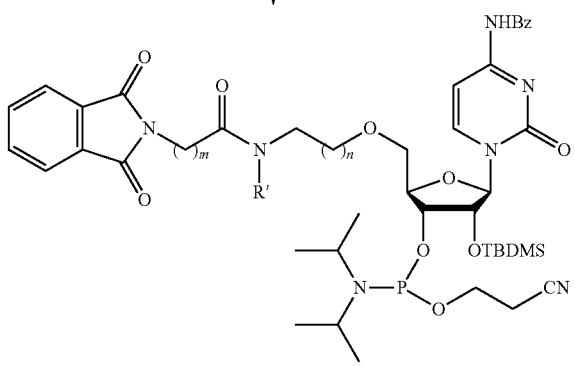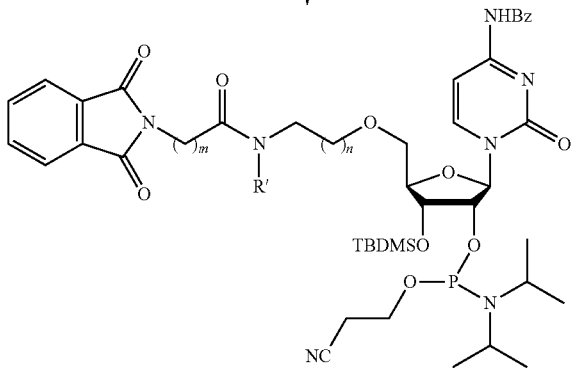

122 R' = H, n = 1, m = 5,
123 R = H, n = 2, m = 5
124 R = Me, n = 1, m = 5,
125 R = Me, n = 2, m = 5

126 R' = H, n = 1, m = 5,
127 R = H, n = 2, m = 5
128 R = Me, n = 1, m = 5,
129 R = Me, n = 2, m = 5

$^a$(i) (a) Ac$_2$O/Py, (b) Triazole, TEA, 4-chlorophenyl dichlorophosphate/MeCN, (c) NH$_4$OH and (d) Pentaflurophenyl benzoate/Py (ii) TBDMS-Cl, Imidazole/Py; (iii) diisopropylamine tetrazolide, 2-cyanoethyl-N,N,N',N'-tetraisopropylphosphoramidite/CH$_2$Cl$_2$ The synthesis of certain compounds is described in Scheme 6, below. Compound 130, shown in Scheme 6, is obtained as reported in Liu and Austin, J. Org. Chem. 66:8643, 2001). Step (i) and (iii) (b) are performed as reported in the literature (Chem. Rev., 1954, 54, 1); step (ii) (a) is performed according to literature procedures (J. Org. Chem., 1993, 58, 2334); step (ii) (b), (iii) (a) and (iv) (b) are performed as reported in the literature (Bioorg. Med. Chem. Lett., 2003, 13, 1713); step (iii) (c) is performed as reported in Dubowchik and Radia (Tetrahedron Lett. 38:5257, 1997); step (iv) (a) is performed as reported in the literature (Organic Lett., 2001, 3, 1809); step (v) is performed as reported in Corey and Venkateswarlu (J. Am. Chem. Soc. 94:6190, 1972) and step (vi) is performed as reported by Fraser et al. (Tetrahedron Lett. 41:1523, 2000).

Scheme 6$^a$

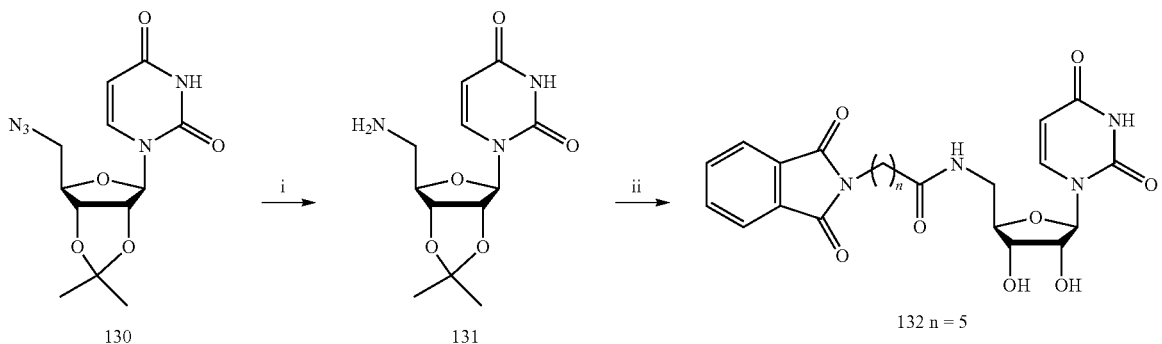

130    131    132 n = 5

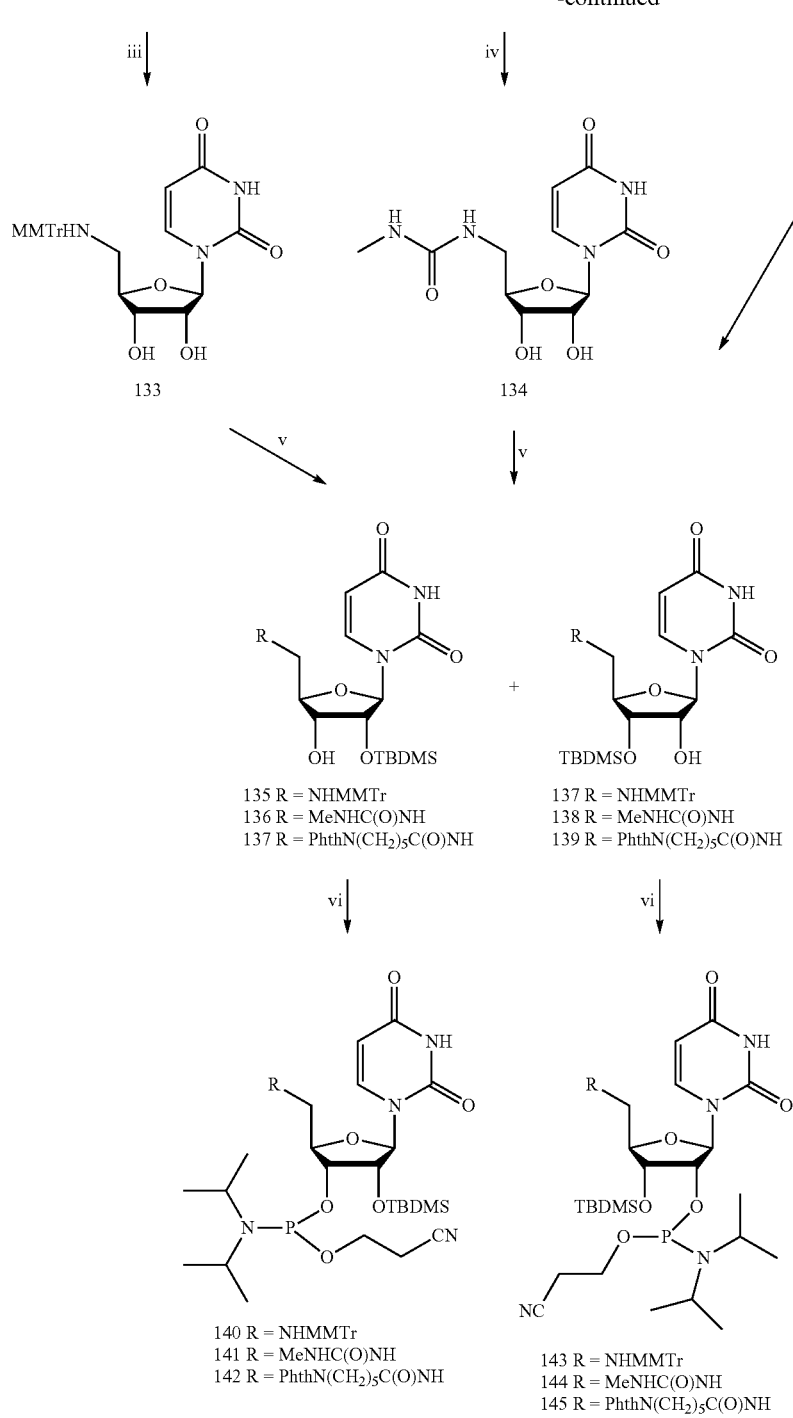

<sup>a</sup> (i) H₂, Pd—C (10%)/MeOH 1 atm; (ii) (a) N-Phthalimido-6-aminocaproic acid, DCC, DMAP, HOBT and (b) HCOOH—H₂O; (iii) (a) HCOOH—H₂O, (b) H₂ Pd—C (10%)/MeOH 1 atm and (c) MMTr—Cl, TEA/CH₂Cl₂; (iv) (a) CDI (carbonyldiimidazole)/THF, MeNH₂ or p-Nitrophenylchloroformate, DMAP/Py, MeNH₂ and (b) HCOOH—H₂O (v) TBDMS—Cl, Imidazole/Py; (vi) diisopropylamine tetrazolide, 2-cyanoethyl-N,N,N',N'-tetraisopropylphosphoramidite/CH₂Cl₂

The synthesis of certain compounds is described in Scheme 7, below. Compound 146 is obtained as reported in Liu and Austin (J. Org. Chem., 2001, 66, 8643). Step (i) (b) and (iii) (c) are performed as reported in the literature (Chem. Rev., 1954, 54, 1); step (ii) (a) is performed according to literature procedures (J. Org. Chem., 1993, 58, 2334); step (ii) (b), (iii) (b) and (iv) (b) are performed as reported in the literature (Bioorg. Med. Chem. Lett., 2003, 13, 1713); step (iii) (d) is performed as reported in Dubowchik and Radia (Tetrahedron Lett., 1997, 38, 5257); step (iv) (a) is performed as reported in the literature (Organic Lett., 2001, 3, 1809); step (v) is performed as reported in Corey and Venkateswarlu (J. Am. Chem. Soc., 1972, 94, 6190) and step (vi) is performed as reported by Fraser et al. (Tetrahedron Lett., 2000, 41, 1523)

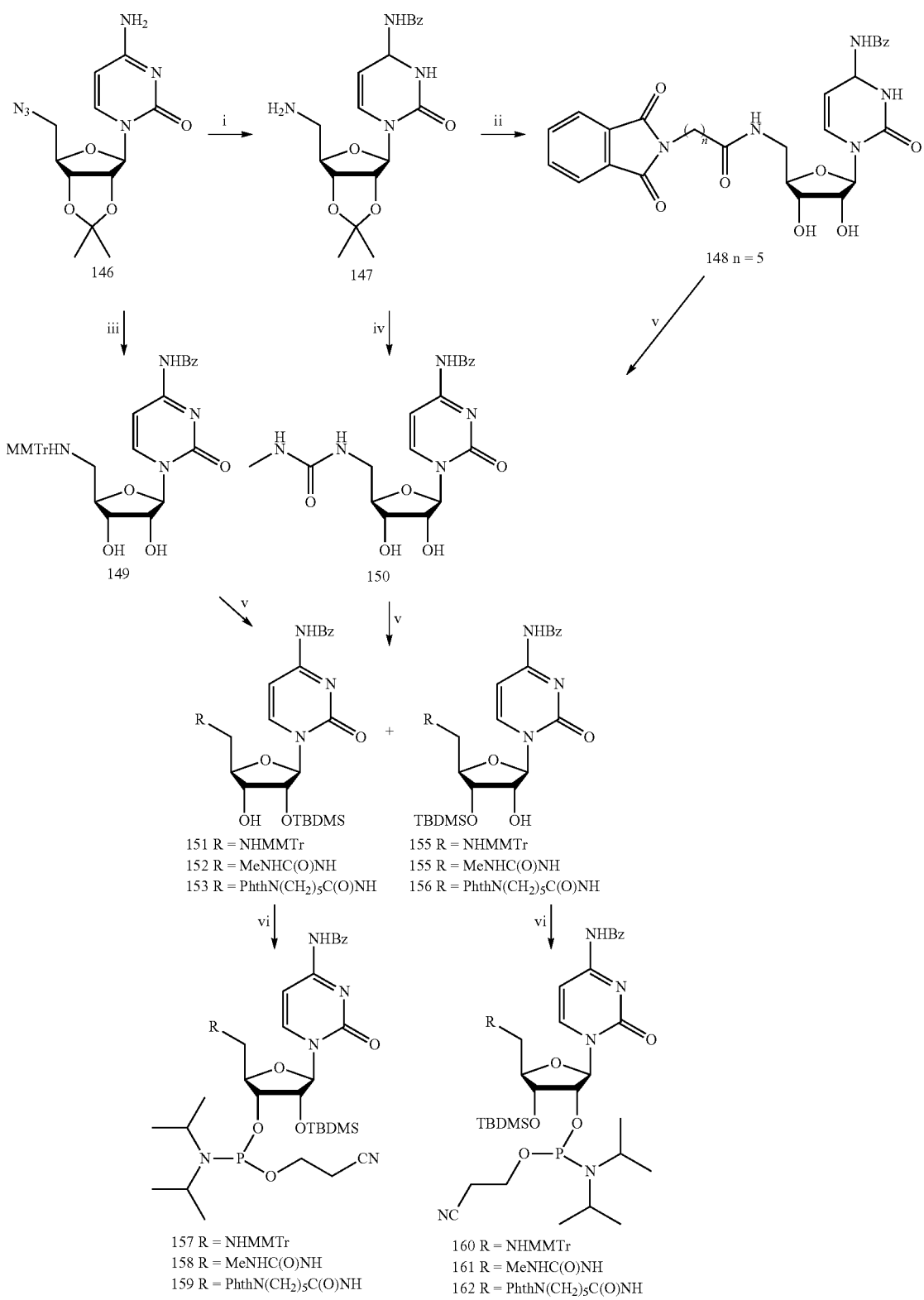

Scheme 7[a]

[a](i) (a) Bz₂O/Py and (b) H₂, Pd-C (10%)/MeOH 1 atm; (ii) (a) N-Phthalimido-6-aminocaproic acid, DCC, DMAP, HOBT and (b) HCOOH-H₂O; (iii) (a) Bz₂O/Py, (b) HCOOH-H₂O, (c) H₂, Pd-C (10%)/MeOH 1 atm and (d) MMTr-Cl/Py; (iv) (a) CDI (carbonyldiimidazole)/THF, MeNH₂ or p-Nitrophenylchloroformate, DMAP/Py, MeNH₂ and (b) HCOOH-H₂O (v) TBDMS-Cl, Imidazole/Py; (vi) diisopropylamine tetrazolide, 2-cyanoethyl-N,N,N′,N′-tetraisopropylphosphoramidite/CH₂Cl₂

The synthesis of certain compounds is described in Scheme 8, below. Compound 163 is obtained as reported in Liu and Austin (J. Org. Chem., 2001, 66, 8643).
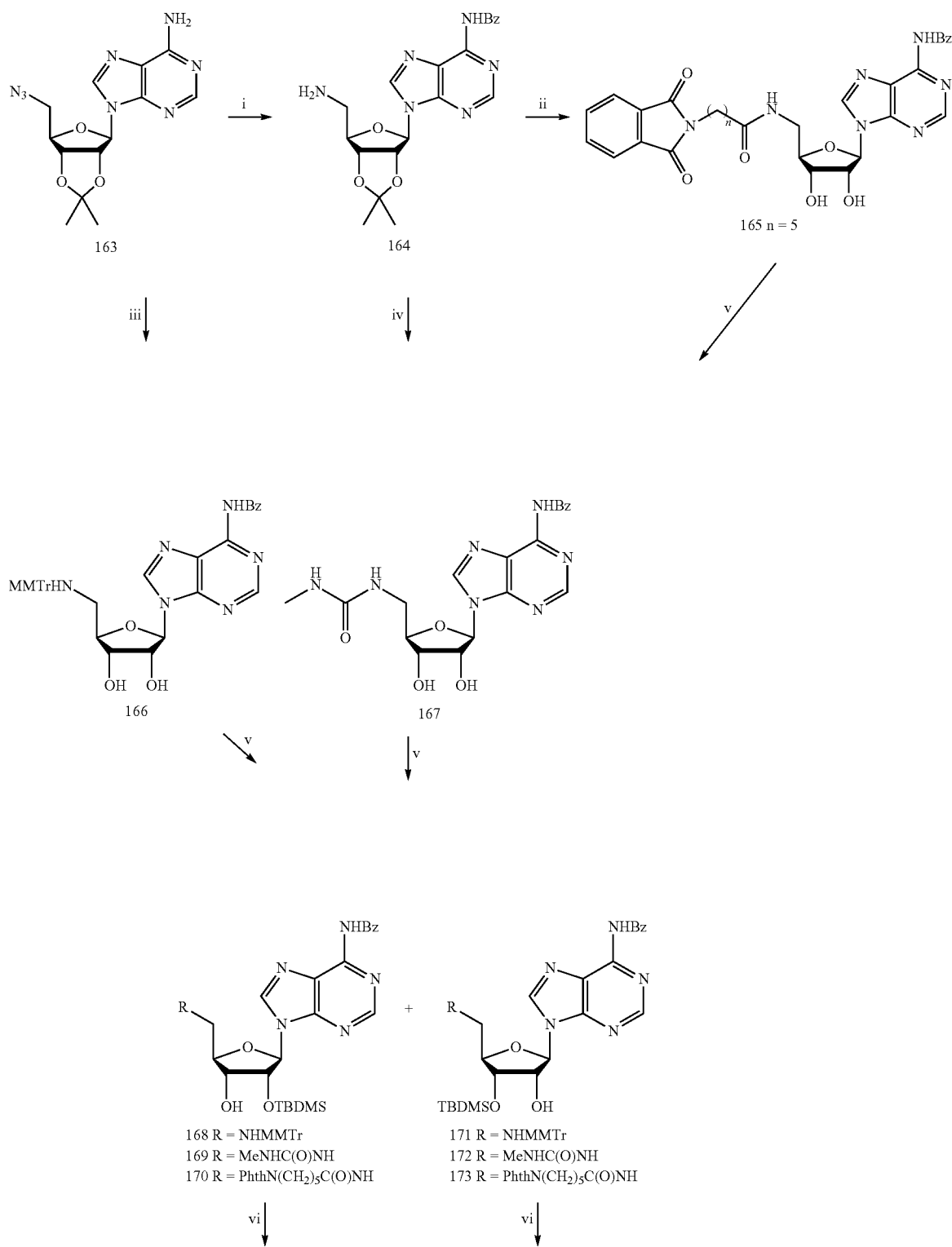

-continued

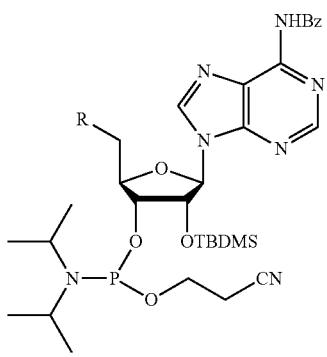

174 R = NHMMTr
175 R = MeNHC(O)NH
176 R = PhthN(CH$_2$)$_5$C(O)NH

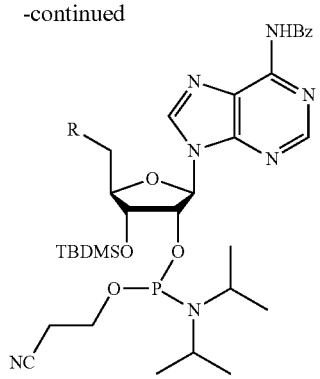

177 R = NHMMTr
178 R = MeNHC(O)NH
179 R = PhthN(CH$_2$)$_5$C(O)NH $^a$(i) (a) Bz$_2$O/Py and (b) H$_2$, Pd-C (10%)/MeOH 1 atm; (ii) (a) N-Phthalimido-6-aminocaproic acid, DCC, DMAP, HOBT and (b) HCOOH-H$_2$O; (iii) (a) Bz$_2$O/Py, (b) HCOOH-H$_2$O, (c) H$_2$, Pd-C (10%)/MeOH 1 atm and (d) MMTr-Cl/Py; (iv) (a) CDI (carbonyldiimidazole)/THF, MeNH$_2$ or p-Nitrophenylchloroformate, DMAP/Py, MeNH$_2$ and (b) HCOOH-H$_2$O (v) TBDMS-Cl, Imidazole/Py; (vi) diisopropylamine tetrazolide, 2-cyanoethyl-N,N,N′,N′-tetraisopropylphosphoramidite/CH$_2$Cl$_2$ The synthesis of certain compounds is described in Scheme 9, below. Compound 180 is obtained as reported in Liu and Austin (J. Org. Chem., 2001, 66, 8643).

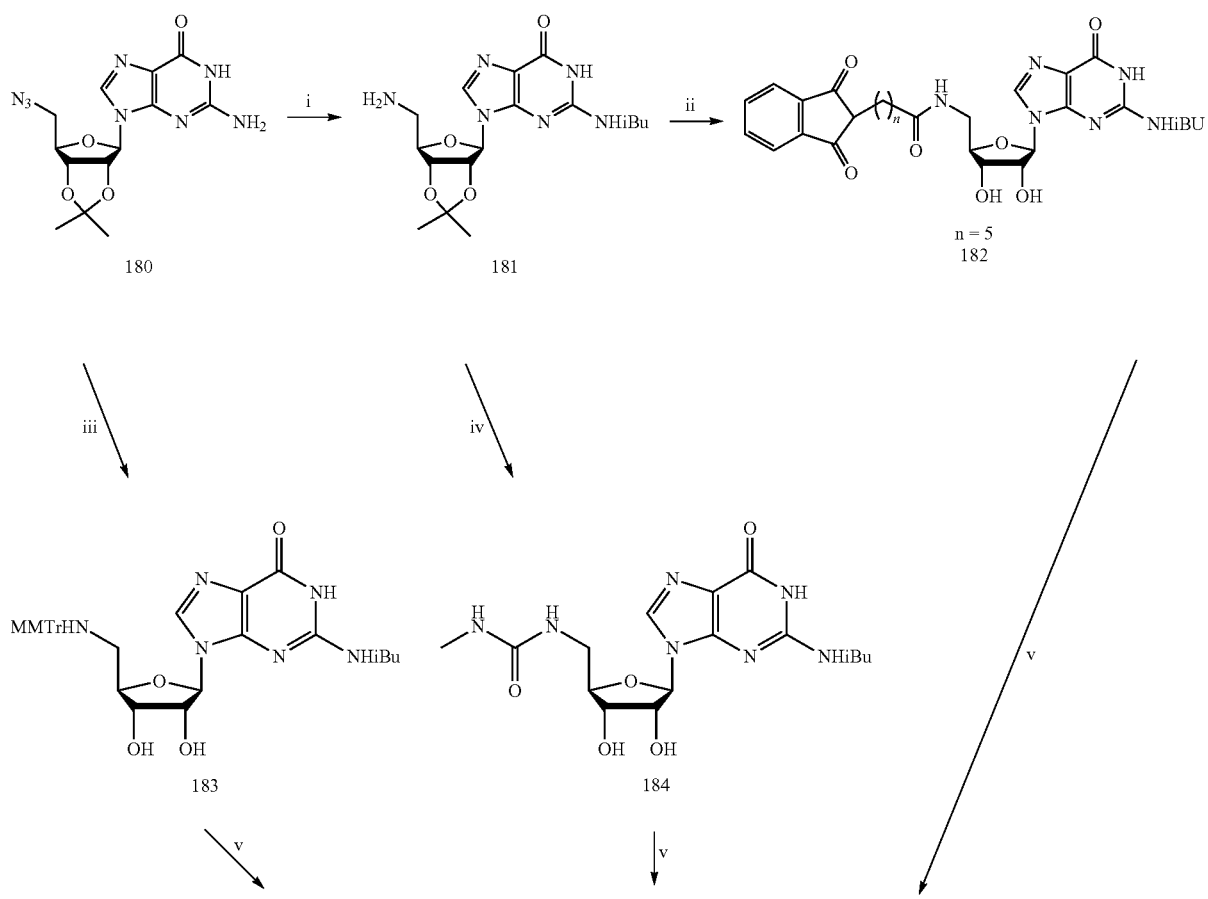

-continued

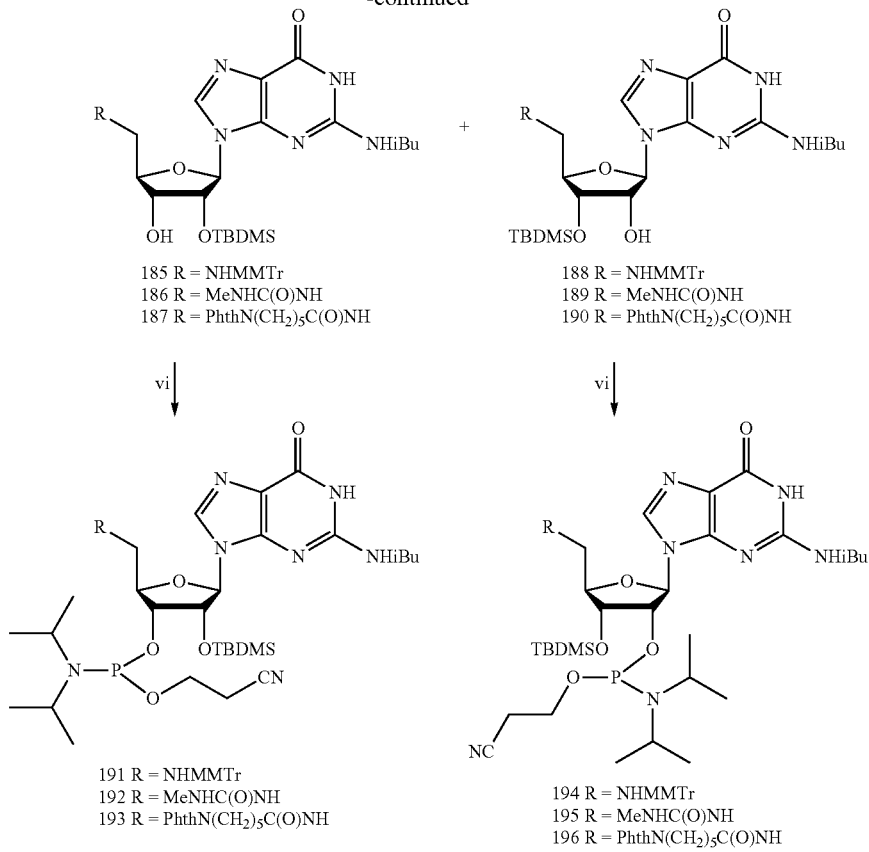

185 R = NHMMTr
186 R = MeNHC(O)NH
187 R = PhthN(CH$_2$)$_5$C(O)NH

188 R = NHMMTr
189 R = MeNHC(O)NH
190 R = PhthN(CH$_2$)$_5$C(O)NH

191 R = NHMMTr
192 R = MeNHC(O)NH
193 R = PhthN(CH$_2$)$_5$C(O)NH

194 R = NHMMTr
195 R = MeNHC(O)NH
196 R = PhthN(CH$_2$)$_5$C(O)NH $^a$ (i) (a) iBuCOCl/Py and (b) H$_2$, Pd—C (10%)/MeOH 1 atm; (ii) (a) N-Phthalimido-6-aminocaproic acid, DCC, DMAP, HOBT and (b) HCOOH—H$_2$O; (iii) (a) iBuCOCl/Py, (b) HCOOH—H$_2$O; (c) H$_2$, Pd—C (10%)/MeOH 1 atm and (d) MMTr—Cl/Py; (iv) (a) CDI (carbonyldiimidazole)/THF, MeNH$_2$ or p-Nitrophenylchloroformate, DMAP/Py, MeNH$_2$ and (b) HCOOH—H$_2$O (v) TBDMS—Cl, Imidazole/Py; (vi) diisopropylamine tetrazolide, 2-cyanoethyl-N,N,N′,N′-tetraisopropylphosphoramidite/CH$_2$Cl$_2$ Targeting The oligonucleotide agents featured in the invention, e.g., oligonucleotide agents that target miRNAs or pre-miRNAs, can be targeted to particular tissues or cell types. For example, an oligonucleotide agent can be targeted to the liver, kidney, a cell of the nervous system, or a muscle cell. For targeting to the liver, for example, an oligonucleotide agent can include an SRMS containing a ligand that targets the liver, e.g., a lipophilic moiety. Lipophilic moieties include lipid, cholesterols, oleyl, retinyl, or cholesteryl residues. Other lipophilic moieties that can function as liver-targeting agents include cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. An oligonucleotide agent can also be targeted to the liver by association with a low-density lipoprotein (LDL), such as lactosylated LDL. Polymeric carriers complexed with sugar residues can also function to target oligonucleotide agents to the liver.

Conjugation of an oligonucleotide agent with a serum albumin (SA), such as human serum albumin, can also be used to target the oligonucleotide agent to a non-kidney tissue.

An oligonucleotide agent targeted to a tissue by an SRMS targeting moiety described herein can target a gene expressed in the tissue. For example, an oligonucleotide agent targeted to the liver, can target p21(WAF1/DIP1), P27(KIP1), beta-catenin, or c-MET, such as for treating a cancer of the liver. In another embodiment, the oligonucleotide agent can target apoB-100, such as for the treatment of an HDL/LDL cholesterol imbalance; dyslipidemias, e.g., familial combined hyperlipidemia (FCHL), or acquired hyperlipidemia; hypercholesterolemia; statin-resistant hypercholesterolemia; coronary artery disease (CAD); coronary heart disease (CHD); or atherosclerosis.

A targeting agent that incorporates a sugar, e.g., galactose and/or analogues thereof, can be useful. These agents target, for example, the parenchymal cells of the liver. For example, a targeting moiety can include more than one or preferably two or three galactose moieties, spaced about 15 angstroms from each other. The targeting moiety can alternatively be lactose (e.g., three lactose moieties), which is glucose coupled to a galactose. The targeting moiety can also be N-Acetyl-Galactosamine, N-Ac-Glucosamine. A mannose or mannose-6-phosphate targeting moiety can be used for macrophage targeting.

The oligonucleotide agents of the invention can also be targeted to the kidney, e.g., by incorporation of an SRMS containing a ligand that targets the kidney.

An oligonucleotide agent targeted to the kidney by an SRMS targeting moiety described herein can target a gene expressed in the kidney.

Ligands on SRMSs can include folic acid, glucose, cholesterol, cholic acid, Vitamin E, Vitamin K, or Vitamin A.

Conjugation with Ligands to Promote Entry into Cells

Oligonucleotide agents, such as an miRNA oligonucleotide agents targeting miRNAs or pre-miRNAs, can be modified so as to enhance entry into cells, e.g., an endocytic or non-endocytic mechanism. A ligand that increases cell permeability can be attached to an oligonucleotide agent in a number of ways, such as by attachment to an SRMS, e.g., pyrroline-based SRMS.

In one embodiment, an oligonucleotide can be conjugated to a polyarginine that will enhance uptake into a wide range of cell-types. While not being bound by theory, the enhanced uptake is believed to be by a nonendocytic route. In another embodiment, an oligonucleotide can be conjugated to a guanidium analog of an aminoglycoside to promote cell permeability.

In another embodiment, an oligonucleotide can be conjugated with a lipophilic moiety. The lipophilic moiety can be attached at the nitrogen atom of a pyrroline-based SRMS. Examples of lipophilic moieties include cholesterols, lipid, oleyl, retinyl, or cholesteryl residues. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine. Cholesterol is a particularly preferred example.

The ligand that enhances cell permeability can be attached at the 3' terminus, the 5'terminus, or internally. The ligand can be attached to an SRMS, e.g., a pyrroline-based SRMS at the 3' terminus, the 5'terminus, or at an internal linkage. The attachment can be direct or through a tethering molecule. Tethers, spacers or linkers discussed herein can be used to attach the moiety to the SRMS.

An oligonucleotide agent to which one or more cell-permeability ligands is conjugated (called an "OA-cell permeability conjugate") can be delivered in vivo, e.g., to a cell, such as a cell of a tissue in a subject, such as a mammalian subject (e.g., a human or mouse). Alternatively, or in addition, the oligonucleotide agent can be delivered in vitro, e.g., to a cell in a cell line. Cell lines can be, for example, from a vertebrate organism, such as a mammal (e.g., a human or a mouse). Delivery of an OA-cell permeability conjugate to a cell line can be in the absence of other transfection reagents. For example, delivery of an OA-cell permeability conjugate to a cell can be in the absence of, or optionally, in the presence of, Lipofectamine™ (Invitrogen, Carlsbad, Calif.), Lipofectamine 2000™, TransIT-TKO™ (Mirus, Madison, Wis.), FuGENE 6 (Roche, Indianapolis, Ind.), polyethylenimine, X-tremeGENE Q2 (Roche, Indianapolis, Ind.), DOTAP, DOSPER, or Metafectene™ (Biontex, Munich, Germany), or another transfection reagent. Exemplary cell lines can be provided by the American Type Culture Collection (ATCC) (Manassas, Va.). An OA-cell permeability conjugate can be delivered to a cell line, such as any cell line described herein, to target a specific gene for downregulation.

In one example, an oligonucleotide agent-lipophilic conjugate can be delivered to a primary cell line, e.g., a synoviocyte (such as type B), cardiac myocyte, keratinocyte, hepatocyte, smooth muscle cell, endothelial cell, or dermal fibroblast cell line.

Oligonucleotide Agent Structure

An oligonucleotide agent that is NAT ("nucleic acid targeting") includes a region of sufficient complementarity to the target gene, and is of sufficient length in terms of nucleotides, such that the oligonucleotide agent forms a duplex with the target nucleic acid. The oligonucleotide agent can modulate the function of the targeted molecule. For example, when the targeted molecule is an mRNA or pre-mRNA, the NAT can inhibit gene expression; when the target is an miRNA, the NAT will inhibit the miRNA function and will thus up-regulate expression of the mRNAs targeted by the particular miRNA; when the target is a region of a pre-mRNA the affects splicing, the NAT can alter the choice of splice site and thus the mRNA sequence; when the NAT functions as an miRNA, expression of the targeted mRNA is inhibited. For ease of exposition the term nucleotide or ribonucleotide is sometimes used herein in reference to one or more monomeric subunits of an oligonucleotide agent. It will be understood herein that the usage of the term "ribonucleotide" or "nucleotide" herein can, in the case of a modified RNA or nucleotide surrogate, also refer to a modified nucleotide, or surrogate replacement moiety at one or more positions.

A NAT oligonucleotide agent is, or includes, a region that is at least partially, and in some embodiments fully, complementary to the target RNA. It is not necessary that there be perfect complementarity between the oligonucleotide agent and the target, but the correspondence must be sufficient to enable the oligonucleotide agent, or a cleavage product thereof, to modulate (e.g., inhibit) target gene expression.

An oligonucleotide agent will preferably have one or more of the following properties:

(1) it will be of the Formula 1, 2, 3, or 4 described below;
(2) it will have a 5' modification that includes one or more phosphate groups or one or more analogs of a phosphate group;
(3) it will, despite modifications, even to a very large number of bases specifically base pair and form a duplex structure with a homologous target RNA of sufficient thermodynamic stability to allow modulation of the activity of the targeted RNA;
(4) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, all of the nucleotide sugars can contain e.g., 2'OMe, 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. (Generally, it is preferred that a modified moiety at the 2' sugar position will be able to enter into hydrogen-bonding which is more characteristic of the 2'-OH moiety of a ribonucleotide than the 2'-H moiety of a deoxyribonucleotide. A preferred oligonucleotide agent will: exhibit a $C_{3'}$-endo pucker in all, or at least 50, 75, 80, 85, 90, or 95% of its sugars; exhibit a C$_{3'}$-endo pucker in a sufficient amount of its sugars that it can give rise to a the RNA-characteristic A-family-type helix; will have no more than 20, 10, 5, 4, 3, 2, or 1 sugar which is not a C$_{3'}$-endo pucker structure.

Preferred 2'-modifications with C3'-endo sugar pucker include:

2'-OH, 2'-O-Me, 2'-O-methoxyethyl, 2'-O-aminopropyl, 2'-F, 2'-O—CH2-CO—NHMe, 2'-O—CH2-CH2-O—CH2-CH2-N(Me)2, LNA (5) regardless of the nature of the modification, and even though the oligonucleotide agent can contain deoxynucleotides or modified deoxynucleotides, it is preferred that DNA molecules, or any molecule in which more than 50, 60, or 70% of the nucleotides in the molecule are deoxyribonucleotides, or modified deoxyribonucleotides which are deoxy at the 2' position, are excluded from the definition of oligonucleotide agent.

Preferred 2'-modifications with a C2'-endo sugar pucker include:

2'-H, 2'-Me, 2'-S-Me, 2'-Ethynyl, 2'-ara-F.

Sugar modifications can also include L-sugars and 2'-5'-linked sugars.

As used herein, "specifically hybridizable" and "complementary" are terms that are used to indicate a sufficient degree of complementarity such that stable and specific binding occurs between a compound of the invention and a target RNA molecule in the case of NAT oligonucleotides agents that bind target RNAs. Specific binding requires a sufficient lack of complementarity to non-target sequences under conditions in which specific binding is desired, i.e., under physiological conditions in the case of in vivo assays or therapeutic treatment, or in the case of in vitro assays, under conditions in which the assays are performed. It has been shown that a single mismatch between targeted and non-targeted sequences are sufficient to provide discrimination for siRNA targeting of an mRNA (Brummelkamp et al., *Cancer Cell*, 2002, 2:243).

In one embodiment, a NAT oligonucleotide agent is "sufficiently complementary" to a target RNA, such that the oligonucleotide agent inhibits production of protein encoded by the target mRNA. The target RNA can be, e.g., a pre-mRNA, mRNA, or miRNA endogenous to the subject. In another embodiment, the oligonucleotide agent is "exactly complementary" (excluding the SRMS containing subunit(s)) to a target RNA, e.g., the target RNA and the oligonucleotide agent can anneal to form a hybrid made exclusively of Watson-Crick base pairs in the region of exact complementarity. A "sufficiently complementary" target RNA can include a region (e.g., of at least 7 nucleotides) that is exactly complementary to a target RNA. Moreover, in some embodiments, the oligonucleotide agent specifically discriminates a single-nucleotide difference. In this case, the oligonucleotide agent only down-regulates gene expression if exact complementarity is found in the region the single-nucleotide difference.

Oligonucleotide agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (*Nucleic Acids Res.*, 1994, 22:2183-2196). Such rare or unusual RNAs, often termed modified RNAs, are typically the result of a post transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

As nucleic acids are polymers of subunits or monomers, many of the modifications described below occur at a position which is repeated within a nucleic acid, e.g., a modification of a base, or a phosphate moiety, or a non-linking O of a phosphate moiety. In some cases the modification will occur at all of the subject positions in the nucleic acid but in many, and infact in most cases it will not. By way of example, a modification may only occur at a 3' or 5' terminal position, may only occur in a terminal regions, e.g. at a position on a terminal nucleotide or in the last 2, 3, 4, 5, or 10 nucleotides of a strand. The ligand can be at attached at the 3' end, the 5' end, or at an internal position, or at a combination of these positions. For example, the ligand can be at the 3' end and the 5' end; at the 3' end and at one or more internal positions; at the 5' end and at one or more internal positions; or at the 3' end, the 5' end, and at one or more internal positions. E.g., a phosphorothioate modification at a non-linking O position may only occur at one or both termini, or may only occur in a terminal region, e.g., at a position on a terminal nucleotide or in the last 2, 3, 4, 5, or 10 nucleotides of the oligonucleotide. The 5' end can be phosphorylated.

Modifications and nucleotide surrogates are discussed below.

FORMULA 1

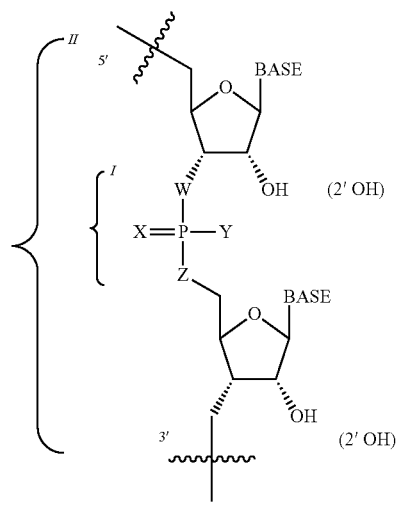

The scaffold presented above in Formula 1 represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula 1 represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, e.g., can render oligoribonucleotides more stable to nucleases. Unmodified oligoribonucleotides may also be less than optimal in terms of offering tethering points for attaching ligands or other moieties to an oligonucleotide agent.

Modified nucleic acids and nucleotide surrogates can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein.);

(ii) alteration, e.g., replacement, of a constituent of the ribose sugar, e.g., of the 2' hydroxyl on the ribose sugar, or wholesale replacement of the ribose sugar with a structure other than ribose, e.g., as described herein;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, e.g. a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid but rather modified simply indicates a difference from a naturally occurring molecule.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Specific modifications are discussed in more detail below.

The Phosphate Group

The phosphate group is a negatively charged species. The charge is distributed equally over the two non-linking oxygen atoms (i.e., X and Y in Formula 1 above). However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of X or Y is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both X and Y which eliminate the chiral center, e.g. phosphorodithioate formation, may be desirable in that they cannot produce diastereomer mixtures. Thus, X can be any one of S, Se, B, C, H, N, or OR (R is alkyl or aryl). Thus Y can be any one of S, Se, B, C, H, N, or OR (R is alkyl or aryl). Replacement of X and/or Y with sulfur is preferred.

The phosphate linker can also be modified by replacement of a linking oxygen (i.e., W or Z in Formula 1) with nitrogen (bridged phosphoroamidates), sulfur (bridged phosphorothioates) and carbon (bridged methylenephosphonates). The replacement can occur at a terminal oxygen (position W (3') or position Z (5'). Replacement of W with carbon or Z with nitrogen is preferred.

Candidate agents can be evaluated for suitability as described below.

The Sugar Group

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge or ethylene bridge (e.g., 2'-4'-ethylene bridged nucleic acid (ENA)), to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_nAMINE$, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), (OCH$_2$CH$_2$OCH$_3$, a PEG derivative), exhibit nuclease stabilities comparable to those modified with the robust phosphorothioate modification.

"Deoxy" modifications include hydrogen (i.e. deoxyribose sugars); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C— allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

The modification can also entail the wholesale replacement of a ribose structure with another entity at one or more sites in the oligonucleotide agent. These modifications are described in section entitled Sugar Replacements for SRMSs.

Candidate modifications can be evaluated as described below.

Replacement of the Phosphate Group

The phosphate group can be replaced by non-phosphorus containing connectors (cf. Bracket I in Formula 1 above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates (see Bracket II of Formula 1 above). While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. A preferred surrogate is a PNA surrogate.

Candidate modifications can be evaluated as described below.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Preferred modifications include the addition of a methylphosphonate at the 3'-most terminal linkage; a 3' C5-aminoalkyl-dT; 3' cationic group; or another 3' conjugate to inhibit 3'-5' exonucleolytic degradation.

Terminal modifications useful for modulating activity include modification of the 5' end with phosphate or phosphate analogs. E.g., in preferred embodiments oligonucleotide agents are 5' phosphorylated or include a phosphoryl analog at the 5' terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking anoligonucleotide agent to another moiety; modifications useful for this include mitomycin C.

Candidate modifications can be evaluated as described below.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are less preferred for promoting stability, but they can be useful for other reasons, e.g., some, e.g., 2,6-diaminopurine and 2 amino purine (e.g., 2-amino adenine), are fluorescent. Modified bases can reduce target specificity. This should be taken into consideration in the design of oligonucleotide agents.

Candidate modifications can be evaluated as described below.

Evaluation of Candidate Oligonucleotide Agents

One can evaluate a candidate oligonucleotide agent, e.g., a modified oligonucleotide agent, for a selected property by exposing the agent or modified molecule and a control molecule to the appropriate conditions and evaluating for the presence of the selected property. For example, resistance to a degradent can be evaluated as follows. A candidate modified RNA (and preferably a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled, preferably prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to inhibit gene expression. For example, a cell, e.g., a mammalian cell, such as a mouse or human cell, can be co-transfected with a plasmid expressing a fluorescent protein, e.g., GFP, and a candidate oligonucleotide agent homologous to the transcript encoding the fluorescent protein (see, e.g., WO 00/44914). For example, a modified oligonucleotide agent homologous to the GFP mRNA can be assayed for the ability to inhibit GFP expression by monitoring for a decrease in cell fluorescence, as compared to a control cell, in which the transfection did not include the candidate oligonucleotide agent, e.g., controls with no agent added and/or controls with a non-modified RNA added. Efficacy of the candidate agent on gene expression can be assessed by comparing cell fluorescence in the presence of the modified and unmodified oligonucleotide agent. In an alternative functional assay, a candidate oligonucleotide agent homologous to an endogenous mouse gene, preferably a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by an oligonucleotide agent would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target RNA, or by Western blot to assay for a decrease in the level of target protein, as compared to a negative control. Controls can include cells in which with no agent is added and/or cells in which a non-modified RNA is added.

An oligonucleotide agent that targets an miRNA ore pre-miRNA can be assayed by monitoring expression of the transcript targeted by the miRNA. For example, an oligonucleotide agent designed to bind an miRNA that targets GFP can be assessed by monitoring for an increase in cell fluorescence, as compared to a control cell, in which the transfection did not include the candidate oligonucleotide agent, e.g., controls with no agent added and/or controls with a non-modified RNA added. In another example, an oligonucleotide agent designed to bind an miRNA that targets an endogenous enzyme can be assessed by monitoring for an increase in enzyme activity, as compared to a control cell. The effect of the modified oligonucleotide agent on target miRNA levels can be verified by Northern blot to assay for a decrease in the level of the target miRNA.

REFERENCES

General References

The oligoribonucleotides and oligoribonucleosides used in accordance with this invention may be with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., *Tetrahedron*, 1992, 48, 2223-2311 and Beaucage, S. L. and Iyer, R. P., *Tetrahedron*, 1993, 49, 6123-6194, or references referred to therein.

Modification described in WO 00/44895, WO01/75164, or WO02/44321 can be used herein.

The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or U.S. Pat. No. 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.*, 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489, 677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Bases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references can be disclosed in the above section on base modifications.

Preferred Oligonucleotide Agents

Preferred oligonucleotide agents have the following structure (see Formula 2 below):

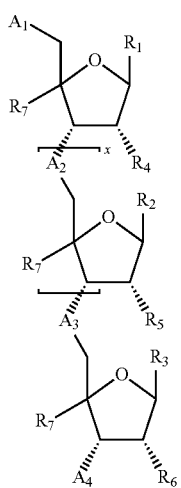

FORMULA 2

Referring to Formula 2 above, $R^1$, $R^2$, and $R^3$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

$R^4$, $R^5$, and $R^6$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_mCH_2CH_2NHR^9$; $NHC(O)R^8$; cyano; mercapto, $SR^8$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, or ureido; or $R^4$, $R^5$, or $R^6$ together combine with $R^7$ to form an [—O—$CH_2$—] covalently bound bridge between the sugar 2' and 4' carbons.

$A^1$ is:

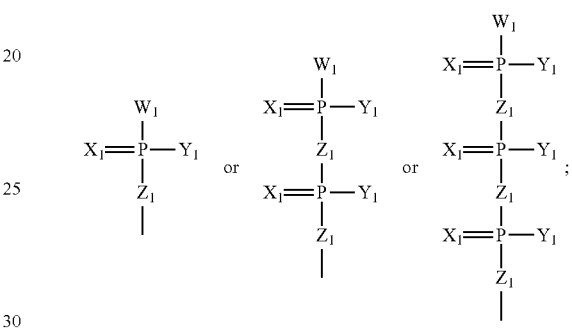

H; OH; $OCH_3$; $W^1$; an abasic nucleotide; or absent;

(a preferred A1, especially with regard to anti-sense strands, is chosen from 5'-monophosphate ((HO)$_2$(O)P—O-5'), 5'-diphosphate ((HO)$_2$(O)P—O—P(HO)(O)—O-5'), 5'-triphosphate ((HO)$_2$(O)P—O—(HO)(O)P—O—P(HO)(O)—O-5'), 5'-guanosine cap (7-methylated or non-methylated) (7m-G-O-5'-(HO)(O)P—O—(HO)(O)P—O—P(HO)(O)—O-5'), 5'-adenosine cap (Appp), and any modified or unmodified nucleotide cap structure (N—O-5'-(HO)(O)P—O—(HO)(O)P—O—P(HO)(O)—O-5'), 5'-monothiophosphate (phosphorothioate; (HO)$_2$(S)P—O-5'), 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g. RP(OH)(O)—O-5'-, (OH)$_2$(O)P-5'-$CH_2$—), 5'-alkyletherphosphonates (R=alkylether=methoxymethyl (MeOCH$_2$—), ethoxymethyl, etc., e.g. RP(OH)(O)—O-5'-)).

$A^2$ is:

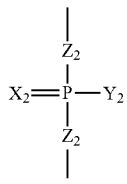

$A^3$ is:

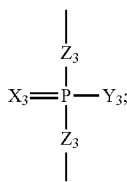

and
$A^4$ is:

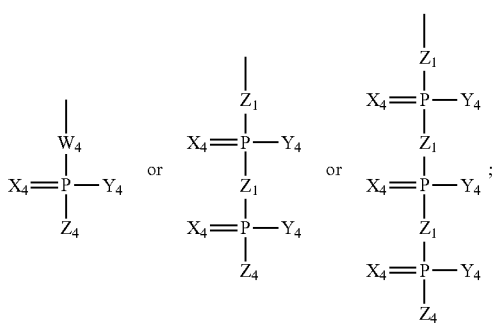

H; $Z^4$; an inverted nucleotide; an abasic nucleotide; or absent.

$W^1$ is OH, $(CH_2)_nR^{10}$, $(CH_2)_nNHR^{10}$, $(CH_2)_nOR^{10}$, $(CH_2)_nSR^{10}$; $O(CH_2)_nR^{10}$; $O(CH_2)_nOR^{10}$, $O(CH_2)_nNR^{10}$, $O(CH_2)_nSR^{10}$; $O(CH_2)_nSS(CH_2)_nOR^{10}$, $O(CH_2)_nC(O)OR^{10}$, $NH(CH_2)_nR^{10}$; $NH(CH_2)_nNR^{10}$; $NH(CH_2)_nOR^{10}$, $NH(CH_2)_nSR^{10}$; $S(CH_2)_nR^{10}$, $S(CH_2)_nNR^{10}$, $S(CH_2)_nOR^{10}$, $S(CH_2)_nSR^{10}O(CH_2CH_2O)_mCH_2CH_2OR^{10}$; $O(CH_2CH_2O)_mCH_2CH_2NHR^{10}$, $NH(CH_2CH_2NH)_mCH_2CH_2NHR^{10}$; Q-$R^{10}$, O-Q-$R^{10}$N-Q-$R^{10}$, S-Q-$R^{10}$ or —O—. $W^4$ is O, $CH_2$, NH, or S.

$X^1$, $X^2$, $X^3$, and $X^4$ are each, independently, O or S.

$Y^1$, $Y^2$, $Y^3$, and $Y^4$ are each, independently, OH, O$^-$, O$R^8$, S, Se, $BH_3^-$, H, $NHR^9$, $N(R^9)_2$ alkyl, cycloalkyl, aralkyl, aryl, or heteroaryl, each of which may be optionally substituted.

$Z^1$, $Z^2$, and $Z^3$ are each independently O, $CH_2$, NH, or S. $Z^4$ is OH, $(CH_2)_nR^{10}$, $(CH_2)_nNHR^{10}$, $(CH_2)_n$ $OR^{10}$, $(CH_2)_nSR^{10}$; $O(CH_2)_nR^{10}$; $O(CH_2)_nOR^{10}$, $O(CH_2)_nNR^{10}$, $O(CH_2)_nSR^{10}$, $O(CH_2)_nSS(CH_2)_nOR^{10}$, $O(CH_2)_nC(O)OR^{10}$; $NH(CH_2)_nR^{10}$; $NH(CH_2)_nNR^{10}$; $NH(CH_2)_nOR^{10}$, $NH(CH_2)_nSR^{10}$; $S(CH_2)_nR^{10}$, $S(CH_2)_nNR^{10}$, $S(CH_2)_nOR^{10}$, $S(CH_2)_nSR^{10}O(CH_2CH_2O)_mCH_2CH_2OR^{10}$, $O(CH_2CH_2O)_mCH_2CH_2NHR^{10}$, $NH(CH_2CH_2NH)_mCH_2CH_2NHR^{10}$; Q-$R^{10}$, O-Q-$R^{10}$N-Q-$R^{10}$, S-Q-$R^{10}$.

X is 5-100, chosen to comply with a length for an oligonucleotide agent described herein.

$R^7$ is H; or is together combined with $R^4$, $R^5$, or $R^6$ to form an [—O—$CH_2$—] covalently bound bridge between the sugar 2' and 4' carbons.

$R^8$ is alkyl, cycloalkyl, aryl, aralkyl, heterocyclyl, heteroaryl, amino acid, or sugar; $R^9$ is $NH_2$, alkylamino, dialkylamino, heterocyclyl, arylamino, diaryl amino, heteroaryl amino, diheteroaryl amino, or amino acid; and $R^{10}$ is H; fluorophore (pyrene, TAMRA, fluorescein, Cy3 or Cy5 dyes); sulfur, silicon, boron or ester protecting group; intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipohilic carriers (cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino; alkyl, cycloalkyl, aryl, aralkyl, heteroaryl; radiolabelled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles); or an oligonucleotide agent. M is 0-1,000,000, and n is 0-20. Q is a spacer selected from the group consisting of abasic sugar, amide, carboxy, oxyamine, oxyimine, thioether, disulfide, thiourea, sulfonamide, or morpholino, biotin or fluorescein reagents.

Preferred oligonucleotide agents in which the entire phosphate group has been replaced have the following structure (see Formula 3 below):

FORMULA 3

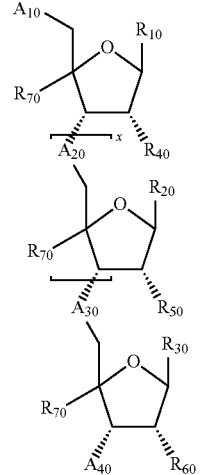

Referring to Formula 3, $A^{10}$-$A^{40}$ is L-G-L; $A^{10}$ and/or $A^{40}$ may be absent, in which L is a linker, wherein one or both L may be present or absent and is selected from the group consisting of $CH_2(CH_2)_g$; $N(CH_2)_g$; $O(CH_2)_g$; $S(CH_2)_g$. G is a functional group selected from the group consisting of siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

$R^{10}$, $R^{20}$, and $R^{30}$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6,N6-dimethyladenine, 2,6-diaminopurine, 5-amino-allyl-uracil, N3-methyluracil substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases.

$R^{40}$, $R^{50}$, and $R^{60}$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_mCH_2CH_2R^9$; $NHC(O)R^8$; cyano; mercapto, $SR^7$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, and ureido groups; or $R^{40}$, $R^{50}$, or $R^{60}$ together combine with $R^{70}$ to form an [—O—CH$_2$—] covalently bound bridge between the sugar 2' and 4' carbons.

X is 5-100 or chosen to comply with a length for an oligonucleotide agent described herein.

$R^{70}$ is H; or is together combined with $R^{40}$, $R^{50}$, or $R^{60}$ to form an [—O—CH$_2$—] covalently bound bridge between the sugar 2' and 4' carbons.

$R^8$ is alkyl, cycloalkyl, aryl, aralkyl, heterocyclyl, heteroaryl, amino acid, or sugar; and $R^9$ is $NH_2$, alkylamino, dialkylamino, heterocyclyl, arylamino, diaryl amino, heteroaryl amino, diheteroaryl amino, or amino acid. M is 0-1,000,000, n is 0-20, and g is 0-2.

Preferred nucleoside surrogates have the following structure (see Formula 4 below):

SLR$^{100}$-(M-SLR$^{200}$)$_x$-M-SLR$^{300}$      FORMULA 4

S is a nucleoside surrogate selected from the group consisting of mophilino, cyclobutyl, pyrrolidine and peptide nucleic acid. L is a linker and is selected from the group consisting of CH$_2$(CH$_2$)$_g$; N(CH$_2$)$_g$; O(CH$_2$)$_g$; S(CH$_2$)$_g$; —C(O)(CH$_2$)$_n$— or may be absent. M is an amide bond; sulfonamide; sulfinate; phosphate group; modified phosphate group as described herein; or may be absent.

$R^{100}$, $R^{200}$, and $R^{300}$ are each, independently, H (i.e., abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6,N6-dimethyladenine, 2,6-diaminopurine, 5-amino-allyl-uracil, N3-methyluracil substituted 1,2,4-triazoles, 2-pyridinones, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases.

X is 5-100, or chosen to comply with a length for an oligonucleotide agent described herein; and g is 0-2.

Nuclease Resistant Monomers

The monomers and methods described herein can be used to prepare an oligonucleotide agent, that incorporates a nuclease resistant monomer (NRM).

An oligonucleotide agent can include monomers which have been modified so as to inhibit degradation, e.g., by nucleases, e.g., endonucleases or exonucleases, found in the body of a subject. These monomers are referred to herein as NRMs, or nuclease resistance promoting monomers or modifications. In many cases these modifications will modulate other properties of the oligonucleotide agent as well, e.g., the ability to interact with a protein, e.g., a transport protein, e.g., serum albumin, or a member of the RISC (RNA-induced Silencing Complex), or the ability of the first and second sequences to form a duplex with one another or to form a duplex with another sequence, e.g., a target molecule.

While not wishing to be bound by theory, it is believed that modifications of the sugar, base, and/or phosphate backbone in an oligonucleotide agent can enhance endonuclease and exonuclease resistance, and can enhance interactions with transporter proteins and one or more of the functional components of the RISC complex. Preferred modifications are those that increase exonuclease and endonuclease resistance and thus prolong the half-life of the oligonucleotide agent prior to interaction with the RISC complex, but at the same time do not render the oligonucleotide agent resistant to endonuclease activity in the RISC complex. Again, while not wishing to be bound by any theory, it is believed that placement of the modifications at or near the 3' and/or 5' end of the oligonucleotide agent can result in agents that meet the preferred nuclease resistance criteria delineated above.

Modifications that can be useful for producing oligonucleotide agents that meet the preferred nuclease resistance criteria delineated above can include one or more of the following chemical and/or stereochemical modifications of the sugar, base, and/or phosphate backbone:

(i) chiral (S$_P$) thioates. Thus, preferred NRMs include nucleotide dimers with an enriched for or having a pure chiral form of a modified phosphate group containing a heteroatom at the nonbridging position, e.g., Sp or Rp, at the position X, where this is the position normally occupied by the oxygen. The atom at X can also be S, Se, Nr$_2$, or Br$_3$. When X is S, enriched or chirally pure Sp linkage is preferred. Enriched means at least 70, 80, 90, 95, or 99% of the preferred form. Such NRMs are discussed in more detail below;

(ii) attachment of one or more cationic groups to the sugar, base, and/or the phosphorus atom of a phosphate or modified phosphate backbone moiety. Thus, preferred NRMs include monomers at the terminal position derivatized at a cationic group. As the 5' end of an oligonucleotide agent should have a terminal —OH or phosphate group, this NRM is preferably not used at the 5' end of the agent. The group should be attached at a position on the base which minimizes interference with H bond formation and hybridization, e.g., away from the face which interacts with the complementary base on the other strand, e.g, at the 5' position of a pyrimidine or a 7-position of a purine. These are discussed in more detail below;

(iii) nonphosphate linkages at the termini. Thus, preferred NRMs include Non-phosphate linkages, e.g., a linkage of 4 atoms which confers greater resistance to cleavage than does a phosphate bond. Examples include 3' CH2-NCH$_3$—O—CH2-5' and 3' CH2-NH—(O=)—CH2-5'.;

(iv) 3'-bridging thiophosphates and 5'-bridging thiophosphates. Thus, preferred NRM's can included these structures;

(v) L-RNA, 2'-5' linkages, inverted linkages, a-nucleosides. Thus, other preferred NRM's include: L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; monomers having an alpha linkage at the 1' site on the sugar, e.g., the structures described herein having an alpha linkage;

(vi) conjugate groups. Thus, preferred NRM's can include e.g., a targeting moiety or a conjugated ligand described herein, e.g., conjugated with the monomer, e.g., through the sugar, base, or backbone;

(vi) abasic linkages. Thus, preferred NRM's can include an abasic monomer, e.g., an abasic monomer as described herein (e.g., a nucleobaseless monomer); an aromatic or heterocyclic or polyheterocyclic aromatic monomer as described herein; and (vii) 5'-phosphonates and 5'-phosphate prodrugs. Thus, preferred NRM's include monomers, preferably at the terminal position, e.g., the 5' position, in which one or more atoms of the phosphate group are derivatized with a protecting group, which protecting group or groups, are removed as a result of the action of a component in the subject's body, e.g, a carboxyesterase or an enzyme present in the subject's body. E.g., a phosphate prodrug in which a carboxy esterase cleaves the protected molecule resulting in the production of a thioate anion which attacks a carbon adjacent to the O of a phosphate and resulting in the production of an unprotected phosphate.

One or more different NRM modifications can be introduced into an oligonucleotide agent or into a sequence of an oligonucleotide agent. An NRM modification can be used more than once in a sequence or in an oligonucleotide agent. As some NRM's interfere with hybridization the total number incorporated, should be such that acceptable levels of oligonucleotide agent/target RNA duplex formation are maintained.

Chiral S$_P$ Thioates

A modification can include the alteration, e.g., replacement, of one or both of the non-linking (X and Y) phosphate oxygens and/or of one or more of the linking (W and Z) phosphate oxygens. Formula X below depicts a phosphate moiety linking two sugar/sugar surrogate-base moieties, SB$_1$ and SB$_2$.

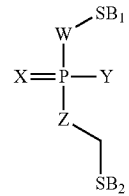

FORMULA X

In certain embodiments, one of the non-linking phosphate oxygens in the phosphate backbone moiety (X and Y) can be replaced by any one of the following: S, Se, BR$_3$ (R is hydrogen, alkyl, aryl, etc.), C (i.e., an alkyl group, an aryl group, etc.), H, NR$_2$ (R is hydrogen, alkyl, aryl, etc.), or OR (R is alkyl or aryl). The phosphorus atom in an unmodified phosphate group is achiral. However, replacement of one of the non-linking oxygens with one of the above atoms or groups of atoms renders the phosphorus atom chiral; in other words a phosphorus atom in a phosphate group modified in this way is a stereogenic center. The stereogenic phosphorus atom can possess either the "R" configuration (herein R$_P$) or the "S" configuration (herein S$_P$). Thus if 60% of a population of stereogenic phosphorus atoms have the R$_P$ configuration, then the remaining 40% of the population of stereogenic phosphorus atoms have the S$_P$ configuration.

In some embodiments, oligonucleotide agents have phosphate groups in which a phosphate non-linking oxygen has been replaced by another atom or group of atoms, may contain a population of stereogenic phosphorus atoms in which at least about 50% of these atoms (e.g., at least about 60% of these atoms, at least about 70% of these atoms, at least about 80% of these atoms, at least about 90% of these atoms, at least about 95% of these atoms, at least about 98% of these atoms, at least about 99% of these atoms) have the S$_P$ configuration. Alternatively, oligonucleotide agents having phosphate groups in which a phosphate non-linking oxygen has been replaced by another atom or group of atoms may contain a population of stereogenic phosphorus atoms in which at least about 50% of these atoms (e.g., at least about 60% of these atoms, at least about 70% of these atoms, at least about 80% of these atoms, at least about 90% of these atoms, at least about 95% of these atoms, at least about 98% of these atoms, at least about 99% of these atoms) have the R$_P$ configuration. In other embodiments, the population of stereogenic phosphorus atoms may have the S$_P$ configuration and may be substantially free of stereogenic phosphorus atoms having the R$_P$ configuration. In still other embodiments, the population of stereogenic phosphorus atoms may have the R$_P$ configuration and may be substantially free of stereogenic phosphorus atoms having the S$_P$ configuration. As used herein, the phrase "substantially free of stereogenic phosphorus atoms having the R$_P$ configuration" means that moieties containing stereogenic phosphorus atoms having the R$_P$ configuration cannot be detected by conventional methods known in the art (chiral HPLC, $^1$H NMR analysis using chiral shift reagents, etc.). As used herein, the phrase "substantially free of stereogenic phosphorus atoms having the S$_P$ configuration" means that moieties containing stereogenic phosphorus atoms having the S$_P$ configuration cannot be detected by conventional methods known in the art (chiral HPLC, $^1$H NMR analysis using chiral shift reagents, etc.).

In a preferred embodiment, modified oligonucleotide agents contain a phosphorothioate group, i.e., a phosphate groups in which a phosphate non-linking oxygen has been replaced by a sulfur atom. In an especially preferred embodiment, the population of phosphorothioate stereogenic phosphorus atoms may have the $S_P$ configuration and be substantially free of stereogenic phosphorus atoms having the $R_P$ configuration.

Phosphorothioates may be incorporated into oligonucleotide agents using dimers e.g., formulas X-1 and X-2. The former can be used to introduce phosphorothioate

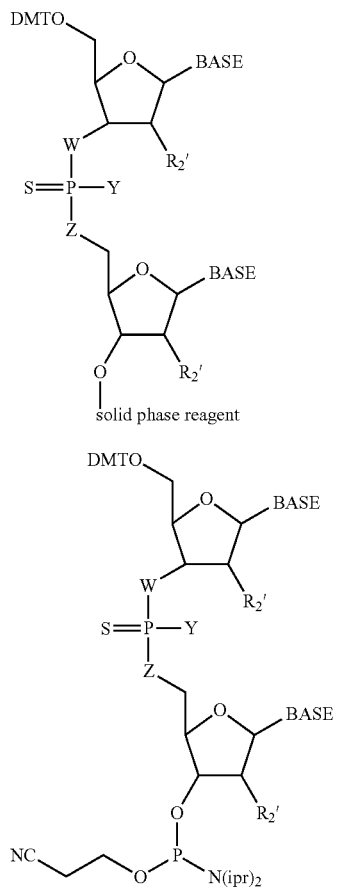

at the 3' end of a strand, while the latter can be used to introduce this modification at the 5' end or at a position that occurs e.g., 1, 2, 3, 4, 5, or 6 nucleotides from either end of the strand. In the above formulas, Y can be 2-cyanoethoxy, W and Z can be O, $R_{2'}$ can be, e.g., a substituent that can impart the C-3 endo configuration to the sugar (e.g., OH, F, OCH$_3$), DMT is dimethoxytrityl, and "BASE" can be a natural, unusual, or a universal base.

X-1 and X-2 can be prepared using chiral reagents or directing groups that can result in phosphorothioate-containing dimers having a population of stereogenic phosphorus atoms having essentially only the $R_P$ configuration (i.e., being substantially free of the $S_P$ configuration) or only the $S_P$ configuration (i.e., being substantially free of the $R_P$ configuration). Alternatively, dimers can be prepared having a population of stereogenic phosphorus atoms in which about 50% of the atoms have the $R_P$ configuration and about 50% of the atoms have the $S_P$ configuration. Dimers having stereogenic phosphorus atoms with the $R_P$ configuration can be identified and separated from dimers having stereogenic phosphorus atoms with the $S_P$ configuration using e.g., enzymatic degradation and/or conventional chromatography techniques.

Cationic Groups

Modifications can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=NH$_2$; alkylamino, dialkylamino, heterocyclyl, arylamino, diaryl amino, heteroaryl amino, or diheteroaryl amino, ethylene diamine, polyamino); aminoalkoxy, e.g., O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino); amino (e.g. NH$_2$; alkylamino, dialkylamino, heterocyclyl, arylamino, diaryl amino, heteroaryl amino, diheteroaryl amino, or amino acid); or NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino).

Nonphosphate Linkages

Modifications can also include the incorporation of nonphosphate linkages at the 5' and/or 3' end of a strand. Examples of nonphosphate linkages which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methyl phosphonate and hydroxylamino groups.

3'-bridging thiophosphates and 5'-bridging thiophosphates; locked-RNA, 2'-5' linkages, inverted linkages, α-nucleosides; conjugate groups; abasic linkages; and 5'-phosphonates and 5'-phosphate prodrugs are also linkages that can be included in oligonucleotide agents.

Referring to formula X above, modifications can include replacement of one of the bridging or linking phosphate oxygens in the phosphate backbone moiety (W and Z). Unlike the situation where only one of X or Y is altered, the phosphorus center in the phosphorodithioates is achiral which precludes the formation of oligonucleotide agents containing a stereogenic phosphorus atom.

Modifications can also include linking two sugars via a phosphate or modified phosphate group through the 2' position of a first sugar and the 5' position of a second sugar. Also contemplated are inverted linkages in which both a first and second sugar are eached linked through the respective 3' positions. Modified RNA's can also include "abasic" sugars, which lack a nucleobase at C-1'. The sugar group can also contain one or more carbons that possess the opposite stereochemical configuration than that of the corresponding carbon in ribose. Thus, a modified oligonucleotide agent can include nucleotides containing e.g., arabinose, as the sugar. In another subset of this modification, the natural, unusual, or universal base may have the α-configuration. Modifications can also include L-RNA.

Modifications can also include 5'-phosphonates, e.g., P(O)(O$^-$)$_2$—X—O$^{5'}$-sugar (X=CH2, CF2, CHF and 5'-phosphate prodrugs, e.g., P(O)[OCH2CH2SC(O) R]$_2$CH$_2$C$^{5'}$-sugar. In the latter case, the prodrug groups may be decomposed via reaction first with carboxy esterases. The remaining ethyl thiolate group via intramolecular $S_N2$ displacement can depart as episulfide to afford the underivatized phosphate group.

Modification can also include the addition of conjugating groups described elsewhere herein, which are preferably attached to an oligonucleotide agent through any amino group available for conjugation.

Nuclease resistant modifications include some which can be placed only at the terminus and others which can go at any position. Generally, these modifications can inhibit hybridization so it is preferably to use them only in terminal regions, and preferable to not use them at the cleavage site or in the cleavage region of a sequence.

Modifications which interfere with or inhibit endonuclease cleavage should not be inserted in the region of an oligonucleotide agent which is subject to RISC mediated cleavage, e.g., the cleavage site or the cleavage region. As used herein cleavage site refers to the nucleotide on either side of the cleavage site on the target or on the oligonucleotide agent strand which hybridizes to it. Cleavage region means an nucleotide with 1, 2, or 3 nucleotides of the cleave site, in either direction.)

Such modifications can be introduced into the terminal regions, e.g., at the terminal position or with 2, 3, 4, or 5 positions of the terminus.

An oligonucleotide agent can have the following:

an NRM modification at or within 1, 2, 3, 4, 5, or 6 positions from the 3' end;

an NRM modification at or within 1, 2, 3, 4, 5, or 6 positions from the 5' end (5' end NRM modifications are preferentially not at the terminus but rather at a position 1, 2, 3, 4, 5, or 6 away from the 5' terminus of the oligonucleotide agent);

an NRM modification at or within 1, 2, 3, 4, 5, or 6 positions from the 3' end and which has a NRM modification at or within 1, 2, 3, 4, 5, or 6 positions from the 5' end;

an NRM modification at the cleavage site or in the cleavage region;

an NRM modification at the cleavage site or in the cleavage region and one or more of an NRM modification at or within 1, 2, 3, 4, 5, or 6 positions from the 3' end, an NRM modification at or within 1, 2, 3, 4, 5, or 6 positions from the 5' end, or NRM modifications at or within 1, 2, 3, 4, 5, or 6 positions from both the 3' and the 5' end (5' end NRM modifications are preferentially not at the terminus but rather at a position 1, 2, 3, 4, 5, or 6 away from the 5' terminus of the oligonucleotide agent).

Ribose Mimics

The monomers and methods described herein can be used to prepare an oligonucleotide agent, that incorporates a ribose mimic.

Thus, an aspect of the invention features an oligonucleotide agent that includes a secondary hydroxyl group, which can increase efficacy and/or confer nuclease resistance to the agent. Nucleases, e.g., cellular nucleases, can hydrolyze nucleic acid phosphodiester bonds, resulting in partial or complete degradation of the nucleic acid. The secondary hydroxy group confers nuclease resistance to an oligonucleotide agent by rendering the oligonucleotide agent less prone to nuclease degradation relative to an oligonucleotide agent that lacks the modification. While not wishing to be bound by theory, it is believed that the presence of a secondary hydroxyl group on the oligonucleotide agent can act as a structural mimic of a 3' ribose hydroxyl group, thereby causing it to be less susceptible to degradation.

The secondary hydroxyl group refers to an "OH" radical that is attached to a carbon atom substituted by two other carbons and a hydrogen. The secondary hydroxyl group that confers nuclease resistance as described above can be part of any acyclic carbon-containing group. The hydroxyl may also be part of any cyclic carbon-containing group, and preferably one or more of the following conditions is met (1) there is no ribose moiety between the hydroxyl group and the terminal phosphate group or (2) the hydroxyl group is not on a sugar moiety which is coupled to a base. The hydroxyl group is located at least two bonds (e.g., at least three bonds away, at least four bonds away, at least five bonds away, at least six bonds away, at least seven bonds away, at least eight bonds away, at least nine bonds away, at least ten bonds away, etc.) from the terminal phosphate group phosphorus of the oligonucleotide agent. In preferred embodiments, there are five intervening bonds between the terminal phosphate group phosphorus and the secondary hydroxyl group.

Preferred oligonucleotide agent delivery modules with five intervening bonds between the terminal phosphate group phosphorus and the secondary hydroxyl group have the following structure (see formula Y below):

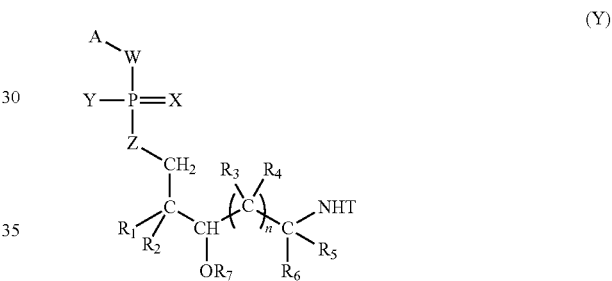

(Y)

Referring to formula Y, A is an oligonucleotide agent, including any oligonucleotide agent described herein. The oligonucleotide agent may be connected directly or indirectly (e.g., through a spacer or linker) to "W" of the phosphate group. These spacers or linkers can include e.g., —$(CH_2)_n$—, —$(CH_2)_nN$—, —$(CH_2)_nO$—, —$(CH_2)_nS$—, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents.

The oligonucleotide agents can have a terminal phosphate group that is unmodified (e.g., W, X, Y, and Z are O) or modified. In a modified phosphate group, W and Z can be independently NH, O, or S; and X and Y can be independently S, Se, $BH_3^-$, $C_1$-$C_6$ alkyl, $C_6$-$C_{10}$ aryl, H, O, O$^-$, alkoxy or amino (including alkylamino, arylamino, etc.). Preferably, W, X and Z are O and Y is S.

$R_1$ and $R_3$ are each, independently, hydrogen; or $C_1$-$C_{100}$ alkyl, optionally substituted with hydroxyl, amino, halo, phosphate or sulfate and/or may be optionally inserted with N, O, S, alkenyl or alkynyl.

$R_2$ is hydrogen; $C_1$-$C_{100}$ alkyl, optionally substituted with hydroxyl, amino, halo, phosphate or sulfate and/or may be optionally inserted with N, O, S, alkenyl or alkynyl; or, when n is 1, $R_2$ may be taken together with $R_4$ or $R_6$ to form a ring of 5-12 atoms.

$R_4$ is hydrogen; $C_1$-$C_{100}$ alkyl, optionally substituted with hydroxyl, amino, halo, phosphate or sulfate and/or may be optionally inserted with N, O, S, alkenyl or alkynyl; or, when n is 1, $R_4$ may be taken together with $R_2$ or $R_5$ to form a ring of 5-12 atoms.

$R_5$ is hydrogen, $C_1$-$C_{100}$ alkyl optionally substituted with hydroxyl, amino, halo, phosphate or sulfate and/or may be optionally inserted with N, O, S, alkenyl or alkynyl; or, when n is 1, $R_5$ may be taken together with $R_4$ to form a ring of 5-12 atoms.

$R_6$ is hydrogen, $C_1$-$C_{100}$ alkyl, optionally substituted with hydroxyl, amino, halo, phosphate or sulfate and/or may be optionally inserted with N, O, S, alkenyl or alkynyl, or, when n is 1, $R_6$ may be taken together with $R_2$ to form a ring of 6-10 atoms;

$R_7$ is hydrogen, $C_1$-$C_{100}$ alkyl, or $C(O)(CH_2)_qC(O)NHR_9$; T is hydrogen or a functional group; n and q are each independently 1-100; $R_8$ is $C_1$-$C_{10}$ alkyl or $C_6$-$C_{10}$ aryl; and $R_9$ is hydrogen, C1-C10 alkyl, C6-C10 aryl or a solid support agent.

Preferred embodiments may include one of more of the following subsets of oligonucleotide agent delivery modules.

In one subset of oligonucleotide agent delivery modules, A can be connected directly or indirectly through a terminal 3' or 5' ribose sugar carbon of the oligonucleotide agent.

In another subset of Oligonucleotide agent delivery modules, X, W, and Z are O and Y is S.

In still yet another subset of oligonucleotide agent delivery modules, n is 1, and $R_2$ and $R_6$ are taken together to form a ring containing six atoms and $R_4$ and $R_5$ are taken together to form a ring containing six atoms. Preferably, the ring system is a trans-decalin. For example, the Oligonucleotide agent delivery module of this subset can include a compound of Formula (Y-1):

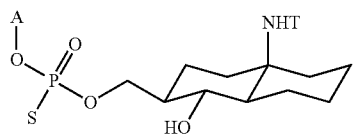

The functional group can be, for example, a targeting group (e.g., a steroid or a carbohydrate), a reporter group (e.g., a fluorophore), or a label (an isotopically labelled moiety). The targeting group can further include protein binding agents, endothelial cell targeting groups (e.g., RGD peptides and mimetics), cancer cell targeting groups (e.g., folate Vitamin B12, Biotin), bone cell targeting groups (e.g., bisphosphonates, polyglutamates, polyaspartates), multivalent mannose (for e.g., macrophage testing), lactose, galactose, N-acetyl-galactosamine, monoclonal antibodies, glycoproteins, lectins, melanotropin, or thyrotropin.

As can be appreciated by the skilled artisan, methods of synthesizing the compounds of the formulae herein will be evident to those of ordinary skill in the art. The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Delivery Module

The monomers and methods described herein can be used to prepare an oligonucleotide agent, e.g., conjugated oligonucleotide agent described herein, that can be used with a drug delivery conjugate or module.

The oligonucleotide agents can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane, e.g., an endosome membrane); and (c) a targeting group, e.g., a cell or tissue targeting agent, e.g., a lectin, glycoprotein, lipid or protein, e.g., an antibody, that binds to a specified cell type such as a kidney cell.

An oligonucleotide agent can be linked, e.g., coupled or bound, to the modular complex. The oligonucleotide agent can interact with the condensing agent of the complex, and the complex can be used to deliver an oligonucleotide agent to a cell, e.g., in vitro or in vivo. For example, the complex can be used to deliver an oligonucleotide agent to a subject in need thereof, e.g., to deliver an oligonucleotide agent to a subject having a disease or disorder.

The fusogenic agent and the condensing agent can be different agents or the one and the same agent. For example, a polyamino chain, e.g., polyethyleneimine (PEI), can be the fusogenic and/or the condensing agent.

The delivery agent can be a modular complex. For example, the complex can include a carrier agent linked to one or more of (preferably two or more, more preferably all three of):

(a) a condensing agent (e.g., an agent capable of attracting, e.g., binding, a nucleic acid, e.g., through ionic interaction), (b) a fusogenic agent (e.g., an agent capable of fusing and/or being transported through a cell membrane, e.g., an endosome membrane), and (c) a targeting group, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, Neproxin, or an RGD peptide or RGD peptide mimetic.

Carrier Agents

The carrier agent of a modular complex described herein can be a substrate for attachment of one or more of: a condensing agent, a fusogenic agent, and a targeting group. The carrier agent would preferably lack an endogenous enzymatic activity. The agent would preferably be a biological molecule, preferably a macromolecule. Polymeric biological carriers are preferred. It would also be preferred that the carrier molecule be biodegradable.

The carrier agent can be a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or lipid. The carrier molecule can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Other useful carrier molecules can be identified by routine methods.

A carrier agent can be characterized by one or more of: (a) is at least 1 Da in size; (b) has at least 5 charged groups, preferably between 5 and 5000 charged groups; (c) is present in the complex at a ratio of at least 1:1 carrier agent to fusogenic agent; (d) is present in the complex at a ratio of at least 1:1 carrier agent to condensing agent; (e) is present in the complex at a ratio of at least 1:1 carrier agent to targeting agent.

Fusogenic Agents

A fusogenic agent of a modular complex described herein can be an agent that is responsive to, e.g., changes charge depending on, the pH environment. Upon encountering the pH of an endosome, it can cause a physical change, e.g., a change in osmotic properties which disrupts or increases the permeability of the endosome membrane. Preferably, the fusogenic agent changes charge, e.g., becomes protonated, at pH lower than physiological range. For example, the fusogenic agent can become protonated at pH 4.5-6.5. The fusogenic agent can serve to release the oligonucleotide agent into the cytoplasm of a cell after the complex is taken up, e.g., via endocytosis, by the cell, thereby increasing the cellular concentration of the oligonucleotide agent in the cell.

In one embodiment, the fusogenic agent can have a moiety, e.g., an amino group, which, when exposed to a specified pH range, will undergo a change, e.g., in charge, e.g., protonation. The change in charge of the fusogenic agent can trigger a change, e.g., an osmotic change, in a vesicle, e.g., an endocytic vesicle, e.g., an endosome. For example, the fusogenic agent, upon being exposed to the pH environment of an endosome, will cause a solubility or osmotic change substantial enough to increase the porosity of (preferably, to rupture) the endosomal membrane.

The fusogenic agent can be a polymer, preferably a polyamino chain, e.g., polyethyleneimine (PEI). The PEI can be linear, branched, synthetic or natural. The PEI can be, e.g., alkyl substituted PEI, or lipid substituted PEI.

In other embodiments, the fusogenic agent can be polyhistidine, polyimidazole, polypyridine, polypropyleneimine, mellitin, or a polyacetal substance, e.g., a cationic polyacetal. In some embodiment, the fusogenic agent can have an alpha helical structure. The fusogenic agent can be a membrane disruptive agent, e.g., mellittin.

A fusogenic agent can have one or more of the following characteristics: (a) is at least 1 Da in size; (b) has at least 10 charged groups, preferably between 10 and 5000 charged groups, more preferably between 50 and 1000 charged groups; (c) is present in the complex at a ratio of at least 1:1 fusogenic agent to carrier agent; (d) is present in the complex at a ratio of at least 1:1 fusogenic agent to condensing agent; (e) is present in the complex at a ratio of at least 1:1 fusogenic agent to targeting agent.

Other suitable fusogenic agents can be tested and identified by a skilled artisan. The ability of a compound to respond to, e.g., change charge depending on, the pH environment can be tested by routine methods, e.g., in a cellular assay. For example, a test compound is combined or contacted with a cell, and the cell is allowed to take up the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in endosome population in the cells. The test compound can be labeled. In another type of assay, a modular complex described herein is constructed using one or more test or putative fusogenic agents. The modular complex can be constructed using a labeled nucleic acid instead of the oligonucleotide. The ability of the fusogenic agent to respond to, e.g., change charge depending on, the pH environment, once the modular complex is taken up by the cell, can be evaluated, e.g., by preparation of an endosome preparation, or by microscopy techniques, as described above. A two-step assay can also be performed, wherein a first assay evaluates the ability of a test compound alone to respond to, e.g., change charge depending on, the pH environment; and a second assay evaluates the ability of a modular complex that includes the test compound to respond to, e.g., change charge depending on, the pH environment.

Condensing Agent

The condensing agent of a modular complex described herein can interact with (e.g., attracts, holds, or binds to) an oligonucleotide agent and act to (a) condense, e.g., reduce the size or charge of the oligonucleotide agent and/or (b) protect the oligonucleotide agent, e.g., protect the oligonucleotide agent against degradation. The condensing agent can include a moiety, e.g., a charged moiety, that can interact with a nucleic acid, e.g., an oligonucleotide agent, e.g., by ionic interactions. The condensing agent would preferably be a charged polymer, e.g., a polycationic chain. The condensing agent can be a polylysine (PLL), spermine, spermidine, polyamine, pseudopeptide-polyamine, peptidomimetic polyamine, dendrimer polyamine, arginine, amidine, protamine, cationic lipid, cationic porphyrin, quarternary salt of a polyamine, or an alpha helical peptide.

A condensing agent can have the following characteristics: (a) at least 1 Da in size; (b) has at least 2 charged groups, preferably between 2 and 100 charged groups; (c) is present in the complex at a ratio of at least 1:1 condensing agent to carrier agent; (d) is present in the complex at a ratio of at least 1:1 condensing agent to fusogenic agent; (e) is present in the complex at a ratio of at least 1:1 condensing agent to targeting agent.

Other suitable condensing agents can be tested and identified by a skilled artisan, e.g., by evaluating the ability of a test agent to interact with a nucleic acid, e.g., an oligonucleotide agent. The ability of a test agent to interact with a nucleic acid, e.g., an oligonucleotide agent, e.g., to condense or protect the oligonucleotide agent, can be evaluated by routine techniques. In one assay, a test agent is contacted with a nucleic acid, and the size and/or charge of the contacted nucleic acid is evaluated by a technique suitable to detect changes in molecular mass and/or charge. Such techniques include non-denaturing gel electrophoresis, immunological methods, e.g., immunoprecipitation, gel filtration, ionic interaction chromatography, and the like. A test agent is identified as a condensing agent if it changes the mass and/or charge (preferably both) of the contacted nucleic acid, compared to a control. A two-step assay can also be performed, wherein a first assay evaluates the ability of a test compound alone to interact with, e.g., bind to, e.g., condense the charge and/or mass of, a nucleic cid; and a second assay evaluates the ability of a modular complex that includes the test compound to interact with, e.g., bind to, e.g., condense the charge and/or mass of, a nucleic acid.

Amphipathic Delivery Agents

The oligonucleotide agents described herein can be used with an amphipathic delivery conjugate or module, such as those described herein and those described in copending, co-owned U.S. Provisional Application Ser. No. 60/455,050, filed on Mar. 13, 2003, and International Application Serial No. PCT/US04/07070, filed Mar. 8, 2004, which is hereby incorporated by reference.

Oligonucleotide Production

An oligonucleotide agent can be produced, e.g., in bulk, by a variety of methods. Exemplary methods include: organic synthesis and RNA cleavage, e.g., in vitro cleavage.

Organic Synthesis

A large bioreactor, e.g., the OligoPilot II from Pharmacia Biotec AB (Uppsala Sweden), can be used to produce a large amount of an oligonucleotide agent. The OligoPilotII reactor can efficiently couple a nucleotide using only a 1.5 molar excess of a phosphoramidite nucleotide. To make an RNA strand, ribonucleotides amidites are used. Standard cycles of monomer addition can be used to synthesize the oligonucleotide agent.

Organic synthesis can be used to produce a discrete oligonucleotide agent species. The complementary of the species to a particular target gene can be precisely specified. For example, the species may be complementary to a region that includes a polymorphism, e.g., a single nucleotide polymorphism. Further the location of the polymorphism can be precisely defined. In some embodiments, the polymorphism is located in an internal region, e.g., at least 4, 5, 7, or 9 nucleotides from one or both of the termini.

An oligonucleotide agent preparation can be prepared in a solution (e.g., an aqueous and/or organic solution) that is appropriate for formulation. For example, the oligonucleotide agent preparation can be precipitated and redissolved in pure double-distilled water, and lyophilized. The dried oligonucleotide agent can then be resuspended in a solution appropriate for the intended formulation process.

Synthesis of modified and nucleotide surrogate oligonucleotide agents is discussed below.

Formulation

The oligonucleotide agents described herein can be formulated for administration to a subject.

For ease of exposition the formulations, compositions and methods in this section are discussed largely with regard to unmodified oligonucleotide agents. It should be understood, however, that these formulations, compositions and methods can be practiced with other oligonucleotide agents, e.g., modified oligonucleotide agents, and such practice is within the invention.

A formulated oligonucleotide agent composition can assume a variety of states. In some examples, the composition is at least partially crystalline, uniformly crystalline, and/or anhydrous (e.g., less than 80, 50, 30, 20, or 10% water). In another example, the oligonucleotide agent is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the oligonucleotide agent composition is formulated in a manner that is compatible with the intended method of administration (see, below).

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An oligonucleotide agent preparation can be formulated in combination with another agent, e.g., another therapeutic agent or an agent that stabilizes an oligonucleotide agent, e.g., a protein that complexes with an oligonucleotide agent. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the oligonucleotide agent preparation includes a second oligonucleotide agent, e.g., a second oligonucleotide agent that can modulate gene expression with respect to a second gene, or with respect to the same gene. Still other preparation can include at least three, five, ten, twenty, fifty, or a hundred or more different oligonucleotide agent species. Such oligonucleotide agents can modulate gene expression with respect to a similar number of different genes.

In one embodiment, the oligonucleotide agent preparation includes at least a second therapeutic agent (e.g., an agent other than an RNA or a DNA). For example, an oligonucleotide agent composition for the treatment of a viral disease, e.g. HIV, might include a known antiviral agent (e.g., a protease inhibitor or reverse transcriptase inhibitor). In another example, an oligonucleotide agent composition for the treatment of a cancer might further comprise a chemotherapeutic agent.

Oligonucleotide agents described herein can be formulated for delivery in a membranous molecular assembly, e.g., a liposome or a micelle. In one embodiment, a preparation including an oligonucleotide agent can be formulated as an emulsion that includes a surfactant.

Targeting

For ease of exposition the formulations, compositions and methods in this section are discussed largely with regard to unmodified oligonucleotide agents. It should be understood, however, that these formulations, compositions and methods can be practiced with other oligonucleotide agents, e.g., modified oligonucleotide agents, and such practice is within the invention.

In some embodiments, an oligonucleotide agent, or a DNA which encodes an oligonucleotide agent, or precursor thereof, is targeted to a particular cell. For example, a liposome or particle or other structure that includes an oligonucleotide agent can also include a targeting moiety that recognizes a specific molecule on a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell. For example, the targeting moiety can recognize a cancer-specific antigen of the kidney (e.g., G250, CA15-3, CA19-9, CEA, or HER2/neu) or a viral antigen, thus delivering the oligonucleotide agent to a cancer cell or a virus-infected cell. Exemplary targeting moieties include antibodies (such as IgM, IgG, IgA, IgD, and the like, or a functional portions thereof), ligands for cell surface receptors (e.g., ectodomains thereof).

Table 6 provides a number of antigens which can be used to target an oligonucleotide agent to a selected cell, such as when targeting of the oligonucleotide agent to a tissue other than the kidney is desired.

TABLE 6

Targeting Antigens

| ANTIGEN | Exemplary tumor tissue |
| --- | --- |
| CEA (carcinoembryonic antigen) | colon, breast, lung |
| PSA (prostate specific antigen) | prostate cancer |
| CA-125 | ovarian cancer |
| CA 15-3 | breast cancer |
| CA 19-9 | breast cancer |
| HER2/neu | breast cancer |
| α-feto protein | testicular cancer, hepatic cancer |
| β-HCG (human chorionic gonadotropin) | testicular cancer, choriocarcinoma |
| MUC-1 | breast cancer |
| Estrogen receptor | breast cancer, uterine cancer |
| Progesterone receptor | breast cancer, uterine cancer |
| EGFr (epidermal growth factor receptor) | bladder cancer |

In one embodiment, the targeting moiety is attached to a liposome. For example, U.S. Pat. No. 6,245,427 describes a method for targeting a liposome using a protein or peptide. In another example, a cationic lipid component of the liposome is derivatized with a targeting moiety. For example, WO 96/37194 describes converting N-glutaryldioleoylphosphatidyl ethanolamine to a N-hydroxysuccinimide activated ester. The product was then coupled to an RGD peptide.

Targeting to the Kidney

The kidney is an important site of gene expression. Aspects of the invention relate to silencing genes expressed in the kidney, e.g., to treat disorders of or related to the kidney. Accordingly, the invention includes compositions and methods for delivering oligonucleotide agents to the kidney. The invention also includes compositions and methods for minimizing delivery of oligonucleotide agents to the kidney.

An oligonucleotide agent composition of the invention can be one that has been modified to alter distribution in favor of the kidney. A composition of the invention includes an oligonucleotide agent, e.g., an oligonucleotide agent described herein.

One aspect of the invention provides a method for treating a human having or at risk for having a disorder of the kidney. The method of treatment includes administering an oligonucleotide agent to the human, wherein the oligonucleotide agent targets a nucleic acid, e.g., an RNA expressed in the kidney. In one embodiment, the human is suffering from a disorder characterized by elevated or otherwise unwanted expression of a nucleic acid, e.g., elevated gene expression levels or elevated RNA levels, in the kidney. The unwanted expression levels can correspond to a gene encoding a chemokine, such as RANTES, MCPJ or osteopontin; or a gene encoding a complement factor or a growth factor (e.g., Transforming growth factor-beta (TGFbeta), Platelet derived growth factor (PDGF), IGF-1, IGF-2 or Vascular endothelial growth factor (VEGF)). In another embodiment, the gene can encode an inflammatory cytokine, such as IL1alpha or TNFalpha; a fibrogenic cytokine; a vasoactive protein, such as angiotensin II or ET1; or a growth factor receptor, such as KDR (VEGF receptor), an epidermal growth factor receptor, or a fibroblast growth factor receptor.

In one embodiment, the oligonucleotide agent targets an miRNA expressed in the kidney. In another embodiment, the human is suffering from a disorder characterized by overexpression or accumulation of the miRNA in the kidney, or decreased expression of a nucleic acid that is the target of the miRNA expressed in the kidney. Administration of the oligonucleotide agent to the subject, or to a cell of the kidney of the subject, can result in the pairing of the oligonucleotide agent with the target miRNA and the subsequent downregulation of the miRNA.

In one embodiment, the oligonucleotide agent is substantially identical to an miRNA normally expressed in kidney tissue, and in another embodiment, the human is suffering from a disorder characterized by decreased expression of the miRNA in the kidney. Administration of the oligonucleotide agent to the subject, or to a cell of the kidney, at least partially rescues the function of the downregulated miRNA.

In one embodiment, the human has or is at risk for having renal vascular hypertension, a uretar obstruction, diabetes, diabetic nephropathy, glomerular sclerosis, glomerular nephritis, systemic lupus erythematosis, HIV-associated nephropathy, renal fibrosis, proteinurea, renal carcinoma, Fanconi's syndrome or Bartter's syndrome. In another embodiment, an oligonucleotide agent targeting the kidney can be administered to a subject in shock, or the agent can be administered before, during, and/or following a kidney transplant.

In one embodiment, the oligonucleotide agent targets a growth factor, such as TGFbeta, or a growth factor receptor, and the human has or is at risk for having diabetic nephropathy, progressive renal disease, chronic tissue injury, or glomerulosclerosis. In one embodiment, the oligonucleotide agent targets a growth factor, such as TGFbeta, and the human has had or is going to have a kidney transplant, or has been identified as a candidate for a kidney transplant.

In one embodiment, the oligonucleotide agent targets PDGF and the human has had or is going to have a kidney transplant, or has been identified as a candidate for a kidney transplant.

In one embodiment, the oligonucleotide agent targets a vasoconstrictor, such as angiotensin II, or a vasoconstrictor receptor, such as angiotensin receptor I, and the human has or is at risk for having angiotensin II-dependent hypertension or type II diabetes, or the human is in a hyperglycemic state.

In one embodiment, the oligonucleotide agent targets a vasoconstrictor, such as endothelin-1 (ET-1), or an ET-1 receptor, such as ETA or ETB, and the human has or is at risk for having an autosomal-dominant polycystic kidney disease and/or chronic renal disease. For example, the human can have an autosomal-dominant polycystic kidney disease, and in one embodiment, the patient's condition has progressed to a chronic renal disease.

In one embodiment, the oligonucleotide agent targets a transcription factor, such as a ligand-activated transcription factor, e.g., the nuclear hormone receptor peroxisome proliferator-activated receptor (PPAR), and the human has or is at risk for having diabetic nephropathy, a kidney tumor, or glomerulosclerosis. In one embodiment the oligonucleotide agent targets PPAR-alpha, PPAR beta/delta, or PPAR gamma.

In one embodiment, the oligonucleotide agent targets a growth factor receptor, such as an IGF receptor (e.g., IGFR1), the VEGF receptor KDR, an epidermal growth factor receptor, or a fibroblast growth factor receptor, and the human has or is at risk for having a renal cell carcinoma, diabetic nephropathy, renal hypertrophy, glomerular enlargement, increased urinary albumin excretion, and/or diabetes.

In one embodiment, the oligonucleotide agent targets a costimulatory molecule, e.g., B7-1, B7-2, ICOS, CD40, and/or CD154, and the human has or is at risk for having an autoimmune disease or transplant rejection.

In one embodiment, the oligonucleotide agent targets a chemokine, such as MCP-1, RANTES and/or osteopontin, and the human has or is at risk for having systemic hypertension, renal parenchymal injury, an acute or chronic rejection of a kidney allograft, or chronic hypoxia-induced hypertension.

One aspect of the invention provides an oligonucleotide agent that targets a complement component, such as complement factor C3, C4, C5 or B. An oligonucleotide that targets a complement component can be desirable, e.g., to inhibit the immune response.

In one aspect, the invention provides for a method of delivering an oligonucleotide agent to the kidney of a subject, e.g., a mammalian subject, such as a mouse or a human. In one embodiment, the oligonucleotide agent can be delivered to a cell or cells in the glomerulus of the kidney, e.g., glomerular endothelial cells, glomerular epithelial cells, mesangial cells, and the like; and/or the oligonucleotide agent can be delivered to the proximal tubular cells of the kidney. For example, an oligonucleotide agent can be delivered to the proximal tubular cells of the kidney for treatment of shock, uretar obstruction, diabetes, proteinuria, renal carcinoma, or a tubular defect disease, such as Fanconi or Bartter's syndrome. An oligonucleotide agent directed to the treatment of a renal transplant patient can also be directed to the proximal tubular cells of the kidney. In one embodiment, an oligonucleotide directed to the proximal tubular cells of the kidney will further be delivered to the interstitium and other downstream cells. It is preferable that the oligonucleotide agent silences a target gene at the target site within the kidney.

An oligonucleotide agent delivered to the kidney, e.g., the proximal tubular cells of the kidney, can be an unmodified oligonucleotide agent. In one embodiment, the oligonucleotide agent can be stabilized with phosphodiester linkages. In another embodiment, the 3' end of the oligonucleotide agent can be modified by a cationic group, e.g., an alkyl amine (such as an 2'O-alkyl amine), polyamine, cationic peptide, or cationic amino acid. The modification can be an external or terminal cationic residue. In another embodiment, the oligonucleotide agent can be modified with a sugar, e.g., a glycoconjugate or alkylglycoside component, e.g., glucose, mannose, 2-deoxy-glucose, or an analog thereof. In another embodiment, the oligonucleotide agent can be conjugated to an enzyme substrate, e.g., a substrate for which the relative enzyme is present in a higher amount, as compared to the enzyme level in other tissues of the body. For example, the oligonucleotide agent can be conjugated to a substrate of γ-glutamyl transferase or n-acetyl-γ-glutamyl transferase.

In one embodiment, the oligonucleotide agent can be conjugated to a folic acid or folic acid derivative, e.g., γ-folate, α-folate, 5-methyl tetrahydrofolic acid, a pteridine analog, or an alternative analog thereof.

In one embodiment, the oligonucleotide agent of the invention can be conjugated to a protein that will accumulate in the kidney when administered systematically. For example, the oligonucleotide agent can be conjugated to a lysozyme, cytochrome-c or aprotinin protein. In one embodiment, the oligonucleotide agent can be conjugated to a lysine residue of the protein.

In one embodiment, an oligonucleotide agent targeted to the kidney can be conjugated to a low molecular weight polyethylene glycol (PEG) molecule, or guanidium group, and in another embodiment, the oligonucleotide agent can be conjugated to an RGD peptide, peptide analog, or peptide mimetic or derivative thereof. An oligonucleotide conjugated to an RGD peptide, peptide analog, or peptide mimetic can bind to an $\alpha_v\beta_3$ integrin.

Synthetic Integrin Inhibitors

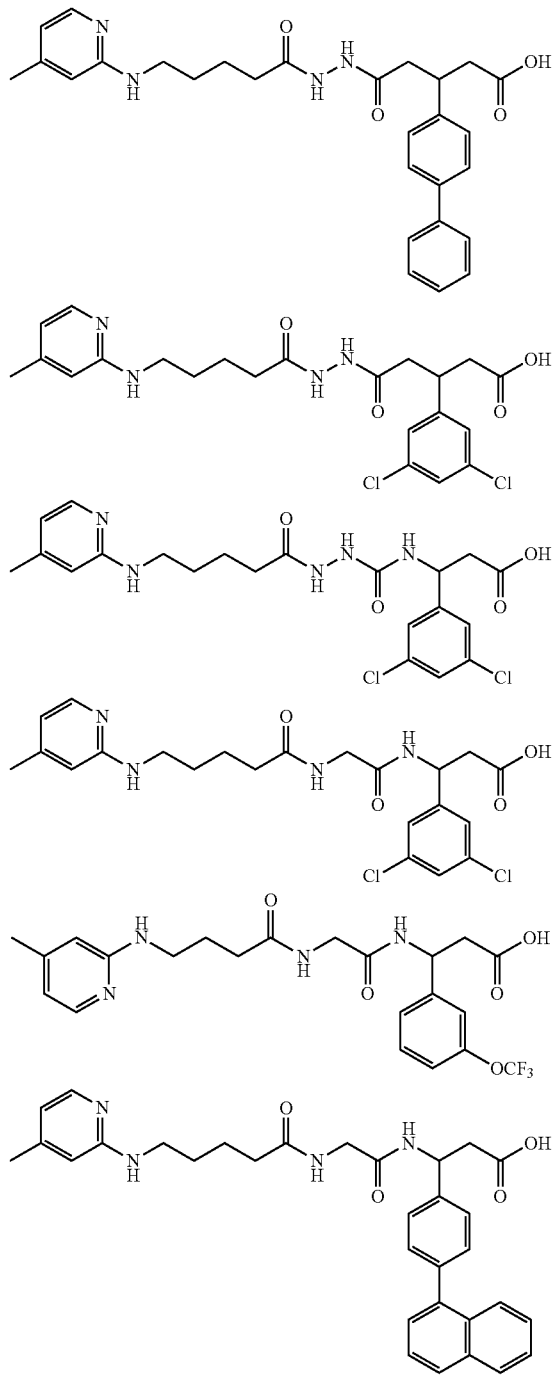

-continued

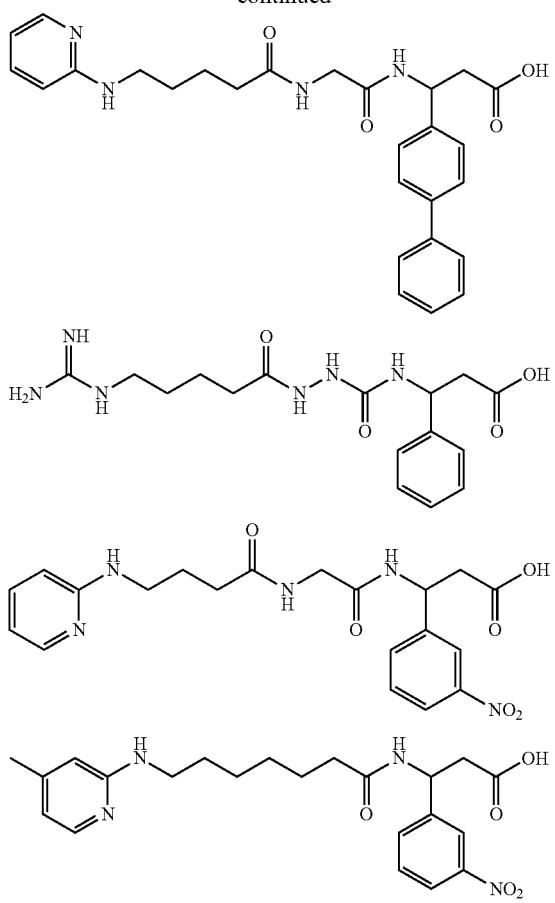

Ref: Goodman, S. L.; Hölzemann, G.; Sulyok, G. A. G.; Kessler, H. *J. Med. Chem.* 2002, 45, 1045-1051.

TABLE 8

| R | base | spacer |
|---|---|---|
| (Carboxamide)[a] | guanidine | m-C$_6$H$_4$— |
| none | guanidine | ω-C$_4$H$_8$— |
| none | guanidine | m-C$_6$H$_4$— |
| 4-F | guanidine | m-C$_6$H$_4$— |
| 4-Cl | guanidine | m-C$_6$H$_4$— |
| 4-Br | guanidine | m-C$_6$H$_4$— |
| 4-OCH$_3$ | guanidine | m-C$_6$H$_4$— |
| 4-OCF$_3$ | guanidine | guanidine |
| (1-naphthyl)[a] | guanidine | m-C$_6$H$_4$— |
| 3-Cl, 5-Cl | guanidine | m-C$_6$H$_4$— |
| (H)[a] | 2-NH$_2$-pyridine | ω-C$_4$H$_8$— |
| none | 2-NH$_2$-pyridine | ω-C$_4$H$_8$— |
| 4-F | 2-NH$_2$-pyridine | ω-C$_4$H$_8$— |
| 4-Cl | 2-NH$_2$-pyridine | ω-C$_4$H$_8$— |
| 4-Br | 2-NH$_2$-pyridine | ω-C$_4$H$_8$— |
| 4-OCH$_3$ | 2-NH$_2$-pyridine | ω-C$_4$H$_8$— |
| 4-OCF$_3$ | 2-NH$_2$-pyridine | ω-C$_4$H$_8$— |

TABLE 8-continued

| R | base | spacer |
|---|---|---|
| (1-naphthyl)[a] | 2-NH$_2$-pyridine | ω-C$_4$H$_8$— |
| 3-Cl, 5-Cl | 2-NH$_2$-pyridine | ω-C$_4$H$_8$— |

[a]Instead of substituted phenyl ring

Ref: Sulyok, G. A. G.; Gibson, C.; Goodman, S. L.; Hölzemann, G.; Wiesner, M.; Kessler H. *J. Med. Chem.* 2001, 44, 1938-1950

In a preferred embodiment, at least 30%, 40%, 50%, 60%, 70%, 80%, 90% or more of the oligonucleotide agent administered to the subject is successfully targeted to the kidney. In a preferred embodiment between 30-90%, 40-80% or 50-70% 50-80%, or 50-90% of the oligonucleotide agent administered to the subject is successfully targeted to the kidney.

In any of the embodiments described above, the oligonucleotide agent/conjugate can have additional modifications, such as a stabilizing modification. For example, a linker molecule can tether a protein, PEG or RGD peptide to the oligonucleotide agent. Exemplary linkers are described infra, and can include amino linkers (e.g., aminooxy linkers), thiol linkers, carboxyl linkers, aldehyde linkers, haloacetyl linkers, and the like.

In another aspect, the invention features an conjugate oligonucleotide agent. The conjugate includes an oligonucleotide agent coupled to, e.g., linked to, a ligand or therapeutic agent. The oligonucleotide agent is optionally coupled to the ligand or therapeutic agent by a linker (e.g., a peptide linker or other linker described herein). The ligand can function to, e.g., affect the distribution of the oligonucleotide agent in the body and/or to target the oligonucleotide agent to a particular tissue or cell.

The ligand can be placed at an end of the oligonucleotide agent, preferably at the 3'end of an oligonucleotide agent. The ligand can also be placed at the 5'end, or within the middle of the oligonucleotide agent. In some embodiments, more than one ligand can be coupled to the oligonucleotide agent. For example, a ligand can be coupled to the 3' end of an oligonucleotide agent; a ligand can be coupled to an end, e.g., a 3' end, and to the middle of an oligonucleotide agent; a ligand can be coupled to the 3' end and the 5' of an oligonucleotide agent; a ligand can be coupled to the 3' end, the 5' end, and to one or more internal positions of an oligonucleotide agent.

In one embodiment, the ligand of a conjugated oligonucleotide agent is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including, but not limited to parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In a preferred embodiment, the lipid or lipid based ligand is a phosphorothioate. In this embodiment, it is preferred that the number of sulfurs on the phosphorothioate not be so prevalent that they interfere with binding to a serum protein, e.g., HSA.

In another embodiment, the ligand is a peptide or peptoid. Peptoids, in particular amphipathic species, such as Antennapedia or tat, are preferred.

In another embodiment, the ligand is a polyethylene glycol (PEG) or derivatives thereof. A PEG can, e.g., allow the agent to be kept in circulation. A PEG is intrinsically amphipathic, and can promote stability, particularly if coupled at the 3'end of the oligonucleotide agent.

In another embodiment, the ligand is a charged group or moiety, e.g., a polyamine or cationic group or moiety. This type of linker moiety, e.g., because of its charge, e.g., its negative charge, can help overcome the resistance of entry of the oligonucleotide agent into a cell. Preferably, these are conjugated at the 3' end, but they can also be at the 5' end or within the middle of the oligonucleotide molecule. Exemplary polyamines include polyarginine, polylysine, polyhistidine, polypreprozine, or polymorpholinos, polyornithine.

In another embodiment, the ligand is a vitamin or other moiety that is taken up by a target cell, e.g., a proliferating cell. These are particularly useful for treating disorders characterized by unwanted cell proliferation, e.g., of the malignant or non-malignant type, e.g., cancer cells. Exemplary vitamins are B vitamin, e.g., folic acid, B12, riboflavin, biotin, pyridoxal or other vitamins or nutrients taken up by cancer cells. Also included are HSA and low density lipoprotein (LDL).

In another embodiment, the ligand is a cell-permeation agent, preferably a helical cell-permeation agent. Preferably, the agent is amphipathic. An exemplary agent is a peptide such as tat or Antennapodia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a targeting agent. The targeting agent can be a sugar, a peptide, e.g., an RGD containing peptide.

Another useful targeting agent is one that incorporates a sugar, e.g., galactose and/or analogs thereof. These are useful because they target the liver, in particular, the parenchymal cells of the liver. In a preferred embodiment, the targeting agent includes more than one galactose moiety, preferably two or three. Preferably, the targeting agent includes 3 galactose moieties, e.g., spaced about 15 angstroms from each other. The targeting agent can be lactose. Lactose is a glucose coupled to a galactose. Preferably, the targeting agent includes three lactoses. The targeting agent can also be N-Acetyl-Galactosamine, N-Ac-Glucosamine. A mannose, or mannose-6-phosphate targeting agent can be used for macrophage targeting.

Peptides that target markers enriched in proliferating cells can be used. E.g., RGD containing peptides and peptidomimetics can target cancer cells, in particular cells that exhibit an $I_v\theta_3$ integrin. Thus, one could use RGD peptides, cyclic peptides containing RGD, RGD peptides that include D-amino acids, as well as synthetic RGD mimics. In additional to RGD, one can use other moieties that target the $I_v$-$\theta_3$ integrin ligand. Generally, such ligands can be used to control proliferating cells and angiogenesis. Preferred conjugates of this type include an oligonucleotide agent that targets PECAM-1, VEGF, or other cancer gene, e.g., a cancer gene described herein.

In one embodiment, an oligonucleotide agent is linked, e.g., directly linked, e.g., covalently, or non-covalently linked, to the targeting agent, e.g., a targeting agent described herein. This is referred to as a "conjugation" approach. In another embodiment, the targeting agent (e.g., the same targeting agent) is simply mixed with the oligonucleotide agent. This is referred to as a "complexing" approach. In a complexing approach, the oligonucleotide agent can be mixed with, e.g., a cationic molecule, e.g., a cationic lipid, e.g., with or without a targeting group, e.g., with or without a sugar or an RGD construct described herein. In some embodiments, the oligonucleotide agent is mixed with a polymer-based system, e.g., with or without a targeting group. In other embodiments, the oligonucleotide agent is mixed with a nanoparticle.

The conjugate oligonucleotide agents described herein can include a targeting agent that targets the oligonucleotide agent to a desired target cell or tissue. The target cell or tissue can be a cancer cell, a cell of the vasculature, e.g, tumor vasculature, an angiogenic cell, e.g., a tumor angiogenic cell, or an endosome. A preferred target is the kidney. In another embodiment, the liver e.g., the parenchymal cells of the liver, is a preferred target.

The methods and compositions of the invention, e.g., the conjugates described herein, can be used with any of the oligonucleotide agents described herein. In addition, the methods and compositions of the invention can be used for the treatment of any disease or disorder described herein, and for the treatment of any subject, e.g., any animal, any mammal, such as any human.

The methods and compositions of the invention, e.g., the conjugates described herein, can be used with any dosage and/or formulation described herein, as well as with any route of administration described herein.

As used herein, "conjugated" means two entities are associated, e.g., with sufficient affinity that the therapeutic benefit of the association between the two entities is realized. Conjugated can include covalent or noncovalent bonding as well as other forms of association, such as entrapment, e.g., of one entity on or within the other, or of either or both entities on or within a third entity, such as a micelle. Particularly preferred forms of conjugation are by covalent bonding, e.g., those described herein. An entity can be conjugated to an oligonucleotide agent, e.g., at the 3' or 5' terminus or internally. It is preferred that an entity is conjugated to the oligonucleotide agent in such a way as to preserve the ability of the oligonucleotide agent to mediate inhibition of gene expression.

Treatment of Ocular Disease

The oligonucleotide agents featured in the invention can be used to treat an ocular disease, such as age-related macular degeneration (AMD), glaucoma, cataract, optic nerve atrophy, diabetic retinopathy (DR), or retinitis pigmentosa. Table 9 summarizes gene targets for oligonucleotide agents described herein for the treatment of an ocular disease.

TABLE 9

Potential gene targets for treatment of ocular disease.

| Disease | Gene | OMIM number | Reference |
| --- | --- | --- | --- |
| AMD, DME | VEGF | 192240 | Husain et al., 2002 |
| AMD, DME, glaucoma | PKC-beta | 176970 | Clark & Yario, 2003 |
| AMD, DR | ACE | 106180 | Sjolie & Chaturvedi., 2002 |
| AMD, DR | angiotensin II receptor | 106165 | Sjolie & Chaturvedi., 2002 |
| AMD, DR | MMPs-2, -9, -13 and -14 | 120360, 120361, 600108, 600754 | Scatena, 2000 |
| AMD, DR | Integrins alpha v beta 3 and alpha v beta 5 | 193210, 173470, 147561 | Friedlander et al., 1996 |
| AMD, DR | GH1 | 139250 | Smith et al., 1997 |
| AMD, DR | IGF-I | 147440 | Smith et al., 1997 |
| AMD, DR, glaucoma | C-raf kinase (Raf-1) | 164760 | Danis et al. 2003, Hecquet et al. 2002 |
| Glaucoma, DR | Ras | | Hecquet et al. 2002 |
| Glaucoma, DR | cyclin D1 | 168461 | Hecquet et al. 2002 |
| Glaucoma | Carbonic anhydrases XII (CA12), II (CA2), IV (CA4) | 603263, 259730, 114760 | Liao et al., 2003 |
| Glaucoma | myosin light chain kinase | 600922 | Clark & Yario, 2003 |
| Glaucoma, DR | nitric oxide synthase | 163731 | Wilson, 1999; Clark & Yorio, 2003 |
| Glaucoma, DR | TNF-α | 191160 | Wilson, 1999; Clark & Yorio, 2003 |
| Glaucoma, DR | TNF-α receptor | 191190 | Wilson, 1999; Clark & Yorio, 2003 |
| Glaucoma, DR | Bcl-2, Bel-XL | | Wilson, 1999; Clark & Yorio, 2003 |

In one embodiment, an oligonucleotide agent targets VEGF or protein kinase C for the treatment of, e.g., AMD and diabetic macular edema (DME).

In another embodiment, an oligonucleotide agent is used as a therapy for the treatment of AMD or DR, by targeting, e.g., angiotensin converting enzyme (ACE), angiotensin II receptor, growth factors (e.g., c-Abl, c-Kit, platelet-derived growth factor (PDGF), epidermal growth factor (EGF), insulin-like growth factor (IGF), growth hormone 1 (GH1), insulin-like growth factor-I (IGF-I), or c-raf kinase (raf-1), or their receptors), an inhibitor of matrix metalloproteinases (MMPs)-2, -9, -13 or -14, integrin alpha v beta 3, or alpha v beta 5.

In one embodiment, an oligonucleotide agent targets a caspase, Bcl family member, nitric oxide synthase, endothelin, TNF-α or TNF-α receptor, ERK2, MEK1/2, or cyclin D1. These oligonucleotide agents can be useful for the treatment of, e.g., glaucoma, retinitis pigmentosa, cataract formation, retinoblastoma, retinal ischemia, DR, or an ocular diseases involving the posterior segment, such as a viral infection or vitreoretinopathy.

In one embodiment, an oligonucleotide agent targets a carbonic anhydrase (CA2, CA4, and CA12) or protein kinase, e.g., protein kinase C or myosin light chain kinase. These oligonucleotide agents can be useful for the treatment of, e.g., glaucoma.

In one embodiment, an oligonucleotide agent targets an adhesion molecule, cytokine, chemokine, MMPs, or tissue inhibitor of metalloproteinase (TIMPs). These oligonucleotide agents can be useful for the treatment of, e.g., immunologic challenge, wounding, infection, genetic disease, diabetes, or vitamin A deficiency.

In one embodiment, an oligonucleotide agent targets NOS-II. These oligonucleotide agents can be useful for the treatment of, e.g., uveitis.

In one embodiment, an oligonucleotide agent targets cyclin D1, e.g., to decrease cell proliferation in cells of the eye, e.g., retinal pigment epithelium cells.

In one embodiment, the oligonucleotide agent targets an miRNA expressed in the eye. In another embodiment, the human is suffering from a disorder characterized by increased expression or accumulation of the miRNA in the eye, or decreased expression of a nucleic acid that is the target of the miRNA expressed in the eye. Administration of the oligonucleotide agent to the subject, e.g., to the eye of the subject, results in the pairing of the oligonucleotide agent with the target miRNA and the subsequent downregulation of the miRNA.

In one embodiment, the oligonucleotide agent is substantially identical to an miRNA normally expressed in the eye, and in another embodiment, the human is suffering from a disorder characterized by decreased expression of the miRNA in the eye. Administration of the oligonucleotide agent to the subject, e.g., to the eye of the subject, at least partially rescues the function of the downregulated miRNA.

An oligonucleotide agent useful for treating an ocular disease can be delivered to the eye by, e.g., iontophoresis (e.g., transcorneoscleral iontophoresis), topically (e.g., by a patch or disk, or by eye drops), or by intravitreal injection. The oligonucleotide agent can be formulated in sterically stabilized liposomes.

Targeting to the Liver

Aspects of the invention relate to silencing genes expressed in the liver, or to upregulating genes that are regulated by one or more endogenous miRNAs. Accordingly, the invention includes compositions and methods for delivering oligonucleotide agents to the liver, e.g., to treat disorders of or related to the liver.

An oligonucleotide agent composition of the invention can be one that has been modified to alter distribution in favor of the liver. A composition of the invention includes an oligonucleotide agent, e.g., an oligonucleotide agent described herein.

An oligonucleotide agent directed to the liver can target apoB-100 to treat a disorder characterized by elevated or otherwise unwanted expression of apoB-100, elevated or otherwise unwanted levels of cholesterol, and/or disregulation of lipid metabolism. The oligonucleotide agent can be administered to an individual at risk for the disorder to delay onset of the disorder or a symptom of the disorder. These disorders include HDL/LDL cholesterol imbalance; dyslipidemias, e.g., familial combined hyperlipidemia (FCHL), acquired hyperlipidemia; hypercholestorolemia; statin-resistant hypercholesterolemia; coronary artery disease (CAD) coronary heart disease (CHD) atherosclerosis. In one embodiment, the oligonucleotide agent that targets apoB-100 is administered to a subject diagnosed as having statin-resistant hypercholesterolemia.

The apoB-100 oligonucleotide agent can be administered in an amount sufficient to reduce levels of serum LDL-C and/or HDL-C and/or total cholesterol in a subject. In one embodiment, the oligonucleotide agent is administered in an amount sufficient to reduce the risk of myocardial infarction the subject.

In one embodiment, expression levels of apoB-100 are decreased in the liver following administration of the apoB-100 oligonucleotide agent. For example, the oligonucleotide agent can be complexed with a moiety that targets the liver, e.g., an antibody or ligand that binds a receptor on the liver.

In other embodiments, an oligonucleotide agent targeted to the liver can modulate expression of, e.g., beta-catenin or glucose-6-phosphatase RNA, to treat a liver-related disorder.

In another embodiment, the oligonucleotide agent targets an miRNA or pre-miRNA expressed in the liver. In another embodiment, the human is suffering from a disorder characterized by overexpression or accumulation of the miRNA in the liver, or decreased expression of a nucleic acid that is the target of the miRNA expressed in the liver. Administration of the oligonucleotide agent to the subject, or to a cell of the lung of the subject, can result in the pairing of the oligonucleotide agent with the target miRNA and the subsequent downregulation of the miRNA.

In one embodiment, the oligonucleotide agent is substantially identical to an miRNA normally expressed in liver tissue, and in another embodiment, the human is suffering from a disorder characterized by decreased expression of the miRNA in the liver. Administration of the oligonucleotide agent to the subject, or to a cell of the liver, at least partially rescues the function of the downregulated miRNA.

Treatment of Pulmonary Disease

An oligonucleotide agent featured in the invention can be used for treating a patient diagnosed as having a pulmonary disease, e.g., chronic bronchitis (including chronic bronchitis), emphysema, asthma (including pediatric asthma), chronic obstructive pulmonary disease (COPD), lung cancer, or a respiratory infection.

In one embodiment, an oligonucleotide agent targets, e.g., a stress kinase (such as JNK, MAPK, or p38), a redox sensitive transcription factor (such as NF-kappa B, KJE, or AP-1), interleukin-5 (IL-5) or the IL-5 receptor, phosphodiesterase 4, ICAM-1, CD11/CD18, E-selectin, interleukin-10, stem cell factor (SCF), MUC5AC, or adenosine A1 receptor. These oligonucleotide agents can be useful for the treatment of, e.g., COPD or asthma, such as bronchial asthma.

Other gene targets for the treatment of COPD include beta-2 adrenergic receptor, leukotriene $D_4$, 5'-lipoxygenase, interleukin-8, MCP-1, TNF-alpha, epidermal growth factor receptor, tyrosine kinase, MUC4, MUC8, and matrix-degrading proteinases, such as serine elastase, ELA2, OMIM 130130 and neutrophil elastase.

TABLE 10

Potential gene targets for treatment of pulmonary disease.

| Disease | Gene | OMIM number | Reference |
| --- | --- | --- | --- |
| asthma | adenosine A1 receptor | 102755 | Ball et al., 2003 |
| Cancer | Bcl family | | Koty et al., 2002 |
| asthma and COPD | Beta-2 adrenergic receptor | 109690 | Barnes, 1999 |
| asthma and COPD | CD11/CD18 | 600065 | Barnes, 1999 |
| asthma and COPD | E-selectin | 131210 | Barnes, 1999 |
| Cancer | farnesyl transferase | 134635, 134636 | Scharovsky et al., 2000 |
| asthma and COPD | ICAM-1 | 147840 | Barnes, 1999 |
| asthma | IL-5 | 147850 | Blumchen et al., 2001 |
| asthma | IL-5 receptor | | Blumchen et al., 2001 |
| asthma and COPD | interleukin-10 | 124092 | Barnes, 1999 |
| asthma and COPD | interleukin-8 | 146930 | Barnes, 1999 |
| asthma and COPD | leukotriene $D_4$ | | Barnes, 1999 |
| asthma and COPD | MAP-kinase | | Barnes, 1999 |
| asthma and COPD | matrix metalloproteinases | | Shapiro, 2002 |
| asthma and COPD | MCP-1 | 158105 | Barnes, 1999 |

TABLE 10-continued

Potential gene targets for treatment of pulmonary disease.

| Disease | Gene | OMIM number | Reference |
|---|---|---|---|
| COPD | MUC-4 and MUC-8 | 158372, 601932 | Barnes, 1999 |
| asthma | MUC5AC | 158373 | Fahy, 2002 |
| asthma and COPD | neutrophil elastase | 130130 | Wright et al., 2002 |
| asthma and COPD | Phosphodiesterase 4 | | Barnes, 1999 |
| Cancer | polo-like kinase-1 | 602098 | Spankuch-Schmitt et al., 2002 |
| Cancer | R2 small subunit component of human ribonucleotide reductase | 180390 | Lee et al., 2003 |
| Cancer | ras | | Scharovsky et al., 2000 |
| asthma | SCF | 184745 | Finotto et al., 2001 |
| asthma and COPD | serine elastase | | Wright et al., 2002 |
| asthma and COPD | serine proteinases | | Shapiro, 2002 |
| Cancer | Stat3 | 102582 | Song et al., 2003 |
| asthma and COPD | TNF-alpha | 191160 | Barnes, 1999 |
| Cancer | VEGF receptors | 191306 | Pavco et al., 2003 |
| Viral diseases | viral RNA polymerase genes | | Paddle, 2003; Mizuta et al., 1999 |

Oligonucleotide agents described herein can be useful in the treatment of pathogenic infection. For example, a human infected with influenza A can be administered an oligonucleotide agent that targets influenza A PB2 or PA genes. Oligonucleotide agents that target genes of pathogens such as influenza A can also be useful in the treatment of victims of biowarfare attack.

An oligonucleotide agent can target a ras family gene or farnesyl transferase, Stat3, the R2 small subunit component of human ribonucleotide reductase, a Bcl gene (e.g., Bcl-2), polo-like kinase-1 (PLK1), a VEGF receptors, anti-Flt-1 (VEGFR-1) or anti-KDR (VEGFR-2). These oligonucleotide agents would be useful for treating a lung cancer.

An oligonucleotide agent can target SCR, SCF, or the p65 subunit of NF-kappa B for the inhibition or treatment of a pulmonary reaction to an allergen. For example, these oligonucleotide agents can be used to inhibit or treat lung inflammation.

An oligonucleotide agent that targets a gene encoding the p65 subunit of NF-kappa B can be used to treat pneumonitis.

In one embodiment, the oligonucleotide agent targets an miRNA expressed in a tissue of the pulmonary system, e.g., in the lung. In another embodiment, the human is suffering from a disorder characterized by overexpression or accumulation of the miRNA in the lung, or decreased expression of a nucleic acid that is the target of the miRNA expressed in the lung. Administration of the oligonucleotide agent to the subject, or to a cell of the lung of the subject, can result in the pairing of the oligonucleotide agent with the target miRNA and the subsequent downregulation of the miRNA.

An oligonucleotide agent useful for the treatment of asthma can be delivered directly to the lung, e.g., via an inhaled aerosol. A liposomal delivery agent can be used to deliver an oligonucleotide agent to the lung. Oligonucleotide agents, and oligonucleotide agents that include phosphorothioate linkages in particular, can be administered via inhalation, and can subsequently localize to the bronchiolar and alveolar epithelium and endothelium. An oligonucleotide agent can be administered via inhalation at a dosage less than about 15 mg/kg, e.g., less than 12 mg/kg, 10 mg/kg, 8 mg/kg, 6 mg/kg, 5 mg/kg, 4 mg/kg, 3 mg/kg, 2 mg/kg, 1 mg/kg, 0.1 mg/kg, or 0.001 mg/kg.

An oligonucleotide agent can be administered by intratracheal instillation, intranasally, or intravenously for the treatment of a pulmonary disorder.

Treatment of Viral Infection

An oligonucleotide agent, e.g., a conjugated oligonucleotide agent, can be used to target a viral gene, e.g., a gene of a hepatitis C virus (HCV), hepatitis B virus (HBV), hepatitis A virus (HAV), HIV, Epstein-Barr virus, Respiratory syncytial virus, cytomegalovirus (CMV), human papilloma virus (HPV), or influenza, e.g., influenza A.

An oligonucleotide agent can be used to treat a viral infection or a cancer. For example, an oligonucleotide agent can target an HPV, e.g., HPV 16, 18, 31, 33, or 45, for the treatment of cervical neoplasia. An oligonucleotide agent can target, e.g., E6, E7, or MCP-1 of HPV. In addition, or in an alternative, an oligonucleotide agent can target nucleolin in the host subject.

An oligonucleotide agent for the treatment of an HIV infection can target, e.g., the gag, tat, vpr, rev, env, nef, pol, vir, or gp120 gene of the HIV virus.

An oligonucleotide agent that targets a viral gene can be delivered to a subject in the form of a recombinant adenovector or by retroviral-delivery. Delivery can be directly to a tumor tissue, for example.

In one embodiment, the oligonucleotide agent targets an miRNA expressed by a pathogen, e.g., a viral pathogen or bacterial pathogen. For example, an oligonucleotide agent can target an miRNA expressed in a virus, such as a herpesvirus. The herpesvirus can be, for example, an Epstein-Barr virus (EBV or HHV4), a gammaherpesvirus (e.g., a Kaposi sarcoma-associated virus (KSHV or HHV8), a mouse gammaherpesvirus 68 (MHV68)), or a betaherpesvirus (e.g., a human cytomegalovirus (HCMV or HHV5)) (see Pfeffer et al., Science 304:734-736, 2004, and Pfeffer et al., Nature Methods 2:269-276, 2005). Administration of the oligonucleotide agent to the subject results in the pairing of the oligonucleotide agent with the target miRNA and the subsequent decrease in the interaction with the pathogenic miRNA with its target, e.g., a target miRNA endogenous to the pathogen or to the host subject. This interaction results in a decrease in infection of the host by the pathogen.

Other Exemplary Therapeutic Gene Targets

An oligonucleotide agent, e.g., a conjugated oligonucleotide agent described herein, can inhibit a gene involved in cellular adhesion, e.g., ICAM-1, VCAM-1, or ELAM-1.

An oligonucleotide agent can inhibit a gene required for the regulation of cellular proliferation, e.g., c-myb, vascular endothelial growth factor (VEGF), Ha-ras, A-raf kinase, c-raf kinase, or MRP.

An oligonucleotide agent can inhibit a gene involved in the pathogenesis of disease, e.g., beta-thalassemia.

An oligonucleotide agent can inhibit a gene involved in the pathogenesis of disease caused by a pathogen. For example, a *plasmodium* can cause malaria PS1 or PSII, or a shistosoma can cause bloodfluke infections. An oligonucleotide agent that targets a gene of the pathogen can be used to treat the disease.

In one embodiment, the oligonucleotide agent binds an miRNA involved in the pathogenesis of disease.

An oligonucleotide agent can also be administered to human at risk for or afflicted with a neurological disease or disorder, e.g., Alzheimer Disease or Parkinson Disease. For example, an oligonucleotide agent can target an amyloid-family gene, e.g., APP; a presenilin gene, e.g., PSEN1 and PSEN2, or α-synuclein.

An oligonucleotide agent can be administered to a human to treat a neurodegenerative trinucleotide repeat disorder, e.g., Huntington disease (HD), dentatorubral pallidoluysian atrophy (DRPLA) or a spinocerebellar ataxia, e.g., SCA1, SCA2, SCA3 (Machado-Joseph disease), SCA7 or SCA8. For example, an oligonucleotide agent can decrease expression of an HD, DRPLA, SCA1, SCA2, MJD1, CACNL1A4, SCA7, or SCA8 gene.

Oligonucleotide agents featured in the invention can be used to treat a disease of the pancreas, e.g. pancreatitis, pancreatic cancer, diabetes or hyperglycemia. For example, an oligonucleotide agent that targets Ras, JNK, or survivin can be useful for treatment of pancreatic cancer. In one embodiment, the oligonucleotide agent can target an miRNA expressed in the pancreas, e.g., miR-375, such as for the treatment of diabetes. In another embodiment, the oligonucleotide agent is substantially identical to an miRNA expressed in the pancreas, e.g., miR-375.

Oligonucleotide agents featured in the invention can be used to treat a disease of the gut, e.g. gastroenteritis.

Route of Delivery

The oligonucleotide agents described herein can be administered by various routes of delivery, e.g., by ocular, pulmonary, intravenous, topical, rectal, anal, or vaginal, delivery, e.g. as described in International Application Serial No. PCT/US2004/11829, filed Apr. 16, 2004. The contents of this reference are incorporated herein in their entirety.

Dosage

In one aspect, the invention features a method of administering an oligonucleotide agent, to a subject (e.g., a human subject). The method includes administering a unit dose of the oligonucleotide agent, e.g., a microRNA, antisense RNA, decoy RNA or aptamer, that targets an RNA, e.g., an miRNA, or protein in the subject (e.g., an endogenous or pathogen target RNA or protein). In one embodiment, the unit dose is less than 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of oligonucleotide agent (e.g. about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of oligonucleotide agent per kg of bodyweight.

The defined amount can be an amount effective to treat or prevent a disease or disorder, e.g., a disease or disorder associated with the target RNA, such as an RNA present in the kidney. The unit dose, for example, can be administered by injection (e.g., intravenous or intramuscular), an inhaled dose, or a topical application. Particularly preferred dosages are less than 2, 1, or 0.1 mg/kg of body weight.

In a preferred embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has a viral infection and the modality is an antiviral agent other than an oligonucleotide agent. In another embodiment, the subject has atherosclerosis and the effective dose of an oligonucleotide agent is administered in combination with, e.g., after surgical intervention, e.g., angioplasty.

In one embodiment, a subject is administered an initial dose and one or more maintenance doses of an oligonucleotide agent, or a precursor, e.g., a larger oligonucleotide agent which can be processed into an oligonucleotide agent, or a DNA which encodes an oligonucleotide agent, or precursor thereof. The maintenance dose or doses are generally lower than the initial dose, e.g., one-half less of the initial dose. A maintenance regimen can include treating the subject with a dose or doses ranging from 0.01 μg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time, which will vary depending upon the nature of the particular disease, its severity and the overall condition of the patient. In preferred embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the oligonucleotide agent pharmaceutical composition includes a plurality of oligonucleotide agent species. In another embodiment, the oligonucleotide agent species has sequences that are non-overlapping and non-adjacent to another species with respect to a naturally occurring target sequence. In another embodiment, the plurality of oligonucleotide agent species is specific for different naturally occurring target genes. In another embodiment, the oligonucleotide agent is allele specific.

In some cases, a patient is treated with an oligonucleotide agent in conjunction with other therapeutic modalities. For example, a patient being treated for a kidney disease, e.g., early stage renal disease, can be administered an oligonucleotide agent specific for a target gene known to enhance the progression of the disease in conjunction with a drug known to inhibit activity of the target gene product. For example, a patient who has early stage renal disease can be treated with an oligonucleotide agent that targets an SGLT2 RNA, in conjunction with the small molecule phlorizin, which is known to block sodium-glucose cotransport and to subsequently reduce single nephron glomerular filtration rate. In another example, a patient being treated for a cancer of the kidney can be administered an oligonucleotide agent specific for a target essential for tumor cell proliferation in conjunction with a chemotherapy.

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

The concentration of the oligonucleotide agent composition is an amount sufficient to be effective in treating or preventing a disorder or to regulate a physiological condition in humans. The concentration or amount of oligonucleotide agent administered will depend on the parameters determined for the agent and the method of administration, e.g. nasal, buccal, pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an oligonucleotide agent, e.g., a double-stranded oligonucleotide agent or a DNA which encodes an oligonucleotide agent, or precursor thereof) can include a single treatment or, preferably, can include a series of treatments. It will also be appreciated that the effective dosage of an oligonucleotide agent used for treatment may increase or decrease over the course of a particular treatment. Changes in dosage may result and become apparent from the results of diagnostic assays as described herein. For example, the subject can be monitored after administering an oligonucleotide agent composition. Based on information from the monitoring, an additional amount of the oligonucleotide agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g. a gene that produces a target RNA. The transgenic animal can be deficient for the corresponding endogenous RNA. In another embodiment, the composition for testing includes an oligonucleotide agent that is complementary, at least in an internal region, to a sequence that is conserved between the target RNA in the animal model and the target RNA in a human.

In one aspect, the invention features a method that includes: administering a first amount of a composition that comprises an oligonucleotide agent or a DNA which encodes an oligonucleotide agent, e.g., a double-stranded oligonucleotide agent or precursor thereof) to a subject, wherein the oligonucleotide agent is substantially complementary to a target nucleic acid; evaluating an activity associated with a protein encoded by the target nucleic acid; wherein the evaluation is used to determine if a second amount should be administered. In a preferred embodiment the method includes administering a second amount of the composition, wherein the timing of administration or dosage of the second amount is a function of the evaluating. The method can include other features described herein.

In another aspect, the invention features a method of administering a source of an oligonucleotide agent to a subject. The method includes administering or implanting a source of an oligonucleotide agent. In one embodiment, the source releases the oligonucleotide agent over time, e.g. the source is a controlled or a slow release source, e.g., a microparticle that gradually releases the oligonucleotide agent. In another embodiment, the source is a pump, e.g., a pump that includes a sensor or a pump that can release one or more unit doses.

In one aspect, the invention features a pharmaceutical composition that includes a NAT oligonucleotide agent or a DNA which encodes an oligonucleotide agent, including a nucleotide sequence sufficiently complementary to a target RNA to allow duplex formation with a target nucleic acid. The target RNA can be a transcript of an endogenous human gene. In one embodiment, the oligonucleotide agent (a) is about 5 to about 100 nucleobases long, e.g., about 8 to about 75, e.g., about 8 to about 50 nucleotides long, e.g., about 15 to about 30 nucleotides long, e.g., 15, 16, 17, 18, 19, 20, 21, 22, 23, 24, or 25 nucleotides; and (b) is complementary to an endogenous target RNA In one embodiment, the pharmaceutical composition can be an emulsion, microemulsion, cream, jelly, or liposome.

In certain other aspects, the invention provides kits that include a suitable container containing a pharmaceutical formulation of an oligonucleotide agent or a DNA which encodes an oligonucleotide agent or a precursor of an oligonucleotide agent). In certain embodiments the individual components of the pharmaceutical formulation may be provided in one container. Alternatively, it may be desirable to provide the components of the pharmaceutical formulation separately in two or more containers, e.g., one container for an oligonucleotide agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

In another aspect, the invention features a device, e.g., an implantable device, wherein the device can dispense or administer a composition that includes an oligonucleotide agent, or a precursor, e.g., a larger oligonucleotide agent which can be processed into an oligonucleotide agent, or a DNA which encodes an oligonucleotide agent. The oligonucleotide agent can inhibit expression of an endogenous transcript. In one embodiment, the device is coated with the composition. In another embodiment the oligonucleotide agent is disposed within the device. In another embodiment, the device includes a mechanism to dispense a unit dose of the composition. In other embodiments the device releases the composition continuously, e.g., by diffusion. Exemplary devices include stents, catheters, pumps, artificial organs or organ components (e.g., artificial heart, a heart valve, etc.), and sutures.

The invention is further illustrated by the following examples, which should not be construed as further limiting.

EXAMPLES

Example 1

Diethyl 2-azabutane-1,4-dicarboxylate AA

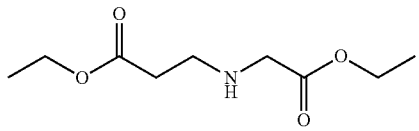

A 4.7M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until the completion of reaction was ascertained by TLC (19 h). After 19 h which it was partitioned with dichloromethane (3×100 mL). The organic layer was dried with anhydrous sodium sulfate, filtered and evaporated. The residue was distilled to afford AA (28.8 g, 61%).

Example 2

3-{Ethoxycarbonylmethyl-[6-(9H-fluoren-9-yl-methoxycarbonyl-amino)-hexanoyl]-amino}-propionic acid ethyl ester AB

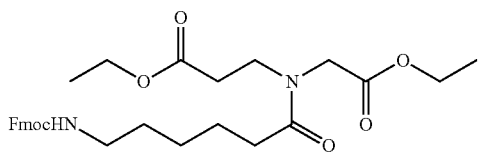

Fmoc-6-amino-hexanoic acid (9.12 g, 25.83 mmol) was dissolved in dichloromethane (50 mL) and cooled with ice. Diisopropylcarbodiimide (3.25 g, 3.99 mL, 25.83 mmol) was added to the solution at 0° C. It was then followed by the addition of Diethyl 2-azabutane-1,4-dicarboxylate (5 g, 24.6 mmol) and dimethylamino pyridine (0.305 g, 2.5 mmol). The solution was brought to room temperature and stirred further for 6 h. the completion of the reaction was ascertained by TLC. The reaction mixture was concentrated in vacuum and to the ethylacetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB

Example 3

3-[(6-Amino-hexanoyl)-ethoxycarbonylmethyl-amino]-propionic acid ethyl ester AC

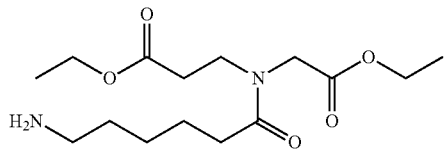

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated in vacuum and the residue water was added and the product was extracted with ethyl acetate. The crude product was purified by converting into hydrochloride salt.

Example 4

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

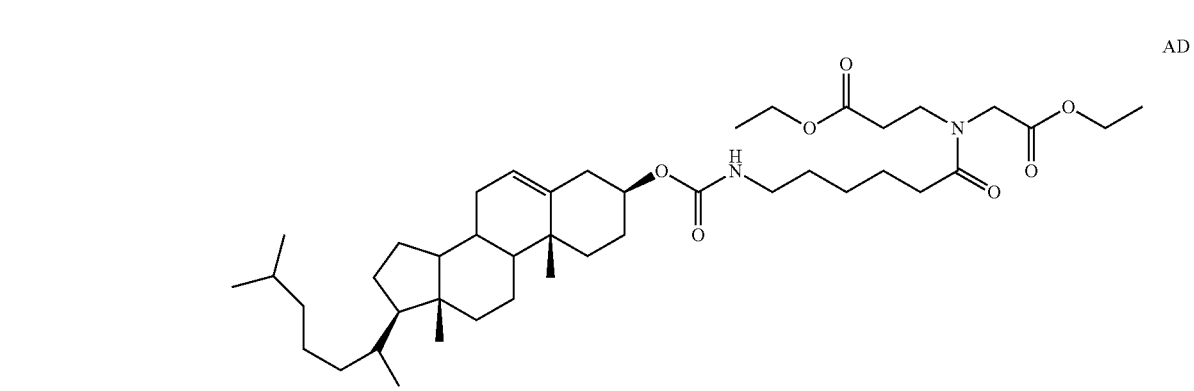 [SMILES: CCOC(=O)CCN(CC(=O)OCC)C(=O)CCCCCNC(=O)O[C@H]1CC[C@@]2(C)C(=CCC3C2CC[C@@]2(C)C3CC[C@@H]2C(C)CCCC(C)C)C1]

Hydrochloride salt of 3-[(6-Amino-hexanoyl)-ethoxycarbonylmethyl-amino]-propionic acid ethyl ester AC (4.7 g, 14.8 mmol) was taken in dichloromethane. The suspension was cooled to 0° C. with ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified flash chromatography (10.3 g, 92%).

Example 5

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]hexanoyl}-4-oxo-pyrrolidine-3-carboxylic acid ethyl ester AE

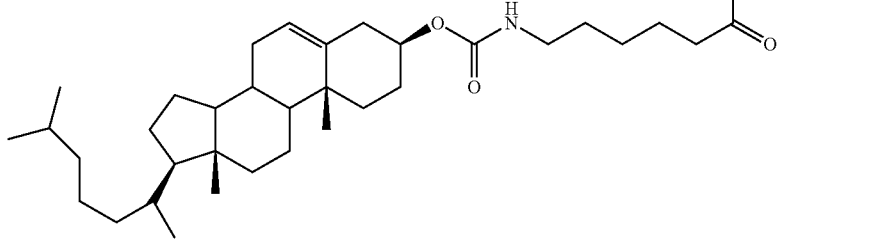

Potassium t-butoxide (1.1 g, 9.8 mmol) was slurried in 30 mL of dry toluene. The mixture was cooled to 0° C. and 5 g (6.6 mmol) of diester was added slowly with stirring within 20 mins. The temperature was kept below 5° C. during the addition. The stirring was continued for 30 mins at 0° C. and 1 mL of glacial acetic acid was added, immediately followed by 4 g of $NaH_2PO_4 \cdot H_2O$ in 40 mL of water The resultant mixture was extracted with two 100 mL of dichloromethane and the combined organic extracts were washed twice with 10 mL of phosphate buffer, dried, and evaporated to dryness. The residue was dissolved in 60 mL of toluene, cooled to 0° C. and extracted with three 50 mL portions of cold pH 9.5 carbonate buffer. The aqueous extracts were converted to pH 3 with phosphoric acid, and extracted with five 40 mL portions of chloroform which were combined, dried and evaporated to a residue. The residue was purified by column chromatography using 25% ethylacetate/hexanes to afford 1.9 g of β-ketoester was obtained (39%).

Example 6

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

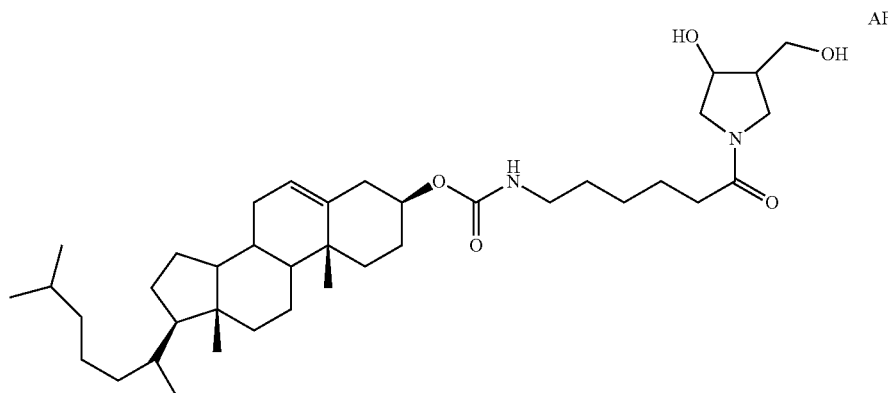 [SMILES: CC(C)CCCC(C)[C@H]1CCC2C3CC=C4C[C@@H](OC(=O)NCCCCCC(=O)N5CC(O)C(CO)C5)CC[C@]4(C)C3CC[C@@]21C]

Methanol (2 mL) was added dropwise over a period of 1 h to a refluxing mixture of ketoester AE (1.5 g, 2.2 mmol) and sodium borohydride (0.226 g, 6 mmol) in tetrahydrofuran (10 mL). Stirring is continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated in vacuum to yield the product which purified by column chromatography (10% MeOH/CHCl$_3$). (89%).

Example 7

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

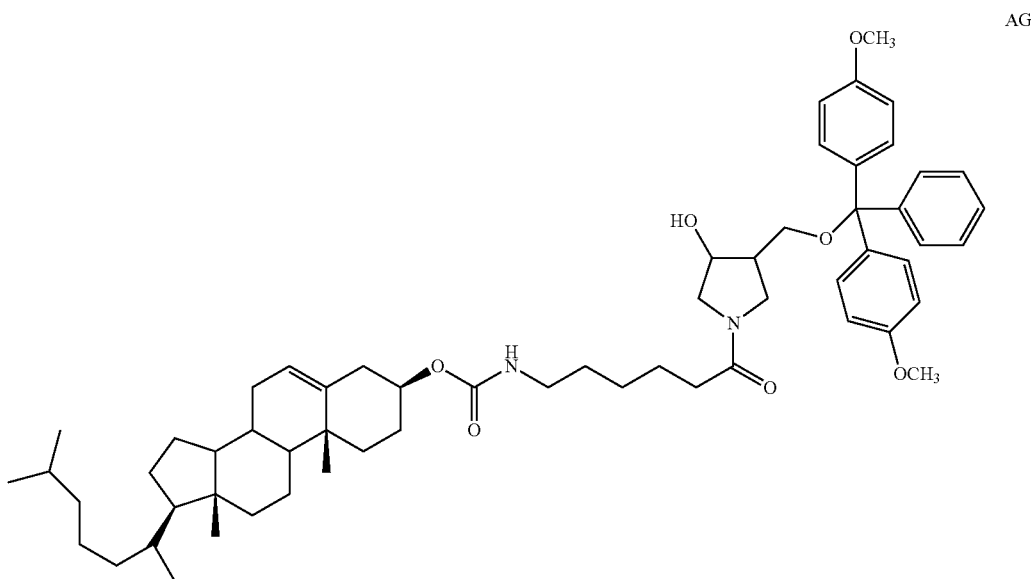 [SMILES: COc1ccc(C(OCC2CN(C(=O)CCCCCNC(=O)O[C@H]3CC[C@@]4(C)C(=CCC5C4CC[C@@]4(C)C5CC[C@@H]4C(C)CCCC(C)C)C3)CC2O)(c2ccccc2)c2ccc(OC)cc2)cc1]

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature for overnight. The reaction was quenched by the addition of methanol. The reaction mixture was concentrated in vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, R$_f$=0.5 in 5% MeOH/CHCl$_3$). (1.75 g, 95%)

Example 8

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

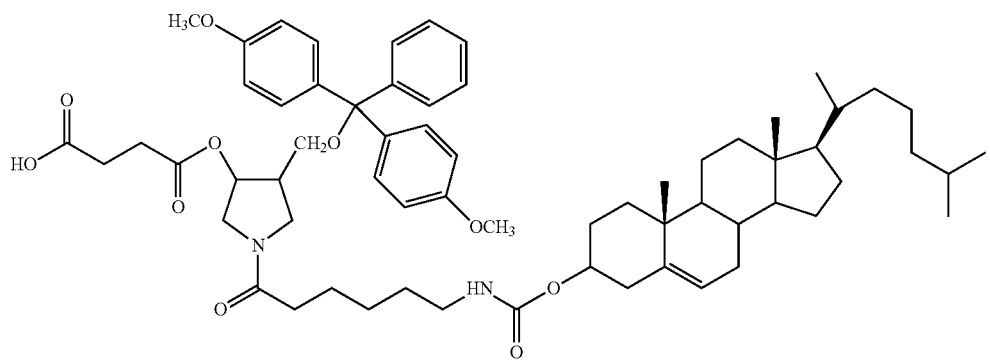

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Example 9

Cholesterol Derivatised CPG AI

Succinate AH (0.254 g, 0.242 mmol) was dissolved in mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using wrist-action shaker (5 mins). Long chain alkyl amine-CPG (LCAA-CPG) (1.5 g, 61 μm/g) was added. The suspension was agitated for 2 h. The CPG was filtered through a sintered funnel and washed with acetonitrile, dichloromethane and ether successively. Unreacted amino groups were masked using acetic anhydride/pyridine. The loading capacity of the CPG was measured by taking UV measurement. (37 μM/g).

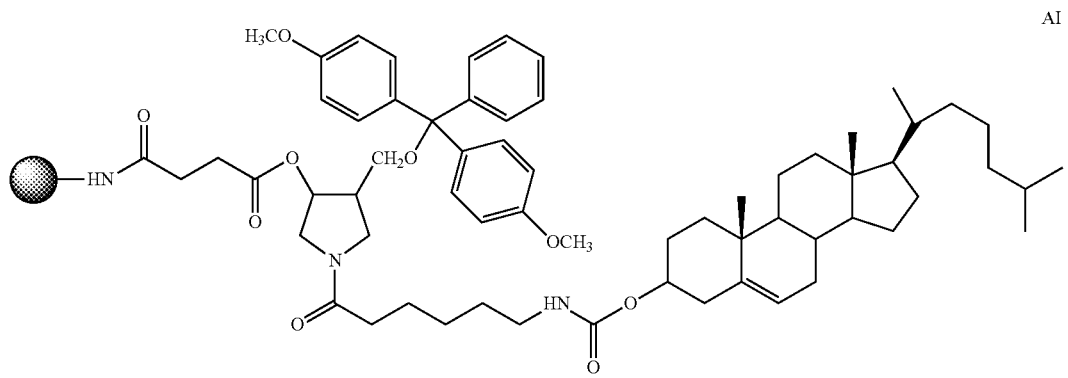

Example 10

(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl)phosphoramidite AJ

AJ

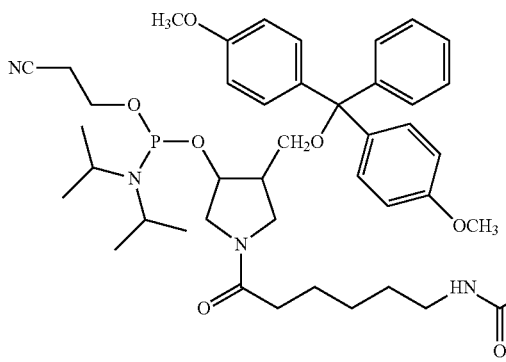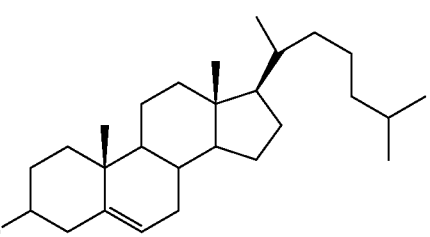

Compound AG (0.15 g, 0.158 mmol) was coevaporated with toluene (5 mL). To the residue N,N-tetraisopropylammonium tetrazolide (0.0089 g, 0.079 mmol) was added and the mixture was dried over $P_2O_5$ in a vacuum oven for overnight at 40° C. The reaction mixture was dissolved in the mixture of anhydrous acetonitrile/dichloromethane (2; 1, 1 mL) and 2-cyanoethyl-N,N,N',N'-tetraisopropylphosphoramidite (0.0714 g, 0.0781 mL, 0.237 mmol) was added. The reaction mixture was stirred at ambient temperature for overnight. The completion of the reaction was ascertained by TLC (1; 1 ethyl acetate:hexane). The solvent was removed under reduced pressure and the residue was dissolved in ethyl acetate (10 mL) and washed with 5% $NaHCO_3$ (4 mL) and brine (4 mL). The ethyl acetate layer was dried over anhydrous $Na_2SO_4$ and concentrated under reduced pressure. The resulting mixture was chromatographed (50:49:1, EtOAc:Hexane:triethlyamine) to afford AJ as white foam (0.152 g, 84%).

Example 11

RNA Synthesis, Deprotection and Purification Protocol

1. Synthesis:

The RNA molecules were synthesized on a 394 ABI machine using the standard 93 step cycle written by the manufacturer with modifications to a few wait steps as described below. The solid support was controlled pore glass (CPG, 1 μmole, 500 Å, Glen Research, Sterling Va.) and the monomers were RNA phosphoramidites with standard protecting groups ($N^6$-benzoyl-5'-O-dimethoxytrityladenosine-2' tbutyldimethylsilyl-3'-O—N,N'-diisopropyl-2-cyanoethylphosphoramidite, 5'-O-dimethoxytrityluridine-2' tbutyldimethylsilyl-3'-O—N,N'-diisopropyl-2-cyanoethylphosphoramidite, $N^2$-isobutyryl-5'-O-dimethoxytrityl-guanosine-2'tbutyldimethylsilyl, 3'-O—N,N'-diisopropyl-2-cyanoethylphosphoramidite, and $N^4$-benzoyl-5'-O-dimethoxytritylcytidine-2'tbutyldimethylsilyl-3'-O—N,N'-diisopropyl-2-cyanoethylphosphoramidite from Chemgenes Corp MA) used at a concentration of 0.15M in acetonitrile ($CH_3CN$) and a coupling time of 7.5 min. The activator was thiotetrazole (0.25M), For the PO-oxidation Iodine/Water/Pyridine was used and the PS-oxidation Beaucage reagent 0.5M solution in acetomitrile was used. All reagents for synthesis were also from Glen Research.

2. Deprotection-I (Oligomer Cleavage, Base and Phosphate Deprotection)

After completion of synthesis the controlled pore glass (CPG) was transferred to a screw cap vial (Fisher, catalog number 03-340-5N) or a screw cap RNase free microfuge tube. The oligonucleotide was cleaved from the CPG with simultaneous deprotection of base and phosphate groups with 1.0 mL of a mixture of ethanolic ammonia [ammonia: ethanol (3:1)] for 6 hours to overnight at 55° C. The vial was cooled briefly on ice and then the ethanolic ammonia mixture was transferred to a new microfuge tube. The CPG was washed with 3×0.25 mL portions of 50% acetonitrile (70% $CH_3CN$ for cholesterol and such hydrophobic conjugated oligomers). The approximate 1.75 mL of solution is best divided equally into two microfuge tubes, capped tightly and then cooled at −80° C. for 15 min, before drying in a speed vac/lyophilizer for about 90 min.

3. Deprotection-II (Removal of 2' TBDMS Group)

The white residue obtained was resuspended in 200 μL of triethylamine trihydrofluoride (TEA.3HF, Aldrich) and heated at 65° C. for 1.5 h to remove the tertbutyldimethylsilyl (TBDMS) groups at the 2'position. The reaction was then quenched with 400 μL of isopropoxytrimethylsilane (iPrOMe₃Si Aldrich) and further incubated on the heating block leaving the caps open for 15 min; (This causes the volatile isopropxytrimethylsilylfluoride adduct to vaporize). The residual quenching reagent was removed by drying in a speed vac. The oligomer was then precipitated in anhydrous methanol (MeOH, 800 μL). The liquid was removed very carefully after spinning in a centrifuge for 5 minutes on the highest speed available. Residual methanol was removed by drying briefly in a speed vac after freezing at −80° C. The crude RNA was obtained as a white fluffy material in the microfuge tube.

4. Quantitation of Crude Oligomer or Raw Analysis

Samples were dissolved in 50% aqueous acetonitrile (0.5 mL) and quantitated as follows: Blanking was first performed with 50% aqueous acetonitrile alone (1 mL).

5 μL of sample and 995 μL of 50% acetonitrile, were mixed well in a microfuge tube, transferred to cuvette and absorbance reading obtained at 260 nm. The crude material is dried down and stored at −20° C.

5. Purification of Oligomers

The crude oligomers were analyzed and purified by HPLC (Mono Q Pharmacia Biotech 5/50). The buffer system is A=100 mM Tris HCl 10% HPLC grade acetonitrile pH=8, B=100 mM Tris-HCl pH 8, 10% HPLC grade acetonitrile 1 M NaCl, flow 1.0 mL/min, wavelength 260 nm. For the unmodified RNA 21mer a gradient of 0-0.6M NaCl is usually adequate. One can purify a small amount of material (~5 OD) and analyze by CGE or MS. Once the identity of this material is confirmed the crude oligomer can then be purified using a larger amount of material. i.e 40 OD's per run, flow rate of 1 mL/min and a less sensitive wavelength of 280 nm to avoid saturation of the detector. Fractions containing the full length oligonucleotides are then pooled together, evaporated and finally desalted as described below.

6. Desalting of Purified Oligomer

The purified dry oligomer was then desalted using either C-18 Sepak cartridges (Waters) or Sephadex G-25M (Amersham Biosciences). The cartridge was conditioned with 10 mL each of acetonitrile, followed 50% acetonitrile, 100 mM buffer (this can be triethylammonium acetate, sodium acetate or ammonium acetate). Finally the purified oligomer dissolved thoroughly in 10 mL RNAse free water was applied to the cartridge with very slow dropwise elution. The cartridge was washed with water (10 mL) to remove salts. And finally the salt free oligomer was eluted with 50% acetonitrile or 50% methanol directly into a screw cap vial.

7. Capillary Gel Electrophoresis (CGE) and Electrospray LC/Ms 14 of approximately 0.04 OD oligomer is first dried down, redissolved in water (24) and then pipetted in special vials for CGE and LC/MS analysis. In general, desalting should be carried out prior to analysis.

Example 14

5' Cholesterol-CUUACGCUGAGUACUUCGAdTdT-3' (SEQ ID NO: 24)

Compound 14-a was used to synthesize oligonucleotide conjugates where cholesterol was conjugated at the 5' end of RNA molecules.

The phosphoramidite 14-a was dissolved in acetomitrile/methylene chloride 1:1 solution to give a 0.2M solution. This was used for the terminal coupling during the oligonucleotide synthesis. For the PO-oxidation Iodine/Water/Pyridine was used and the PS-oxidation Beaucage reagent 0.5M solution in acetomitrile was used. The diamathoxy triotyl group was removed in the synthesizer.

Example 15 siRNA Modifications Enhanced Duplex Stability

Radiolabel Method for Monitoring Serum Stability of siRNA Duplexes:

siRNA duplexes were prepared at a stock concentration of 1 µM in which either the sense (S) or antisense strand (AS) contained a trace amount of 5'-$^{32}$P labeled material (e.g. $^{32}$P-S/AS and S/$^{32}$P-AS). The presence of the end-labeled sense or antisense strand allowed for monitoring of the individual strand within the context of the siRNA duplex. Therefore, two duplex preparations were made for each siRNA sequence tested. siRNA duplexes were incubated in 90% human serum at a final concentration of 100 nM duplex. Samples were removed and quenched in a stop mix at appropriate times. For a typical time course, 10 seconds, 15 minutes, 30 minutes, 1 hour, 2 hours and 4 hours time points were taken. Samples were analyzed by denaturing polyacrylamide gel electrophoresis along with a control sample (4 hour buffer-alone incubation) and a partial alkaline hydrolysis ladder of the labeled sense or antisense strand as a marker. The gel was imaged using a Fuji phosphorimager to detect the full length sense and antisense strands along with any degradation fragments that were generated by serum nucleases during incubation.

Since there is the possibility of losing the 5' phosphate label due to phosphatase activity in the serum, an alternative to 5' end labeling is to place an internal $^{32}$P or $^{33}$P label within either the sense or antisense strand. This labeling method is much more laborious than 5' end labeling and currently we have no evidence that dephosphorylation occurs during serum incubation.

A series of chemical modifications that fall into the following categories; backbone modification, sugar modification, nucleobase modification and 3' conjugate, were tested and showed enhanced serum stability as compared to a unmodified siRNA duplex. A description of each modification, its location within the siRNA duplex, and the serum stability data follows.

Serum Stability of Unmodified Parent Duplex:

The unmodified parent duplex, AL-DUP-1000, was used to establish the serum stability baseline for evaluating the effect of chemical modifications on nuclease resistance.

AL-DUP-1000

```
ALN-SEQ-1000
                                       SEQ ID NO: 24
5'-CUUACGCUGAGUACUUCGAdTdT-3'

ALN-SEQ-1001
                                       SEQ ID NO: 25
3'dTdTGAAUGCGACUCAUGAAGCU-5'
```

Figure 14:
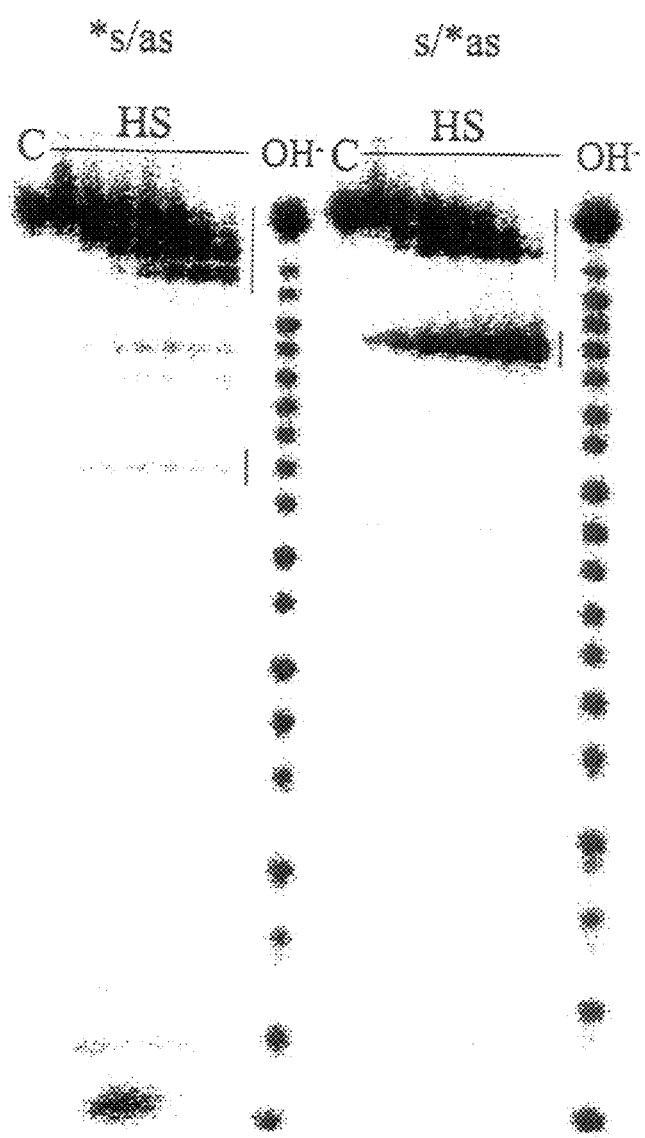
FIG. 14 is a denaturing gel analysis of the human serum stability assay for AL-DUP-1000. C is the 4 hour time point for siRNA duplex incubated in PBS buffer alone, OH— is the partial alkaline hydrolysis marker, *s/as represents siRNA duplex containing 5' end-labeled sense RNA and s/*as represents duplex containing 5' end-labeled antisense RNA. Samples were incubated in 90% human serum and time points were assayed at 10 seconds, 5 min, 15 min, 30 min, 1 hour, 2 hours and 4 hours. Black lines to the right of bands indicate exonucleolytic degradation fragments and the red lines highlight a few of the endonucleolytic degradation fragment.

AL-DUP-1000 was subjected to the serum stability assay to evaluate its inherent nuclease resistance and to define its degradation pattern (FIG. 14). Denaturing gel electrophoresis was used analyze AL-DUP-1000 in a human serum stability assay. An siRNA duplex containing 5' end-labeled sense RNA (*s/as) and a duplex containing 5' end-labeled antisense RNA (as/s*) were each incubated in 90% human serum and time points were assayed at 10 seconds, 5 min, 15 min, 30 min, 1 hour, 2 hours and 4 hours. The control was a 4 hour time point for siRNA duplex incubated in PBS buffer alone, OH— was the partial alkaline hydrolysis marker. This unmodified duplex was observed to be degraded by both 3'-5' exonucleases and endonucleases (FIG. 14).

Cleavage of the 3' end of both the sense and antisense strands by 3'-5' exonucleases occurs within the first 5 minutes of incubation resulting in the loss of the 3' terminal dT residues (top vertical lines in s*/as and s/as* panels of FIG. 14). In addition to exonuclease degradation, both strands were cleaved by endonucleases. There was a major endonuclease site at position sixteen of the antisense strand (bottom vertical lines in s*/as and s/as* panels of FIG. 14) that appears as early as 10 seconds. Very little full length sense or antisense strand was remaining after 1 hour in human serum. Chemical modifications were introduced within the context of the parent duplex to evaluate their effect on nuclease resistance. These chemical modifications fall within one of the following classes: backbone modification, sugar modification, nucleobase modification, cationic modification and conjugate.

Backbone Modifications Enhanced Nuclease Resistance:

Specific phosphodiester linkages of the siRNA duplex were replaced by either phosphorothioate or methylphosphonate and their stability was evaluated in the human serum stability assay. Table 11 contains the sequences of the duplexes tested. Substitution of the phosphodiester linkage at the 3' end of both the sense and antisense strands inhibited exonucleolytic degradation of the 3' overhangs (FIGS. 15A and 15B) as compared to the unmodified parent duplex (refer to FIG. 14). Full length starting material was present for four hours for both the sense and antisense strands. The endonucleolytic cleavage pattern seen in the unmodified duplex was unchanged. Similar results were obtained for duplexes that contained additional phosphorothioates at their 3' ends (data not shown). The placement of phosphorothioates at the endonucleolytic cleavage sites (duplexes 1419, 1420 and 1421) did not inhibit endonucleolytic cleavage at these sites (data not shown). In summary, a single phosphorothioate or methylphosphonate between the two 3' terminal nucleotides was sufficient to protect the 3' ends from exonuclease degradation. Additional phosphorothioates at the 3' ends appear to enhance this effect, which may be necessary for long term exposure to serum nucleases.

TABLE 11 siRNA duplexes containing backbone modifications.

| Alnylam Duplex | Duplex Sequence | Alnylam Sequence |
|---|---|---|
| AL-DUP-1393 | 5'-CUUACGCUGAGUACUUCGAdT*dT-3'<br>3'-dT*dTGAAUGCGACUCAUGAAGCU-5' | AL-SEQ-1026<br>AL-SEQ-1027 |
| AL-DUP-1394 | 5'-CUUACGCUGAGUACUUCGA*dT*dT-3'<br>3'-dT*dT*GAAUGCGACUCAUGAAGCU-5' | AL-SEQ-1028<br>AL-SEQ-1029 |
| AL-DUP-1395 | 5'-CUUACGCUGAGUACUUCG*A*dT*dT-3'<br>3'-dT*dT*G*AAUGCGACUCAUGAAGCU-5' | AL-SEQ-1030<br>AL-SEQ-1031 |
| AL-DUP-1396 | 5'-CUUACGCUGAGUACUUC*G*A*dT*dT-3'<br>3'-dT*dT*G*A*AUGCGACUCAUGAAGCU-5' | AL-SEQ-1032<br>AL-SEQ-1033 |
| AL-DUP-1419 | 5'-CUUACGCUGAGU*ACUUCGAdTdT-3'<br>3'-dTdTGAAUGCGACUCA*UGAAGCU-5' | AL-SEQ-2182<br>AL-SEQ-2184 |
| AL-DUP-1420 | 5'-CUU*ACGCUGAGU*ACUUCGAdTdT-3'<br>3'-dTdTGAA*UGCGACUCA*UGAAGCU-5' | AL-SEQ-2183<br>AL-SEQ-2185 |
| AL-DUP-1421 | 5'-CUU*ACGCUGAGU*ACUUCGAdT*dT-3'<br>3'-dT*dTGAA*UGCGACUCA*UGAAGCU-5' | AL-SEQ-2186<br>AL-SEQ-2188 |
| AL-DUP-1329 | 5'-CUUACGCUGAGUACUUCGAdTmpdT-3'<br>3'-dTmpdTGAAUGCGACUCAUGAAGCU-5' | AL-SEQ-1038<br>AL-SEQ-1039 |

(*= phosphorothioate, mp = methylphosphonate)

SEQ IS NOs 26-41, respectively.

Sugar Modifications Enhanced Nuclease Resistance:

The effect of replacing the 2'OH with 2'OMe was evaluated at the sites of endonucleolytic cleavage as well as at the 3' ends of the siRNA duplex. The duplexes tested in the human serum stability assay are shown in Table 12. Some of these duplexes also contained phosphorothioate linkages to evaluate whether the combination of the two modifications enhance nuclease resistance more significantly. Substitution of the terminal dT residues with 2'OMe-U (AL-DUP-1027) reduced 3'-5' exonuclease degradation slightly over the unmodified parent duplex (data not shown); however, the extent of exonuclease protection by 2'OMe-U was far less than that achieved by placing a

TABLE 12 siRNA duplexes containing 2'OMe Substitutions

| Alnylam Duplex | Duplex Sequence | Alnylam Sequence |
|---|---|---|
| AL-DUP-1027 | 5'-CUUACGCUGAGUACUUCGA<u>UU</u>-3'<br>3'-<u>UU</u>GAAUGCGACUCAUGAAGCU-5' | AL-SEQ-1006<br>AL-SEQ-1007 |
| AL-OUP-1036 | 5'-C*UUACGCUGAGUACUUCGA<u>U</u>*<u>U</u>-3'<br>3'-<u>U</u>*<u>U</u>GAAUGCGACUCAUGAAGC*U-5' | AL-SEQ-1008<br>AL-SEQ-1009 |
| AL-DUP-13ff | 5'-C*<u>UU</u>ACGCUGAGUACUUCGA<u>U</u>,<u>U</u>,-3'<br>3'-<u>U</u>*<u>U</u>GAA<u>U</u>GCGACUCAUGAAGC*U-5' | AL-SEQ-gggg<br>AL-SEQ-hhhh |

TABLE 12-continued siRNA duplexes containing 2'OMe Substitutions

| Alnylam Duplex | Duplex Sequence | Alnylam Sequence |
|---|---|---|
| AL-DUP-1363 | 5'-C*U<u>U</u>ACGCUGAG<u>U</u>ACUUCGA<u>U</u>*<u>U</u>-3'<br>3'-<u>U</u>*<u>U</u>GAA<u>U</u>GCGACUCA<u>U</u>GAAGC*<u>U</u>-5' | AL-SEQ-1162<br>AL-SEQ-1163 |

(<u>U</u> = 2'OMe-uridine, *= phosphorothioate)

Figure 15A:
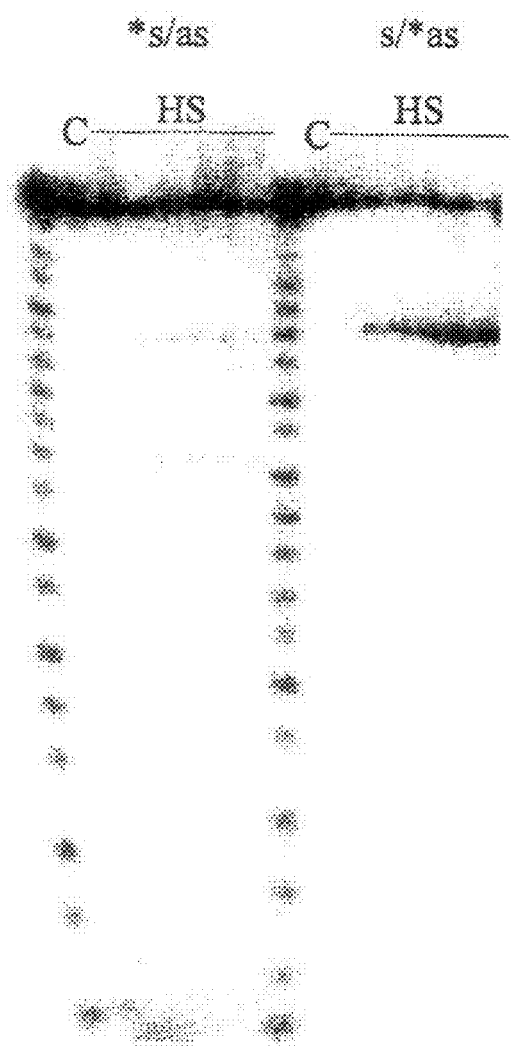
FIG. 15A is a denaturing gel analysis of the human serum stability assay for AL-DUP-1393. C is the 4 hour time point for each siRNA duplex incubated in PBS buffer alone, *s/as represents siRNA duplex containing 5' end-labeled sense RNA and s/*as represents duplex containing 5' end-labeled antisense RNA. Samples were assayed at 10 seconds, 15 min, 30 min, 1 hour, 2 hours and 4 hours.
Figure 15B:
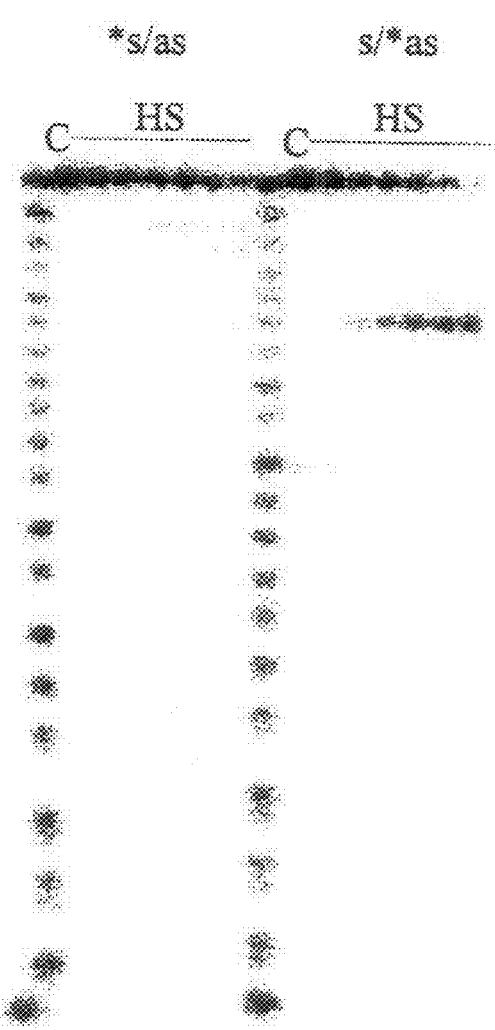
FIG. 15B is a denaturing gel analysis of the human serum stability assay for AL-DUP-1329. The lanes are labeled and the experiment was performed as described for FIG. 15A.
Figure 16:
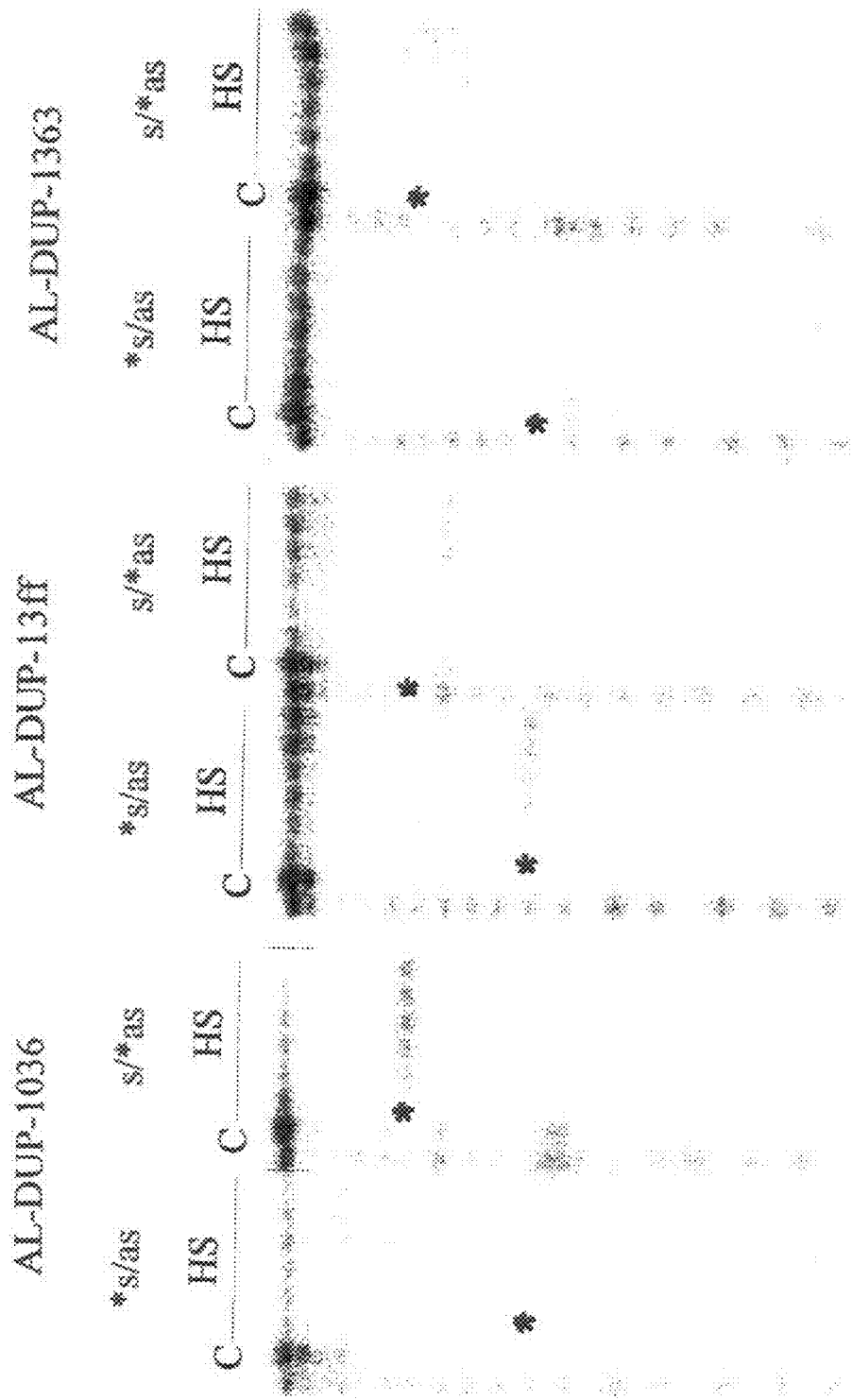
FIG. 16 is a denaturing gel analysis of AL-DUP-1036, AL-DUP-13ff, and AL-DUP-1363 (see Table 12 for sequences). Black vertical lines highlight regions where exonuclease cleavage is suppressed, stars indicate sites of strong endonucleolytic cleavage in the antisense strand and weaker endonucleolytic cleavage in the sense strand. C is the 4 hour time point for each siRNA duplex incubated in PBS buffer alone, *s/as represents siRNA duplex containing 5' end-labeled sense RNA and s/*as represents duplex containing 5' end-labeled antisense RNA. Samples were assayed at 10 seconds, 15 min, 30 min, 1 hour, 2 hours and 4 hours.

SEQ ID NOs 42-49, respectively.

phosphorothioate between the two terminal dT residues (see FIG. 15A). Addition of a single phosphorothioate between the two terminal 2'OMe-uridine residues effectively inhibited 3'-5' exonucleolytic cleavage as seen in FIG. 16 for duplexes AL-DUP-1036, AL-DUP-13ff, and AL-DUP-1363. 2'OMe substitution on its own was much more effective at protecting from endonucleolytic cleavage when placed at the internal cleavage sites. The parent duplex was cleaved 3' of U at two UpA sites within the duplex. Both strands are cleaved due to the symmetry of this dinucleotide repeat and mapping data was used to confirm the sites of cleavage (data not shown). Placement of 2'OMe at the strong endonucleolytic site ((FIG. 16, star in s/*as gel, AL-DUP-13ff) resulted in inhibition of cleavage at this site. The second, weaker endonucleolytic site (FIG. 16, black star in *s/as), however, was slightly enhanced when the strong site was protected with 2'OMe (FIG. 16, compare AL-DUP-13ff to AL-DUP-1036). Protection of both sites with 2'OMe (AL-DUP-1363) resulted in reduced endonucleolytic cleavage at both sites (FIG. 16). The inhibitory effect of the 2'OMe substitution is consistent with the mechanism of endonucleolytic cleavage, which requires the 2'OH as a nucleophile in the cleavage reaction. 2'OMe modification will also be an effective means to protect the 3' overhang of single overhang siRNA duplexes where the 3' overhang is composed of ribonucleotides. In this situation, 2'OMe substitution can be used to block the possible loss of the terminal two nucleotides by endonucleolytic cleavage and phosphorothioate can be used to protect from exonuclease degradation.

Cationic Modifications Enhanced Nuclease Resistance:

The effect of three different cationic chemical modifications on nuclease resistance was tested and compared to the parent unmodified duplex. The structures of the three cationic modifications tested are shown below.

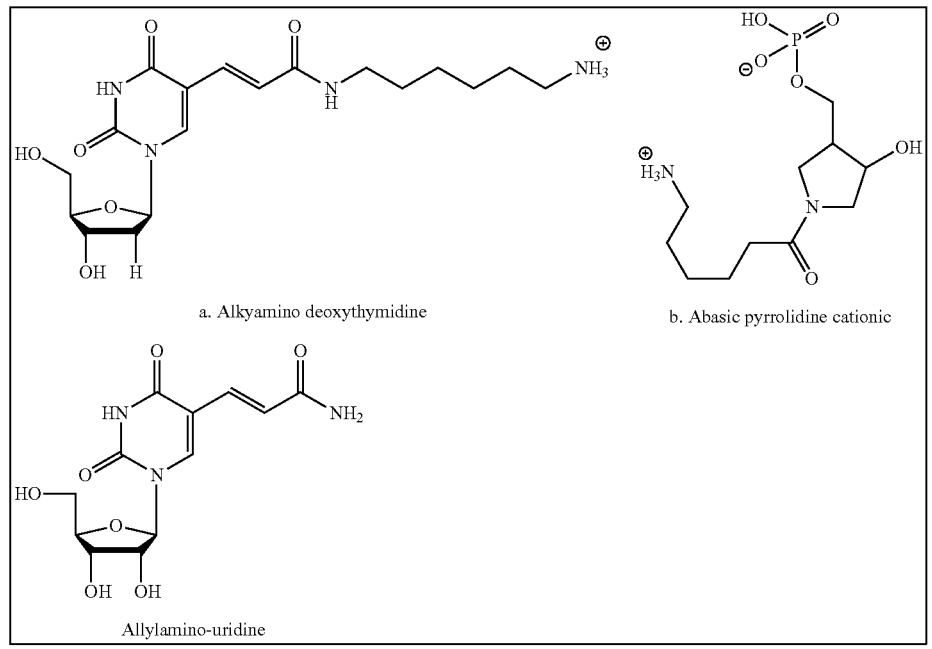

a. Alkyamino deoxythymidine
b. Abasic pyrrolidine cationic
Allylamino-uridine

TABLE 13 siRNA duplexes containing cationic substances

| Alnylam Duplex | Duplex Sequence | Alnylam Sequence |
|---|---|---|
| AL-DUP-10aa | 5'-CUUACGCUGAGUACUUCGAdTaadT-3'<br>3'-aadTdTGAAUGCGACUCAUGAAGCU-5' | AL-SEQ-1017<br>AL-SEQ-1018 |
| AL-DUP-10bb | 5'-CUUACGCUGAGUACUUCGAaadTaadT-3'<br>3'-aadTaadTGAAUGCGACUCAUGAAGCU-5' | AL-SEQ-1015<br>AL-SEQ-1016 |

TABLE 13-continued siRNA duplexes containing cationic substances

| Alnylam Duplex | Duplex Sequence | Alnylam Sequence |
|---|---|---|
| AL-DUP-1ccc | 5'-CUUACGCUGAGUACUUCGAdTdTAbP-3'<br>3'-AbPdTdTGAAUGCGACUCAUGAAGCU-5' | AL-SEQ-dddd<br>AL-SEQ-eeee |
| AL-DUP-1403 | 5'-C*UaaUACGCUGAGUACUUCGAU*U-3'<br>3'-U*UGAAaaUGCGACUCAUGAAGC*U-5' | AL-SEQ-2080<br>AL-SEQ-2081 |
| AL-DUP-1406 | 5'-C*UaaUACGCUGAGaaUACUUCGAU*U-3'<br>3'-U*UGAAaaUGCGACUCAaaUGAAGC*U-5' | AL-SEQ-2082<br>AL-SEQ-2083 |

(aadT = alkylamine-dt, abP = abasic pyrrolidine cationic, aaU = allylamine-U, *= phosphorothioate, U = 2'OMe-U)

SEQ ID NOs 50-59, respectively.

Figure 17:
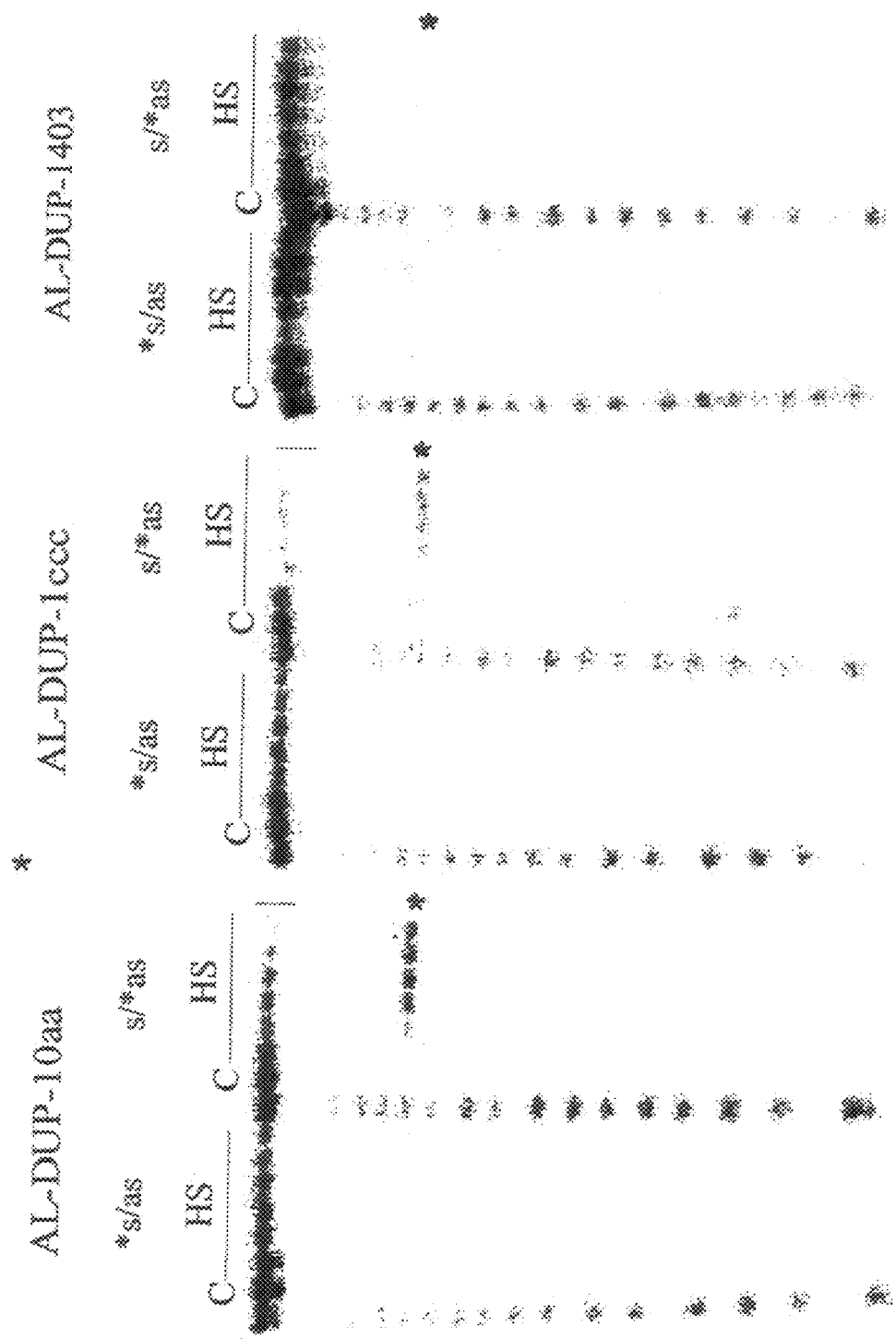
FIG. 17. Human serum stability profile of siRNA duplexes containing cationic modifications. Denaturing gel analysis of AL-DUP-10aa (alkylamino-dT), AL-DUP-1ccc (abasic pyrrolidine cationic), and AL-DUP-1403 (see Table 13 for sequences). Black line highlights region where exonuclease cleavage is suppressed and red star indicates site of strong endonucleolytic cleavage in the antisense strand. C is the 4 hour time point for each siRNA duplex incubated in PBS buffer alone, *s/as represents siRNA duplex containing 5' end-labeled sense RNA and s/*as represents duplex containing 5' end-labeled antisense RNA. Samples were assayed at 10 seconds, 15 min, 30 min, 1 hour, 2 hours and 4 hours.

The sequences of the duplexes assayed in the human serum stability assay are shown in Table 13. Both alkylamino-dT and abasic pyrrolidine cationic modifications were placed at the 3' terminal overhang to evaluate their effect on 3'-5' exonuclease degradation. Allylamino-uridines were placed at the internal endonucleolytic cleavage sites to evaluate their ability to inhibit endonucleolytic cleavage. As seen in FIG. 17, replacing the 3' terminal dT residue with a single alkylamino-dT efficiently inhibited 3'-5' exonucleolytic degradation (FIG. 17, AL-DUP-10aa, left gel image). Replacement of both dT residues in the overhang with alkylamino-dT resulted in a similar extent of inhibition (data not shown). Addition of an abasic pyrrolidine cationic modification at the 3' terminus of each strand also protected against exonucleolytic degradation (FIG. 17, middle gel image). Both the alkylamino-dT and abasic pyrrolidine modifications protected from 3'-5' exonucleolytic cleavage up to 23 hours (data not shown). Placement of allylamino-U at the internal cleavage sites inhibited endonucleolytic cleavage as shown in FIG. 17 for duplex AL-DUP-1403. The ends of this duplex were stabilized from exonucleolytic degradation by 2'OMe-U and phosphorothioate substitutions in order to separate the two different cleavage events. Endonucleolytic cleavage was inhibited at both internal cleavage sites by allylamino-U substitution for AL-DUP-1406 (data not shown).

3' Conjugates Enhanced Nuclease Resistance:

Conjugation of naproxen and ibuprofen to the 3' end of the siRNA were tested for their ability to inhibit 3'-5' exonucleolytic degradation. The structure of naproxen is shown in below:

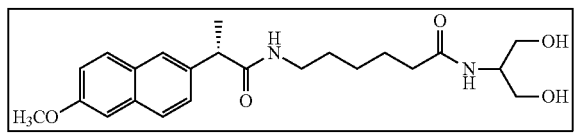 [SMILES: COc1ccc2cc([C@H](C)C(=O)NCCCCCC(=O)NC(CO)CO)ccc2c1]

Figure 18:
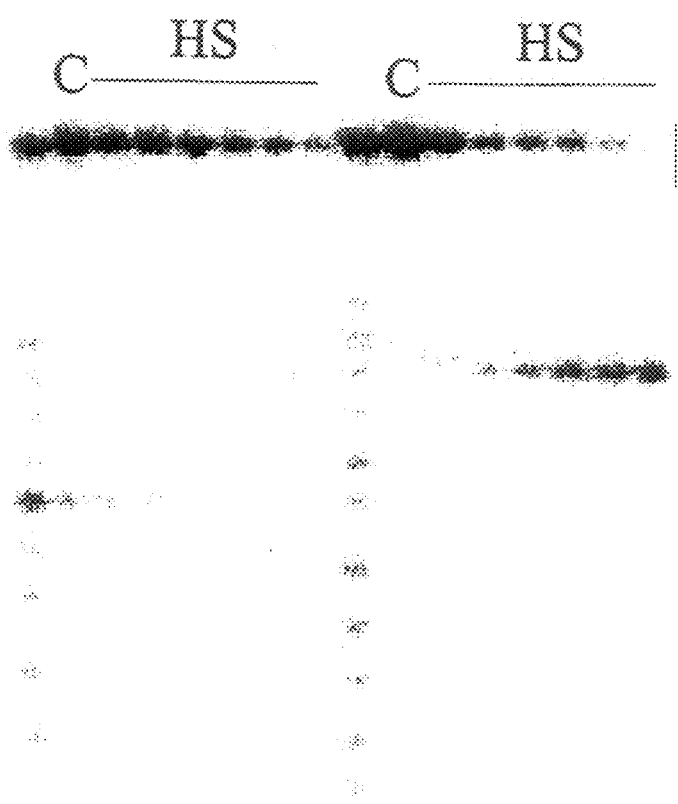
FIG. 18 is a denaturing gel analysis of the human serum stability assay for AL-DUP-1069. The black vertical line highlights the region where exonuclease cleavage is suppressed. C is the 4 hour time point for each siRNA duplex incubated in PBS buffer alone, *s/as represents siRNA duplex containing 5' end-labeled sense RNA and s/*as represents duplex containing 5' end-labeled antisense RNA. Samples were assayed at 10 seconds, 15 min, 30 min, 1 hour, 2 hours and 4 hours.

Table 14 lists the siRNAs that were tested in the human serum stability assay. Conjugation of either naproxen or ibuprofen to the 3' end inhibited exonucleolytic degradation. FIG. 18 shows the serum stability data for the naproxen modified duplex (AL-DUP-1069) and similar results were obtained for AL-DUP1413. Presumably the conjugates inhibit exonucleolytic cleavage by sterically blocking the exonuclease from binding to the 3' end of the siRNA duplex. Similar data was also obtained for AL-DUP-1069 in pooled mouse serum.

TABLE 14 siRNA duplexes containing 3' conjugates.

| Alnylam Duplex | Duplex Sequence | SEQ ID NO: |
|---|---|---|
| AL-DUP-1069 | 5'-CUUACGCUGAGUACUUCGA dTdTNap-3' | 60 |
|  | 3'-NapdTdTGAAUGCGACUCA UGAAGCU-5' | 61 |
| AL-DUP-1413 | 5'-CUUACGCUGAGUACUUCGA dTdTIbu-3' | 62 |
|  | 3'-NapdTdTGAAUGCGACUCA UGAAGCU-5' | 61 |

(Nap = Naproxen, Ibu = Ibuprofen)

Additional examples describing monomer synthesis and conjugation strategies are described in Appendix I, which is expressly included as part of the disclosure of this application.

Example 16

Silencing of microRNAs with Single Stranded iRNA Agents

Figure 19A:
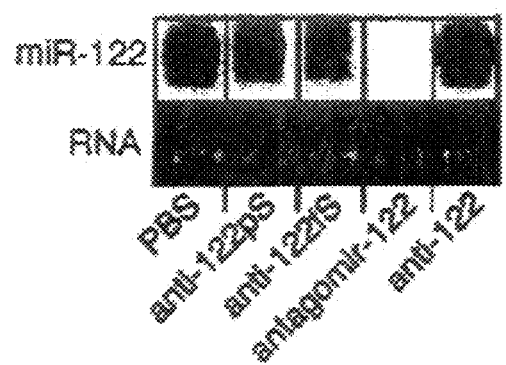
FIG. 19A is a panel of Northern blots of total RNA (15 µg) isolated from mouse liver 24 h after injection of differently modified RNAs (240 mg/kg) targeting miR-122. Samples were separated in 14%-polyacrylamide gels in the absence of formamide, and the membranes were probed for miR-122. Ethidium bromide staining of tRNA is shown as a loading control.
Figure 19B:
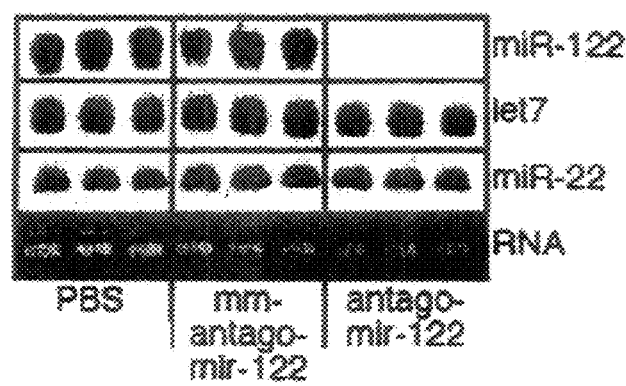
FIG. 19B is a panel of Northern blots of total RNA (15 µg) isolated from mouse liver 24 h after injection of differently modified RNAs (240 mg/kg) against miR-122. Samples were separated in 14%-polyacrylamide gels in the absence of formamide, and the membranes were probed for miR-122, let7, and miR-22 RNAs. Ethidium bromide staining of tRNA is shown as a loading control.

Chemically-stabilized, cholesterol-conjugated single-stranded RNAs complementary to miRNAs were designed and synthesized. These single-stranded modified RNAs are referred to herein as "antagomirs" (see below). To explore the potential of these synthetic RNAs to silence endogenous miRNAs, antagomir-122 was designed to target miR-122, an miRNA expressed in the liver. The sequence of antagomir-122 is shown in Table 15. Antagomir-122 was administered to mice by intravenous injection in a small volume (0.2 ml, 80 mg/kg, 3 consecutive days) and normal pressure. Administration of antagomir-122 resulted in a striking reduction of endogenous miR-122 levels as detected by Northern blot analysis (FIG. 19A). Administration of unmodified single-stranded RNA (anti-122) had no effect on hepatic miR-122 expression levels (FIG. 19A), while injection of unconjugated, but chemically-stabilized single-stranded RNAs with partial (pS) or complete (fS) phosphorothioate backbone and 2'-O-methyl sugar modifications (anti-122fS, anti-122pS, see Table 15) led to an incomplete effect (FIG. 19A). The effects of antagomir-122 were found to be specific as animals injected with a control antagomir-122 derivative that harbored four mismatch mutations (mm-antagomir-122) had no effect on miR-122 expression in the liver. Furthermore, expression levels of miR-let7 and miR-22 were unaffected in antagomir-122 and mm-antagomir-122 treated mice, suggesting that silencing was miRNA-specific (FIG. 19B). The structure of the single stranded RNAs injected into mice is described in Table 15.

TABLE 15

Antagomirs

Figure 19C:
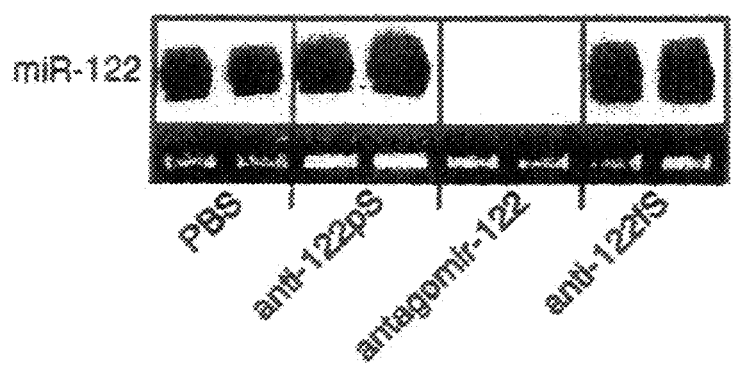
FIG. 19C is a panel of Northern blots of total RNA (15 µg) isolated from mouse liver 24 h after injection of differently modified RNAs (240 mg/kg) against miR-122. Samples were separated in 14%-polyacrylamide gels in the presence of 20% formamide, and the membranes were probed for miR-122. Ethidium bromide staining of tRNA is shown as a loading control.

| RNA | Sequence | AL-SQ NO: | SEQ ID NO: |
|---|---|---|---|
| anti-122 | 5'-ACAAACACCAUUGUCACACUCCA-3' | 3033 | 93 |
| anti-122pS | 5'-a$_s$c$_s$aaacaccauugucacac$_s$u$_s$c$_s$c$_s$a-3' | 3226 | 94 |
| anti-122fS | 5'-a$_s$c$_s$a$_s$a$_s$a$_s$c$_s$a$_s$c$_s$c$_s$a$_s$u$_s$u$_s$g$_s$u$_s$c$_s$a$_s$c$_s$a$_s$c$_s$u$_s$c$_s$c$_s$a-3' | 3037 | 95 |
| antagomir-122 | 5'-a$_s$c$_s$aaacaccauugucacacu$_s$c$_s$c$_s$a$_s$-Chol-3' | 3038 | 96 |
| mm-antagomir-122 | 5'-a$_s$c$_s$acacaacacugucacauu$_s$c$_s$c$_s$a$_s$-Chol-3' | 3040 | 97 |
| antagomir-122(I) | 5'-u$_s$g$_s$gagugugacaaugguu$_s$u$_s$g$_s$u$_s$-Chol-3' | 3223 | 98 |
| antagomir-122(II) | 5'-u$_s$g$_s$gaaggugacaguguguu$_s$u$_s$g$_s$u$_s$-Chol-3' | 3224 | 99 |
| antagomir-122(III) | 5'-u$_s$c$_s$acgcgagccgaacgaac$_s$a$_s$a$_s$a$_s$-Chol-3' | 3230 | 100 |
| antagomir-16 | 5'-c$_s$g$_s$ccaauauuuacgugcug$_s$c$_s$u$_s$a$_s$-Chol-3' | 3227 | 101 |
| antagomir-192 | 5'-g$_s$g$_s$cugucaauucauaggu$_s$c$_s$a$_s$g$_s$-Chol-3' | 3228 | 102 |
| antagomir-194 | 5'-u$_s$c$_s$cacauggaguugcuguu$_s$a$_s$c$_s$a$_s$-Chol-3' | 3229 | 103 | lower case letters represent 2'-O-methyl modified nucleotides; subscript 's' represent phosphorothioate linkage; "Chol" indicates cholesterol conjugate MiR-122 is expressed at high levels in hepatocytes with over 50,000 copies per cell (Chang J. et al., *RNA Biology* 1:2, 106-113, 2004). To determine whether the silencing of miR-122 following antagomir treatment was caused by stoichiometric duplex formation between miR-122 and antagomir-122 or by catalytic degradation of miR-122, total RNA from livers of mice treated with unconjugated single-stranded anti-miR-122 RNAs (anti-122fS, anti-122pS) or antagomir-122 were examined under stringent, formamide-containing denaturing conditions (FIG. 19C). No difference in miR-122 levels could be detected between PBS and unconjugated anti-miR-122 RNA-treated livers, showing that the decrease in miR-122 levels observed under non-stringent conditions was not caused by degradation, but instead by the formation of miR-122/RNA duplexes. In contrast, miR-122 remained undetectable in livers of mice treated with antagomir-122. These data suggest that the silencing of miRNA-122 in livers of mice treated with antagomir-122 was due to degradation of the miRNA, and the ability of antagomir-122, but not unconjugated anti-122 RNAs, to result in miR-122 degradation may be due to efficient delivery of antagomirs to hepatocytes.

Figure 20A:
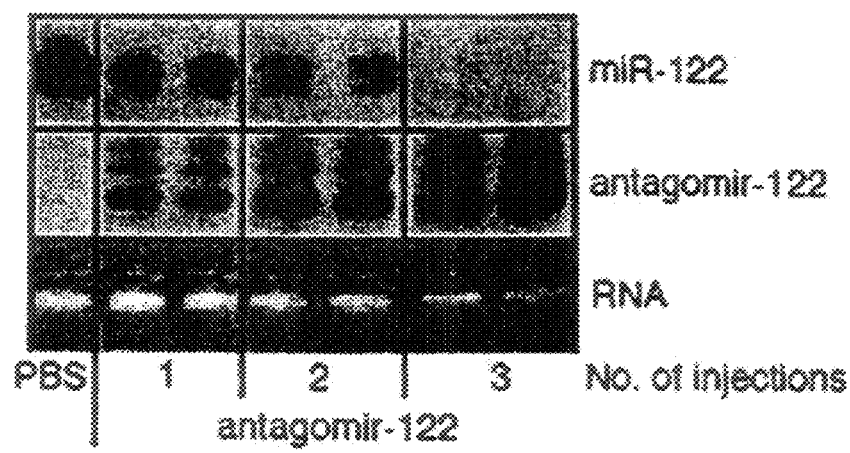
FIG. 20A is a panel of Northern blots of total RNA (15 µg) isolated from mouse livers. RNA was isolated 24 h after injection of 80 mg/kg bodyweight antagomir-122 (n=2) on 1, 2, or 3 consecutive days as indicated. Membranes were probed for both the endogenous miR-122 and the injected antagomir-122. Ethidium bromide staining of tRNA is shown as a loading control.

To determine the dose of antagomir-122 that can completely silence miR-122, mice were injected with 80, 160 or 240 mg/kg bodyweight antagomir-122 and miR-122 expression levels were measured. The highest dose (240 mg/kg bodyweight) resulted in a complete loss of miR-122 signal and was subsequently used for all other experiments (FIG. 20A).

Figure 20B:
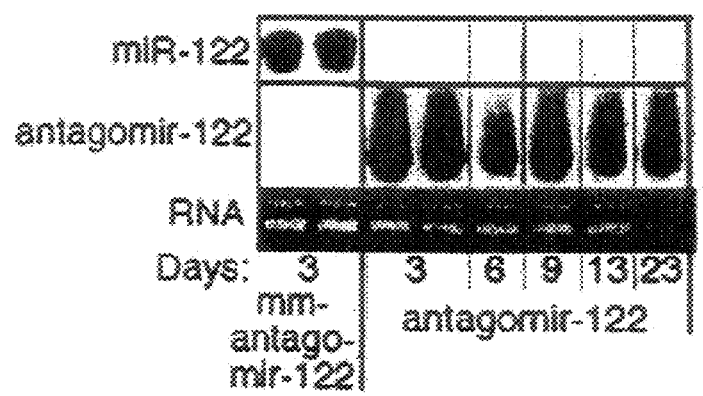
FIG. 20B is a panel of Northern blots of total RNA (15 µg) isolated from mouse livers. RNA was isolated 3, 6, 9, 13, and 23 days after injection of antagomir-122. Membranes were probed for both the endogenous miR-122 and the injected antagomir-122. Ethidium bromide staining of tRNA is shown as a loading control.
Figure 21A:
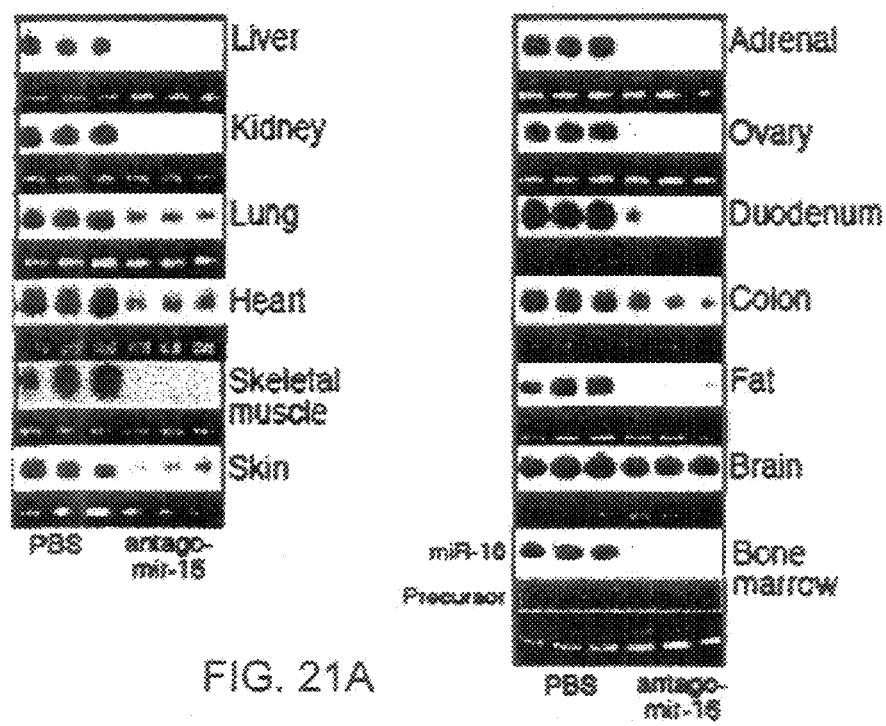
FIG. 21A is a panel of Northern blots of total RNA (10-30 µg) isolated from different mouse tissues 24 h after injection of antagomir-16 (n=3). Membranes were probed for miR-16. The precursor miR-16 transcript was visible on Northern blots of bone marrow and expression was similar in all mice. Ethidium bromide staining of tRNA is shown as a loading control.
Figure 21B:
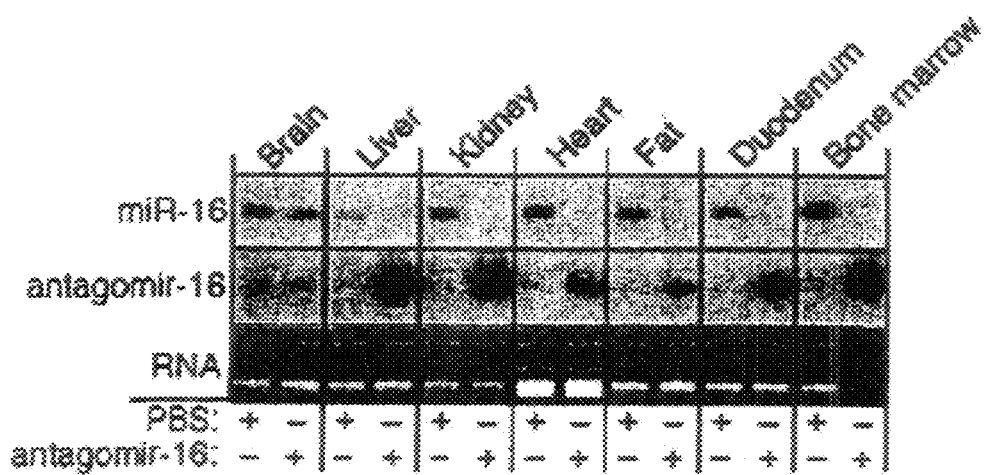
FIG. 21B is a panel of Northern blots of total RNA (10-30 µg) isolated from different mouse tissues 24 h after injection of antagomir-16 (n=3). Total RNA from 3 mice were pooled for the detection of miR-16 and the injected antagomir-16. Ethidium bromide staining of tRNA is shown as a loading control.

The duration of silencing with antagomir-122 was also measured. Levels of miR-122 were undetectable for as long as 23 days post-injection (FIG. 20B), indicating that silencing of miRNAs using antagomirs is long lasting. The injected antagomirs were well tolerated even during the course of the prolonged treatment; no alterations in bodyweight or serum markers of liver toxicity (alanine amino-transferase) were detected. To test the bioavailability of antagomirs in vivo and their ability to silence miRNA expression in different tissues, mice were injected with antagomir-16 directed to miR-16, which is abundantly expressed in all tissues (miR-16 is predicted to target one or both of Activin type II receptor gene, which is involved in TGFbeta signaling, and Hox-A5I (John et al., *PLoS Biology* 2:1862-1878, 2004; correction in *PLoS Biology* 3:1328, 2005)). Tissues were harvested one day after the final injection, and miRNA expression levels were compared to PBS-injected mice. Northern blot analysis revealed that expression of miR-16 was efficiently silenced in all tissues tested except brain (FIG. 21A). Antagomir-16 did not affect the expression of the 89 nt precursor of miR-16 as detected in bone marrow. The bioavailability of antagomir-16 was also assessed by Northern blotting in the above mentioned tissue samples. In concordance with the ability to silence miR-16 levels, significant levels of antagomir-16 were detected in all tissues except brain (FIG. 21B). Together, these data demonstrate that antagomirs achieve broad biodistribution and can efficiently silence miRNAs in most tissues in vivo.

Many miRNA genes have been found to be located in close proximity and to be coordinately transcribed. These polycistronic miRNA genes are transcribed to generate long primary transcripts (pri-miRNAs), which are processed by multiple enzymes in the nucleus and cytoplasm to generate the mature miRNA. To investigate if antagomirs targeting polycistronic miRNAs retain their target specificity with no effect on the expression of neighboring miRNAs, mice were injected with antagomirs targeting either miR-192 or miR-194 of the bicistronic cluster miR-192/194. Administration of antagomir-192 into mice resulted in silencing of miR-192 in liver and kidney, with no effect on the expression levels of miR-194. Conversely, injection of antagomir-194 into mice abolished miR-194 expression but had no demonstrable effect on the miR-192 levels compared to PBS-injected mice. These data demonstrate that antagomirs have the ability to differentially silence specific miRNAs that derive from the same primary transcript.

MicroRNAs are believed to bind to imperfect complementary target sites in 3'UTRs of mRNAs and interfere with translation and possibly mRNA stability. Therefore, silencing of miRNAs would be expected to result in a corresponding increase in target protein and possibly mRNA levels. To test this prediction, the expression of aldolase A, a gene that is repressed in hepatocytes and predicted to be the target of miR-122, was examined. The aldolase-A mRNA has a conserved nucleus with perfect sequence complementarity to miR-122 between nucleotides 29 and 36 downstream of the open reading frame. Aldolase-A expression was increased 4-5 fold in livers of mice injected with antagomir-122 compared to scrambled control (mm-antagomir-122). This regulation was observed in multiple experiments and different time points after injection. The target was also independently confirmed by cloning the 3'UTR Aldolase-A downstream of the luciferase open reading frame and cotransfecting this vector with control miRNAs (miR-124 (5'-UAAGGCACGCGGUGAAUGCCA-3 (SEQ ID NO: 104); see Krek et al., *Nature Genetics* 37:495-500, 2005, and Lim et al., *Nature* 433:769-773, 2005) and miR-192) and miR-122 into HEK293 cells, which lack miR-122 expression. Cotransfection of miR-122 resulted in a significant reduction in luciferase activity compared to miR-124 and miR-192 transfected cells. Together, these data indicate that aldolase-A is a physiological target of miR-122.

The upregulation of aldolase-A in mice treated with antagomir-122 demonstrates functional silencing of this miRNA. Aldolase-A is a housekeeping gene expressed in all cells. This gene is produced in large amounts in muscle where it can be as much as 5% of total cellular protein. In adult liver, aldolase-A expression is repressed and aldolase-B is produced. Conversely, dedifferentiated hepatocytes and transformed liver cells have increased aldolase-A expression levels and can even replace aldolase-B. Expression of miR-122 shows an inverse relationship with aldolase-A expression, with highest levels in differentiated adult hepatocytes and complete absence in undifferentiated cells such as HepG2. In contrast, the mRNA levels of aldolase-B, which lacks miR-122 target sites, was unaffected by antagomir-122. These findings provide non-genetic, pharmacologic evidence in mammals that microRNAs define tissue-specific gene expression.

The data demonstrate that antagomirs, single-stranded cholesterol-conjugated RNAs complementary to specific miRNAs, are effective inhibitors of miRNAs in vivo. The results also suggest that this process is highly specific and likely to occur in the cytosol since it does not affect the miRNA precursor or non-targeted miRNAs of common polycistronic precursors.

Methods

Synthesis of Antagomirs

RNAs were synthesized using commercially available 5'-O-(4,4'-dimethoxytrityl)-2'-O-methyl-3'-O-(2-cyanoethyl-N,N-diisopropyl) RNA phosphoramidite monomers of 6-N-benzoyladenosine (ABz), 4-N-benzoylcytidine (CBz), 2-N-isobutyrylguanosine (GiBu), and uridine (U), according to standard solid phase oligonucleotide synthesis protocols (Damha and Ogilvie, *Methods Mol. Biol.* 20:81-114, 1993). For antagomirs, i.e., cholesterol conjugated RNAs, the synthesis started from a controlled-pore glass solid support carrying a cholesterol-hydroxyprolinol linker (Manoharan et al., U.S. Pat. Appl. Publ. 20050107325). Antagomirs with phosphorothioate backbone at a given position were achieved by oxidation of phosphite with phenylacetyl disulfide (PADS) during oligonucleotide synthesis (Cheruvallath et al., *Nucleosides Nucleotides* 18:485-492, 1999). After cleavage and de-protection, antagomirs were purified by reverse-phase high-performance liquid chromatography, while the unconjugated RNA oligonucleotides were purified by anion-exchange high-performance liquid chromatography. Purified oligonucleotides were characterized by ES mass spectrometry and capillary gel electrophoresis.

Animals.

All animal models were maintained in C57Bl/6J background on a 12 hours light/dark cycle in a pathogen-free animal facility at Rockefeller University. Six week old mice received, on one to three consecutive days, tail vein injections of saline or different RNAs. RNAs were administered at doses of 80 mg/kg body weight in 0.2 ml per injection. Measurements of miRNA levels in tissues were performed 24 h after the last injection unless indicated otherwise. Tissues were harvested, snap frozen and stored at −80° C.

Northern Blotting Analysis.

Total RNA was isolated using the Trizol reagent (Invitrogen, Carlsbad, Calif.) and ethanol precipitation. RNA was separated at 45 mA on 14%-polyacrylamide gels that contained 8 M urea and 20% formamide. Antisense probes were designed according to the "microRNA registry" (Griffiths-Jones, *NAR* 32:D109-D111, 2004).

RT-PCR.

Extraction of total RNA, synthesis of cDNA, and PCR were carried out as described in Shih et al., *Proc. Natl. Acad. Sci. U.S.A.* 99:3818-3823, 2002.

Assay of Luciferase Activity.

The mouse full length aldolase-A 3'UTR was PCR-amplified using the following primers: 5' d-(CCAGAGCT-GAACTAAGGCTGCTCCA)-3' (SEQ ID NO: 105) and 5' d-(CCCCTTAAATAGTTGTTTAT TGGCA)-3' (SEQ ID NO: 106) and cloned downstream of the stop codon in pRL-TK (Promega). HEK293 cells were cultured in 24-well plates and each transfected with 50 ng of pRL-TK (Rr-luc), 50 ng of pGL3 control vector (Pp-luc) (Promega) and 200 ng of double-stranded siRNA (Dharmacon). Cells were harvested and assayed 24-30 h post-transfection.

Statistical Analysis.

Results are given as mean±s.d. Statistical analyses were performed by using Student's t-test, and the null hypothesis was rejected at the 0.05 level.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of inhibiting a target gene comprising providing a conjugate to a cell, wherein the conjugate comprises an oligonucleotide agent that can target a substantially complementary miRNA and a ligand, and wherein at least one subunit having a formula (I) is incorporated into said oligonucleotide agent:

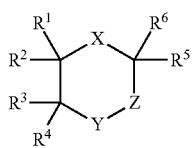

(I)

wherein:

X is $N(CO)R^7$, $NR^7$ or $CH_2$;

Y is $NR^8$, O, S, $CR^9R^{10}$, or absent;

Z is $CR^{11}R^{12}$ or absent;

Each of $R^1$, $R^2$, $R^3$, $R^4$, $R^9$, and $R^{10}$ is, independently, H, $OR^a$, $OR^b$, $(CH_2)_nOR^a$, or $(CH_2)_nOR^b$, provided that at least one of $R^1$, $R^2$, $R^3$, $R^4$, $R^9$, and $R^{10}$ is $OR^a$ or $OR^b$ and that at least one of $R^1$, $R^2$, $R^3$, $R^4$, $R^9$, and $R^{10}$ is $(CH_2)_nOR^a$, or $(CH_2)_nOR^b$;

Each of $R^5$, $R^6$, $R^{11}$, and $R^{12}$ is, independently, H, $C_1$-$C_6$ alkyl optionally substituted with 1-3 $R^{13}$, or $C(O)NHR^7$; or $R^5$ and $R^{11}$ together are $C_3$-$C_8$ cycloalkyl optionally substituted with $R^{14}$;

$R^7$ is $R^d$; or $C_1$-$C_{20}$ alkyl substituted with $NR^cR^d$ or $NHC(O)R^d$;

$R^8$ is $C_1$-$C_6$ alkyl;

$R^{13}$ is hydroxy, $C_1$-$C_4$ alkoxy, or halo;

$R^{14}$ is $NR^cR^7$;
$R^a$ is:

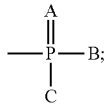

$R^b$ is:

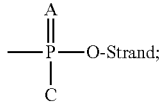

Each of A and C is, independently, O or S;
B is OH, O⁻, or

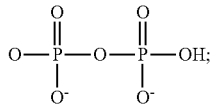

$R^c$ is H or $C_1$-$C_6$ alkyl;
$R^d$ is the ligand; and
n is 1-4.

2. The method of claim 1, wherein said conjugate is administered to an organism.

3. The method of claim 1, wherein said cell is outside an organism.

4. The method of claim 3, wherein said cell is a cell of a cell line.

5. A method of modulating expression of a target gene in a subject, the method comprising administering an conjugate to a subject, wherein the conjugate comprises an oligonucleotide agent that can target a substantially complementary miRNA and a ligand, wherein at least one subunit having a formula (I) is incorporated into said oligonucleotide agent:

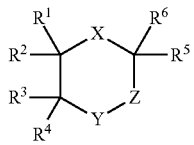

wherein:
X is $N(CO)R^7$, $NR^7$ or $CH_2$;
Y is $NR^8$, O, S, $CR^9R^{10}$, or absent;
Z is $CR^{11}R^{12}$ or absent;
Each of $R^1$, $R^2$, $R^3$, $R^4$, $R^9$, and $R^{10}$ is, independently, H, $OR^a$, $OR^b$, $(CH_2)_nOR^a$, or $(CH_2)_nOR^b$, provided that at least one of $R^1$, $R^2$, $R^3$, $R^4$, $R^9$, and $R^{10}$ is $OR^a$ or $OR^b$ and that at least one of $R^1$, $R^2$, $R^3$, $R^4$, $R^9$, and $R^{10}$ is $(CH_2)_nOR^a$, or $(CH_2)_nOR^b$;
Each of $R^5$, $R^6$, $R^{11}$, and $R^{12}$ is, independently, H, $C_1$-$C_6$ alkyl optionally substituted with 1-3 $R^{13}$, or $C(O)NHR^7$; or $R^5$ and $R^{11}$ together are $C_3$-$C_8$ cycloalkyl optionally substituted with $R^{14}$;
$R^7$ is $R^d$; or $C_1$-$C_{20}$ alkyl substituted with $NR^cR^d$ or $NHC(O)R^d$;

$R^8$ is $C_1$-$C_6$ alkyl;
$R^{13}$ is hydroxy, $C_1$-$C_4$ alkoxy, or halo;
$R_{14}$ is $NR^cR^7$;
$R^a$ is:

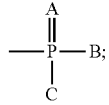

$R^b$ is:

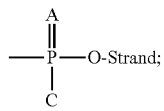

Each of A and C is, independently, O or S;
B is OH, O⁻, or

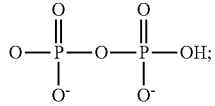

$R^c$ is H or $C_1$-$C_6$ alkyl;
$R^d$ is the ligand; and
n is 1-4.

6. A method of treating a kidney, ocular, or viral disorder, said method comprising administering a conjugate to a subject, wherein the conjugate comprises an oligonucleotide agent that can target a substantially complementary miRNA and a ligand, wherein at least one subunit having a formula (I) is incorporated into said oligonucleotide agent:

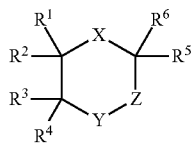

wherein:
X is $N(CO)R^7$, $NR^7$ or $CH_2$;
Y is $NR^8$, O, S, $CR^9R^{10}$, or absent;
Z is $CR^{11}R^{12}$ or absent;
Each of $R^1$, $R^2$, $R^3$, $R^4$, $R^9$, and $R^{10}$ is, independently, H, $OR^a$, $OR^b$, $(CH_2)_nOR^a$, or $(CH_2)_nOR^b$, provided that at least one of $R^1$, $R^2$, $R^3$, $R^4$, $R^9$, and $R^{10}$ is $OR^a$ or $OR^b$ and that at least one of $R^1$, $R^2$, $R^3$, $R^4$, $R^9$, and $R^{10}$ is $(CH_2)_nOR^a$, or $(CH_2)_nOR^b$;
Each of $R^5$, $R^6$, $R^{11}$, and $R^{12}$ is, independently, H, $C_1$-$C_6$ alkyl optionally substituted with 1-3 $R^{13}$, or $C(O)NHR^7$; or $R^5$ and $R^{11}$ together are $C_3$-$C_8$ cycloalkyl optionally substituted with $R^{14}$,
$R^7$ is $R^d$; or $C_1$-$C_{20}$ alkyl substituted with $NR^cR^d$ or $NHC(O)R^d$;
$R^8$ is $C_1$-$C_6$ alkyl;
$R^{13}$ is hydroxy, $C_1$-$C_4$ alkoxy, or halo;
$R^{14}$ is $NR^cR^7$;

$R^a$ is:

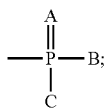

$R^b$ is:

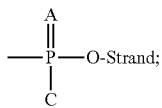

Each of A and C is, independently, O or S;
B is OH, O⁻, or

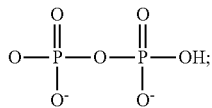

$R^c$ is H or $C_1$-$C_6$ alkyl;
$R^d$ is the ligand; and
n is 1-4.

7. The method of claim 1, wherein X is N(CO)$R^7$ or $NR^7$, Y is $CR^9R^{10}$, and Z is absent.

8. The method of claim 7, wherein $R^7$ is $(CH_2)_5NHR^d$ or $(CH_2)_5NHC(O)R^d$.

9. The method of claim 1, wherein the $R^d$ ligand is a steroid radical optionally tethered to at least one carbohydrate radical; a folic acid radical; a carbohydrate radical; a vitamin A radical; a vitamin E radical; a vitamin K radical; or a vitamin B 12 radical.

10. The method of claim 9, wherein the $R^d$ ligand is a carbohydrate cholesterol radical.

11. The method of claim 1, wherein the miRNA is selected from the group consisting of miR-21, miR-16, miR-22, miR-122, miR-155, miR-192, miR-194, and miR-375.

12. The method of claim 5, wherein X is N(CO)$R^7$ or $NR^7$, Y is $CR^9R^{10}$, and Z is absent.

13. The method of claim 12, wherein $R^7$ is $(CH_2)_5NHR^d$ or $(CH_2)_5NHC(O)R^d$.

14. The method of claim 5, wherein the $R^d$ ligand is a steroid radical optionally tethered to at least one carbohydrate radical; a folic acid radical; a carbohydrate radical; a vitamin A radical; a vitamin E radical; a vitamin K radical; or a vitamin B 12 radical.

15. The method of claim 14, wherein the $R^d$ ligand is a carbohydrate cholesterol radical.

16. The method of claim 5, wherein the miRNA is selected from the group consisting of miR-21, miR-16, miR-22, miR-122, miR-155, miR-192, miR-194, and miR-375.

17. The method of claim 6, wherein X is N(CO)$R^7$ or $NR^7$, Y is $CR^9R^{10}$, and Z is absent.

18. The method of claim 17, wherein $R^7$ is $(CH_2)_5NHR^d$ or $(CH_2)_5NHC(O)R^d$.

19. The method of claim 6, wherein the $R^d$ ligand is a steroid radical optionally tethered to at least one carbohydrate radical; a folic acid radical; a carbohydrate radical; a vitamin A radical; a vitamin E radical; a vitamin K radical; or a vitamin B 12 radical.

20. The method of claim 19, wherein the $R^d$ ligand is a carbohydrate cholesterol radical.

21. The method of claim 6, wherein the miRNA is selected from the group consisting of miR-21, miR-16, miR-22, miR-122, miR-155, miR-192, miR-194, and miR-375.

* * * * *

UNITED STATES PATENT AND TRADEMARK OFFICE
CERTIFICATE OF CORRECTION

| | | |
|---|---|---|
| PATENT NO. | : 9,453,222 B2 | Page 1 of 1 |
| APPLICATION NO. | : 14/582284 | |
| DATED | : September 27, 2016 | |
| INVENTOR(S) | : Manoharan et al. | |

It is certified that error appears in the above-identified patent and that said Letters Patent is hereby corrected as shown below:

In the Claims

In Claim 10, Column 278, Line 2, delete "carbohydrate cholesterol radical" and insert in its place -- cholesterol radical --.

In Claim 15, Column 278, Line 16, delete "carbohydrate cholesterol radical" and insert in its place -- cholesterol radical --.

In Claim 20, Column 278, Line 31, delete "carbohydrate cholesterol radical" and insert in its place -- cholesterol radical --.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 106

<210> SEQ ID NO 1
<211> LENGTH: 16
<212> TYPE: PRT
<213> ORGANISM: Artificial Sequence

```
<220> FEATURE:
<223> OTHER INFORMATION: Exemplary Cell Permeation Peptide

<400> SEQUENCE: 1

Arg Gln Ile Lys Ile Trp Phe Gln Asn Arg Arg Met Lys Trp Lys Lys
 1               5                  10                  15

<210> SEQ ID NO 2
<211> LENGTH: 14
<212> TYPE: PRT
<213> ORGANISM: Artificial Sequence
<220> FEATURE:
<223> OTHER INFORMATION: Exemplary Cell Permeation Peptide

<400> SEQUENCE: 2

Gly Arg Lys Lys Arg Arg Gln Arg Arg Arg Pro Pro Gln Cys
 1               5                  10

<210> SEQ ID NO 3
<211> LENGTH: 27
<212> TYPE: PRT
<213> ORGANISM: Artificial Sequence
<220> FEATURE:
<223> OTHER INFORMATION: Exemplary Cell Permeation Peptide

<400> SEQUENCE: 3

Gly Ala Leu Phe Leu Gly Trp Leu Gly Ala Ala Gly Ser Thr Met Gly
 1               5                  10                  15

Ala Trp Ser Gln Pro Lys Lys Lys Arg Lys Val
            20                  25

<210> SEQ ID NO 4
<211> LENGTH: 18
<212> TYPE: PRT
<213> ORGANISM: Artificial Sequence
<220> FEATURE:
<223> OTHER INFORMATION: Exemplary Cell Permeation Peptide

<400> SEQUENCE: 4

Leu Leu Ile Ile Leu Arg Arg Arg Ile Arg Lys Gln Ala His Ala His
 1               5                  10                  15

Ser Lys

<210> SEQ ID NO 5
<211> LENGTH: 26
<212> TYPE: PRT
<213> ORGANISM: Artificial Sequence
<220> FEATURE:
<223> OTHER INFORMATION: Exemplary Cell Permeation Peptide

<400> SEQUENCE: 5

Gly Trp Thr Leu Asn Ser Ala Gly Tyr Leu Leu Lys Ile Asn Leu Lys
 1               5                  10                  15

Ala Leu Ala Ala Leu Ala Lys Lys Ile Leu
            20                  25

<210> SEQ ID NO 6
<211> LENGTH: 18
<212> TYPE: PRT
<213> ORGANISM: Artificial Sequence
<220> FEATURE:
<223> OTHER INFORMATION: Exemplary Cell Permeation Peptide

<400> SEQUENCE: 6

Lys Leu Ala Leu Lys Leu Ala Leu Lys Ala Leu Lys Ala Ala Leu Lys
```

Leu Ala

<210> SEQ ID NO 7
<211> LENGTH: 9
<212> TYPE: PRT
<213> ORGANISM: Artificial Sequence
<220> FEATURE:
<223> OTHER INFORMATION: Exemplary Cell Permeation Peptide

<400> SEQUENCE: 7

Arg Arg Arg Arg Arg Arg Arg Arg Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Exemplary Cell Permeation Peptide

<400> SEQUENCE: 8

Lys Phe Phe Lys Phe Phe Lys Phe Phe Lys
1               5                   10

<210> SEQ ID NO 9
<211> LENGTH: 37
<212> TYPE: PRT
<213> ORGANISM: Artificial Sequence
<220> FEATURE:
<223> OTHER INFORMATION: Exemplary Cell Permeation Peptides

<400> SEQUENCE: 9

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 10
<211> LENGTH: 31
<212> TYPE: PRT
<213> ORGANISM: Artificial Sequence
<220> FEATURE:
<223> OTHER INFORMATION: Exemplary Cell Permeation Peptides

<400> SEQUENCE: 10

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Exemplary Cell Permeation Peptides

<400> SEQUENCE: 11

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys

```
            20                  25                  30

<210> SEQ ID NO 12
<211> LENGTH: 36
<212> TYPE: PRT
<213> ORGANISM: Artificial Sequence
<220> FEATURE:
<223> OTHER INFORMATION: Exemplary Cell Permeation Peptides

<400> SEQUENCE: 12

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 13
<211> LENGTH: 12
<212> TYPE: PRT
<213> ORGANISM: Artificial Sequence
<220> FEATURE:
<223> OTHER INFORMATION: Exemplary Cell Permeation Peptides

<400> SEQUENCE: 13

Arg Lys Cys Arg Ile Val Val Ile Arg Val Cys Arg
1               5                   10

<210> SEQ ID NO 14
<211> LENGTH: 42
<212> TYPE: PRT
<213> ORGANISM: Artificial Sequence
<220> FEATURE:
<223> OTHER INFORMATION: Exemplary Cell Permeation Peptides

<400> SEQUENCE: 14

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 15
<211> LENGTH: 13
<212> TYPE: PRT
<213> ORGANISM: Artificial Sequence
<220> FEATURE:
<223> OTHER INFORMATION: Exemplary Cell Permeation Peptides

<400> SEQUENCE: 15

Ile Leu Pro Trp Lys Trp Pro Trp Trp Pro Trp Arg Arg
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 16

Ala Ala Val Ala Leu Leu Pro Ala Val Leu Leu Ala Leu Leu Ala Pro
1               5                   10                  15
```

```
<210> SEQ ID NO 17
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 17

Ala Ala Leu Leu Pro Val Leu Leu Ala Ala Pro
 1               5                  10

<210> SEQ ID NO 18
<211> LENGTH: 13
<212> TYPE: PRT
<213> ORGANISM: Human immunodeficiency virus

<400> SEQUENCE: 18

Gly Arg Lys Lys Arg Arg Gln Arg Arg Pro Pro Gln
 1               5                  10

<210> SEQ ID NO 19
<211> LENGTH: 16
<212> TYPE: PRT
<213> ORGANISM: Drosophila Antennapedia

<400> SEQUENCE: 19

Arg Gln Ile Lys Ile Trp Phe Gln Asn Arg Arg Met Lys Trp Lys Lys
 1               5                  10                  15

<210> SEQ ID NO 20
<211> LENGTH: 21
<212> TYPE: DNA
<213> ORGANISM: Artificial Sequence
<220> FEATURE:
<223> OTHER INFORMATION: "Dual targeting" siRNAs
<220> FEATURE:
<221> NAME/KEY: misc_feature
<222> LOCATION: 20, 21
<223> OTHER INFORMATION: n = dT= deoxythymidine

<400> SEQUENCE: 20
uaccagcacc caggugcugn n                                              21

<210> SEQ ID NO 21
<211> LENGTH: 21
<212> TYPE: DNA
<213> ORGANISM: Artificial Sequence
<220> FEATURE:
<223> OTHER INFORMATION: "Dual targeting" siRNAs
<220> FEATURE:
<221> NAME/KEY: misc_feature
<222> LOCATION: 20, 21
<223> OTHER INFORMATION: n = dT= deoxythymidine

<400> SEQUENCE: 21
ccgggcaucc ggacgaguun n                                              21

<210> SEQ ID NO 22
<211> LENGTH: 21
<212> TYPE: DNA
<213> ORGANISM: Artificial Sequence
<220> FEATURE:
<223> OTHER INFORMATION: Dual targeting  siRNA
<220> FEATURE:
<221> NAME/KEY: misc_feature
<222> LOCATION: 1, 2
<223> OTHER INFORMATION: n = dT= deoxythymidine
```

<400> SEQUENCE: 22
nnaugguagu gggucgacga c          21

<210> SEQ ID NO 23
<211> LENGTH: 21
<212> TYPE: DNA
<213> ORGANISM: Artificial Sequence
<220> FEATURE:
<223> OTHER INFORMATION: "Dual targeting" siRNAs
<220> FEATURE:
<221> NAME/KEY: misc_feature
<222> LOCATION: 1, 2
<223> OTHER INFORMATION: n = dT= deoxythymidine

<400> SEQUENCE: 23
nnggcccguc gcccagcuca a          21

<210> SEQ ID NO 24
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n =  deoxythymidine

<400> SEQUENCE: 24
cuuacgcuga guacuucgan n          21

<210> SEQ ID NO 25
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n =  deoxythymidine

<400> SEQUENCE: 25
ucgaaguacu cagcguaagn n          21

<210> SEQ ID NO 26
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20
<223> OTHER INFORMATION: n = deoxythymidine, phosphorothioate linkage
<220> FEATURE:
<221> NAME/KEY: misc_feature
<222> LOCATION: 21
<223> OTHER INFORMATION: n = deoxythymidine

<400> SEQUENCE: 26
cuuacgcuga guacuucgan n          21

<210> SEQ ID NO 27
<211> LENGTH: 21
<212> TYPE: DNA
<213> ORGANISM: Artificial Sequence
<220> FEATURE:
<223> OTHER INFORMATION: Synthetically generated siRNA

```
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine, phosphorothioate linkage

<400> SEQUENCE: 27
ucgaaguacu cagcguaagn n                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 19
<223> OTHER INFORMATION: n =  adenine, phosphorothioate linkage
<220> FEATURE:
<221> NAME/KEY: misc_feature
<222> LOCATION: 20
<223> OTHER INFORMATION: n = deoxythymidine, phosphorothioate linkage
<220> FEATURE:
<221> NAME/KEY: misc_feature
<222> LOCATION: 21
<223> OTHER INFORMATION: n = deoxythymidine

<400> SEQUENCE: 28
cuuacgcuga guacuucgnn n                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20, 21
<223> OTHER INFORMATION: n = deoxythymidine phosphorothioate linkage

<400> SEQUENCE: 29
ucgaaguacu cagcguaagn n                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 18
<223> OTHER INFORMATION: n =  guanine phosphorothioate linkage
<220> FEATURE:
<221> NAME/KEY: misc_feature
<222> LOCATION: 19
<223> OTHER INFORMATION: n =  adenine, phosphorothioate linkage
<220> FEATURE:
<221> NAME/KEY: misc_feature
<222> LOCATION: 20
<223> OTHER INFORMATION: n = deoxythymidine, phosphorothioate linkage
<220> FEATURE:
<221> NAME/KEY: misc_feature
<222> LOCATION: 21
<223> OTHER INFORMATION: n = deoxythymidine

<400> SEQUENCE: 30
```
cuuacgcuga guacuucnnn n                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 19
<223> OTHER INFORMATION: n =guanine phosphorothioate linkage
<220> FEATURE:
<221> NAME/KEY: misc_feature
<222> LOCATION: 20, 21
<223> OTHER INFORMATION: n = deoxythymidine, phosphorothioate linkage

<400> SEQUENCE: 31
ucgaaguacu cagcguaann n                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 17
<223> OTHER INFORMATION: n = cytosine phosphorothioate linkage
<220> FEATURE:
<221> NAME/KEY: misc_feature
<222> LOCATION: 18
<223> OTHER INFORMATION: n =  guanine phosphorothioate linkage
<220> FEATURE:
<221> NAME/KEY: misc_feature
<222> LOCATION: 19
<223> OTHER INFORMATION: n = adenine phosphorothioate linkage
<220> FEATURE:
<221> NAME/KEY: misc_feature
<222> LOCATION: 20
<223> OTHER INFORMATION: n = deoxythymidine, phosphorothioate linkage
<220> FEATURE:
<221> NAME/KEY: misc_feature
<222> LOCATION: 21
<223> OTHER INFORMATION: n = deoxythymidine

<400> SEQUENCE: 32
cuuacgcuga guacuunnnn n                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 17, 18
<223> OTHER INFORMATION: n = adenine phosphorothioate linkage
<220> FEATURE:
<221> NAME/KEY: misc_feature
<222> LOCATION: 19
<223> OTHER INFORMATION: n = guanine phosphorothioate linkage
<220> FEATURE:
<221> NAME/KEY: misc_feature
<222> LOCATION: 20, 21
<223> OTHER INFORMATION: n = deoxythymidine phosphorothioate linkage

<400> SEQUENCE: 33
ucgaaguacu cagcgunnnn n                                              21

```
<210> SEQ ID NO 34
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 12
<223> OTHER INFORMATION: n =  uridine phosphorothioate linkage
<220> FEATURE:
<221> NAME/KEY: misc_feature
<222> LOCATION: 20, 21
<223> OTHER INFORMATION: n = deoxythymidine

<400> SEQUENCE: 34
cuuacgcuga gnacuucgan n                                                 21

<210> SEQ ID NO 35
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 8
<223> OTHER INFORMATION: n = adenine, phosphorothioate linkage
<220> FEATURE:
<221> NAME/KEY: misc_feature
<222> LOCATION: 20, 21
<223> OTHER INFORMATION: n =  deoxythymidine

<400> SEQUENCE: 35
ucgaaguncu cagcguaagn n                                                 21

<210> SEQ ID NO 36
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 3, 12
<223> OTHER INFORMATION: n =  uridine phosphorothioate linkage
<220> FEATURE:
<221> NAME/KEY: misc_feature
<222> LOCATION: 20, 21
<223> OTHER INFORMATION: n = deoxythymidine

<400> SEQUENCE: 36
cunacgcuga gnacuucgan n                                                 21

<210> SEQ ID NO 37
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 8, 17
<223> OTHER INFORMATION: n =  adenine phosphorothioate linkage
<220> FEATURE:
<221> NAME/KEY: misc_feature
<222> LOCATION: 20, 21
<223> OTHER INFORMATION: n = deoxythymidine

<400> SEQUENCE: 37
ucgaaguncu cagcgunagn n                                                 21
```

```
<210> SEQ ID NO 38
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 3, 12
<223> OTHER INFORMATION: n = uridine phosphorothioate linkage
<220> FEATURE:
<221> NAME/KEY: misc_feature
<222> LOCATION: 20
<223> OTHER INFORMATION: n =  deoxythymidine phosphorothioate linkage
<220> FEATURE:
<221> NAME/KEY: misc_feature
<222> LOCATION: 21
<223> OTHER INFORMATION: n = deoxythymidine

<400> SEQUENCE: 38
cunacgcuga gnacuucgan n                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 8, 17
<223> OTHER INFORMATION: n = adenine, phosphorothioate linkage
<220> FEATURE:
<221> NAME/KEY: misc_feature
<222> LOCATION: 20
<223> OTHER INFORMATION: n =deoxythymidine
<220> FEATURE:
<221> NAME/KEY: misc_feature
<222> LOCATION: 21
<223> OTHER INFORMATION: n = deoxythymidine, phosphorothioate linkage

<400> SEQUENCE: 39
ucgaaguncu cagcgunagn n                                              21

<210> SEQ ID NO 40
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20
<223> OTHER INFORMATION: n = methylphosphonate deoxythymidine
<220> FEATURE:
<221> NAME/KEY: misc_feature
<222> LOCATION: 21
<223> OTHER INFORMATION: n = deoxythymidine

<400> SEQUENCE: 40
cuuacgcuga guacuucgan n                                              21

<210> SEQ ID NO 41
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20
<223> OTHER INFORMATION: n =deoxythymidine
```

```
<220> FEATURE:
<221> NAME/KEY: misc_feature
<222> LOCATION: 21
<223> OTHER INFORMATION: n = methylphosphonate deoxythymidine

<400> SEQUENCE: 41
ucgaaguacu cagcguaagn n                                          21

<210> SEQ ID NO 42
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20, 21
<223> OTHER INFORMATION: n = 2'OMe-uridine

<400> SEQUENCE: 42
cuuacgcuga guacuucgan n                                          21

<210> SEQ ID NO 43
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20, 21
<223> OTHER INFORMATION: n =  2'OMe-uridine

<400> SEQUENCE: 43
ucgaaguacu cagcguaagn n                                          21

<210> SEQ ID NO 44
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = cytosine phosphorothioate linkage
<220> FEATURE:
<221> NAME/KEY: misc_feature
<222> LOCATION: 20
<223> OTHER INFORMATION: n = 2'OMe-uridine phosphorothioate linkage
<220> FEATURE:
<221> NAME/KEY: misc_feature
<222> LOCATION: 21
<223> OTHER INFORMATION: n = 2'OMe-uridine

<400> SEQUENCE: 44
nuuacgcuga guacuucgan n                                          21

<210> SEQ ID NO 45
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 2
<223> OTHER INFORMATION: n = cytosine phosphorothioate linkage
<220> FEATURE:
<221> NAME/KEY: misc_feature
<222> LOCATION: 20
```

<223> OTHER INFORMATION: n = 2'OMe-uridine
<220> FEATURE:
<221> NAME/KEY: misc_feature
<222> LOCATION: 21
<223> OTHER INFORMATION: n = 2'OMe-uridine phosphorothioate linkage

<400> SEQUENCE: 45
ungaaguacu cagcguaagn n                                              21

<210> SEQ ID NO 46
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = cytosine phosphorothioate linkage
<220> FEATURE:
<221> NAME/KEY: misc_feature
<222> LOCATION: 3, 21
<223> OTHER INFORMATION: n = 2'OMe-uridine
<220> FEATURE:
<221> NAME/KEY: misc_feature
<222> LOCATION: 20
<223> OTHER INFORMATION: n = 2'OMe-uridine, phosphorothioate linkage

<400> SEQUENCE: 46
nunacgcuga guacuucgan n                                              21

<210> SEQ ID NO 47
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 2
<223> OTHER INFORMATION: n = cytosine phosphorothioate linkage
<220> FEATURE:
<221> NAME/KEY: misc_feature
<222> LOCATION: 16, 20
<223> OTHER INFORMATION: n = 2'OMe-uridine
<220> FEATURE:
<221> NAME/KEY: misc_feature
<222> LOCATION: 21
<223> OTHER INFORMATION: n = 2'OMe-uridine, phosphorothioate linkage

<400> SEQUENCE: 47
ungaaguacu cagcgnaagn n                                              21

<210> SEQ ID NO 48
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = cytosine phosphorothioate linkage
<220> FEATURE:
<221> NAME/KEY: misc_feature
<222> LOCATION: 3, 12, 21
<223> OTHER INFORMATION: n = 2'OMe-uridine
<220> FEATURE:
<221> NAME/KEY: misc_feature
<222> LOCATION: 20
<223> OTHER INFORMATION: n = 2'OMe-uridine, phosphorothioate linkage

<400> SEQUENCE: 48
nunacgcuga gnacuucgan n                                    21

<210> SEQ ID NO 49
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 2
<223> OTHER INFORMATION: n = cytosine phosphorothioate linkage
<220> FEATURE:
<221> NAME/KEY: misc_feature
<222> LOCATION: 7, 16, 20
<223> OTHER INFORMATION: n = 2'OMe-uridine
<220> FEATURE:
<221> NAME/KEY: misc_feature
<222> LOCATION: 21
<223> OTHER INFORMATION: n = 2'OMe-uridine, phosphorothioate linkage

<400> SEQUENCE: 49
ungaagnacu cagcgnaagn n                                    21

<210> SEQ ID NO 50
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = alkylamine- deoxythymidine

<400> SEQUENCE: 50
cuuacgcuga guacuucgan n                                    21

<210> SEQ ID NO 51
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = alkylamine- deoxythymidine

<400> SEQUENCE: 51
ucgaaguacu cagcguaagn n                                    21

<210> SEQ ID NO 52
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20, 21
<223> OTHER INFORMATION: n = alkylamine- deoxythymidine

```
<400> SEQUENCE: 52
cuuacgcuga guacuucgan n                                              21

<210> SEQ ID NO 53
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20, 21
<223> OTHER INFORMATION: n = alkylamino- deoxythymidine

<400> SEQUENCE: 53
ucgaaguacu cagcguaagn n                                              21

<210> SEQ ID NO 54
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine, abasic pyrrolidine cationic

<400> SEQUENCE: 54
cuuacgcuga guacuucgan n                                              21

<210> SEQ ID NO 55
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20
<223> OTHER INFORMATION: n = deoxythymidine
<220> FEATURE:
<221> NAME/KEY: misc_difference
<222> LOCATION: 21
<223> OTHER INFORMATION: n = deoxythymidine, abasic pyrrolidine cationic

<400> SEQUENCE: 55
ucgaaguacu cagcguaagn n                                              21

<210> SEQ ID NO 56
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = cytosine  phosphorothioate linkage
<220> FEATURE:
<221> NAME/KEY: misc_feature
<222> LOCATION: 3
<223> OTHER INFORMATION: n = alkylamine-uridine
<220> FEATURE:
<221> NAME/KEY: misc_feature
<222> LOCATION: 20
<223> OTHER INFORMATION: n = 2'OMe-uridine, phosphorothioate linkage
```

```
<220> FEATURE:
<221> NAME/KEY: misc_feature
<222> LOCATION: 21
<223> OTHER INFORMATION: n = 2'OMe-uridine

<400> SEQUENCE: 56
nunacgcuga guacuucgan n                                              21

<210> SEQ ID NO 57
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 2
<223> OTHER INFORMATION: n = cytosine phosphorothioate linkage
<220> FEATURE:
<221> NAME/KEY: misc_feature
<222> LOCATION: 16
<223> OTHER INFORMATION: n = alkylamine-uridine
<220> FEATURE:
<221> NAME/KEY: misc_feature
<222> LOCATION: 20
<223> OTHER INFORMATION: n = 2'OMe-uridine
<220> FEATURE:
<221> NAME/KEY: misc_feature
<222> LOCATION: 21
<223> OTHER INFORMATION: n = 2'OMe-uridine phosphorothioate linkage

<400> SEQUENCE: 57
ungaaguacu cagcgnaagn n                                              21

<210> SEQ ID NO 58
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = cytosine phosphorothioate linkage
<220> FEATURE:
<221> NAME/KEY: misc_feature
<222> LOCATION: 3, 12
<223> OTHER INFORMATION: n = alkylamino-uridine
<220> FEATURE:
<221> NAME/KEY: misc_feature
<222> LOCATION: 20
<223> OTHER INFORMATION: n = 2'OMe-uridine phosphorothioate linkage
<220> FEATURE:
<221> NAME/KEY: misc_feature
<222> LOCATION: 21
<223> OTHER INFORMATION: n = 2'OMe-uridine

<400> SEQUENCE: 58
nunacgcuga guacuucgan n                                              21

<210> SEQ ID NO 59
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 2
<223> OTHER INFORMATION: n = cytosine  phosphorothioate linkage
<220> FEATURE:
<221> NAME/KEY: misc_feature
<222> LOCATION: 7, 16
```

```
<223> OTHER INFORMATION: n = alkylamine-uridine
<220> FEATURE:
<221> NAME/KEY: misc_feature
<222> LOCATION: 20
<223> OTHER INFORMATION: n = 2'OMe-uridine
<220> FEATURE:
<221> NAME/KEY: misc_feature
<222> LOCATION: 21
<223> OTHER INFORMATION: n = 2'OMe-uridine, phosphorothioate linkage

<400> SEQUENCE: 59
ungaaguacu cagcgnaagn n                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine, naproxen conjugate

<400> SEQUENCE: 60
cuuacgcuga guacuucgan n                                              21

<210> SEQ ID NO 61
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine, naproxen conjugate

<400> SEQUENCE: 61
ucgaaguacu cagcguaagn n                                              21

<210> SEQ ID NO 62
<211> LENGTH: 21
<212> TYPE: DNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine, ibuprofen conjugate

<400> SEQUENCE: 62
cuuacgcuga guacuucgan n                                              21

<210> SEQ ID NO 63
<211> LENGTH: 21
<212> TYPE: RNA
<213> ORGANISM: Artificial Sequence
```

```
<220> FEATURE:
<223> OTHER INFORMATION: Exemplary oligonucleotide agent
<220> FEATURE:
<221> NAME/KEY: misc_feature
<222> LOCATION: 21
<223> OTHER INFORMATION: n =  uridine phosphorothioate linkage

<400> SEQUENCE: 63
gcacauagga gagaugagcu n                                                   21

<210> SEQ ID NO 64
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 21
<223> OTHER INFORMATION: n =  uridine phosphorothioate linkage

<400> SEQUENCE: 64
gucaucacac ugaauaccaa n                                                   21

<210> SEQ ID NO 65
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine phosphorothioate linkage

<400> SEQUENCE: 65
caucacacug aauaccaaun n                                                   21

<210> SEQ ID NO 66
<211> LENGTH: 22
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 1
<223> OTHER INFORMATION: n = 2'-O-Methyl modified uridine
      phosphorothioate linkage
<220> FEATURE:
<221> NAME/KEY: misc_feature
<222> LOCATION: 2, 19
<223> OTHER INFORMATION: n = 2'-O-Methyl modified cytosine
      phosphorothioate
<220> FEATURE:
<221> NAME/KEY: misc_feature
<222> LOCATION: 3, 8, 13, 14, 17, 18
<223> OTHER INFORMATION: n = 2'-O-Methyl modified adenine
<220> FEATURE:
<221> NAME/KEY: misc_feature
<222> LOCATION: 4, 6, 10, 11, 15
<223> OTHER INFORMATION: n = 2'-O-Methyl modified cytosine
<220> FEATURE:
<221> NAME/KEY: misc_feature
<222> LOCATION: 5, 7, 9, 12, 16
<223> OTHER INFORMATION: n = 2'-O-Methyl modified guanine
<220> FEATURE:
<221> NAME/KEY: misc_feature
<222> LOCATION: 20, 21, 22
```

```
<223> OTHER INFORMATION: n = 2'-O-Methyl modified adenine
      phosphorothioate linkage

<400> SEQUENCE: 66
nnnnnnnnnn nnnnnnnnnn nn                                            22

<210> SEQ ID NO 67
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 1, 11, 15, 16, 17
<223> OTHER INFORMATION: n = 2'-O-Methyl modified cytosine
<220> FEATURE:
<221> NAME/KEY: misc_feature
<222> LOCATION: 2, 10, 19
<223> OTHER INFORMATION: n = 2'-O-Methyl modified uridine
<220> FEATURE:
<221> NAME/KEY: misc_feature
<222> LOCATION: 20
<223> OTHER INFORMATION: n = deoxythymidine phosphorothioate linkage
<220> FEATURE:
<221> NAME/KEY: misc_feature
<222> LOCATION: 21
<223> OTHER INFORMATION: n = deoxythymidine

<400> SEQUENCE: 67
nngggaaagn naagnnnann n                                             21

<210> SEQ ID NO 68
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 1, 6, 12, 13, 14
<223> OTHER INFORMATION: n = 2'-O-Methyl modified cytosine
<220> FEATURE:
<221> NAME/KEY: misc_feature
<222> LOCATION: 2, 4, 10, 19
<223> OTHER INFORMATION: n = 2'-O-Methyl modified uridine
<220> FEATURE:
<221> NAME/KEY: misc_feature
<222> LOCATION: 20
<223> OTHER INFORMATION: n = deoxythymidine phosphorothioate linkage
<220> FEATURE:
<221> NAME/KEY: misc_feature
<222> LOCATION: 21
<223> OTHER INFORMATION: n = deoxythymidine

<400> SEQUENCE: 68
nngngnaagn gnnnaagann n                                             21

<210> SEQ ID NO 69
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 4, 7, 9, 14, 16, 17
<223> OTHER INFORMATION: n = 2'-deoxy-2'-fluoro modified uridine
<220> FEATURE:
<221> NAME/KEY: misc_feature
<222> LOCATION: 5, 8, 10, 15, 19
<223> OTHER INFORMATION: n = 2'-deoxy-2'-fluoro modified cytosine
<220> FEATURE:
```

```
<221> NAME/KEY: misc_feature
<222> LOCATION: 20
<223> OTHER INFORMATION: n = deoxythymidine phosphorothioate linkage
<220> FEATURE:
<221> NAME/KEY: misc_feature
<222> LOCATION: 21
<223> OTHER INFORMATION: n = deoxythymidine

<400> SEQUENCE: 69
ggannannnn aagnnnnann n                                              21

<210> SEQ ID NO 70
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n = deoxythymidine phosphorothioate linkage

<400> SEQUENCE: 70
acugcagggu gaagaauuan n                                              21

<210> SEQ ID NO 71
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n =  uridine phosphorothioate linkage

<400> SEQUENCE: 71
gcacauagga gagaugagcn n                                              21

<210> SEQ ID NO 72
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20
<223> OTHER INFORMATION: n =  cytosine phosphorothioate linkage
<220> FEATURE:
<221> NAME/KEY: misc_feature
<222> LOCATION: 21
<223> OTHER INFORMATION: n =  uridine phosphorothioate linkage

<400> SEQUENCE: 72
gaacugugug ugagaggucn n                                              21

<210> SEQ ID NO 73
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n = thymidine phosphorothioate linkage

<400> SEQUENCE: 73
ccagguuuuu uucuuacuun n                                              21
```

```
<210> SEQ ID NO 74
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n = thymidine phosphorothioate linkage

<400> SEQUENCE: 74
uuccucaaau caauuaccan n                                              21

<210> SEQ ID NO 75
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n = deoxythymidine phosphorothioate linkage

<400> SEQUENCE: 75
ggaaggcucc cuugauggan n                                              21

<210> SEQ ID NO 76
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n = deoxythymidine phosphorothioate linkage

<400> SEQUENCE: 76
gacacagugu guuugauuun n                                              21

<210> SEQ ID NO 77
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n = deoxythymidine phosphorothioate linkage

<400> SEQUENCE: 77
ugccaagcca gauucucuun n                                              21

<210> SEQ ID NO 78
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n = deoxythymidine phosphorothioate linkage

<400> SEQUENCE: 78
```
cucaggaauu cagugccuun n                                              21

<210> SEQ ID NO 79
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n = deoxythymidine

<400> SEQUENCE: 79
cuggacuucc agaagaacan n                                              21

<210> SEQ ID NO 80
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20
<223> OTHER INFORMATION: n = adenine phosphorothioate linkage

<400> SEQUENCE: 80
gucaucacac ugaauaccan u                                              21

<210> SEQ ID NO 81
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 21
<223> OTHER INFORMATION: n = uridine phosphorothioate linkage

<400> SEQUENCE: 81
gucaucacac ugaauaccaa n                                              21

<210> SEQ ID NO 82
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 21
<223> OTHER INFORMATION: n = guanine phosphorothioate linkage

<400> SEQUENCE: 82
gcaccaucuu cuucaaggac n                                              21

<210> SEQ ID NO 83
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 21
<223> OTHER INFORMATION: n = guanine phosphorothioate linkage

<400> SEQUENCE: 83
agguguaugg cuucaacccu n                                              21

<210> SEQ ID NO 84
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 21
<223> OTHER INFORMATION: n = uridine phosphorothioate linkage

<400> SEQUENCE: 84
gugaucagac ucaauacgaa n                                              21

<210> SEQ ID NO 85
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 7, 8, 10, 12, 13, 14
<223> OTHER INFORMATION: n = 2'-O-Methyl modified uridine
<220> FEATURE:
<221> NAME/KEY: misc_feature
<222> LOCATION: 19
<223> OTHER INFORMATION: n = 2'-O-Methyl modified cytosine
<220> FEATURE:
<221> NAME/KEY: misc_feature
<222> LOCATION: 21
<223> OTHER INFORMATION: n = adenine phosphorothioate linkage

<400> SEQUENCE: 85
ggaaucnnan annngaucna n                                              21

<210> SEQ ID NO 86
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 21
<223> OTHER INFORMATION: n = uridine phosphorothioate linkage

<400> SEQUENCE: 86
ccacaugaag cagcacgacu n                                              21

<210> SEQ ID NO 87
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 21
<223> OTHER INFORMATION: n = uridine phosphorothioate linkage

<400> SEQUENCE: 87
gucaucacac ugaauaccaa n                                              21

<210> SEQ ID NO 88
<211> LENGTH: 23
<212> TYPE: RNA

```
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 21
<223> OTHER INFORMATION: n = 2'-O-Methyl modified cytosine
      phosphorothioate linkage
<220> FEATURE:
<221> NAME/KEY: misc_feature
<222> LOCATION: 22
<223> OTHER INFORMATION: n = 2'-O-Methyl modified adenine
      phosphorothioate linkage
<220> FEATURE:
<221> NAME/KEY: misc_feature
<222> LOCATION: 23
<223> OTHER INFORMATION: n = cytosine  phosphorothioate linkage

<400> SEQUENCE: 88
auugguauuc agugugauga nnn                                           23

<210> SEQ ID NO 89
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n = deoxythymidine

<400> SEQUENCE: 89
cuuacgcuga guacuucgan n                                             21

<210> SEQ ID NO 90
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20, 21
<223> OTHER INFORMATION: n = deoxythymidine

<400> SEQUENCE: 90
ucgaaguacu cagcguaagn n                                             21

<210> SEQ ID NO 91
<211> LENGTH: 21
<212> TYPE: RNA
<213> ORGANISM: Artificial Sequence
<220> FEATURE:
<223> OTHER INFORMATION: Exemplary oligonucleotide agent
<220> FEATURE:
<221> NAME/KEY: misc_feature
<222> LOCATION: 20
<223> OTHER INFORMATION: n =  adenine phosphorothioate linkage

<400> SEQUENCE: 91
gucaucacac ugaauaccan u                                             21

<210> SEQ ID NO 92
<211> LENGTH: 21
<212> TYPE: DNA
<213> ORGANISM: Artificial Sequence
<220> FEATURE:
<223> OTHER INFORMATION: Exemplary oligonucleotide agent
<220> FEATURE:
<221> NAME/KEY: misc_feature
```

```
<222> LOCATION: 20, 21
<223> OTHER INFORMATION: n = deoxythymidine

<400> SEQUENCE: 92
ucgaaguacu cagcguaagn n                                              21

<210> SEQ ID NO 93
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 93
acaaacacca uugucacacu cca                                            23

<210> SEQ ID NO 94
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = 2'-O-Methyl modified adenine
      phosphorothioate linkage
<220> FEATURE:
<221> NAME/KEY: misc_feature
<222> LOCATION: 2, 19, 21, 22
<223> OTHER INFORMATION: n = 2'-O-Methyl modified cytosine
      phosphorothioate linkage
<220> FEATURE:
<221> NAME/KEY: misc_feature
<222> LOCATION: 20
<223> OTHER INFORMATION: n = 2'-O-Methyl modified uridine
      phosphorothioate linkage
<220> FEATURE:
<221> NAME/KEY: misc_difference
<222> LOCATION: 3,4, 5, 6, 7, 8, 9, 10, 11, 12, 13, 14, 15, 16, 17, 18
<223> OTHER INFORMATION: 2'-O-Methyl modified nucleotides

<400> SEQUENCE: 94
nnaaacacca uugucacann nna                                            23

<210> SEQ ID NO 95
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1,3, 4, 5, 7, 10, 16, 18
<223> OTHER INFORMATION: n = 2'-O-Methyl modified adenine
      phosphorothioate linkage
<220> FEATURE:
<221> NAME/KEY: misc_feature
<222> LOCATION: 2, 6, 8, 9, 15, 17, 19, 21, 22
<223> OTHER INFORMATION: n = 2'-O-Methyl modified cytosine
      phosphorothioate linkage
<220> FEATURE:
<221> NAME/KEY: misc_feature
<222> LOCATION: 11, 12, 14, 20
<223> OTHER INFORMATION: n = 2'-O-Methyl modified uridine
      phosphorothioate linkage
<220> FEATURE:
<221> NAME/KEY: misc_feature
<222> LOCATION: 13
<223> OTHER INFORMATION: n = 2'-O-Methyl modified guanine
      phosphorothioate linkage
<220> FEATURE:
<221> NAME/KEY: misc_difference
```

```
<222> LOCATION: 23
<223> OTHER INFORMATION: 2'-O-Methyl modified adenine

<400> SEQUENCE: 95
nnnnnnnnnn nnnnnnnnnn nna                                        23

<210> SEQ ID NO 96
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 23
<223> OTHER INFORMATION: n = 2'-O-Methyl modified adenine
      phosphorothioate linkage
<220> FEATURE:
<221> NAME/KEY: misc_feature
<222> LOCATION: 2, 21, 22
<223> OTHER INFORMATION: n = 2'-O-Methyl modified cytosine
      phosphorothioate linkage
<220> FEATURE:
<221> NAME/KEY: misc_feature
<222> LOCATION: 20
<223> OTHER INFORMATION: n = 2'-O-Methyl modified uridine
      phosphorothioate linkage
<220> FEATURE:
<221> NAME/KEY: misc_difference
<222> LOCATION: 3, 4, 5, 6, 7, 8, 9, 10, 11, 12, 13, 14, 15, 16, 17, 18,
      19
<223> OTHER INFORMATION: 2'-O-Methyl modified nucleotides

<400> SEQUENCE: 96
nnaaacacca uugucacacn nnn                                        23

<210> SEQ ID NO 97
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 23
<223> OTHER INFORMATION: n = 2'-O-Methyl modified adenine
      phosphorothioate linkage
<220> FEATURE:
<221> NAME/KEY: misc_feature
<222> LOCATION: 2, 21, 22
<223> OTHER INFORMATION: n = 2'-O-Methyl modified cytosine
      phosphorothioate linkage
<220> FEATURE:
<221> NAME/KEY: misc_feature
<222> LOCATION: 20
<223> OTHER INFORMATION: n = 2'-O-Methyl modified uridine
      phosphorothioate linkage
<220> FEATURE:
<221> NAME/KEY: misc_difference
<222> LOCATION: 3, 4, 5, 6, 7, 8, 9, 10, 11, 12, 13, 14, 15, 16, 17, 18,
      19
<223> OTHER INFORMATION: 2'-O-Methyl modified nucleotides

<400> SEQUENCE: 97
nnacacaaca cugucacaun nnn                                        23

<210> SEQ ID NO 98
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
```

```
<221> NAME/KEY: misc_feature
<222> LOCATION: 1, 20, 21, 23
<223> OTHER INFORMATION: n = 2'-O-Methyl modified uridine
      phosphorothioate
<220> FEATURE:
<221> NAME/KEY: misc_feature
<222> LOCATION: 2, 22
<223> OTHER INFORMATION: n = 2'-O-Methyl modified guanine
      phosphorothioate
<220> FEATURE:
<221> NAME/KEY: misc_difference
<222> LOCATION: 3, 4, 5, 6, 7, 8, 9, 10, 11, 12, 13, 14, 15, 16, 17, 18,
      19
<223> OTHER INFORMATION: 2'-O-Methyl modified nucleotides

<400> SEQUENCE: 98
nngaguguga caauggugun nnn                                             23

<210> SEQ ID NO 99
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 20, 21, 23
<223> OTHER INFORMATION: n = 2'-O-Methyl modified uridine
      phosphorothioate linkage
<220> FEATURE:
<221> NAME/KEY: misc_feature
<222> LOCATION: 2, 22
<223> OTHER INFORMATION: n = 2'-O-Methyl modified guanine
      phosphorothioate linkage
<220> FEATURE:
<221> NAME/KEY: misc_difference
<222> LOCATION: 3, 4, 5, 6, 7, 8, 9, 10, 11, 12, 13, 14, 15, 16, 17, 18,
      19
<223> OTHER INFORMATION: 2'-O-Methyl modified nucleotides

<400> SEQUENCE: 99
nngaagguga caguuugun nnn                                              23

<210> SEQ ID NO 100
<211> LENGTH: 22
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = 2'-O-Methyl modified uridine
      phosphorothioate linkage
<220> FEATURE:
<221> NAME/KEY: misc_feature
<222> LOCATION: 2, 19
<223> OTHER INFORMATION: n = 2'-O-Methyl modified cytosine
      phosphorothioate linkage
<220> FEATURE:
<221> NAME/KEY: misc_feature
<222> LOCATION: 20, 21, 22
<223> OTHER INFORMATION: n = 2'-O-Methyl modified adenine
      phosphorothioate linkage
<220> FEATURE:
<221> NAME/KEY: misc_difference
<222> LOCATION: 3, 4, 5, 6, 7, 8, 9, 10, 11, 12, 13, 14, 15, 16, 17, 18
<223> OTHER INFORMATION: 2'-O-Methyl modified nucleotides

<400> SEQUENCE: 100
nnacgcgagc cgaacgaann nn                                              22

<210> SEQ ID NO 101
```

```
<211> LENGTH: 22
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 20
<223> OTHER INFORMATION: n = 2'-O-Methyl modified cytosine
      phosphorothioate linkage
<220> FEATURE:
<221> NAME/KEY: misc_feature
<222> LOCATION: 2, 19
<223> OTHER INFORMATION: n = 2'-O-Methyl modified guanine
      phosphorothioate linkage
<220> FEATURE:
<221> NAME/KEY: misc_feature
<222> LOCATION: 21
<223> OTHER INFORMATION: n = 2'-O-Methyl modified uridine
      phosphorothioate linkage
<220> FEATURE:
<221> NAME/KEY: misc_feature
<222> LOCATION: 22
<223> OTHER INFORMATION: n = 2'-O-Methyl modified adenine
      phosphorothioate linkage
<220> FEATURE:
<221> NAME/KEY: misc_difference
<222> LOCATION: 3, 4, 5, 6, 7, 8, 9, 10, 11, 12, 13, 14, 15, 16, 17, 18
<223> OTHER INFORMATION: 2'-O-Methyl modified nucleotides

<400> SEQUENCE: 101
nnccauauau uacgugcunn nn                                             22

<210> SEQ ID NO 102
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 2, 21
<223> OTHER INFORMATION: n = 2'-O-Methyl modified guanine
      phosphorothioate linkage
<220> FEATURE:
<221> NAME/KEY: misc_feature
<222> LOCATION: 18
<223> OTHER INFORMATION: n = 2'-O-Methyl modified uridine
      phosphorothioate linkage
<220> FEATURE:
<221> NAME/KEY: misc_feature
<222> LOCATION: 19
<223> OTHER INFORMATION: n = 2'-O-Methyl modified cytosine
      phosphorothioate linkage
<220> FEATURE:
<221> NAME/KEY: misc_feature
<222> LOCATION: 20
<223> OTHER INFORMATION: n = 2'-O-Methyl modified adenine
      phosphorothioate linkage
<220> FEATURE:
<221> NAME/KEY: misc_difference
<222> LOCATION: 3, 4, 5, 6, 7, 8, 9, 10, 11, 12, 13, 14, 15, 16, 17
<223> OTHER INFORMATION: 2'-O-Methyl modified  nucleotides

<400> SEQUENCE: 102
nncugucaau ucauaggnnn n                                              21

<210> SEQ ID NO 103
<211> LENGTH: 22
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
```

```
<222> LOCATION: 1, 19
<223> OTHER INFORMATION: n = 2'-O-Methyl modified uridine
      phosphorothioate linkage
<220> FEATURE:
<221> NAME/KEY: misc_feature
<222> LOCATION: 2, 21
<223> OTHER INFORMATION: n = 2'-O-Methyl modified cytosine
      phosphorothioate linkage
<220> FEATURE:
<221> NAME/KEY: misc_feature
<222> LOCATION: 20, 22
<223> OTHER INFORMATION: n = 2'-O-Methyl modified adenine
      phosphorothioate linkage
<220> FEATURE:
<221> NAME/KEY: misc_difference
<222> LOCATION: 3, 4, 5, 6, 7, 8, 9, 10, 11, 12, 13, 14, 15, 16, 17, 18
<223> OTHER INFORMATION: 2'-O-Methyl modified nucleotides

<400> SEQUENCE: 103
nncacaugga guugcugunn nn                                                    22

<210> SEQ ID NO 104
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 104
uaaggcacgc ggugaaugcc a                                                     21

<210> SEQ ID NO 105
<211> LENGTH: 25
<212> TYPE: DNA
<213> ORGANISM: Artificial Sequence
<220> FEATURE:
<223> OTHER INFORMATION: Primer

<400> SEQUENCE: 105
ccagagctga actaaggctg ctcca                                                 25

<210> SEQ ID NO 106
<211> LENGTH: 25
<212> TYPE: DNA
<213> ORGANISM: Artificial Sequence
<220> FEATURE:
<223> OTHER INFORMATION: Primer

<400> SEQUENCE: 106
ccccttaaat agttgtttat tggca                                                 25
```